(12) United States Patent
Mohler et al.

(10) Patent No.: US 11,866,717 B2
(45) Date of Patent: Jan. 9, 2024

(54) MODIFIED PLANTS AND METHODS OF DETECTING PATHOGENIC DISEASE

(71) Applicant: INSIGNUM AGTECH, LLC., Whitestown, IN (US)

(72) Inventors: Kyle Mohler, Whitestown, IN (US); Marcelo German, Whitestown, IN (US)

(73) Assignee: INSIGNUM AGTECH, LLC., Whitestown, IN (US)

( * ) Notice: Subject to any disclaimer, the term of this patent is extended or adjusted under 35 U.S.C. 154(b) by 0 days.

(21) Appl. No.: 17/934,252

(22) Filed: Sep. 22, 2022

(65) Prior Publication Data

US 2023/0026144 A1    Jan. 26, 2023
US 2023/0193300 A9    Jun. 22, 2023

Related U.S. Application Data

(63) Continuation of application No. PCT/US2021/023631, filed on Mar. 23, 2021.

(60) Provisional application No. 62/994,036, filed on Mar. 24, 2020.

(51) Int. Cl.
| | |
|---|---|
| *C12N 15/82* | (2006.01) |
| *A01G 7/06* | (2006.01) |
| *A01M 7/00* | (2006.01) |
| *C07K 14/415* | (2006.01) |

(52) U.S. Cl.
CPC .......... *C12N 15/8212* (2013.01); *A01G 7/06* (2013.01); *A01M 7/0089* (2013.01); *C07K 14/415* (2013.01); *C12N 15/825* (2013.01); *C12N 15/8239* (2013.01)

(58) Field of Classification Search
None
See application file for complete search history.

(56) References Cited

U.S. PATENT DOCUMENTS

| | | | |
|---|---|---|---|
| 6,100,451 A | 8/2000 | Chappell et al. | |
| 6,140,555 A * | 10/2000 | Reichert | C12N 15/8207 800/278 |
| 6,709,867 B2 * | 3/2004 | Grotewold | C12N 15/8271 435/468 |
| 9,605,271 B2 * | 3/2017 | Takatsuji | C12N 15/8261 |
| 2012/0110698 A1 | 5/2012 | Wan et al. | |
| 2019/0259108 A1 | 8/2019 | Bongartz et al. | |
| 2020/0200683 A1 | 6/2020 | Aronov | |

FOREIGN PATENT DOCUMENTS

| | | |
|---|---|---|
| WO | 2003/084312 A2 | 10/2003 |
| WO | 2020/257791 | 12/2020 |

OTHER PUBLICATIONS

Garcia-Muniz et al. Induction of mRNA accumulation corresponding to a gene encoding a cell wall hydroxyproline-rich glycoprotein by fungal elicitors. Plant Mol. Biol. Nov. 1, 1998;38(4):623-32. (Year: 1998).*
Doferus R et al. Differential interactions of promoter elements in stress responses of the *Arabidopsis* Adh gene. Plant Physiol. Aug. 1994;105(4):1075-87. (Year: 1994).*
Fiedler et al. A complex ensemble of cis-regulatory elements controls the expression of a Vicia faba non-storage seed protein gene. Plant Mol Biol. Jul. 1993;22(4):669-79. (Year: 1993).*
PCT International Search Report and Written Opinion completed by the ISA/US dated Jun. 11, 2021 and issued in connection with PCT/US2021/023631.
GenBank Accession No. AC240204 "Solanum lycopersicum strain Heinz 1706 chromosome 1 clone hba-33m2 map 1, complete sequence" Mar. 16, 2010 [online]. [Retrieved on Jun. 11, 2021). Retrieved from the internet: <URL: https://www.ncbi.nlm.nih.gov/nuccore/AC240204> Entire document; sequence residues 61726-63875.
Johnson, David S et al. "Genome-wide mapping of in vivo protein-DNA interactions." Science (New York, N.Y.) vol. 316,5830 (2007): 1497-502. doi:10.1126/science.1141319.
Gupta, Shobhit et al. "Quantifying similarity between motifs." Genome biology vol. 8,2 (2007): R24. doi: 10.1186/gb-2007-8-2-r24.
Bailey, T L, and C Elkan. "Fitting a mixture model by expectation maximization to discover motifs in biopolymers." Proceedings. International Conference on Intelligent Systems for Molecular Biology vol. 2 (1994): 28-36.
Tu, Xiaoyu et al. "Reconstructing the maize leaf regulatory network using ChIP-seq data of 104 transcription factors." Nature communications vol. 11, 1 5089. Oct. 9, 2020, doi:10.1038/s41467-020-18832-8.
Tello-Ruiz, Marcela Karey et al. "Gramene: A Resource for Comparative Analysis of Plants Genomes and Pathways." Methods in molecular biology (Clifton, N.J.) vol. 2443 (2022): 101-131. doi:10.1007/978-1-0716-2067-0_5.

* cited by examiner

*Primary Examiner* — Cynthia E Collins
(74) *Attorney, Agent, or Firm* — Barnes & Thornburg LLP

(57) ABSTRACT

Genetically modified plants and methods of detecting diseases by a relevant color change in the genetically modified plant compared to a non-genetically modified plant are provided. Also disclosed is a system for remote detection of pathogens on crops and a methods for treating crops under a pathogenic attack.

24 Claims, 2 Drawing Sheets

Specification includes a Sequence Listing.

SEQUENCE LISTING

```
Sequence total quantity: 90
SEQ ID NO: 1            moltype = DNA  length = 2150
FEATURE                 Location/Qualifiers
source                  1..2150
                        mol_type = other DNA
                        organism = Solanum lycopersicum
SEQUENCE: 1
gtgaacaaat cgaatataca tatttatcgt tttgaacggc aagataactt gccatcacta   60
taacttctgc cacaactttc tgtccttggg agagcactct ttgggtagca ttttgtgcac  120
attaaataaa tctccacggt ataaatacca tgcaaatata tataaaccgc ataatgtaag  180
ctctatatga tagactcgac ttagaaaata ttgagagatc atttaaacaa gataaaaaac  240
aaattaaatt gctcgaatat tgtttactag tatatatact atggttgaaa tttctttttc  300
agaaggtaga acaaaattta attgtccaat caattatata ttctcactaa atccagcctc  360
tcatcttctt ttcattgatt atatagtact cctagtaacg tataatagaa atggtaatta  420
gggagttcaa tatatatagt gaaacatcga agtaaggaaa tgttacgtta tagatattca  480
tcaaaattaa cgacgatttc tttactatat ttatttattg attggttttc aaaattggct  540
aataattgtg ccaattaaaa gctagtaacc attcaattaa taattctttt acaacctaca  600
aactttaaac tcaacattct tatttcttcc ctattaaaac ccatccatgt tctcatttaa  660
actcaaaaat gaaatactcc atttggattg cttgtttaat tatctttgct atatttcatt  720
cttcacaagg tcaaaactgt cccaaaattt atcttattcc tcataatgaa gcacgtagac  780
aagttggagt cggacatatg acatgaaata tgtggacact atagtcaaat tgtttggcgt  840
aattcggtac gtgttggttg tgctaaggtt caatgcaata acgggtggta ttttataact  900
tgcaattatg atccatcggg taattatatt ggacaacgtc cttatgatga tccacagggt  960
aattttattc catgagcaat attttttatcg attttttccta gaaattaatc tagtttgatc 1020
aattaaggaa aaaaaatctt taatggataa tggatagacc aagaaaaaac catatgaatc 1080
ccattattat aaaaaataat aattgtttta atgggtcaaa gtactatata gttgtcacat 1140
cctaaagctt ttatttattt atttattatt attagtatta ttattaaatg gcggctttta 1200
tgtttctgat ataagtagt tgcaaaatca ctttacggag gctgctctta acaacatgta 1260
gttgttttaa ggtttaacaa tgtcgaaact tatcataaaa tatgacttag gtcacattcc 1320
tttcccaatt catgtgatat tatagtttaa aataaattat aaatatggtg tgatcatgca 1380
ttatctcatt aaaaataaat aattgtttca aaattaatat aaaatatata attatctttt 1440
tatattgatt taaaaaagaa atgatgagac aggcaagtga aatattctgt tccatctaac 1500
ctttaacaaa aaaagaaaaa aaacacgaga agaaattgac gacatctata tatagcagat 1560
aataagatat agtaatgatt taatcgaccg gaaaaaagaa gttagtttaa gcaataatcg 1620
tttcgtaatt cgataagaaa caaatcacat gtatggttgg aagacataaa ataagttatc 1680
cacgtataat attaatataa gcgattgaca atttaaaaat ttgcataata actaatacat 1740
atctaaatta tgaaggaatt tatatatata tatatatata tatttatttt aggaattgag 1800
cagatgaaac aattaagtct aactcacacc ctatatcttg aagagaggag aactgccaag 1860
ccttatagtc agtgcaccga tctcattaat aattaatata cgtagaattt ttaacttttt 1920
taatatctat ataattaatc ttcgcataac ttataccaac ataaataaca tatagattta 1980
ctcataatta acctgattaa tcaatcgcca atccaacgaa cctaaatggt ttttcatcaa 2040
gaataacgag tggcggctct tatcatttaa gcgaatagtt gtatgatgtg acatgtcatt 2100
ctctgacttt ctcaacctaa tcttatatac aatttttttt tcaaataatc              2150
```

```
SEQ ID NO: 2              moltype = DNA  length = 2131
FEATURE                   Location/Qualifiers
source                    1..2131
                          mol_type = other DNA
                          organism = Solanum lycopersicum
SEQUENCE: 2
gtacctagat ctgaaaatat aaaattgtag ggacaactcg ttacatgtca taatataagt    60
caaacagatg gaaatatttt tttattggcg gcttttggaa cattttcaag tatactatag   120
tatatgaaaa ttcattaaaa ttttaataag tgtttagatt tgaatttata agtttaaaga   180
aataataaat tcaatattaa ttaaaaagct taaagattcg aacattaagt taaactgata   240
attaaatgag tcgatataca aaaagaaaa agaaaaaga agaagataat tttatataaa    300
agtcaacttt taaaaatcac ttaccccatt aatatcttcc ttctaaaaga cgttatcctt   360
tagtatctga attcataact tgaaatagca aaaaagggct ttcactttca attgcgattc   420
aatgcctaag ctaagaattc aacattattt aaatattgat attgtattaa aattcattac   480
ttccaaaact cttttattat aaaaaaataa aataaaatac aattgggcgt tcgtattgct   540
taaataattg caatgttact taaaaaattc tattaaaaca atttaagttc ttttattctg   600
cccaagcagt tacacgttgt tgatttcaga ctcctccggt agagccaaca accattcagt   660
gaattgtctt gtgttactaa gtttcaagtc gttcactgaa tccttcacga tgttttggtg   720
gcaggtacta gtacatctac cgatcaaaat caaatccaaa aactcttgca tgttccaaaa   780
ttaaactcaa atatacaatc atctcattta aactcaagaa tatcttatta tgaaccaaca   840
aacaaagacg accatgatga caacgataaa aaatcaatac tccctccgtc cagaaatatt   900
tgtcatgtta cgcttatcga aagtcaattt tgattgattt ctaaaggtaa attaaatcac   960
attaattcga tactttaaac caaaaaaatt aaatattcta aaacaatatg aaaagtacta  1020
taaattacaa tcttttcata ttaatatgat aaaaaaatgt atcttcaaat gttagtcaaa  1080
gttttatag tttgagtcta taaatagaaa ccataacaaa caatatcgga cggaggaaac  1140
ataaaacaaa aatcaatatc gaacaaatta ttcaatcaat aacaaaaatc attgctagtt  1200
ctatatctag taaccaatta gggatagatt attcaaaact ttgcatatta gagatagatt  1260
agtaacgaaa ttcataacta atttcaaaat tcattttct cgtgtgaaac aagacctaca   1320
tagcttgtat cgaataaaaa aaaaattcaa acttttaagg ttccactcat ctctacgcct  1380
acccatttgc tcaactttt tgactgtaga atgcatgcac attttcaatt aattattatg   1440
tccacttgat aaatatgcta taaataattt aatataaaaa tccactatat atacgacg    1500
gaaaaaaata atcaagggaa aaaaggcaat tgtctgtaaa caaaaattac aaatttgtaa  1560
ttcaaaatttt taagttatt ttatttatga aaacataacc aataaaaatt atgaagagaa  1620
ttctctacta actaaatttc tcatgaaaaa atgttcaaaa aaaattagga aatttccac    1680
aattttaggt ttcatgccct gccatgcatt tttccgattt gttgtatata ctaaactaaa  1740
taattttaaaa ttaatatata gttaaacaca aaactaataa tacgtatata tcacttaatt  1800
aaaaaatatc ttctctttt ttttaatca ttataaat cataatgtgt taatgcataa      1860
attttcaaaa tagcaaaaag ttgaactgtg aaatatgact ggagtgaaca aaatatatta  1920
cttataatag gctgtactca tattatattg gcggcttttt ttttcaagtg gagatatttt  1980
ggatacaatt tttttttta attttctata tatgttata acaagtgcca atatttatat    2040
gattaatgtc catagtgaaa aaaagccgcc ataccactat ataaacccct agctcgatat  2100
gcaaatatat cctacaactt cttatactaa a                                 2131

SEQ ID NO: 3              moltype = DNA  length = 2968
FEATURE                   Location/Qualifiers
source                    1..2968
                          mol_type = other DNA
                          organism = Solanum lycopersicum
SEQUENCE: 3
tcagtcaatt atgctaccta acaagcccca ctattttatt agcataaaat tgatagggca    60
aaaaatatga cttttcttag attgagcgtt ttgttcaagt tcattgtatt gtgattgata   120
ttgtcttcat tagtgagaat acttaatttt tccaaaaaat atagagaaaa agaaaatgag   180
aaacgaaatt aaaaaaattta gagttgaaac ttcatcaata agacgaatgt ttagatagtt   240
aatcaactga tttattaaga tttacaattg ctatgataaa atacagcggt gttttttctt   300
cttttcaatt ttatcttacc catagttata tttttcatcc aatttagtat tattagcaaa   360
agatatagat attgagatat gacacaacca tccctagact atgatcgaaa tgacaaagat   420
atatcctaac taaactaagg tcctattaca ctttaacttc ttttttttg tggtaatttt    480
atacattttt taacttacgt gacacacttt tgtgactcca cgtagttgagg tgcgtgaaaa  540
atgtttgaat atcatcttac tttagtttag ataagattct agaatttcag tcataacgta   600
ggagatactt atgctttata tcagatttga tgaagatgat gaaaaatgaa taagaaagga   660
ataaatatat aataaacaaa aataattaat tttaaaagat gattttacct gatttaaaat   720
taaattaatc gaacttcaac ataagtaccg aacgtcatac ttggaaaaac aagaaaaaaa   780
ttgctcaattt gagttttttc ctcgtattga tcaattgaac aaccatttat tatggtaccgt  840
acaattcatc gactccatca cactactaga tttgaacttt atacttaaat tttaatattt   900
tcttcatatg gacaaatatt acattattat atactttaaa tagttaatat gatattccat   960
gacgttcttc acagggtatg acttggtatt ctatacaaaa aattatactt ttaattaaca  1020
ctttcttcct tgccctcttc ttttttgtcta ctttatgtta gcaccgaaaa ataattaggt  1080
gtcatgcgaa aattaacaaa gcaaactccg aaaagtcaa tcataagtaa gggacaacct   1140
gagaaattaa atatactaaa agtcacgaag atttaatgtg gttcggtaca ccaacctaca  1200
tccacaaagg agatgaacaa tcttttgtat tcttcccta atcaaatttc tccaagtccc    1260
taagactata ctgtgaatgt tgattaactt gaaagaacaa acctttattt agaaagtccg   1320
aagcctttc ctacaagaaa aagactagct aattataaag accttacgtt ttccttttag    1380
aaaaatgaaa atttattatg ataagaaact caggacaatt aatcccaac agtctctcta   1440
tgttaaatta tgtgatggtg tttaaggaa tataaaattt aataatattt tcttaaaaaa    1500
gtttaaggtc aaaataatta tagaggaaac caattcaaat ttatgttaga gcgttcgact  1560
acataagtca tcgatcttta aattttttt ttggatcaat ataatataga aacaaataga    1620
gaaagtactt acacatggta ttttttaacc taagaagata tatgataaat tcgccgggga   1680
gatctttag agatgtttgg agtctacatt aaggttatta aagacatgta tgtggaaaca   1740
```

```
aaacctgagt taggaaaatg ggagatgact taaaatattt cccaatattg tgatgggatt   1800
gcaccatgga ttaaccctag cttgtcatat tcatttatgc ctaagtgatg actatattgg   1860
gatgatatat aaaaggggag gtgttgtgat atgatattcg tagatgacat agtatttata   1920
atttgtcaag tcgtgtagtg aagttaatga taaattgaaa gtttggagag agccatggaa   1980
tctaaaggtt tcaagttaag cagggctaag aaagaacacc gcagtgcaa gttttgtaac   2040
ttgatgcatg agatagagtg gaagtaaaga tatacactag taatatactc aagagagaaa   2100
accgcaagta tcttgtcttt aatttaagga aactgagcaa ttgatgatga cgttacatat   2160
tgtattaaag cagtgtgagt aaaaagaagc tcaccaccgg ggtatttaag tgtgatacga   2220
atgtgttgcc tgttgccaat gattaaaaga taagttttac aaagtgatag ttatgttaga   2280
ccaacactag tgcatgaggg tgagtgttgg ctacccaaga atgtccacgt tcaaaagatg   2340
agggtagcaa atataaggat gttcagacgg attagtggag aaatgtacta agagagatat   2400
gattattaac aatgctatac atgccgagat aaggtgagag tagtgacctc catgacacag   2460
aagataatgg aagcaagatt aagataattc agacatatat aaagactagc taggagtgag   2520
gatgtactag tgagaaggtg tgaaagactg attatagtaa aagtctattt gaaacgaact   2580
tctcgatcct gcaaagattg agataaggta taaatagata cattttcgt ttaagttaaa   2640
gcttatttag gaaccaaagg gtaaaaaaca agacttgttc ctaacatgaa ggcaaattaa   2700
gttactcaac ttcacatagt tggttgttta attttccata tattaaatgg aatcaacctt   2760
ttttttttaaa attttccatc acctactcac tagatttgaa ctttcttcat tcccacttgg   2820
acttggttat tctacttgac taaatttac tattcattaa acttctttat agggcaactt   2880
gacttggctt tttccacact accttttcttg gtcttcttct tcttcttcat cttattacct   2940
atataagaag caattttatg ttaccttta                                      2968

SEQ ID NO: 4         moltype = DNA   length = 2988
FEATURE              Location/Qualifiers
source               1..2988
                     mol_type = other DNA
                     organism = Solanum lycopersicum
SEQUENCE: 4
cctttacatt gaagagggaa ggatagaact tttggtattt cattgttgat aaagagttta   60
acaatgtttc ttttcgtgtt ttcaaagatt tgaaaagcat aattttttgtc atctaatagg   120
ccatgctttt taagcgtaac atctaaaatg acgacatttc aaacattata tttttttta   180
tcacccttg aaagtgttga ctaaaattta aaaatgtggc atttgatcaa tgacggcacc   240
ttttgatggt ttatgccaca atttttaggg atcgttgaag agctaaaata ttatagtgtg   300
acttagttgg ttagtcatct aaaatttcac gatacaaagc tcacttcctt attatccta   360
taactcgatg agaatatgtg atgtatttat ttaagatgtt atcaacaaaa tctaagatac   420
tctccgtgca agtaggctaa tcatgaaaca aatatgttat atttaatctt ccacttgatt   480
cgatccacaa atcaaattaa ataataagaa ttctataaaa tcttcttta cttccaattc   540
tcatgtcaac atatcaatat agaatgattt taacaaattc attggctaaa tctcttcac   600
caagctaagt tcacttattt cacttacctt accgaaatct atatagaatg attttaacaa   660
ttgcattaaa aaacatgata tcaatttgtc aacaatttat aagaaaccaa tgactactta   720
accaaataaa gaacatgtcc cctgtagttt taattttg cccttaatt tataatttat   780
aatttgcttc actcaaagag tgtttaaaaa aagtggccaa aaatgtttgt gacattgaaa   840
ataaaaataa aaatcacgag acaaaataaa tttacaaggt ccttaaaaag                                     900
aaatatttgt aaggtacgag ttatgcttta cgagacataa tttggtacaa attatgcttt   960
acaaaaaaaa attgtaagat acaagttatg ctttacgaga cataaattga tacaaattat  1020
gccttacaaa agaaaaaatt gtaagataca agttatgctt tacgagacat aatttgattt  1080
tacaaaattt ccatcaatag aggtacaaga tcaatttcaa aacacacaaa taagatgaaa  1140
ttataattaa aaaaatagtt tgattgataa tttttttatca aatagataat attaaaataa  1200
aagttaaata tcattacaag agaaaggtat taacaaaatc ttgtatattt attgttatat  1260
agattgagtc aaagggtttg acattttctt taggttgaag aaaaaataaa tgttcttttc  1320
ctacgtgttc ataatgttac aatccaaatt gtacatctca ttaactattc cacgaaaagg  1380
ttcacataaa atttttgag atattctatg ataaaattcg aattaaatct ttttttctct  1440
tattatattt ataatgaaac aattcatca ttgtatcaca tatttacaat ctatattaat  1500
aaaaaattta ttttatttt atatcgatcc attaaatcaa ttaaatccta ataaactaag  1560
cttataagtt taattaaagt tcgctaagaa ctttattaat aaccttcata ttttaagtat  1620
tattatatta taacatgaac gtccttaatt atccgttacc actaacattt gtcctattaa  1680
taaacccgtg aatgattgta cctaatatta ttaaaattac atttatgtaa ttatgttaac  1740
gatgaatgag tcaataagca atacaaaaaa gaaatattaa aaaattatta tcttattaca  1800
tactatcaat taaagtatta ctttttatat atattatctt tttaataca cttaattcca  1860
aaagtaaatt caaaccatca atatcgggat gactagacat attttagtga acttcatta  1920
tcaaaatagt gtttctttt ttaaaaaaat ctctgtcatt tagtaatctt aatctttat  1980
aactaaataa aatacaaaaa aaaggttcca aattatattt atagtaaat aaaagcaatg  2040
attctagaat atataagcac acatttattt ggaaaatcat attgcattgt gatcttcaat  2100
ttgacgtaaa ttaattaatt attgataaa tattcacga ttctgataat tagtacctat  2160
cttgtttatc attatataat tacaatgatt acaaacaaaa tgttgtgccta tataaattta  2220
attacacagc taaatctata tttatgtttg actcaaattt atgcaactg tatggtgcat  2280
gcatggtaag ctcaattcta gaagcagaaa gaaaaatgag aaaaaaggaa aaaaaaaac  2340
tacttctagc tagctagcac ataaatgact tttttctctt cgtttgacaa aatcatactc  2400
cttcctttca atttattttt cattttacac catacttagc aaattataaa taatttaaaa  2460
aataattttta cttcattctt taacaaaatt tattcgaaat tttacaaata atataaaagc  2520
tattttaaaa aattgcaaga atatataaa aaataaata cttaccccat ttaaaaagaa  2580
tgacatcctt tcttttttag tctgtttaaa atagaatgat cttttttctt ttctggtaac  2640
aattttcacc ctgatatgtt taaagtcaca aaattaaaaa aataatttta tacatttgac  2700
ataattttaa tttatgatca catgatcaaa aaaatttta cttttttatcaa  2760
gtcaaactag attattttta gtaaaattga gggagcaact aataatcaac taatatgaat  2820
atgaaaggga gggagttata atggctcaaa aatgtcaaag tcaaccaata tgaataaaag  2880
tttggtccac taatattaaa aatttgaaca attcaacaat agtggcttaa tccataacaa  2940
tattcaattt tcccatacat ctataaatac tcccccctcc ccatacttt                2988
```

| SEQ ID NO: 5 | moltype = DNA  length = 2328 |
|---|---|
| FEATURE | Location/Qualifiers |
| source | 1..2328 |
| | mol_type = other DNA |
| | organism = Solanum lycopersicum |

SEQUENCE: 5

```
tgaaaacata gacaaatctc gctcgtctct ctcatcttgc tcgctactct catatctcag   60
tcgcgtatct ggtgtcccat atacatgtga ttcacatcag atacatgtat ttagtgtgta  120
tctagagtga ttctcatgta tatgtgatgt aatagataga caaatttcgt ttgactctct  180
tcctatttca atgtatctgt tagcaaaaaa acatatatct tggtgtatca aacttaaaat  240
ctagtacaaa attattaatt aataaataaa atgtgattac ataaaattat agaaaaaatt  300
agtaaatatg ataattttaa acttttgtct tcgcttagta attttctttc aaagaattga  360
agaaataatc ataatgtgaa taaaattgtt gaacagaaca tgttttgttc attagacatt  420
agttttagtt gtaatgtgct cataaggcag gagcggaact atcttatatc agcgacgcat  480
tttcatcaaa aaattacatg atctatataa gtcaaatttt aatttaatga ttatatatat  540
tagtgttgat atatttttgt aagatttagt atagtgatta aggaattgcg aaacttattt  600
aaggttgtgc attttattct ttatagttta tagcaacatt attttattac tttatattta  660
gacactcttt aataaataat aaaaatctca aaggtaggag ttcctatcat ttcaataagt  720
cacatagata taaatagtgt aatttcgtgt ttattggtta tgactataac ttttcaatta  780
tattgaccga gttaatttat ttgtaaattt aattatgatc aaatccattt tttcattaa   840
ttcagcatta cacatttttct atttaaaagt atataatatt attttgtgga ttataagaat  900
taactcttta taaattaaag ggaacaagtt gttaacaatt aaataacaca aagtaacttt  960
tttcaataca ttcaacctta tatcaagaaa atgagtatta ccaaatctta ctcatgtcat 1020
aatttgttaa caattgaaca catgcaactt ttaccgataa aggcaaagtt aatttgtgat 1080
caattgatca aatttactac ctcaaaagct caaacttata tgaaaatatc ccaaactttt 1140
gccttgaaaa aactaatttt agagaaaaaa aattagaaat cacaaataga ataaacatgg 1200
taagactttt atatctataa gatcgataat atattgcgct ctataactat agttctgttt 1260
actatggaga tttcagtggt atacttctgt ccgtttagcg aaatatacaa ataatgtaag 1320
tatatacaaa ttttgtattt gaacattagg aattttttcag aactcagttt gtatatttttc 1380
tttgccaata tacaaatacg ataatttatt catgaattgt attcaaatag ttagaataag 1440
catatacaaa attctgaatt ttacaatcaa gaattgaatt atacaaattc taaatttata 1500
caaatcagga aaattatata aaattatacg aataaaacaa atagcaaaat ttgataaaac 1560
tgtagctgcc aattagaatt ttcctaaaca gtagctatga catttaatat gatttaaata 1620
cttattattc tgcacaattt ttcctttcaa aatctttat taaatgaagc cacaaattca 1680
aaatcaccct tttggtctat ggatgccatt cccataaatt actccaattt cattgagcaa 1740
caattttctc aataaaagaa aactttgaaa cggaaatagt aaaattctag aagttttttag 1800
agcaagtttc atcccatgat ttttccacaa gtttgaccaa tatatattac tatttacaca 1860
aactttatta ttctaatata tatgaaactt ctgtgcaagt tctagaaagt tagcaaatgt 1920
tgaaaaaact taagaagaga atgaaaaaata ttttttgtt tgaagcatca tacctataaa 1980
taaattcaat aatatacgtc taaagataat cgagcctcaa tatgaccgca gaatatcagg 2040
tgaaaaataa ttaaagaaag aaaaaaaacag cttgagcttg aggcttttttc tgtttgtgtg 2100
actagtcata aaatgggcac aattggttag cattagttgg tcacctacac aactaaccac 2160
tttgtcccaa atctacctaa ttcctgtgta aactatataa taaaacaaaa taatgtcaaa 2220
ttgttactat ttgtttatcg gtcaccaatt tttaaaaaaa acatcttctt ttgactctcc 2280
ctactcaact tttttcctat ataaacaaac acaacatttc ttattcaa            2328
```

| SEQ ID NO: 6 | moltype = DNA  length = 2452 |
|---|---|
| FEATURE | Location/Qualifiers |
| source | 1..2452 |
| | mol_type = other DNA |
| | organism = Solanum lycopersicum |

SEQUENCE: 6

```
gcagccggtt aaggatatat tgttgttata gcactatctt gctcagaact gtgtatacca   60
agtcaaataa ttttcaaatg tacatgtctc ttttttaaaa gttaaatata tttgcaccta  120
cttttttgcac aaataaatgt gtgcacatta gtttggcgac catgtgtgat gtgtcgtgtc  180
tgtggggttc atagtttggc gcagtagttt gtcgcagcca aagacagttt aaaggaacaa  240
cttcatatat agcaaataaa aaatatatat ttgtatgtta taacaaaatt tgtataattg  300
cgttacataa taaacatata actgtataat tcgctggcct aaattgtata attcgctgac  360
ctatttcgct gcaattgtat aattcgctcg cctatttcac tgcagtttgta taatgcgcaa  420
ttatataatt cgctgaccta ttttgctgga atatgtgtat aaaatttgct ttgcatacaa  480
ttaaatcgaa gtaaaaggtt tatatattgt ataattataa gtgtatatat aggaagaaga  540
tatatgtttt tcgcttgctt tatacaaaaa cagaaacaca atttatacac ttctgttgta  600
taaagcgaga taattcgttg gcgttttttcg ctgtaatatt tgtataaaat ttgcatttgt  660
atacaattgta atcgaagtaa aatatttttta aattgtataa ttaagtgtat agcacgaaaa  720
tatacatttt ttcatgtgt atatacaatt ttctctcgct ttatacaaaa caaaaataca  780
atttatacac ttctgttgca taaagcgaga gaggcaagca gatggagagt ggtgagcgag  840
agttttggaa gagaggcgac tggcaaagac aaaggtttgc tatgaagcac aattaaatca  900
aacagtaact actccattta ttttaggtta ctaatttgct actatataga attatcccttt  960
aataaaattc ttatcatata gtataatata tgaattgaat acccatcatt tcaaaaaatt 1020
aaactagtca tttgaatgtc tatatcatta taaaaccatg tgaaaaatta gattattctt 1080
cgtgtaaatt actcgctcag tcttatttat ctttttagtc tgattcacat aatttttaaa 1140
agttttacat aacatgttta aaatcataaa attaaagaca ttaatatata tttacacatc 1200
tttaattttat gacatatatt tttttttaaa aaatcttttt taattaatt ttaaattaaa 1260
ataataaaaat gaaacacata aataagtaa taataattat catcgtatat tgatgaacaa 1320
atgagttgat gtttgatcct attcttagtc aagcaaatag aagtctaaat tagcactttt 1380
tgttttttaat ttattgatga ttcatgaacc ttgtttgtta aattcaagac tatatattac 1440
agtcaattgt aaaacaaaat gtcttggaaa attagatcct tttattggcc caccaaatag 1500
acctaggaaa cccatacgaa cccagtgaag tcacatcgat gtggagtctc tagaacgtca 1560
aatgtgagtc atccttgctca tccttttgtc gaaatttctt ctattgggtc aaataagaaa 1620
```

```
tatgtgccat tctcgttctt attaaataga cataatatac acttttaatt aaattaatat  1680
gtgtcatgta atgatttgta cgtaaatatg actgatttaa aaataatata ataataattg  1740
ttcaaaatta catagtgaat taatagataa ttacaaaata agttgtcttt ttaaaaatct  1800
tggacaactt caatggtgtc tttacttcgt tttctcttta taaatttaaa gcaaaaaaat  1860
atttatatga tgtcaattga ccaaacacat ggatgacctg gatctaattt cttcgaagag  1920
cattatctca tcttgtttat ttggagtact atctttctt atctcactga atgcctacaa   1980
actaagcata attttattct tctgaagatt agcttgctca taaaaccctc gtatcatttt   2040
gagctatttg taattgaaaa cgatgttttc atcactatta tttattttaa aaaggcgttt   2100
ttttcgagca ataaattctc tttattttaa tggtggtcaa attatgttca atttctttat   2160
cgtacataac aattaactaa actttgaaat atcaacgcaa acaagggggta attaattaaa   2220
ccatgtcaca acccatcaag acaccaacta tataatataa attgaaaaag acgtgcacaa   2280
tttttcactt gtttccttat actttccttt ttctccacga gataaataaa attcataaaa   2340
agagccccac gattaaacga ttacttttct agtattcctt tatgttaaat acctcattaa   2400
actataacat ttttcccccaa caaattaacc aaaatcccct ctaataaaag ct           2452

SEQ ID NO: 7          moltype = DNA   length = 940
FEATURE               Location/Qualifiers
source                1..940
                      mol_type = other DNA
                      organism = Solanum lycopersicum
SEQUENCE: 7
aaggtgtaat gtgaattgag aaatgccatg aaaaatgaaa cttaaaaaaa atcatttctc   60
tctcagtggt agtgaagaga gagcttttgt gcttttatct atagaagcac ttcttccagc   120
tcttaaaaga gatgagaaga tagtctccct tgcaccattg tcatcttcgc tcggtttgga   180
caaatgattg attgataaaa ttatttaact gagtttgcgg attttctaa cacaagtgtg    240
attcactccg tttgttgagt ttgttacagt ttttgcaatt tttagaaca caatatgata    300
tggacataag ggaatcggaa taactgaaaa aagatatgaa gactttcaaa tgttttaaaa   360
atatgttggt aatctcccat aaactatagt gttggttggt gaatttgaac acctttttctg   420
tgagagaatt gactatttgg acatggcata attactaagg tgagcatttc ctccaacagc   480
caactaacaa tcctcccatt ccgtttaatt actcacaaca taattctcag taaaattcca   540
cttcaacttt gttctcataa aaccaaaaaa tccttctgtg ccggagaatt cggtagaata   600
atattttact tttgttattt catcttttcta aatctttgta cccttttaat ttgatacttt   660
ttaatttact ataaaataaa aaaaatatta tagcttctt taaattttt tatcaaattc     720
tgattaaatt tttttttgtca tttagcatta cttaaattca taaaatttaa attttgaatt   780
tatttctttc cgtaaaaaat aagtgtttgt ttgtattatg aaaagtttac tcaaaaggaa    840
aatactttag agtcaacatc gacggtggaa taaacctacc atataccttc tccactcaca    900
agacatttta tttatatata ggcatttaac acaatctcaa                         940

SEQ ID NO: 8          moltype = DNA   length = 1860
FEATURE               Location/Qualifiers
source                1..1860
                      mol_type = other DNA
                      organism = Solanum lycopersicum
SEQUENCE: 8
tcttgtcaag gaccatcctc ttgatgtcta cttcaagcta atctagtaac aaattatgct   60
tgcagctaga ttatatgttt tagctagcct ggttagctac cattttttaca tattaatatg   120
ataaaaaaat attctctaaa atattaataa aagttttaatt taaaaaataa                180
attataacaa attaaaagta gacagaaaaa aaatagtatc taagatcgga agtttgaaag   240
ttcaagagga atatgaatca ctcaatgagt caatatcagt gtcaagagga ttctagtgaa   300
tcccttacc aaataaatta tattttctta aaataaaata ttttttcttcg tatcaagtac    360
acataaatagt aatactaata tatttcgtaa aagaattga gaggtcttat ttttgttgta   420
aggaacacat tagatggatc catctacccc gtgaatgatg tggatatttc atgaaatatt   480
tgaagcaaga aatattcaag tcctggaacc atttcaattg gaaatgaaaa ataattaat   540
atatgattaa agaagaagc atccaaattt cacttgttat gctaaacttg agttacaagg   600
ccaattatgg atatttgatg tgccaacgga tccattaaaa tgtgtcaatg aagtacgata   660
tggttagact aattaaccat tcaatttcag atatttaaa caataattgg ctcttatagc    720
ttagtaaaaa aaagagaaag aaaactaaaa ttgcttggtt ataaaaaaaa ttatgttaaa   780
agttatttca aagtggatga atttataat tttcacacac tccgaacaca attttttaagt   840
ttatgattaa ggcatgatcc gttaaatttt cataatttag ttgtttttctc ttttttttaaa   900
aaaaatgat ttgggaccaa ggcatttta tcgaagaagt atgatgatcc gtaagagaaa    960
tatcctaaga ctatgttcaa tatttttatgt aaataaatat atgttcaaat gtattacacg   1020
tgatgtacaa cattgatata tactatttga ataatgttca ttgaaatttg gtgatatcct    1080
ttgattaaaa taataataat aatatatac aaacttccca taacattgtt gaaaggttca    1140
aagtcttact taatttctgc atgtgttgtt atgttcctgt tcttatcctt aaacttcatt    1200
gaagtttcag aatcctacca agcactttgc ttaattatcc gcaagtacaa gggtggctta   1260
attattcgat tttgttttat atatccacgg gtacctaaag ttttatttat ttattttttt    1320
aacttcagga taattcaaaa ttatagcata atatttgtct ttcatatgag tactgagtaa   1380
atttctcatg tgtaatatcc tacaaattac acaaatcaca ctagtttagc tctatatgat   1440
atgtttgaca atgaaactgt cgtgggttga tcttagatgg atataaagtt ttttttttcgc   1500
aatatcaata tcagtaatat ttatttgtta tagcaggtta attagttata attttttatct   1560
tgtgatataa atatcataat tgtaaactaa ttttccacgt ggaacttata tcatttaacg    1620
aaagttcaat ttggcagaaa aaaatagagt cgtgtgagct ctattgcacc acgtgaatca    1680
ttaaaagccg ccaataaata aataataaaa aaaagtaga gcgtatatat tgtaattgta    1740
cgtaactaag catttagcaa gtagaataaa aaataaataca aaaatttatc aattcatata   1800
atatttttaat tagacaataa tgaatacatc tatccttttt gttctataaa taggtaagag   1860

SEQ ID NO: 9          moltype = DNA   length = 1540
FEATURE               Location/Qualifiers
source                1..1540
```

```
                        mol_type = other DNA
                        organism = Solanum lycopersicum
SEQUENCE: 9
taaaaggttt gttaaactat ttatgttggg tgagataata atatcttatt tgtgtaatgt    60
atacacactc ccttcaactt atatattttg atcattgatg aacaaataat aatatcttta   120
ataatcgtgt gtcgttattt actttacttc aacattttct tgcctttttt ttttgttgtt   180
gtatattgaa tttgaaactt attaatgaat tacttgtagg tgtattcgat atggtctcaa   240
tgtttactgg ttagattttg tggtttagtt tatcgatttt ttatttataa acatgctaaa   300
tcaatgatca ataatttaga taatcaacta tcgatcctta aatacttgat tttttattta   360
attattcgtt agatacgttt aagtcagaac ttcataaata gaaatctaga aatttacaag   420
caaaaacact gcttcattta ttatattaat attaaaataa tataataaca caactttaac   480
aagtgcacaa aacacatcag catcaataca ttgattataa aatgcaaaag aaaataggtt   540
ttgtatttga agtttaaata aagtcattat tatataaata gaaataaaaa taaaaaaaag   600
tagttttaat ataattttat taggttattg atttaatcat taactaaaat tttaaaattg   660
gaagctgaac taatattcta agacggttaa ttcaataacc caaaattgat aaatcaacac   720
agtagtaaca tttttttttta tttaaccttt atcagttaaa cctgttttag acacaactaa   780
atatgaatta gttaataaaa taagttaggc gaaaaaaaaa ggaaatttga cccttttttcc   840
tatcttattt tgattaccat ttgttctcgt aagtcttatt cttgcataaa aaaatcaaaa   900
attctaaaag tatggtgaca actcatctta attttgaata gaagaaacta tttaatttttg   960
attttttcttt atggacggtc tgagaatttt cctattattt tttaaaaaaa tgaaattta  1020
atataaagca gacatattaa taaaaatcta gacacattaa agtattagtt aaaaatagga  1080
tatgaggatt attttttgttg tgtttaattc caaaaacttt cttgcctacg aaccaaaaaa  1140
cattccctgt tttctaaatt cattgggaga gttttataat taattaacct tgaatctcta  1200
gaaaataaag aattaatcat ttttgcagat taggaattag ctatgaattt tttattgttg  1260
ctaacaaatt aaaagacaat tatataatat tgtcattaat atcacttcat gtgatgactt  1320
tctctattcc tcctccaatt taagtggctt gtaaattttc cctttagagg aattttccat  1380
atgatcattc catccattta attctttatg gtaaaaattt ccacaactta tatagtggaa  1440
ttctaaatgt gcaaggtgcc aaaagttgtc acacccctat ataaactacc caataatatg  1500
taactatata tcaaaaataa acaaaaatat gtacacaaac                        1540

SEQ ID NO: 10          moltype = DNA  length = 3012
FEATURE                Location/Qualifiers
source                 1..3012
                       mol_type = other DNA
                       organism = Solanum lycopersicum
SEQUENCE: 10
ttggagcaga aattcaggag gactctaaca aatgttggta aaggtggagc aacttataaa    60
gtacagacag aaactcccaa aaattccata gtttcggtgt caccgcgaac tctggtgttc   120
aaggagaaga atgataaaca aagctatact ttgtcaattc gctctataaag tgatagtgat   180
cagagtagga acgttgggtc aatcacttgg gttgaagaaa atggtaatca ctcagttagg   240
agtcctatag tgatatctag gattattgat gtttggggta gtgatgacta ggacaagagg   300
gaaattatgt acatatgttg tcgacatggg aaaaaataat gtatgcacac aaaagaattc   360
cagtaaacac cttgccaaat atgtttgtgt gtgagagaat tggaagaaag gggaagtgac   420
aacttgttct ttctacttct ctcagcttgc tgtttgggat tgcgcattaa tttcgagatg   480
aggctcctct ccatttttcta tctctccctt tctcaaactc taacttggat gagagacatg   540
tatcatgata aaaagataa tgactgagat ttaattaacc aaagcaatgt tccaaccatt   600
gttaagatag caaatactcc ctccatttca atcggtttat tgatccgttt gaaagaggat   660
atcgctttct ttttctcttt cattttaact tttcacatgg tatgttaaaa ctacaagatt   720
acaaaacgat ttggtatatt ctacatgtct tttttcacgt ggtatgttaa aaccacaaga   780
ttacaaaatg atttggtata ttctacgtgt ctttagttaa aaggacaag attcaaaaaa   840
aaattcatac tctcttaaaa tctatgtcaa atcaaaacta gataaatgaa gaaagtattt   900
acttcaattt ttgaatttct ctaaattctt acatccagtt gttagttctg taattttgtt   960
tgtaattttg agttaatctt tacttggttg agttccatt ttctacaatt tgattaattt  1020
ttgctttaat aactgacaag tcaatgtgta atcaatggcc attaaaatat tgatattaga  1080
ccaaaaacaa tattaaggta tgaccaaatt tgagcgcgat ataatgtttg tattacgtta  1140
caaatgaaat cagaatttaa agcttataaa tatttaattt aatatttttc aagttattga  1200
attcaatgaa ttttttattaa aaatataaga tttgaactaa aatttattgg ttcaatcaaa  1260
tccacacgtc cgaacactta caagaacgag aaatattttta agtaagacc gaaaactgat  1320
tacgggaaa atttgctact tacggaaaaa tgtggcagat ttttggacta tatctgaaaa  1380
ttatggctgt ttctgaaatt cagcattgtt cttcttactc aaccaattttg cagctgaaat  1440
tcgcccaaac aaaacaccgaa tcctccacca aattatccca aatctgagat atgagctctc  1500
cacgacattt ctaatctatt gcaataatat taagtccaaa cgaatcttgt ttgcgtcaaa  1560
gccatttttt cgaacttgag ctttgatgaa gcttcaatgg cggattgtct tcttcttctt  1620
caaattgttc cttataacca cgaaacggac aggaatcaac acgacaaat cgatcaaaac  1680
agtactcatt cggaacagat cctttgactc gggcttcaa cttcttagag taagtttttt  1740
ccttatattt cttaaatggc aacaactgat acatgaaact ttcagctcca tttcaatggc  1800
tatcaacgaa atggtttgga aaccagcagc agattcctca acagattttt cagatttttc  1860
aacttttttct gggtttaatt tgcagtagt tatttagtgt tgaattcgaa aatgaacttg  1920
tgtaaatagg taatttaaat tgaaatccaa taatttgac tgattaggga aaatctattc  1980
aaattaagga tatttatgtt gagtttaata gagagaatat aattagtttc gatagtaatt  2040
aataaacaaa aatactaaat cagagggatt taattactca atattttatc cttttccttt  2100
catttaattg gcccttccca aaatttattt ccacaaaaca tagatatatg ctattttcac  2160
aagtcctaat catgagagaa cgttagggac atttttcttat caaattatcg ataacgagat  2220
tttgaat tgaaatta acggaaattt ttttattcct cataatttag  2280
agatattta tatgttttttt cttttatctc gaatttgtac ctattgtctc tttcaaaaaa  2340
agttaatct tttcccctaaa aataataatt actctctaaa aatatcaaat atggctagaa  2400
tactgcatgt gtgcacgtat aaatttgatt tgtcctatca tgaaatgaat aacatgtata  2460
ttctcaatca gtatataagt aatatctttt cttaagaaag gttatttca agccttaatt  2520
cgttccaat ttattaattt gcaaattact ttcaattcat taaggtagtt ttttttttat  2580
```

```
atttcttttt taaaaaaatt aaaacgctat taatctaggt tatgaaaatc tgaacaaaca    2640
aaggttcaac actacatttg caaagatgaa aaggtttaat taggcttgta gctttagtag    2700
gagatccatc agcctaaaac aatttcagcc attgatttgg tgattagtgg tctaattaaa    2760
gaccaattcc agatgcctgt tattcttttc ccaatatatt aagctgagtg tcggcaatat    2820
taaaatttaa taaaattaat catttttgag tcattcatca aactagggac cacaaaaaaa    2880
gattagtctt ttctaatctt ctttttcttc cttttgatta atcctccaaa ttactaaaca    2940
aatgctttaa atgtcagtaa ctgactcatc aacaagtggg aaagtttaga ttatattatc    3000
gtgtgtgata aa                                                       3012

SEQ ID NO: 11           moltype = DNA  length = 3000
FEATURE                 Location/Qualifiers
source                  1..3000
                        mol_type = other DNA
                        organism = Solanum lycopersicum
SEQUENCE: 11
tataaacaac gaaatgatgt atatatcgtg tttatcctac tcaatataaa tatatttgat     60
acatactact taatgtatca agttctacaa tatctttta atcttattca aatttaaaag    120
gctacataga caatatcaaa tcagttttgt gttatgtatc tacgatcttt aatgttttgtt   180
caatcttatc ctacttagaa ggctatgtat atgtatatat atatcaaaaa ataaccttga    240
tacattaatc ataatgttct ataattagag cagtatatat cagttccaat aataggtatt    300
tgatacataa cagtgacaat attgactact ttattatgta tcaaattatg gtaattatgt    360
aacaaacaaac taacacatag tatcacaatt ctaacactgt tagagcatgt acccgaaaca   420
ttacaataac caattataca actattcaca aaaaatcgac tacacaacat ctcgagatca    480
gatatccaaa aatcgattac acaacatctc tccagccttt tgtgttgta taaatgtata    540
cttgatacat tgtaaatttc cgctcatatt tcttcacctc caagtacaga ctaaggaaga    600
tattcatgat gtatctttc taaattttga caattttga taaaattgca aagggtcttc    660
gataaattgg gagaagaatt tgaatctctc atattttttt aattattttg aatcaaagct    720
gaaagatctt cgatgaactg agagaagaat tgtgaatctc aattttttt gacaattttg    780
aataaaaatg gatagcatct ttacacaatt gtagagggat aaagcaacac tcgtgtctat    840
aatgtctcaa atctccaaat ttttctcaac tcatcaatct ccgagctgta atggctgatt    900
caactcatct cactttctca attcttgaa tgcctcaaca aaatagagat attcacgatg    960
aatcgactca atttttcaat aatttttgaat cgaaattgaa aagatttttg aaaatcttgg   1020
aaaagaaatt tgaaattta atttttgat gttgtttac tttggagaga tttattagca    1080
ctgaaaacaa tattgcataa tttatgaatt ggatattat tttacgtttt tgtttctttt    1140
taagtgcaac cagaatggat ttttttctt tttttaatgc aacaaagga ttttttcttgt    1200
ccgaattaat gtatccgaat gatgagttta tattttcaaa aggtacaaat ttaaaaaaat    1260
tattttaata gaaaagaat aggaatat atatatat atatatatat atatatatat    1320
atatatatat ccgaatgatg agtttatatt ttcaaaaggt acaaatttaa aaaaaatta    1380
ttttaattag aaaaagaata ggaatatat tatatatata tatatatatat    1440
tatatatata tatatatat tattgtcatc tgacttttaa gtccttcatg gactcaacct    1500
aacacatgta ggacaatttc tattgtcaag acctaaatca attggcaaat tttcaataat    1560
taaggtgtgt ttggtagtga gggaatgatt ttttaattaa aagtttatat tattttgtcc    1620
agaaaaatta gtttcttata gacaaggaaa aatgactttt atagtaattg ttgagaaaat    1680
aaattgcacg agtattattc tacacgccta atatcataac cctccgtcac acccttattc    1740
cgatagtgtt tgaattgatt atatataata ttttttaaat aatatttcct acttacgtac    1800
taaaatatca gtaagtaagt aacaaaatca cttttttttt tctaaaaaaa aactatcatc    1860
atatttacca aacacaccct tggtcatggt gtctagtgtt taatatagtc aataatatca    1920
tgctaaccat tgctatacgt attatgtatg acttttaaaa tggtaactaa ttcaattata    1980
gttacaatta tattacaaag atacatttga cacaagtact agtaactctc tagcgggtaga   2040
agcaaatgca ttctttttac aagttcggtg tctaggtcag cttgttctca caactattaa    2100
tatcattacg tacttgctat ctctcacaaa cacatatatc tatttgcatc attaaacatc    2160
gtttttaaaga gacatacagt cgcgacatat atgtatttct gaaaacagt taatcactaa    2220
atacaacctt tgaaaaatg ataaattttg gagtagtaag taaaacttt gaatttcata    2280
ctaaagtccg tatataaatc gaattgtgat aacagatcga cactgcttat acataatcct    2340
tcgtatgcac attgcatcta gaaattagtg acatgctagt agtccaaact ttgaattgtc    2400
aaaatattac agccatgtta gtagctagtg tctcttgtgc aagacttcaa ttatcttgca    2460
tccaagtaat ggatattctt gtttaatccc aagagaaata acaataacat atgcaacgca    2520
attccacaac tggagtctgg agatggtagt ttgttacgaa atcctgtccc tacctcgaga    2580
agatagataa gtttattttt tcgatagact agtcctaaga gaaataataa taacaactc    2640
ttcgggataa ttctacaagt aagatcaaga gagggtagta ctgtgttacg taaccttagg    2700
tagaaaatct gtttccggcg gacttaaaaa tctacaaatt ttcctcaatg gttaatgcaa    2760
caattaattg caaacctgcc taacaaattc cacattattt catccagtca ttttcaccaa    2820
ggaaattag gggctgcaga cttttctaca tcttgtaata aggtgtaaca tttttttccat    2880
tgattaactt gacttgtatg tggaaattag agtaacatag tataaaaatt tcattataaa    2940
atgtgtaatc ttttcttcta tttcatccac tgctcaattt tcttttcttt gccaattacc    3000

SEQ ID NO: 12           moltype = DNA  length = 3000
FEATURE                 Location/Qualifiers
source                  1..3000
                        mol_type = other DNA
                        organism = Solanum lycopersicum
SEQUENCE: 12
caatgtatgt ccattactta gtaagcacat ctttaggatg atcaaattat tcatgtcaac     60
taataaaatt agtagtactc ataaaactcca agtttactac gccatgttgcc ttttgcttta   120
gtaaatttct gatttactat tatatgagta aatttcaatt ttattactgc aagagtaatt    180
tttagattta cttcttctca attactttac cctttaggtc agtcgtgatt caatcattga    240
atgaactaac ctaaagaaaa ttgtgcatgt aaacatatta tttgtgccaa cattattgta    300
aacatcaagt tgcgagataa taatagacac acatgagatc atatagaaga aacatttgtt    360
aggatcatta aatatctaaa caatccactt ggtggatgac taggtccaca aatatctgta    420
```

```
tacgttccta gaacgcagaa aattcaatct caacttttgt ttatggtggt ctcacaatta    480
gtttgccttg ctaacaagta gtacaagaaa aatcaccatt taaaagaact ttaagtttct    540
tccatgaaag tccatttaa ttttctataa ttcgtctaaa ctttatagac taacgatgtc    600
ccggacaatc gtgtcaaact aagaaagtat aggaattagt aaattctta tttaccatag    660
aatgtgcctc aattgcacta attttatcc aatacacgct tgaagataaa gtatgaaact    720
tttctataat acatgtcttc ttagagacat tcttggtgat accacatcat tgatcaaaga    780
tcgcaatttt tcacatgcct agcatggtgg cttacatctc attcccttta gcgaatggat    840
ccatatttta gcatttatca gaagttctca ttcttcatga atggaacaca aacacgtgag    900
cttatcaaat tatgatagct ttagtacctc atttcatatt tatgtgcatt attcaatcac    960
ttgtcttctt cagacatata tgcactaata ttacattcac ttttgtaatg gagtaaattc   1020
agtaaatttc atgactttc atctaaaaca cattagtttt tctttagtca ttattatatc   1080
atcaatatgg tgcattaaga cttaaattca atgtcttatc catataaaag tgtcttaggt   1140
cataaatcga cgggtcttgc acccaatatc ttatcatcat ggtgcatcag gactttaacc   1200
caatgtctta ccctctttgt gtgattagac ataaatctat cgtcttattc ttatgatgcg   1260
ataaaactta aatttatcgt cttgcccata atgaggctta acctcaagcc ttcagaatat   1320
ttgtaatttt accacttttg atgaccatta atatgatcgt acattataat tacacataat   1380
tgagattatt gaattcttat aatcaacatt agtagttaat aaatatagct taatagatta   1440
catcctcgt ataaaggttg aaaacatatc tttcactaaa ttgtgcttat tcaattatta   1500
aaataaaatta agaaattttc ttctcaatcg attaaaatta aacgtataaa aagtcaacaa   1560
gtcactttaa attcttacgt tagatggtac ctccagatct gttacataaa taattataac   1620
ataaagataa atcataccttt gaagatataa gaactttatt gcataactta tgcaagatct   1680
cttttgtact tttcccgtct tcttcataat tcttaagaa taaaacaatc gtggtgataa   1740
tatgttatga aattatataa aatttagaag aagaagaaaa taggaaaaag agaaaagatt   1800
tcttatttat cttgaagtat attcaggatt cattaatctt tcacaaatcg tattacaat   1860
gaaggaaaac cttcatttat agggaaaacc ttacttggtc cccaaataag attactaacc   1920
atatcctaca agaactccac ataattagac attcactgta ataacaaatt gtttataaca   1980
cattccatat tttgtctctc aaatgtgtta acaatcacaa agtgaaagcc gaacagtaga   2040
aattagttga tctggtctaa gtaatcaaga taccagaatg aaagtggaat atatatttg   2100
tgattggcta gcgtcaaact tttaagaaat gcattatgca tatccataag tatattaact   2160
ttgtcgttaa ctggtaattt tgagtggtat aaaattaaat aaatagacat attcattcta   2220
tatgacattt tatattaaag ttttatgttt tttatgacgt tatacatgta ttatatcatg   2280
taacacatta tatatttatt tattttatac aaatttgaat tacctgtaca ataaattcaa   2340
aattaaaaaa tataattatc cgctaaaatt aaattaaaaa tcatatttat gtaatatgtc   2400
aaacgaaaca aagaccaaag tcaaaaccag taacaaattg tttattcttt aattattatt   2460
ttaaaaaatt cttctcaaga ctcggttaaa agtctttttc tgccactcca ttaagttaaa   2520
gaccgactaa aatacatgtg atgtgtggcc aagagcaagc atacacaatg ggctgtgtta   2580
ggtttaattc aaattatttt aattttttt aaaattgat ccataagtaa ataatattat   2640
ttgtaaaata ttttatatat tatttagata aatatatca aaggtggatg aaaaataata   2700
aagaggacac aattaataca aaaatgaaaa ataataaagga ggacacaatt aatacaaaayg   2760
attattttg aaacttatt tcactatatt ccttaacatt cagagacgtt ttttcattt   2820
ttaataaaca taatcatta aaaaaaacat cttccttttg taccaaacag accaaacaag   2880
tcatacttct ccactcagaa taagttaata catgaaaatt caattgaaaa ttcttcacct   2940
cttcgttcta tattttttct ctataaatac caatcatttt ctcaattata attaaaaaga   3000
```

SEQ ID NO: 13          moltype = DNA   length = 3000
FEATURE                Location/Qualifiers
source                 1..3000
                       mol_type = other DNA
                       organism = Solanum lycopersicum
SEQUENCE: 13

```
tctcctcctt taccttcttc tccaactcca attctctaca gatctgagaa taatattcat     60
tgctctgttg cacatagttc aactgatcat cgaccgccgg tttttgttcc tctgatttc    120
cggtaaggta ccggttaatg acggcgtcgg cgctcggatg accaaaagtg aacaaacgct    180
gtcgttttag cgactgaacc ataatagcga tttcagcgcc ggttaaaatg caaagttcgc    240
tagcttttt gaagagacct aaacggcgtt tgctaaaggt aacgtgccta ctgttttgat    300
ttgctattgg tttaattgct attttcctcc gcccttgagt tttcttgacg gcgacggcgg    360
cggagttggc ggcggcgttg gtattgttat taatattcat ggtgggagga aaaggttaat    420
tattatggct tggtaaaatt taattttat agagagtata taacaggtaa aaaataatag    480
taataacgtg taaatcgaag attttatttt gacaaaaaat cggagaatat tttatttact    540
cgttttaaat tgtcgtttta ggaaaaatt gggttacgaa tttgggaact attattatat    600
tagtaataat aaggaattgt ttttcctaaa taggaaataa aaagagttat tgggggaata    660
tttcctataa ttttgggtac taattggaaa acaagaatct ctaataagaa aataaaaata    720
aaataaaata tacgcctagg atttttttt tcttcacatg tgcattaagg tgattattaa    780
acaatttga tataataaca atttagtat tattttttg ttagggtgt tgaagtggta    840
taatggtggc tggtcgatga atatatggat gtatgtgtat aatagtgtcg tgtgaaaaa    900
tcacgtaatt atacaattaa agataacata attcttagaa acttctatca tttgaaataa    960
gtacaaatac ttcattttt cttctctctc ttaatactct gttacatcac ttcacctcta   1020
ttaaatatat atattttac aattttttt ttatacaata tatttgttac aaaagttatt   1080
attgatacat aatttcaatt atttcaaatc taactcagta tgaattagt ttatagttat   1140
gtatctgatg cataaattat atatatgata cacaatttat gtattgtttg ctatgtatgg   1200
cgaagaaaca atgtatccgt gatttttgaa aaatcagaat tattgtaatt tagaaagctt   1260
ttggaataag atgtaattag tgtccaaatt attgaggttt tatactttta tggtaattat   1320
atttttttt tagttaaacg atccttgtgg tgggtcaggg gttgagcaac accctcagac   1380
tttattatta ataataaaa caaaatacaa ggagagggca taaaccttac cttctatcta   1440
agatggttcg gagtcaactt cccaaggaaa gtcaactgct tccccttacaa aaagatgta   1500
atcaaaatac taagcactaa tgaggggact gctctcaata catcgtatct agaaaatata   1560
aactaggggag actctccctt tacaagaaag ctataactaa attagtctat tcaaagtggc   1620
tataattta atatagcta agttgaaaag aagtgagaat aatcaagaag attccttaat   1680
tcttttggtc ttcttccttc taaagctaga catatgcaac aagtcaaagt gattgtaatt   1740
```

-continued

```
agtgtccaaa ttattgaggt ttttgtactt tatggtgatt atataatgta tattgtgcta   1800
aaattttgat tgtattggac aactataagc ccatcaagtt tgacatttat gataggaaaa   1860
aggctcaaat atgtcattaa attttagaa aaagttcatt aatgtcatca gttaaaagtt   1920
tgattcgttt atgccattac ttttaatgaa aaggctgcca ttattttata acggtgattt   1980
tgtaaaacca tttttgatac gtggctaatt ataattcgat cacgtcatca atttttttga   2040
ttaaaaaaac ataactcaaa aaaaaatata aattaatttt tttattaaat aaattgatga   2100
tgtgactgaa ttataattga ccacatcatt aaatttttaa taaaaaaatc aaaattctga   2160
ataaaaatta aattattttt ttaattagaa aaactgatga tgtggctgaa ttataagtgg   2220
ccacgtgtca aaaaataatg atagaatgag tcttttcttt aacggtaatg acatatttta   2280
gccttttttcc ctttatgata atggcacttc cactccaaca agtcgcaatt caagttcaaa   2340
tttgcttcca ttgatcaata ttctatcaaa aaaaaaaaat gtgaaagaga ctagatttta   2400
tcaaaaatat ttgagaattt gtggcggaaa tcaagatagc aaaatagacg attgacaagt   2460
cgataaagaa agtttctttg gaggtcccaa tttaaatcca taaactgtcc tatatagttt   2520
gaactttagt aggcgttatt tctaggatat ttccgtaaga aaatgaatag atttttaat   2580
atttttatttt actagcttga agcaaattaa gacttggtca tttgcataaa agttcatatt   2640
tttgagcggt ctttaatttt ggtctctcaa attcataatt tttaaatttt cgtcctttat   2700
aaagttatat tgcgaatttc taaagaattt ctgtcataag tttagataaa atgtcttgcg   2760
aattagatat taccggac aagttagccc tgtaaaatta ggtcataact aagaacactt   2820
acgcccacaa atttattata tgagaagcag agacaaaaat taaagaccat cgatttgaga   2880
ataaaaattt aaagatcatt aggaaatagg gacaattagt acaaaaacat gactaagact   2940
tgctatagta ttaggttagc tttttgatcc tataaaaact catctgaagg tttgtttagt   3000

SEQ ID NO: 14         moltype = DNA    length = 3000
FEATURE               Location/Qualifiers
source                1..3000
                      mol_type = other DNA
                      organism = Solanum lycopersicum
SEQUENCE: 14
gacagagctg ttttttgccct gcagaactgc aacgggatag ttgaggaggc caccgaggag   60
gagttgatgg atgctatggc tcaggcagac tccactgtga tgttcatttg cccgcatact   120
ggtgtggcat tgactgcgct gttcaagctg agaaacagtg gagtcattgc accaactgat   180
aggactgtgg ttgtgagtac agctcatgga ttgaagttta ctcaatccaa gattgattac   240
cactcaaagg aaataaaaga catggaatgt cggttttcta acccacctgt ggaagtgaaa   300
gcagattttg gatcagttat ggatgttctg aagagctatt tgttgagcca aaattccaag   360
ctatgatgtg ttgtcagttt taaacatagt aagtttgtaa tatgtactcc ttttgtcagc   420
atatggtcat ttatcgccat taatttgccg tatagaaatg accagatggt gattttgttg   480
ttggcagagt tggggagaga aaggctctac attacttttg agagtactac gaactcgagt   540
cctttttatgg aactctgttt tttgtaacag tctgcttttt gtagcattgc tttggtgcat   600
cacaatggaa actgccttaa tttgacctgt tttgttaaat tatatgacct taaagagaat   660
tcacttcgga tactgcagct agaaatttgt ttcttatctg attagtatt cttgtctttt   720
taatcatgca tatcctgtc atgcctagaa ggctctgatt tggctcattg ggttataatg   780
tattcaacag tgcgagtgtg ggactgtaat atacatttat cagttaccat tgtctttgga   840
actaataatc tggattagct tgcatttatc ttctccttcat ctgtttgag ataacttatt   900
taaagttttc acaaacattt atcaatatga atttagccaa gactcgaaca aatgggaaat   960
aaagcatcca atataggtgg tgtcaataaa ttgatttttt ccttagtgac gtgggtacct   1020
aattacctcc taccaacaca aatgctgggc aatctgccca ccaaatcttg tacaggtaga   1080
aagaaaccat ctagtgtgtt tcgcctccat tggaatttga acctgaggct tcatggtttc   1140
cattctcctc cgcttcatta accactgtga acgcaatatg ccaagaccaa ctagtgaaaa   1200
ttacgtttttg ctacatttag ttcggtgttt gtcaagtgtc ttctcattct gattagagac   1260
ttgattgacc ttgtaggaag gtgtatttgg ctgttactac cccaaaatat aagtgacatt   1320
tagaggaact ctactttaag ggagctccta atttgtcttat tgtttttggaa tgaaatttac   1380
cttatattag caatattgat atagtagatt aatatagcat atttaggtag agtaaattga   1440
ttggctttgt gatggttgga cacacttaga aggtaagttt gtttcttgct tggttattat   1500
tacgccaaac aatagagtct ggcaaattgg atataacaaa atgcaatctt gaaaaatcta   1560
ctatggaatt catttttaaa gactaaaaact gagtttagta ttggtagttt ggggaaatgtt   1620
gaagatgcac gtttctaccg gtgatggtt ctacaagtca aactgtatat tagtcaatca   1680
tataccagct atttaacgcg ttgttacagt gttattttga tccttatgaa caactcaaga   1740
cctatttacc tttccattct atattcagtt cagaacttca gattatggtg gactaatggt   1800
atgattggtc taaccataac atctgaatac ttcatgttca atttttctgaa aattgcaatt   1860
tacaacagct tggatgaaga atgtgtgtgt gcttgatgaa atttaggggt taaacgcacg   1920
ctggagtata gactgaaagt gctggctgac aaagaatgag atcaggtgaa gggtaaacgt   1980
ccaaatccca gcttgcatga cttttttgtgt gagtaaaaca aagctggtgt tctcacttca   2040
atactacaga ccttgcattt ttgtcctaca atcttcagtt tctaatgggg tgaggcgctg   2100
aatgatttgc atctcattct ggaagcttga aataacttga agaacagcag tacttctaag   2160
tatcagattt tttctcttaa tctaatcgca tagcttctag aatgttacat ctgttcttca   2220
ttgggtacct gctacctcct agtaacacag ttaatcgtgt cttgaataga tggaaatcgg   2280
ccttactgag atttatggtt tccgttctac ctgattgatc aagaaattcc attttggggt   2340
cctattaaat tcaaattagc gcattgtaga gcttattttt tgggatgat actctaaata   2400
agatttttttt tttttaccat tctcaaatgc ttgaattcga aacctctaat ttcaaacaca   2460
agtcacgacc agtagtagta gcatgagtat atatataccct attgacgtca tagttcatct   2520
cgtgacttag aatatcaatt aaggagtcta atcaaatct atttccgtga ttgtcaaagt   2580
cccaaaactt gaaaattatc ttcaaactt gtttgcaagg attgaatatt gacttccttt   2640
attacaattt atgcaatatt cttttgcatg attagcttca aattaactct caataaacaa   2700
caggaagaaa taacaataca taaattgagg caataataa tgtaactta tgtattgaat   2760
gatgacttaa taatgagaat ggccacttga ctgcacaaaa aaccagagcc cgtgacaccc   2820
cacactttttg cctaaaaagt aaatccaatg aactttcacg gatttccatt tcttacacta   2880
tccacacccca taaccaatca cacaacacac attaaattcc tatctatcta attataacta   2940
tataaacccct ctatttcatt cactttcata cacacacatt attgagacaa agaaatagag   3000
```

| SEQ ID NO: 15 | moltype = DNA length = 3000 |
| --- | --- |
| FEATURE | Location/Qualifiers |
| source | 1..3000 |
| | mol_type = other DNA |
| | organism = Solanum lycopersicum |

SEQUENCE: 15

```
aaatggagac taatgaagta tatatcactc cctctatctg cctaatatta ttattttatc    60
tcacgttcat gacttgaaag cagtatattc agttcaatct gaaaattgta ataataacat   120
ctcgaagcag cagtggatcg ctccatttcc ttcttccatt gtgcacagtt acttcctgta   180
tatgtgagtt ggtggtatgt ttttttttt gtttactgtt tggattaaaa attattgctt   240
ttggtaaaaa aaaaaaagtt agtgaagcat aaggtccact aaaaaagtgg agagtaggcc   300
acttaacatg tgattggctg tctgctttac tgaacaagag aattcagtca ttttcttcat   360
attttcctca tacaatatta ctataacatg ttttcttcac ctaaccatca tattaacata   420
caattagtta attgactctt agataattaa atacataaag tttgttttat ctccttgactt   480
ttaacgatgg atatacaaat tcctattgta ttctattaat ttacttctca ttactttatc   540
aaaaattgtga atacaaacaa tgtaattgtc tagttgaagt agaatatcga tatttacaaa   600
tttttatttct ctattatatt gtttaatatg ttcaaggttg atatgaccac attaatatat   660
gaagatacat tgaattgctg ttagtttttt ttgaatgtat tactaaattc taactaaccc   720
cttctattta atgatgacat atgaagatac attacatgtg ttatttttttt tttttttacct   780
tgatacgttg cttgttgaaa tttgcaagaa agagtcttca actagagatt tttctttttt   840
ttaaaaacaa taaataaata aaatctttgt ttggtataac aaaaaataaa tatgtatgta   900
tatatcaaat catgaaatct ccttatgat tattcttttca cagtccactt ttctctgtg   960
atgatttaaa gttgttgcac ctaacattac tagatttatt ttttcaatca cttctctagat  1020
ggaaagataa cctactttaa ggttttctt tagcttccta agtaagtgat gtttaccatt  1080
ttgaatgatt ctcttgtcac ttgaaataat cctattaatg ctaaacttct attaattcta  1140
aaccgaattc caccaaaaga attttcgtgac gctacttata gtcccattaa ctagtatctt  1200
ggctaatgtg ctttaacaaa atggtatcaa cactacatta ttttttatgta aaaatatcca  1260
gttcacaaaa atcacatgta catctacaac atttaaccac aacttttcta aagcacaatg  1320
agcctttcaa caagacatta tgaactctaa ttcttaacaa ttctaaacca caaaattatg  1380
aactctaatt cttaacaact cacaaaccct cactgatata tgtcctcaaa tctttaagtt  1440
atcccaacttt gaagattata atccaataac acactaaaat taagatttgc attaatatta  1500
caactcaaat gaacacatga aggctaaaac ttgtagttgc attaggacct gattcttcaa  1560
tgtgttcctt caatagtcaa acaacattgg cgaagccaat tggttttgc tctgtgagtg  1620
cacaccttgt tctgagtgac tcaagcac aactcttcag agtgttactc aaaactctct  1680
tgatttaaaa ttctacatca agtaaagttc tttcttaaaa tcaaactcct tgatttcagt  1740
attctccttga cttaatccga agtaaccatt attcgtttat tggttttgc acgcttatct  1800
ttataatgtt agtacagtat atatatatat atatgacctt gttacaaatt cagctccttg  1860
taacaataag tattatgtga actagttata tagggaacct aacagtgagg tccatatgca  1920
attgctaagc ccatattcgc tgagttctgg cccaagtatg ttccatttta ttttgaaagt  1980
taatggctaa gtgggctcat aaaataatgc caccgatac ctatatgcct tcttatttca  2040
tgctacagat tactagtatt tcatattcta caactaaacc ccttaaaatt tgtacaacat  2100
cgggttttat caaaatttct ctccaaatgc ctatctttat atcatgttga aaattgatat  2160
atagaaaaaa tttttggagg gttggggag tagattatca tagatgtgtt atgtatattg  2220
atgaatctac ttgatttata tatacatatt ttgataccat gttatacaat gtgtataaaa  2280
tgattacgag caagccttat aatgtggtag aatattgatt gtcactactg taacatttag  2340
gaaatactac atctgtcatc aagatgcacc atgcatgtgt tcacttgcgt tttcttggag  2400
gaaaaaaaaa aatcctcag ggctaaaaaa aaaggggtg gataataaat ttgttgacta  2460
tttgggtttg gatttcattt ttatttttat aaaaatataa atatagacac tcaaagaag  2520
attcgtgaac tatattttttt ttaaaaaagc agtcgccaag tggcgttttg tgcaaccaca  2580
atttttcag tagaaaaatt ttgacttcac gaacttcctt cgcagagtag tcagcacgcg  2640
ctcttgccaa cattccacgt catctgtatt tgattacgtg cagcacttt taatacccct  2700
ttgttatata aataaactga gcgagttaac tcacttactc ggtttccaat tgagagtcca  2760
acccagtttt tggttgagat tacgatttgt aacccttccg ctttctatcg tttcgaaaaa  2820
gtgcaacctg gtcccaccg aatagactga aaccactcat ttcaagccac gtggaattttc  2880
ttctacttgc tcttctctct tattcatttt ctagcctcta atttatttcc tatttattga  2940
aattgaatca actccgaaaa atactagtgg ctgagatttt tctttgagat tttatgggaa  3000
```

| SEQ ID NO: 16 | moltype = DNA length = 3000 |
| --- | --- |
| FEATURE | Location/Qualifiers |
| source | 1..3000 |
| | mol_type = other DNA |
| | organism = Solanum lycopersicum |

SEQUENCE: 16

```
gttattgata tagttgtggt gaaagtgata agtactcatt tattttaaat cataagtttt    60
aaatttgaat cagatacgga actagacatc aaatgaaaat aaaaataaat taataaataa   120
atttgatgtt atacaataaa aataatgtaa catgaaagca acctcatatc ttcgtcctat   180
acgcttatac ttatacaata aaatattcc tctgcccaat tttcttttat ttctctctct   240
ttcttgtttt atacatacac aaattataca attgatttgt ctacaactgt tttcttttgt   300
atatgtataa cgaattatac aattggtttt attcacatat tgtataacgaa ttatacatat   360
ttatatttgc tatagatcac aattatgcaa acttgctat aacatacgaa tacaaattat   420
gtatttgcta tatgaaaag ttgtcccctaa ataatcacag ttaatccatc tttgtgaaat   480
caaactaaat cataacatat cattctaaaa cactcagcat aacgacataa acagtggga   540
aaatgtatat gattaaagtg ttcaagtgaa atactagact agcttataag gtcgtttatg   600
tatcccacga tctatttata tttataattt attattagaaa taaaatata aataaaaaat   660
taaattatct aaatactctt cttattaacc tattatctta tttaataaaa agagaaaact   720
aattcctaca aaagaaatc aatgtctcac gtatatttta accttgttcc aaatgaaaat   780
tatcactatt taatttcatt taccactaaa caaagaagga taaagtcat tatcgaaatc   840
aacttttcctc aatcaatctt tgaggaattt ctataagaaa ttgacctaaa atcattaatc   900
gatttaagac ttttgtataa aagtacataa attttatttt tacaacacaa aaatttcacac   960
```

-continued

```
atcagaggac taaatctgat tttataaagt ccggcttagc aaagtcaaca aaatcttact  1020
cgactttta  ctcctccaat ttggatattt tgtttgtccc ttttattta  ttattttga   1080
taaataattt ttgcatatta tattctcaat tattcagaga agctaatgtt ttgaaaaaaa  1140
aatagaacaa taaattgatt ttttaattta tcaattaata cagataaaat aaatgtgttc  1200
caaattaaaa ataaccaaac agaaatggac aaatggatga taacaattta aatcttcagt  1260
tctaaatgaa aaattatttc aaactataaa gtaaaaaaaa agaaaaatgt cgttttattg  1320
atttttttta ctaaattgta gaaaattgga tgtttgttta gcattttctt tttgttctta  1380
tacaatactt atgtaaatta gtgaaaatct atatatttta tttatacgca tagaatgtga  1440
aatctagata tattttataat gcgtggatta gaatattaaa atgacaaact tcataatagt  1500
gaatatattt tttaaactaa aaagtaaata aatatcttac attatactct ctatatcata  1560
tttgtactat aatcaaacta aatatcaaaa caaaaaaata attctctcat tttaatctca  1620
acattattaa ttttggcata acaaattctg cataattcat ctccaaatta atatttaaat  1680
tcataaattt tctcataatt tacatatgta ttagttatgc gatatcttaa attacaaaaa  1740
aaacaccatt ttattttat  atttgaataa cttactacat aaatcaacta agtacttaac  1800
atgaattatt tctacataat ttaatatctg cataacttat ctccaaataa acaaccaaac  1860
aactccttag aaacaatagt ctcacaataa aacgcaaaat tatttatct  tacgtttaat   1920
taaagatatt aattaattct gaaaaatcaa aacttttttgt ccaatctctt tctttaaatc  1980
attaatttca taaaatattt ttattaataa aataatatta tgtatcttat cccgcgtacc  2040
aaaggcgaga taattttttta agtaaagagt ttgaaatgga tggtcctgga atactcgtac  2100
tagtctacta taagtggtcc actatatgc  accatttatt agtttgactt gtattatttt  2160
aattttaggg cgacttaaca accaactact agacaaaaaa tcaactaatt tacttgaatg  2220
tgtttgtttc gttagaaata tttttctttt tgtataaaat aaatatattt ttaatttta   2280
atttaatat  ttaattagta agaaaaaata taattacata atttattctt agcaaaaatt  2340
tgtgtagagt gaatgaggtg gaaagtagag gattatatat aagtgacaag ggggtaggat  2400
ggtcaaaata aaagttgaga gtgttaatat tagtccgaag acaatgaact agataagtta  2460
cttattataa ataataagtc tgaaagtgat aatctacttt ttcgattcta aattcttaat  2520
cgaggtgata gcgaaatcgt tattaatccc atgaaagatc tcataggcca ctagggtata  2580
tttggaacaa aaatatttt  ttagaacaac ttacttatct acggtataat ttagcaaaat  2640
actattttct taaaaaaaat aaattaatta tgtcaaatat attagaatat cttttaattt  2700
tgtgatctcg aatttatcac gtagaaagtc aaagttaaaa tattattaaa aatacttttt  2760
tttaaacaaa ctaaaaaata ttttttttga aacagagaaa agtatatgaa ttcagataga  2820
aatgaaatga tcaaggtgca tgcatgactt tgattgtttg gacggaacgg aaaggagatt  2880
tcttacttta gaaattttt  ttttccagta ttttaattta aatatcattt cactcattta  2940
tgtaaaacaa gtttattttt aaaaaatatt tagactaaat aaacatgaaa aatgtttaaa  3000
```

```
SEQ ID NO: 17           moltype = DNA   length = 3000
FEATURE                 Location/Qualifiers
source                  1..3000
                        mol_type = other DNA
                        organism = Solanum lycopersicum
SEQUENCE: 17
atataaataa tatcatattt aataataatt aacagtaagt tttataaatac gatatttagt  60
ttacgattta aaaattcata catcttaata tatgtgtttga gggaaccatg cataaattat  120
gaggcatgta ttattattat tattatttta tgataaatag aaggtaaaat gaataaataaa 180
ataatacaat aatacatata cctagttgca gcaagatttt tagaaaaaaa ttgtatattt  240
ctttctcatc aatatataaa ataacatgaa catgctatgt tactgttgtc ttattctaat  300
attatatgca atcaaacatc ccatttaatc gcaacaataa aaacgacttt taacgatatt  360
aattattaat attaataaag aatgctaaag tcttttttgg tattagttaa gtaccattag  420
aaccaatatc gctaaaggct ttagaaatat attttgtcgc caatgattat ttttgttata  480
gtgaatggtt gagatctttt tactcttaat cttaagtctc gatttaaatt ttatatttaa  540
ttatttttta attaaagatg acgagctcag aataactcta caaaatacaa attcaaatta  600
atcaaatttc acattctgaa aatgaccttt gttaattttt tttaagggaa aagacttaaa  660
tatgccattg aatttttatg ctattatcgt taaagtaaat gctcattcat gctattattt  720
tttaacaatg attttgcaaa attattttg  acacgtggcc aattgtaact cggtcacgtt  780
atcaaattt  ttaattaaaa aataaaaaaa agtgacacaa ttttattca gaagtttaat  840
tatttattg  aaaaatgatg acgtgaccaa ttataattcg atcatttat  taattttaa    900
ataaaaattt ttaaaattaa atttaatttt ttttaattaa aaaaattgat gatatgggag  960
aaaagttaga gtgcatacaa aaattgccac tttcacatta ccaaatggct ttagtcaaga  1020
tttcatcaac tccatgattt ttactataag acaatgtttg gcttagtcaa ttagatgtag  1080
acattgaaaa gatttttcta tagaagaaaa actatatggt atacactaca tatcattatc  1140
ctcacaccca cccacccaat tatcaaagac caactagcct ctcaaaaaga taagtattaa  1200
aaaaaaaatt attcgtattc gatatttata caactatata agatatagag agaagtattt  1260
aaaatacatt tgaatttaac gtaaattatt aatttcatct ttaatatcaa atatattcat  1320
ttgtttggct agctgaactt aaaaaatatcc ttaattttat aagatgagtg aaatacatct  1380
ttatagtttc accagattta ggagtgtttt caacccttct ctcgatttt  tatgaaaagt  1440
ttcatttttc tacaagaatt tgaaccact  tgtatatcag atttagttag ataagtaaaa  1500
aaattcttat aaagctatta ataatttaaa aataaaacta ataatttata tcaaattaaa  1560
aaataattcc attacttctc tacgagatat ttaattaaac aatacattaa gctatactac  1620
attaatattt gacaaaaata ttttacaaat taattaccta aatataaact gacaaatggt  1680
tactttcaaa atgatttttt tgaaaagttt ttcttttttcc aagcaatcag agttaaagtt  1740
tgattaaata aagtattata acataatata aacagtaata aatataaaaa tatatttta   1800
tttataatac ataaaaacac ctatcaaaat atcattaaat tcaaactcat gacaccgtaa  1860
ttttcattac tcattttctt attatataat ttaatgagtg aaactagata attttgaatt  1920
caaaaaatta atattgatgg aataataat  tagcaaacga acgttcttct aagcttccaa  1980
atataatgaa cactattatt attaaggatc gtagttgaaa tgataatact tataatttat  2040
tcttaacgag aggtcttaga aaatataata aactctatta tacgagatct ttcagtgtaa  2100
atttatattt aatcgaattt caacacgaat aatatcgatg agaaaaaaca tgatgagcac  2160
taccaagttt gtaggttcct aaagtccaat caaacttaat atcgtgtcag caagcctttat  2220
ttttatagac catattatat aaaattctcc caatgtcaca actaacaaaa ttaattatca  2280
```

```
aagatagtga cacaacatgt agaaaaaaat aaaaataaaa aatggacaaa attgtcaaca  2340
atgcactgct ttgaatgttg aaattaatac taaagttaag attgttcatg actagaattc  2400
taaaatttca ccaaactttt ccaacaactt atacaccttc cagatcgcga tctaacaatt  2460
tattttaatt ataactttg caacaattta tacatctttt agatcgcgtt aacgattat   2520
tttaattata acttttataa ttattagata atattttgtt tgatatcttc gtcttttcg   2580
atcatgattg ataagataaa ttcaaaagat tttaatagct ttcactctac ttgtactgaa  2640
tacgagtaat tgttcaccat ttgtccaaag gtttatattt tttctgtcta ataatatttg  2700
ttcagtattg acggtggaca cttttttaaa aattataaat aaaaggataa ttttactata  2760
tcactcattg aatatgatta taaatataac gttttaaaaa atgtaataaa aatgactata  2820
actaataata tatcgtggat aagtattatt ggacatttta taataatata gtactgaaca  2880
actattgtcg aacatgatcg agttttatat gactttcaa ggtagggaca aaacttacat   2940
aataatcaac caaaatctca cttcattttt tgtcctataa ataccatcta aaactttcaa  3000

SEQ ID NO: 18         moltype = DNA  length = 3000
FEATURE               Location/Qualifiers
source                1..3000
                      mol_type = other DNA
                      organism = Solanum lycopersicum
SEQUENCE: 18
atctttacaa attttctttt tgcctgttaa aactaagaac aatctaatta aatttttct   60
tttgtatgtt tattgtctct cttttgtat gtaatcctaa tgatttaaag tgccaattta   120
agaattttga aaatcatgtt atattcgaaa agcaaaaaaa taaaaaataa taaaagggtg   180
aagggtgtgg ggagcaaagt gttaaacgta aatgttaatt atgttaaatt aggtgatgat   240
tatgcttttg ataactagta agtaattaat aacaaccaaa tatagcatca tatctggaaa   300
aaatattaat tctttttttt tgaatgaaaa tgatgtaatt gttaaacctt tttgcgtgaa   360
aaaataagat gtgatttgat atgagatcga tgatctcgag agattgata tttcaattta   420
attggttga caaagttata acattttca aattaacatc ctagcttgag aataacataa   480
gcaaaaaacc atataattga taaatcaggt aagataaagc ttcgattatt aatatattac   540
agaaaatttc agatataaat tcaattttta tttttaaatc attgctttag aagtaaacaa   600
taattataga gttggagtaa ggaatctaat acacttaata aaattactct taaatttaa   660
aaggtgaaaa aatttaatat tatatctaa ctagtcgttt gtctatattt tgtagagtta   720
gaaaatcatc gagagttatg gtagagtgat atatttttt attttagtt agaatttcaa   780
attcgagttt tttttaggta taaatcatt tttatcatag aaaattttat tctttaatgt   840
gaaatttttc atcacaaatt taaatttaat ctagctccaa tataaatacg aacgcctaaa   900
aattaaagtc aacatacata gataaattta atatttagct ggtttcaatt actctaaaca   960
atcattttaa tcattccaaa caatcaatca taggcagcaa ttcatgcata cacctcatat   1020
tccttttcac aatgttagaa tttctcgtta atttatatac atctcgatct atcgaatatt   1080
taaatatcat tattatcgaa tttcgaacat tatttataag attatcggtt tattttttt   1140
aaacagtcca atcttcttct tattattatt gtgcttatat aaacaataac tagaatcacg   1200
cttcaatttc aaacaaatta cgcttaatta catgaatcct tacttaatca taccatatca   1260
tttcactcaa actcatttta attttacgtt cactatcagt ctattataac tctacaatct   1320
cgtatacgat ttccgcaccc taatgctaca atactaaaaa aaaaattgaa aatttactga   1380
aaacatggta gcaaaaattc atgaagatga atataagtt tatcttaatt tatacgtcaa   1440
atttatttat ttatttattt tatatttgtt tgacaaaaaa acataaatca tcacccaaca   1500
ataatttca tcaatgaact ccgccgagac ttccgcggat agcccataat tttttattat   1560
tatctttttt tgcactcaaa ctttcattta ttctctttct agtccttttt taaaaattta   1620
tttatatata taagtgag acatataaat tccttttgtt tatactttgg aatatatata   1680
aaaataaata aataaatgtg taacaccgta gaataaggta atcccgtga atattattt    1740
cccttttgtt ggaatgttgg tcaaaacacc aaaatggaac ctaaccaatt acattgtcca  1800
cttgggaata agagtttcat cgaaatcccg aggtctgggt agggtagagt atatgtatac  1860
gttattgcta acttgaggat agagaagtta tcgtcgaaac atcatcgact caagtgaaaa  1920
aatttatgaa gaaatataa cagtaataaa aaaagtagtg taaagtctaa aagaaagaaa   1980
caatgatgac aacaattaca tgtgatattt caagcagacg taacataaga cgagaagtgc  2040
aagagtacaa ctagaactac ggaagacact aataagttta aacctacaca cgacaagaag  2100
agtacaacta gaactacgga agacactaat aagtttaaac ctacacacga caagaagaag  2160
tttcaccctt actaacattc tatcttgata cgcgacctcc acttatttcc tatctagaat  2220
catgtcctcg ataacataaa gctacatcat ttccttgtcta atcacttctc caaaatactt  2280
ctcggactac aattaacctc tcgcacctcc tcactagggt gtcaacgcac ctcctttgca  2340
cacgagaaaa tcatctcaat ctcacttccc tcatcttgtc cgccacaaag accactccta  2400
ccttctctcg aataacctca tccctaattt tctcgctcct aatatatcaa tacatccaca  2460
tctccacaac aaatatcttct gaacatataa gttcttgact aacgagcatc ccactctata  2520
caacaaaact acacgtaaag ccccaaaaag ggttaaaacc atataaattt attatatata  2580
tctatataca cacgtattat tatcctacat ttatgcgaat taaattcatg acctcttcat  2640
cacacattta acaacttttat ttcaaaagta acttacaata aatagatct aatgaataa    2700
actttcaaaa accatattac aatcatttt attattttt agatacaatc ataaaaaggg   2760
tgataagaaa agaaaaaga aaaatattag tactaacttt aacttaagca gttagtggcg   2820
gttactaaag tggttagagg ttaggttaaa atgacaattt aaccttagga cagaaaaaaa  2880
aaccaaacca ctaaccattt aaccatagtt aaagtaaagg tgattttagt tgataaacgg  2940
ccgttaaatt taacgttttc tgttaacagc ctctatataa accaccttca gaggccgtta  3000

SEQ ID NO: 19         moltype = DNA  length = 3000
FEATURE               Location/Qualifiers
source                1..3000
                      mol_type = other DNA
                      organism = Solanum lycopersicum
SEQUENCE: 19
agtaaaatta ttccacatgt gatattcatg tactctttt attatttcaa taatttaca    60
gtttcagata tacaatggaa accaccaaaa tttatttcat ttctaaattg agaggtactc   120
ctgtaaaaca ggaactatta ataaacatca catttctctt gactttatca actatcccat   180
```

```
tctcatcctg tgttgttttg tgtatgtttc tatatctacc tccaacgtaa ctcacttatc    240
atcgaaataa ttggaacggt tttaaaaagt ctaattttag taacgattta aatttggata    300
taaactaatt aaataaacca agtcattgac accttatctt cccatcctca ccacaagaat    360
cgcctatgtt tcaccattag aaaaaccaag ctgaagttaa ctcttttgt tgcttctcag     420
ttcttagctc aattaacaac aactctgttt taaatatggt tacctgtgga ggcctaaaac    480
acttttttga caaaccattc ccagaaaatt caacaattct tgattccact tcttcatgga    540
atcagattaa atcaagaaaa ccaaataaag attcatcctt tatggagatt tttgatgaat    600
taaattctgt ttcatcgttt tcttttaatt atctccctcc attgtccact gccaccacct    660
catcgtcgtc gtcatcatcg acatgttctt ctttataataa ttcgtcatta tctttcgaag   720
caattcacca atctggggtt gaagggaaaa acagagaccc catttatcca ccaagcagtc    780
agaataaaca ttacaagcat agtgatagct tttcttcaag aaattcagat tgtctttcaa    840
tatgtacaga aagccttgga tttgaaagct gtgatgatgt tgaagatatt atgaatgcat    900
tgagcattgg gaatgatcaa gaacacgaag aaattagatc aacaaacatt cataatcagg    960
ggattataag tcatgaatat acaaaaatta aatcaagaac aaataaaggg gcattattgc   1020
ctcctccaat ttcttgcatt ggtagaaatg gaaagccctg tgtttgtttt gaatctttta   1080
gagaaaatgg taggtttatt ctcaaggaag ttaaaattcc tgagtgggaa ttcttgcatg   1140
catgtagaga agatggacga ttgaagctac agattgttca gtcagatgac gaattttcg    1200
atgaagatga agaatatgat gatgattcag aggatgttga aggaagatgaa tcaagtgatg   1260
acgacgacaa tgattatgag aaatgagaag ttggagaatc ttgcttgaaa acaacttagg   1320
aattaaaaaa aatagatatc ataaaaagca gaggcgaagc gaagccaata tttaaaaaca   1380
tacgagttca gatttctaat ccttctaagt tacttagtta catataaata cagtgttcgg   1440
accaagcat tgggacgaac ctgaaacaga aactctagct ccgctcctgc acaaagacaa    1500
aggggtgttt gatttttta tttttatttt ttttggtttt cttgtaaaaa aaaggttta     1560
aaactactct ttttctctct ctgtttcaat tatgaaaata agaggaatc ggaaaatgta    1620
attctgaatt tcagatttag atgatgatgt aaaggtagta gcaagagagt agtaatgttc   1680
atggggtaaa tcaatgtatt cccagcaata acatgaaacg cggaatactc gatttcatgc   1740
tcaaataaaa tttaaacttg tatttatgtg tagcttagta ttttcgattc tgccttgcat   1800
tattaaaatt aaaatgttat tttgtcaatg tgataataca atgtctttgt aattttatac   1860
tttgcaccta atgatgtcta aatatgagtg atttttataaa ttttactagg aattcacaat  1920
gttcatattc tgtgagcata gcaagagata tattcgatat ttatagaagt caatgcagct   1980
aaaggagaaa taaaatatat atatattata tgcatggaat ttcattattt tgggtccaac   2040
ttttatttga ttgaaaacaa tggcgtttta gtcaagttat ttttacttt ttgaccaaaa    2100
aaagtattac tagtttacta tatacgatta aataaacaaa tactctagtc attacaccta   2160
aaacagaaat tcaaaaaata acaaaaaagt atggtaaatg atattattaag aaaggtaaga  2220
agaaatattc cacctaaaag ctaagttgtc taattttact ggttcaattg atgaattcaa   2280
aatatgattt attaatttgt gtttaattt attttatta tgacatatta ttaatttaat    2340
atttaaataa cttctatttt tttaaattat agtaaatcat cctctgttt tttgatattt    2400
ctaaaaagga tatagcaagt caaagatgga gcactgtgat aatacatatt atatcatata   2460
ttcttacgct atgtttgaat cattgttatc tattgtattg taatgtatgg ttattatatc   2520
tacaatgttt cttttgattg ttacttaaaa tgtattatac tgtattgtca aatttcgttg   2580
ttacgtaaca atgaaaaccc ttattttatg aaacaaccaa tttgatgtgt ttccattgtt   2640
acttaatttt ttttttaatta tatctttaca taatatttt aaaatactat tttgcccttt   2700
acttttttta tttaaatcta gaataattaa tgatatttaa ctaaatttat aaattataat   2760
acaatacgat ataatcaaac taaacaatta aaatgttaga ataacaaaca atacaattta   2820
gcaaaatatt gtatctatca tacaatacag tataatagag tataatacaa tacgatatat   2880
tatgaaacaa tggataacaa tgattcaaat aaaatgttaa tatttatgaa tcatattaat   2940
gttaggttag gagtaataaa gagggaatat atactatact tttactatta ttaagaatat   3000
```

```
SEQ ID NO: 20          moltype = DNA   length = 3000
FEATURE                Location/Qualifiers
source                 1..3000
                       mol_type = other DNA
                       organism = Solanum lycopersicum
SEQUENCE: 20
ttcaattatt cgattatcaa tcatacagaa ataaagaaa caattcattt taaagaggaa      60
caaaagaggc aagaactcat tcaaaatgaa aaatacttaa aatagccgaa tttataaaac    120
tttttattac taaatttact gtgaataaaa cttttaaatt caccatttta gcctagaagt   180
aagagagaaa aacatttcca ccaagaattg tcaagaatac tcatatacat gaaaccaata   240
tgataaatgt tctcttcagg acggttcata aataaattat gataaacata tataagatat   300
ttaaaataaa ataaaatata tatatctta atttatcggt tcgattattt cttcaacttt    360
ttaaataaaa tcaagactta tcaattctta agaatcttag aacaaactaa accaaataaa   420
attaaacgat ttaatcaact taatttaatt tttcaatgtg ggtcaatttt tatccaaata   480
cttttacacc cactttttcac catcacaagg ggtaagaact agcaaattat tttgccttaa  540
caaaaactta ctattggtgt agagaaaatt ggttgatttt cttatcaata tatataattt   600
agtacccaat tttcccaaaa ctaaataaaa tatagaatat ccactaaggt ggttacacgt   660
gtacactcaa ccaatgacgg cacttcaaat tcttgataac ggtatcttcc caccttcata   720
tatttcaaca ttttattgtt aaaataaaat cgcacgctct attttatcta aattttattt   780
atagaattat attaagtatg ttattattaa tttttacgta taaatatatt tcatattaaa   840
atcatataag ttgacatcac taagttcgtt ggatttgcat gtagaccaa ttattccagat   900
actcaacatg actcatttaa tattggatta ttgaaatatt tgtaatacat taagaatata   960
attgttaact atttttaattt ttaattatac gtaaatatca aacaaaaata ttaatatgat  1020
cgctatatta gatgataact ataaggagcc tacacaatta acactattta actctattct   1080
ttgcatttat aaaagttac tttagtctta ggttcacaat gtcaaaatct aaacaactaa    1140
aaacgacgag gagtaaggtt tgcaacgacg ataacaaggta ttaggcaaca attagagttg  1200
tgaattgtga gtattaacta tacttttact atattaggca gaattttgc actcaatgag   1260
taacttgatt tatttatttt ttatttcgcc ctaaattatt ggacaagtca tatttgtt    1320
ttgaaaacat tctttattg gctaaatcga aattgaatc gttaaagatc aaaaatcaat   1380
aacaaatatc ttattggttt aacatatta aaataaaaa accataaaat ctaactaata    1440
atatttaata cgaaaacgaa atggactgac acacattcct aaatttttgg tcaaaatttt   1500
```

```
ttcataattt  ccctaaaatc  taaaatatta  aatatttgac  ggaaacaaaa  aattcacttt  1560
taataaatta  tttgaaggac  taaaacagtg  gaagaatata  tttaagaagc  taatttgaac  1620
ctagtgccaa  atataaaggg  accatttttg  tcattttttca  acttgaaaat  ctacgtgtct  1680
taatataaca  ccaaagaatt  aatatttact  gaaaaaatgt  aaaaatgagg  atatggattc  1740
tgaatcactc  aattccaatc  agcaaaaata  aaataaaata  aaataaaata  aaatttaaaa  1800
aataataata  aatgctataa  aatgaccaaa  atgtgtggag  caaaaagtgc  agaaaaaacc  1860
aacaaattgc  attctccatt  cttggaagtg  gccattcttg  atttcttgaa  acaaaggttt  1920
gtttcccttc  acttcttgat  atgtaaagtt  gcaatcttta  taactttcta  ttgctttgct  1980
agtgttttg  ttatatacag  ggggtggagt  tagagggtaa  gttacgcatt  tagtcgtaac  2040
tttagtcaaa  cttcgtaata  atttagtaag  ttaaaatata  ttagaaattt  tcagaattca  2100
taaactttaa  attttaaatt  ttgacttcgc  tttgtgtgac  tatacaatta  cagaaattca  2160
gagtggccat  tgttgaaaga  gagggtggaa  tttgtgtaag  ttttgttttcc  tttcagttct  2220
tgatatataa  agttgcaatc  tttaacattc  tttgttcact  ttctataggt  ttgctaggtt  2280
cggttaaatt  cagtagcttt  agtttaaacc  ctatgcggaa  tagagaatgt  gtaaacttta  2340
aacttcaaat  tttggctccg  catacgacta  gcgactatat  aataataggga  attgagcact  2400
tggcttttgt  atatagcttc  tatgtgtacc  aaaattagaa  aatcaggcga  ttattataat  2460
cttgttgact  aaatatagaa  tgcatccatt  accccccaaaa  agtgtgattc  cactgtcata  2520
ggaggttttt  tttatttcat  tttatttgtg  ctttcaataa  tgtagagtag  ttttacaaag  2580
atcctttctt  tgtgacacat  ggtaggtaat  attgctgatt  ttgttgtagt  tttggggtta  2640
taaagtttca  aattatttat  actggagggt  aggggtgggg  gttgtctata  atgcaggtta  2700
tggttttacg  tgaactcaat  aattattgta  gatactaaga  aatccactca  gtgttcttgc  2760
ggtgtcttgc  ttttgatttc  agcatcactt  gtagttgatt  tgtgtttagat  tatcacatta  2820
ttctgtggct  gtaactgtat  ccttgttagt  tgctttgttt  ctacactgtt  gttttccctc  2880
ttttataccct  attttgatat  gttgtactcg  aacgaggggc  atcggggaac  aacctctttta  2940
cctccgtgag  gtagagctat  ggtctgtgtc  cactctaccc  tccccagatc  cctcttgtag  3000

SEQ ID NO: 21         moltype = DNA   length = 3000
FEATURE               Location/Qualifiers
source                1..3000
                      mol_type = other DNA
                      organism = Solanum lycopersicum
SEQUENCE: 21
tatattttttt  taggagataa  attacactat  ttttttaaaa  taacttgaaa  taaacaaaag    60
attaatatta  aaaaatataa  tttatgtttt  taaatatttt  tcttagtagg  aatggtatgt   120
ctttatagtg  tgtacgcatg  ccttttagtt  tattggatga  ttacataaag  ttgacctaaa   180
tcaactactt  ttttttaatcg  caattgatat  gatttgtatt  tagttagttt  aaaaaaaaata   240
ttttattatt  gaataaaatg  atatatactc  acataaaatat  ttgtaattta  ttataaaatta   300
caaatttaaa  aatatttttaa  attttttattt  ttatatttaa  ttaaattata  tcatataaat   360
cgattgagaa  aataattaat  aagcaatgtt  tatgagtcat  aatagagaaa  gatttgaaac   420
agtaaaaatc  gtatcaagtg  aaaaaacattt  gtctatataa  gtttgtcaaa  gtaatttcaa   480
ttatttatca  aactctcatt  cttagcttaa  ttgaaatgga  gaaacatcta  gaaatttcaa   540
gaaatcacaa  tataagaagc  tacactagac  accaaaatat  aaattaaaaa  aatactccgt   600
ggtacaattg  cacatcaaaa  agttacatta  gagtcttaaa  aagtaactaa   660
aaacattcaa  atgtgagttc  ctgctgaata  ttttgtattc  ttacgatttc  gagaaagttt   720
aatgataaag  agtacagtaa  atttcttaca  agtttttcac  ttttgacaaa  tataaaggta   780
ttacacaaat  ttagctcgat  ttataaagca  taactatttta  aatatatttt  tcgtaataga   840
agtgtgtcga  ataaagaatt  cctgctaatg  cgataaaatt  atgtttttca  cttcctccaa   900
taaacgagta  agtttattct  ttcattaaac  tatttttagcc  tatgctatta  aaaagatatt   960
catatgatat  ttatatttta  atatgattat  cttttgtacac  gaatacttaa  ttattatttt  1020
tattattgtc  taaaatttaa  gataactatt  ttaatttttta  tctatatttta  tccctttttta  1080
atgatacttt  gcatttttaa  gaaaataaat  tacactactt  ttaaaaataa  tttagagtag  1140
attaaaaaaa  taataaaaata  aaatttatat  tcttaaaatat  tttcttaata  aatgtgttttt  1200
atctcgtaac  ttcacttaat  atgacatgga  aaattctaat  caggtctata  tactgtggaa  1260
cacatgactt  ttagttcatt  ggataattaa  cataagttg  acctcaagtc  aacaacttttc  1320
tttaactctc  attttgatatg  attttttttt  agttagttta  aaaaattgat  actttagttt  1380
tgaataaaaat  aatttataat  tttaaatatt  tataagttat  tttaaatgtt  ataaaattaa  1440
taaaaatcat  atcaaattga  attatatcat  ataaattaaa  aaattggaaa  aaattattaa  1500
cgggcaatgt  tcataagtca  taaccaagaa  agactttcaa  cagtagaaag  tgcatcaggt  1560
aaatttctat  gaaattgcta  gttacaataa  acataaaaaa  tgattcctta  ttttttttaaa  1620
tatgttcaaa  atagcactta  agtatcaagt  gaactatttt  tgtcccataa  gtttgtcaaa  1680
gtaagtattt  ttggtttcttt  gtcaattact  tatcaaactc  taattcttaa  gtttaatcga  1740
aatggagaaa  catctagaaa  tttcaagaaa  ttacgacata  aaaagccacg  ccagaaagaa  1800
aatataaaca  aacaaaaagc  tctgtaatat  aattgcacat  ttaaaagtta  tactagtctc  1860
ttaaaaatga  tataaaaaat  aaatatctaa  atttgagttc  ccgctatata  ttttgtattc  1920
ttacaattttc  gataaatatt  aatcataaaa  atatgataaa  tatcagacaa  agttttcact  1980
tttgacaaat  ttaaaagccg  aaactacttt  tttaaaaaat  attttaaaca  tattaaaaaa  2040
gacaaagaga  ttataattta  tattttccat  agacctcacc  aattttttata  ttataatctt  2100
aaaattaaca  taaatgatat  ttttaattaa  tttctcaaac  accgatgacc  gactattgac  2160
tatgtcaaat  tactccaaaa  ttcactcgat  attggaattt  tttattaggt  ctgattatag  2220
tgtggacacg  tgacttttag  ttcattggat  gataaatata  aagttgacct  caagtcaact  2280
accttttttt  ttatctcaat  tgatattatt  ttgcaaaaat  aaaactttat  tttttaatac  2340
aataaattat  acttacataa  gtatttataa  tattttctga  tttactttag  acaataaatt  2400
ttaagaaaat  attttttttaa  tttttaattt  tatttcaaa  ttaaattata  tcatataaat  2460
tgataaacga  aaaagataat  taacaagcaa  tgttcataag  tcttaacgaa  gaaagacttt  2520
caatagtaaa  aagtgaatca  tgtaaattct  catgaaatcg  ctagttacaa  taaatattaa  2580
aaaatgatcc  cttgttttttc  ataatatgtt  caaaatagct  ctttaagtat  caaataaaca  2640
attttttgtcc  gcaccaatca  agaatcccaa  ggaattccaa  aaagtaagt  atttttggtt  2700
tttcatctat  aatccttatg  tttaatcgaa  atagagaaaa  atttagaaat  ttcaagaaat  2760
cacaacataa  gaagtcatac  cagacacaaa  atataaacaa  acaaaaaact  ctgtaacaca  2820
```

| attgtacatc | aaaaagttac | actagattct | taaaaatgat | ataaaaaata | atataaacat | 2880 |
| ccaaatttga | gattccgcta | tatattttgt | gttcttacaa | aaataatcgt | aaaagtataa | 2940 |
| taaatattag | acaaagttct | cacttttgat | aaatataagg | gtcgaaacta | ctctgtggat | 3000 |

```
SEQ ID NO: 22            moltype = DNA   length = 3000
FEATURE                  Location/Qualifiers
misc_feature             1..411
                         note = n is a, c, g, or t
source                   1..3000
                         mol_type = other DNA
                         organism = Solanum lycopersicum
SEQUENCE: 22
```

| nnnnnnnnnn | nnnnnnnnnn | nnnnnnnnnn | nnnnnnnnnn | nnnnnnnnnn | nnnnnnnnnn | 60 |
| nnnnnnnnnn | nnnnnnnnnn | nnnnnnnnnn | nnnnnnnnnn | nnnnnnnnnn | nnnnnnnnnn | 120 |
| nnnnnnnnnn | nnnnnnnnnn | nnnnnnnnnn | nnnnnnnnnn | nnnnnnnnnn | nnnnnnnnnn | 180 |
| nnnnnnnnnn | nnnnnnnnnn | nnnnnnnnnn | nnnnnnnnnn | nnnnnnnnnn | nnnnnnnnnn | 240 |
| nnnnnnnnnn | nnnnnnnnnn | nnnnnnnnnn | nnnnnnnnnn | nnnnnnnnnn | nnnnnnnnnn | 300 |
| nnnnnnnnnn | nnnnnnnnnn | nnnnnnnnnn | nnnnnnnnnn | nnnnnnnnnn | nnnnnnnnnn | 360 |
| nnnnnnnnnn | nnnnnnnnnn | nnnnnnnnnn | nnnnnnnnnn | nnnnnnnnnn | nttgttttgg | 420 |
| ttaatataaa | attttatata | acgttttgaa | attttgtta | atattttgta | cccttttaggc | 480 |
| tccgaccag | ggtttcgtat | ccaagagaat | tcaaatttga | gatttttag | ttaaggatga | 540 |
| aggagtattt | atcgttttct | tacaatcttt | attggtaatt | attattttga | gatcaacaag | 600 |
| ctctagcaat | tgttgtagat | tatatcatga | ttgagtccaa | atttgacatt | tcctataatt | 660 |
| tcagccaaac | aatatttaag | cggataaata | tcatgattta | attcaacggg | ccggcatcta | 720 |
| ctctaacact | aagtaggaga | accatcgatt | ttcaacgatt | taaaacatgc | ggaagattaa | 780 |
| gaaaaactga | gataaatgaa | attacaagat | tttacaagtg | aggagttcta | atacatttct | 840 |
| tagttaagaa | ttgtaaagta | attaacaccc | tagggatcta | atctaaacat | gcacacaaga | 900 |
| gcttctaaga | ttaaaagata | tgaacaaaat | agcaaagaca | caactcccac | cattgcggaa | 960 |
| ggaaaaataa | aagttgttgg | agattatctt | catcttcacc | taatgaaaca | tcatcaaccc | 1020 |
| tgcatccata | ctatgtcaaa | aaggcatagt | agtatcaata | cagtcacacg | tactggtagg | 1080 |
| catcatcaat | caacccgacg | tccaccgcat | aatataagaa | atcaactaga | aagaacatgt | 1140 |
| aataaaaccg | tgtgctcctc | cacctttacc | attttcagac | acctgaaatc | acactagtac | 1200 |
| ccttaaatct | gaccccgta | tccatcaacc | tacttactag | gttcttaatc | atagcttaat | 1260 |
| cattactc | atgaacgagt | ccacaaacac | caccacaagc | actccgacta | accactcaca | 1320 |
| acataccctt | acttctttca | cattaccact | caaccctaag | cccatagtac | attatatcaa | 1380 |
| ggcctactaa | cagtcaaaca | cgaatccctt | tcccaaggta | gaatctatct | gtttacataa | 1440 |
| cgaacactac | ccccactttt | caaccttag | gaacacgatt | aaccctctac | ctaaccaatg | 1500 |
| gtaactcttg | gaaccttggt | cctcattcac | tgtatcacat | tttgatttgg | acttgaccct | 1560 |
| ctccggttaa | tttaacctcg | agatacataa | ccagtttact | caacatagta | gaacaatcat | 1620 |
| cgaaaggtta | ccataatcat | ttatcaatcc | acatattctc | aattgtacat | atatatcca | 1680 |
| caagtcaatg | gtcctctcct | ggaacccata | tccaaaattg | ttagtgtgtc | ggattgtgac | 1740 |
| acccgattca | aatgtatgca | tattagagtg | ttggtacgtg | acatccgatt | cgacatatgt | 1800 |
| atgtatgtcg | gtatgtgaca | cccgatccaa | tgtatatata | ttagtgctgc | ggtacgtaac | 1860 |
| acgcgatcta | atatatctat | gtgtgtcggt | atgtgacacc | cgatccaatg | catgttagta | 1920 |
| tgccgatacg | tgacacctga | tccaatgcat | gctggtgtgt | cgatacgtga | cacccgattc | 1980 |
| aatgcatgtt | ggtatatcgg | tacgtcacac | ccgattcaat | gcatgttggt | atatcggtac | 2040 |
| gtcacatccg | atcccatcag | tacaatcaca | tacacaacaa | acatacttat | attcacccaa | 2100 |
| tcaatcaagt | attaggttga | tgacatgtaa | ttggacatca | ttagtctttt | ccttagattt | 2160 |
| gattcatatg | catcaattct | atacatgtat | acgtataacg | aagccaataa | cagatgtata | 2220 |
| tcacacaaac | atgaatcaca | accatcactt | aatcctaatt | cacgagatag | gtttttttac | 2280 |
| ctcatggtac | acgtcctatg | caacagctag | gatcacagta | taatcattca | ttattttgtc | 2340 |
| cacgaaagcc | tacgcatgaa | ttataccacc | aattaacagt | atactacgca | acgagcacat | 2400 |
| attttataatt | actcaattaa | taaaacctag | cctacatggg | ctccaagcag | ctgtagagaa | 2460 |
| attatcgttc | caatccgaac | tttcgaacga | cgaggctgta | atcgggatct | gcaatctatc | 2520 |
| gacatccta | agctagaaat | ctcttttctcc | ttccttccca | agcttagagc | agccttaga | 2580 |
| gggtttctag | ggtaaccttta | gcctcttttt | gatgttttg | gaagaaggag | aaaacaagat | 2640 |
| ttcgcgttat | ttcactttttg | tcacgtctat | cctgctgggg | cggctactta | tcccgctgtg | 2700 |
| gtgttgccgc | cctagtaaca | tctcgcccgc | tctggcggga | cacctcaaca | ttttcccaat | 2760 |
| gtttattttt | tcctaaataa | cgatggttca | gttcgctaaa | ataaataacc | cataaattta | 2820 |
| atttaataag | tcaactcatt | aatcggtaat | cggtacccgc | tttagagctt | gacaataata | 2880 |
| atattaaata | ctattaaaga | gaaaaaaaga | agaagagaaa | acccctataa | atgttcttat | 2940 |
| aaagctccca | ctcaattgct | caacttatta | atcaatccct | cccccccct | cccccccccc | 3000 |

```
SEQ ID NO: 23            moltype = DNA   length = 3000
FEATURE                  Location/Qualifiers
source                   1..3000
                         mol_type = other DNA
                         organism = Solanum lycopersicum
SEQUENCE: 23
```

| acataattat | tttccctaca | taattatgaa | ataccttat | ctttaaacgt | gtcatgtact | 60 |
| cattcatcca | tatgattaga | cagcattgat | caataattct | catcaaataa | tttgacaccc | 120 |
| gtataaacaa | tttttatct | ttaaatcaca | tttaagaaat | taaacttgcg | atcttatttt | 180 |
| tttcaatgaa | attattcttt | cgtttacgaa | taacgtcttt | tttttttaa | cacatctcct | 240 |
| aaagtatatt | ttccatcatt | ctcaatttct | ttgcgataac | gttattaaag | ttatcacgtg | 300 |
| aatcgactca | ttcataagga | tttatacaac | tcctccctaa | tatgttcata | tctatgttct | 360 |
| tgattcatat | ttaggtcact | taattatggt | catttgacaa | tactattgat | attaatcaga | 420 |
| ataggtccca | tttgtaatta | attttcact | taggttgtgt | tggccaataa | cacatgtcac | 480 |
| aaatcacaat | ataactaata | atatgttcaa | gaaaaatacc | aaaagtgtt | agatattaaa | 540 |
| tccttacaca | aagaagcaa | ttttctgttg | gttcaatttt | attttttttg | gtgtagaaat | 600 |

```
taggtgttag attttaaaga aaattgtcct tgcaaaagta ggtattttgt gataaatgga  660
ccgaaaattg ggtgaagatt tttgagaaat atccacaaat attatttctt tctatcttac  720
tttatatgat ccgcttatta tttttttttt agtctccaaa agaatgatat tcttttatat  780
ttagtaacaa tttaattttt aaatgctcat tttattatta ataaaaatga tttatatgtc  840
atgcaaatat ctatgactta ttttagatca taagtttgaa ctttttttt cctaactcag  900
aggcagattc aggatttcaa atctctaggt gccaacagat tcatcggtta aatcaatttt  960
agccttcagt cgaattattc gtcttttcgg tctatgacaa gtataaacaa taataagatg 1020
acaattaatg tattatatat actacaaatt attttttgcat gagtcatact aattttctat 1080
gcattgtttc aattttatca gatgtcttta aggaagcaaa agtttattgt tttaatttag 1140
atgcttttgc taaaagtcga attcaagatg attttttttct catgtaatat ttgggaaaaa 1200
tcactttagc tcaattggtt gactatttga actctcatgc taccattttg ctttccctac 1260
ctccatatat aaatacaaat ttgtaccca catttgattg agatcataaa ataaacaagt 1320
taaaactttc attatacta taaatatcat taatattcat tattcattta aaattgtact 1380
cgacaatttt catatttga aaacgatcaa tgacgatatc attgcttatg tttacaaata 1440
aatcacgttt tatgtaacac gttagtcaaa tatacttata aattactact ccatattaag 1500
acaactatta gaaacagaaa aaaaaaaaag tgtcgttgtc atattaagga agaagcaagt 1560
taaacttgaa aattaaaaaa ctgccatgcg agcaagttaa aaaaaatact acagcctcta 1620
cgaggttcga cctcgcgacc ttcgtgttag aattatgacc cttagcaccc cccacaaacc 1680
ttactagatc ctcccctgct tatactccat atcaagtcaa attaaatcat ataacagagt 1740
agttagaaaa tatttacata caaattgaca tgagatagaa agtaatattt ttttaaaaat 1800
tcaaaaaaat agtgttttt cttatacatt taagggaaaa ttatatgaaa taacaaacta 1860
taattcaaat taaatgctat agctataatt tattttatt gtgattcgca acaaatatcc 1920
cttttttgc catctaattg gtatacaatt actcattcaa tatacaaatg tagaaaatgt 1980
gtttgtgttt gtgtttgtat aaagcgagag aaaaatgtat acacaaatac aaatacatat 2040
atttctttca tatacactta taattataca aatacagatc ctattataca atttacaata 2100
taaataaatt tacacaaaat tgaacaattg tataaaatta ggtatatcca gcgaattata 2160
caaatcaaaa gctccatagc aaacataaaa tttattattg aacacaatta tacaaactat 2220
agttataaca tataaaatata attttatgt tactacacgt aaaaattgct ctttatttaa 2280
cttagcgatg taattgtttt tagcgaccgc ccaaacatat aacttgccaa aataattct 2340
ctgaatttct ttttgtaaaa attaggtagg atgatatatc ttgagcacgc tatgaatttt 2400
tttggcaccg ttgaaaacat ataatgttgg tttaaacctc ataaatcgtt ctatattaaa 2460
acctcataaa tcctaaacta gttttcactt gttaatcctt ttagttgcgt ttgttggcag 2520
tggcggagct aaaattttta ataaagggtt caaaatatga aagactaaac acatgaacta 2580
atcgaagggg gttcagatct actatatata tataataaat aattttaacc atgtataaat 2640
aataaattta gcgggggat cagaaggctg gctccgcccc tgtttgttgg agttgatatt 2700
tcttgggggt attttagtcc ttagtaatat tttcatattg aaaatggcta aatgttaaaa 2760
gcttgtaaaa tattttgata tattccacgt atctttaatc tatgattaca taattcaaaa 2820
gtccttttac ttttttaaaat tccattcgat caaatcaaaa tcagacaaac aaatcaaatt 2880
gtcttgcgtg caccacttaa acatggccta gctcataatt caccgccaaa aacaccacca 2940
actttctcc tatatataaa caaaacttat ttctccattt tactccaatc tacttcaaca 3000

SEQ ID NO: 24         moltype = DNA  length = 3000
FEATURE               Location/Qualifiers
misc_feature          749..768
                      note = n is a, c, g, or t
source                1..3000
                      mol_type = other DNA
                      organism = Solanum lycopersicum SEQUENCE: 24
cgatcctcat atactatcct ggtaccgaaa cgtggcaccc gatccatatt ctatcttggt   60
gtcggaacgt gacactccga tcctcatata ctattctggt accggaacgt ggcacccgat  120
ccatattcta tcctggtgtc agaacgtgac actccgatcc tcatatacta tcctggtatt  180
ggaacgtggc acccgatccc ctaatctcat tactttcgtt catcaagcct tcttttatac  240
caaggaatca tcattaaaaa agtagattag ggttttcttt tcaagattta ggattcaata  300
gcttcatcat gcttattta tcacaattat ataatcaaa catgcaaaca cacaattaag  360
catatagaag ggtttacaac actacccaat acatatcatt cgctattaag agtttactat  420
gaaagagcat aaaaaccata acctacctcc accgaagatt cgtgatcaag caacaagcta  480
atcttcaaag tctttgcttt cctcttcgtt tctcccttt ctcgttcgat tctctttctc  540
tctcttctgt tcttctatt tttcttattc aggctctctt tcttttaccc taattaacat  600
ataattaaga ataaagatg gcaataataa cccactagtt tactcaaggt tacctctttt  660
agcccccaag taattgagtt attaatatta aaccactaac attataatta taagtcggaa  720
tagtcaaaaa cgtcccttaa aacattaann nnnnnnnnn nnnnnnnnag ttcagagagt  780
cgattttcag tacccatttt tttaaaattt ctaagtgttt tgaaacgaga caccctcgac  840
ggtccgtcgt gcccatgacg gtccgtcgtg gattccgtac tctcagcctg tttttccaga  900
aataaaatct gctgctcaaa acgactaaac agatcgttac aatagatacc aatttaccca  960
tcgttcgtcc ccgaacgatc acaagaagga aaacaagggc gagaaggagt acctgaatct 1020
gtaaacaggt ttgggtatct ttctcgcata tcagcctctt tctcccaagt ggcttcttcg 1080
acgggtcgat tcttccattg aactttgatg gatgcaatct cccttgacct tagcttgtga 1140
acttctctgt ctaaaatggc aacaggttcc tcctcataag acaaattctc atcaagcaaa 1200
atggaatccc aacggatgat gtagtttcca tccccgtggt atcttttcaa catgagacaca 1260
tggaataccg gatgcactcc tgacaaccct ggaggcaagg ctaactcata gccacctcc 1320
cctactcgct taagtatttc aaagggacca atatatcttg ggttaatttt tccccttta 1380
ccaaaacgca tcacccctt catgggtgag accttcagca agacctgttc accctccata 1440
aactccaagt ctctaaccctt gcgatccgca tattccttt gcctactttg cgccgctaga 1500
agcttttctt gaatagattt cacttatatt aacgattccc tcagaagatc agtaccccaa 1560
ggtctaactt caaatgcatc aaaccaccca atgggagacc tacatcttct cccatatagt 1620
gcctcaaatg ggccatatca atgcttgagt gatagctatt gttgtagaat ttattttttg 1680
tcgagtgttt agtttatgat tgctcaattc gttttgtgtt tagattaaaa attctataaa 1740
aagctccttt aattttctaat tatatctttg aattattatg aattttctat tcatgtaact 1800
```

-continued

```
gggtcaaggt agataattgc cggacaattt ttttatgacc ttgtaactag ctaggagaag    1860
aacaattta ttgtcatgtt tactatttc tcacatgaat aattttagga taaataattg     1920
tcatcttaat aaattgatca cctacggaat gtcaattttc aatgtttcat attttctta    1980
gatcttatga ttttaaacat gtcatgtgaa aaattgaaac taaagaattg ctaaaaaga    2040
aataaatatt tttttttaaa aaatattcct ttatagaaaa taaatagtat tttctactaa   2100
attttcttta attaaatgtc ttgaaaaaga gacaactctt ttaagtgtta cgtattatta   2160
gacatttcaa taatttaaag aattcgaact cacaactcta gcacggaaaa tattcaattt   2220
ccatgaccca ttccttatac taacttatca atcagttttg ttaggagttc ataagataat   2280
attgataata tttttataat tttgtaataa atataaaatt tacgaaaaag ttcatatata   2340
ttcgaataaa attatcccat tatttatttg atttaaaatt tgaattttcg ttggaataaa   2400
attcttcgtc cgagagaaaa gtatcttagc tgttcacatg ctaaggaact aggaagtttc   2460
gcctttggtg ggccagtgat tgtatatttt attatttaat atatatcaat ttcctcatca   2520
aattgaaaat gaaagataaa atcaacggta ttttaattgt taatatttc aaataatatt    2580
ttttaattt gtttagtttt aaaattaaaa tacatcaaat atattaaaa ttcattaatt     2640
ttatatggca aagcacgcta catgaaaat taaaaaaag gccatcaaac aaatgaaaag     2700
gaatatcgtt cgtaaaataa attataaata aaaataaatt gaataaatta aaaatataag   2760
tatattttta aagagtgatt tttctatcca ctagatttga ccaaaatgtt ggtgacatga   2820
gcgcacaagt catcgttatt attgtattat tcctaaaaaa aaaatgggga agatgttcaa   2880
acaagcgtct agttagtcaa atataatttt taatattaaa aaattgaata gtcaaacaag   2940
aaaaacatta atatatccct atttttttcc tctataaaata ataaaaaaga ctatacacca  3000

SEQ ID NO: 25          moltype = DNA  length = 3000
FEATURE                Location/Qualifiers
source                 1..3000
                       mol_type = other DNA
                       organism = Solanum lycopersicum
SEQUENCE: 25
aaagggcga aacttattca cataatcgcg tgtttacgcc aagtcaatat atatacatga     60
tcatttgaaa tttatagttt attttacttt attaaattac ataataatgg aaattatatc   120
aaacttctct cacatttcac tcacgtatct tgtatatatt taatttgatt tgcatgtatt   180
tgaaatatat tgacaaattt cgctggcctt aatcccgttc tccctcacct ctcttcctat   240
ttgaaagtat ttgatagtaa aagacatata tttaggttta tctaatttaa aatctagtac   300
gaaattattt attaatgaga taatatataa ttattttaaa ttataagata agaattagta   360
aatatgacaa aaatatttgt ataattagat tcaaacctct atgatcacat taataataat   420
tttgttttct atcagtaatt taaaataata ataataaaat agtaccatgt gttgggatcg   480
aatccacaca cacgcttgat gaattaagaa cacaagaact ttcaagagaa agagaaaga    540
gatctagaga gagaaacaaa gaaaccaata cttcatgata acgccccgtg agtaaacttc   600
cacggcgatg gggtatatat attaataaat cagagtattt tttgttacag agaataaata   660
gtacagccta aaatttaagt gaggccgctg ccctgaaccc ctccttcgga tggggggctc   720
ccgcccccat aacccctgg caacctcacc acgaggtta aaccacgtaa atattggaat     780
ataatagcat atcaaatatt aatcaggctc cacagcctag catcatgatc tagatataat   840
tactacatgt ttccttggccg gtctaactag tcaattatga gaagcttcga aacgtttaa   900
agtatcaatt aacttggtca aacaaacgaa tatcaattca atttaagta tttttaatta   960
tatatatgtt taagttttga tagataatat tgtcctctgt atatacatat tgattgtaca  1020
taaatatata taatccataa ttaaattata aataaaggta cgtataaatt aattagaata  1080
ttatttactc ttagttgctt gactataata acttctaatt ggtgtttatg agttattaca  1140
tattttacat gactaaactt atatatatat atatatatat atatatatat atatgtatat  1200
gtctttttt tttaaatggc tagttaaatt aattctggt ttatatttaa tttagtaaaa    1260
tgaaagtaaa agcaataagt tgaaggtgtg aaggctggaa ataattgcaa agtcttcaaa  1320
gaaaacatat cataccattc acaccataaa attgtaattg gcgaatatga taattattct  1380
tttcattatt aattgaaaat tttcaaattt aattttttgt taaagagtga              1440
ttaaatatat tatttataac tttaaatttt taatatgaat ttaaattaat tagactttaa  1500
aataattatta aacatcaaat caaaaatcag aaagaatata atatgatgta gttgaccaag  1560
tcaagtacct aattgagtcc ttctttaag tactcttcac acctcacttt caaactatct    1620
ttgcatattg aaataaatt taggttaatc aaataaataa atatacaaat aaaaaaattt    1680
aaatttgaag aattaaatat acaaattaat taataggatt ttgatatttt ctttgtatat  1740
ataaaaaata attttaacta tatataaata ataataattt ttataatttt ttaaaataaa  1800
ttccgataga aaactgactc tatgtatatt taaatcatcg tgactcttcc atccgatgac  1860
ttggccaaacg tgcctttggg ggtcaaattt gtgtctatat caaaactaat tttttttttg  1920
tttcttttc tattttaagg ttttgtttaa tcactaaata aaataattc ttttttcttc     1980
tatagtgaaa gtacgcagaa atatggtgat aatatatata taatttataa caaaccaaca   2040
aaatgattat tttatctttt ttcttacgaa aagtctattt tgaggttttt tcaataaata   2100
aacttgatct catccgtgtg cttgctatat atcgaccaaa tgcatgtaga agactcaaga   2160
ctttgcatta aagttgaatt ggtatttcat acgcactcg ctttgaaact cgattaacta    2220
ttatttatat gatgctaaaa cttattaaat gaaaagattt tgattattt tatcaagaag    2280
tattttact gttaaatatt attattttt caatattag atttcttatt taatataagt      2340
gatttgataa aattatctta ttattggttg tttgttaatt cttttgtcaa agtcaaaaat   2400
caacaactat tactgaacag aataaatatg aacaaaacag acaagtgtcc ttctgtccta   2460
aaataagtat taccttagac gaaatcatat tgattaagaa atcaatgaat atgattact    2520
aaattatcct tattaaaaaa aatgtctctt aaaaatcgaa cattattaga aacataaatt   2580
ataatgttat agctcgaaaa tcatacttct gctgtccatt tttaattatc atgttgcact   2640
ttttgaaaat taattttgact aatttaaag ttatgtttaa ttgcataaat ttaatatttt   2700
aaatagaaaa taaaaaacta tacgaaaaat actataaatt ccaatctttt acatatcgat   2760
ataataaaaa taacatcgt aaaatgaaaa ttataacaat acaaataga caaagataat    2820
atactatttt tcattttaaaa ttcctaaaat tacactcatt gatatgagac tttttttccc  2880
taagaatttt tttattttttt taagaacat acatatgaaa acttagacaa acattttgac  2940
tagtaaaaga aacccaaacc aaccactcct ataagtatac caataaacat ttttccaaca   3000

SEQ ID NO: 26          moltype = DNA  length = 2988
```

```
FEATURE              Location/Qualifiers
source               1..2988
                     mol_type = other DNA
                     organism = Solanum lycopersicum
SEQUENCE: 26
taatgcaatt attaatttga ctttatttca aatccgaaag caacaatttc gaatatgatc    60
actcaattat taataattat ctcgcaaaaa ttgtttattt taatttcttt tactagtaat   120
aaagtgtaga tcactattct aatgactcaa ttataaataa ttaataaaaa gtcattattt   180
tttacaacgt aatagtgata tttgcttcat ctttttttacc aacgtttagt tcactgtttt   240
atttcttttg ctaataatag aaaataagac ttcttttttca catcaaataa ttgactcatt   300
tacctttttc ctaagtaata cttaggtcca ataaataaac attgtaatat aataatattc   360
gcatgattat ctttttattt gcctgaaata atgtaagaaa ctatggataa gcatcatagg   420
cgtgttccgc gaaagcatac ctactactga aaattgtaac taatatttttt gtctcacttt   480
tttttattct ttataaatta aatcgaagaa aattaaataa atattttcaa aaaaaacctt   540
cattttttgaa aaatcatgta gcaaaattat ttaaatttat tttcgttcaa taaaatcatc   600
accgaactta ggattatgaa tccccttaaa cttaatgact agaattaagt tggattataa   660
catgtactct ttttttaaaa tatggtgcaa gttacttttca ttggttttga taatgacttc   720
attatagtgg aaatatcatgt ggttcctctc aaaatgtgtg gcatttctat tcaaagatta   780
ttagattatg acatgcaaat tcatgttttt ccgagctttta aaggcaatac ccttttttttt   840
tctcgaaaaaa acgattacta ctttataaca agaagttagg tgttgcaaat tatccaactt   900
aaagctagca tcatatcata attagcacat ggatttagct gttttctaag ctaattaata   960
ctagcttaaa ttagtgctta caaacatgtg agaatgttctc cgtgggacgg ttgtgttcga  1020
tacgtaggaa acatttttttt taaaaaaaag aaaatactaa aatttttttga ggtctatata  1080
attatcaaat atttttgaatt tttttttttgg aaagcaattt aatttaagat tgataaaatta  1140
attattccaaa tgaaaataat aatagaaaaa cagatttcac tagtaatcac attccacgtt  1200
atttgtcctt ccactctaca aggctaaact tccaaccccct tgtcatctata gatttctatg  1260
ttgttgtaag gagtaagtaa ttaaaaaata acgtaagttg tggtgtagcg ataagactgt  1320
ttcatttttta atcagatatt tcaattttga gctttgagta taaaaaaaat tatgttcaga  1380
atgtcaatcc caaataattc atacactgtt taattgaaac tccaacacga gtgcggaatt  1440
ttaagtcaaa taacaaaaat aattttaaaa aaataacgaa aatagacaag ctaagctagc  1500
ctaaatggag caaatggata ggggataagg gttcattgga tcccaatatt tcatttttaa  1560
aactaaaatg cctttcgtagg tatggaggaa actctcctttt gacttgtcta tccttttaaa  1620
tgaccaatga gtccaactta gagctgtttg gccttaaaaa atttaaaatt aaaaaggagc  1680
tgtttggcca accgatgtgg tcattggagg taaaaaataa atttgaaaac aaaaagtggt  1740
aattattatt ttttgaggtg ttaattaata agtaaattct tttccaagta aaattagaaa  1800
tatttttttc atagcaattt aaaagttatg tttttaacaa taatgtgaag cacaatcaaa  1860
gtgcctagtt attttcataa atttacgctg tcattgatga gtctattttta atcaacttaa  1920
aagttaaaata aaaagaagaa aatttaagtc attttttatct tttggaagta cttaataaag  1980
aattaaaata atttaaaatg aataaaaaat gacatttcaa aagttaaata taaatttccc  2040
tattttttttt tacctgacaa ttattaaagt ataattttta ttttttttcga tttaaatcct  2100
tttttctttt ttaaaaaaat ccaaatagac tatatctttt aattcttatc tgatttgatt  2160
cacttttttga ttttatattg gatactctttt aaccaaattt ttttttctatg aaaaggaaga  2220
gttttgaaat aattttttgta agaactttttg gataaaattt ctaataggag tataaacttg  2280
gtacttttttg catatatatc aaacaattag aattagctaa ttcaattgtt ccctaattat  2340
gtttctgctg ttccatatat ggtagtactt aagaagataa tttagtcatt aactgatcaa  2400
cctggttaag tttaaaccaa ctataaaatt ggatatcagc atcaccaaaa cgaacaataa  2460
tacgcaatgc ccttgttttc tcaaatcatt tgctatttat cgatgattaa ttcagaatca  2520
tttttgttaag ttcctattaga aaaataatat tttaattaag aatcaatttg agacatattt  2580
tttattctaa tagtaaaaaa aattattgac atagatcata acatattgta attataatga  2640
gcttgttgta gttacgctaa tttatcttca actgatattt tagattttca atttttaaata  2700
tgtataaaata gatagttaaa tttataccat taaacaaata aacacaaata tacacgtca  2760
acgtaaccta tgtaataaat ataaaacgtt acatctttac ttattttaatt tcatatataaat  2820
ttaaatattt attttatgcat atcaaaactc atacgtaata aacgtaaaaa tgagtttataa  2880
tcaaattttta aaaatcaata aaccaaaatt aaaatggacc ccataagctc aataataaa   2940
catattaggt caatattagg ggccctttttt ttttgtatat aaataaag              2988

SEQ ID NO: 27        moltype = AA  length = 272
FEATURE              Location/Qualifiers
source               1..272
                     mol_type = protein
                     organism = Zea mays
SEQUENCE: 27
MGRRACCAKE GVKRGAWTSK EDDALAAYVK AHGEGKWREV PQKAGLRRCG KSCRLRWLNY    60
LRPNIRRGNI SYDEEDLMII RLHRLLGNRW SLIAGRLPGR TDNEIKNYWN STLGRRAGAG   120
AGAGGSRVVI APDTGSHATP AATSGSGETG QKGAAPRADP DSAGTTTTSA AAVWAPKAVR   180
CTGGLFFFHR DTTPAHAGET ATPMAGGGLG GEAGSSEDCS SAASVSPLVG SQDEPCFSGD   240
GDCDWMDDVR ALASFLESDE DWLRCQTAGQ LA                                 272

SEQ ID NO: 28        moltype = AA  length = 2461
FEATURE              Location/Qualifiers
source               1..2461
                     mol_type = protein
                     organism = Zea mays
SEQUENCE: 28
MALSASRVQQ AEELLQRPAE RQLMRSQLAA AARSINWSYA LFWSISDTQP GVLTWTDGFY    60
NGEVKTRKIS NSVELTSDHL VMQRSDQLRE LYEALLSGEG DRRAAPARPA GSLSPEDLGD   120
TEWYYVVSMT YAFRPGQGLP GRSFASDEHV WLCNAHLAGS KAFPRALLAK SASIQSILCI   180
PVMGGVLELG TTDTVPEAPD LVSRATAAFW EPQCPTYSEE PSSSPSGRAN ETGEAAADDG   240
TFAFEELDHN NGMDIEAMTA AGGHGQEEEL RLREAEALSD DASLEHITKE IEEFYSLCDE   300
```

```
MDLQALPLPL EDGWTVDASN FEVPCSSPQP APPPVDRATA NVAADASRAP VYGSRATSFM    360
AWTRSSQQSS CSDDAAPAAV VPAIEEPQRL LKKVVAGGGA WESCGGATGA AQEMSGTGTK    420
NHVMSERKRR EKLNEMFLVL KSLLPSIHRV NKASILAETI AYLKELQRRV QELESSREPA    480
SRPSETTTRL ITRPSRGNNE SVRKEVCAGS KRKSPELGRD DVERPPVLIM DAGTSNVTVT    540
VSDKDVLLEV QCRWEELLMT RVFDAIKSLH LDVLSVQASA PDGFMGLKIR AQFAGSGAVV    600
PWMISEALRK AIGKRMALSA SRVQQAEELL QRPAERQLMR SQLAAAARSI NWSYALFWSI    660
SDTQPGVLTW TDGFYNGEVK TRKISNSVEL TSDHLVMQRS DQLRELYEAL LSGEGDRRAA    720
PARPAGSLSP EDLGDTEWYY VVSMTYAFRP GQGLPGRSFA SDEHVWLCNA HLAGSKAFPR    780
ALLAKQSASI QSILCIPVMG GVLELGTTDT VPEAPDLVSR ATAAFWEPQC PTYSEEPSSS    840
PSGRANETGE AAADDGTFAF EELDHNNGMD IEAMTAAGGH GQEEELRLRE AEALSDDASL    900
EHITKEIEEF YSLCDEMDLQ ALPLPLEDGW TVDASNFEVP CSSPQPAPPP VDRATANVAA    960
DASRAPVYGS RATSFMAWTR SSQQSSCSDD AAPAAVVPAI EEPQRLLKKV VAGGGAWESC   1020
GGATGAAQEM SGTGTKNHVM SERKRREKLN EMFLVLKSLL PSIHRVNKAS ILAETIAYLK   1080
ELQRRVQELE SSREPASRPS ETTTRLITRP SRGNNESVRK EVCAGSKRKS PELGRDDVER   1140
PPVLIMDAGT SNVTVTVSDK DVLLEVQCRW EELLMTRVFD AIKSLHLDVL SVQASAPDGF   1200
MGLKIRAQFA GSGAVVPWMI SEALRKAIGK RMALSASRVQ QAEELLQRPA ERQLMRSQLA   1260
AAARSINWSY ALFWSISDTQ PGVLTWTDGF YNGEVKTRKI SNSVELTSDH LVMQRSDQLR   1320
ELYEALLSGE GDRRAAPARP AGSLSPEDLG DTEWYYVVSM TYAFRPGQGL PGRSFASDEH   1380
VWLCNAHLAG SKAFPRALLA KSASIQSILC IPVMGGVLEL GTTDTVPEAP DLVSRATAAF   1440
WEPQCPTYSE EPSSSPSGRA NETGEAAADD GTFAFEELDH NNGMDIEAMT AAGGHGQEEE   1500
LRLREAEALS DDASLEHITK EIEEFYSLCD EMDLQALPLP LEDGWTVDAS NFEVPCSSPQ   1560
PAPPPVDRAT ANVAADASRA PVYGSRATSF MAWTRSSQQS SCSDDAAPAA VVPAIEEPQR   1620
LLKKVVAGGG AWESCGGATG AAQEMSGTGT KNHVMSERKR REKLNEMFLV LKSLLPSIHR   1680
VNKASILAET IAYLKELQRR VQELESSREP ASRPSETTTR LITRPSRGNN ESVRKEVCAG   1740
SKRKSPELGR DDVERPPVLI MDAGTSNVTV TVSDKDVLLE VQCRWEELLM TRVFDAIKSL   1800
HLDVLSVQAS APDGFMGLKI RAQFAGSGAV VPWMISEALR KAIGKRMALS ASRVQQAEEL   1860
LQRPAERQLM RSQLAAAARS INWSYALFWS ISDTQPGVLT WTDGFYNGEV KTRKISNSVE   1920
LTSDHLVMQR SDQLRELYEA LLSGEGDRRA APARPAGSLS PEDLGDTEWY YVVSMTYAFR   1980
PGQGLPGRSF ASDEHVWLCN AHLAGSKAFP RALLAKSASI QSILCIPVMG GVLELGTTDT   2040
VPEAPDLVSR ATAAFWEPQC PTYSEEPSSS PSGRANETGE AAADDGTFAF EELDHNNGMD   2100
IEAMTAAGGH GQEEELRLRE AEALSDDASL EHITKEIEEF YSLCDEMDLQ ALPLPLEDGW   2160
TVDASNFEVP CSSPQPAPPP VDRATANVAA DASRAPVYGS RATSFMAWTR SSQQSSCSDD   2220
AAPAAVVPAI EEPQRLLKKV VAGGGAWESC GGATGAAQEM SGTGTKNHVM SERKRREKLN   2280
EMFLVLKSLL PSIHRVNKAS ILAETIAYLK ELQRRVQELE SSREPASRPS ETTTRLITRP   2340
SRGNNESVRK EVCAGSKRKS PELGRDDVER PPVLIMDAGT SNVTVTVSDK DVLLEVQCRW   2400
EELLMTRVFD AIKSLHLDVL SVQASAPDGF MGLKIRAQFA GSGAVVPWMI SEALRKAIGK   2460
R                                                                 2461

SEQ ID NO: 29           moltype = AA  length = 557
FEATURE                 Location/Qualifiers
source                  1..557
                        mol_type = protein
                        organism = Zea mays
SEQUENCE: 29
MALSACPAQE ELLQPAGRPL RKQLAAAARS INWSYSLFWS ISSTQRPRVL TWTDGFYNGE     60
VKTRKISHSV ELTADQLLMQ RSEQLRELYE ALQSGECDRR AARPVGSLSP EDLGDTEWYY    120
VICMTYAFLP GQGLPGRSSA SNEHVWLCNA HLAGSKDFPR ALLAKVPEDP DLINRATAAF    180
REPQCPIYSE QPSSNPSADE TGEAADIAVF EGLDHNAMDM ETAGIAVFEG LDHNAMDET     240
VTAAAGRHGT GQELGEADSP SNASLEHITK GIDEFYNLCE EMDVQPLEDA WIMDGSNFEV    300
PSSALPVDGS SAPADGSRAT SFVAWTRSSQ SCSGEAAAVP VIEEPQKLLK KAVAGGGAWA    360
NTNCGGGGTT VTAQENGAKN HVMLERKRRE KLNEMFLVSL SLVPSIHKVD KASILAETIA    420
YLKELQRRVQ ELESRRQGGS GCVSKKVCVG SNSKRKSPEF AGGAKEHPWV LPMDGTSNVT    480
VTVSDRDVLL EVQCLWEKLL MTRVFDAIKS LHLDALSVQA SALDGFMRLK IGAQFAGSGA    540
VVPGMISQSL RKAIGKR                                                  557

SEQ ID NO: 30           moltype = AA  length = 335
FEATURE                 Location/Qualifiers
source                  1..335
                        mol_type = protein
                        organism = Zea mays
SEQUENCE: 30
MGRAPCCEKV GLKRGRWTAE EDQLLANYIA EHGEGSWRSL PKNAGLLRCG KSCRLRWINY     60
LRADVKRGNI SKEEEDIIIK LHATLGNRWS LIASHLPGRT DNEIKNYWNS HLSRQIHTYR    120
RKYTAGPDDT AIAIDMSKLQ SADRRRGGRT PGRPPKASAS RTKQADADQP GGEAKGPAAA    180
ASSPRHSDVV NPGPNQPNSS SGSTGTAEEE GPSSEDASGP WVLEPIELGD LVWGEADSEM    240
DALMPIGPGG HDSAALEGLG AVGCEAQVDD LFDMDWDGFA AHLWGGPEQD EHSAQLRQAA    300
EPLEVAAAAA AATAARTPDD RELEAFETWL LSDSF                              335

SEQ ID NO: 31           moltype = AA  length = 277
FEATURE                 Location/Qualifiers
source                  1..277
                        mol_type = protein
                        organism = Zea mays
SEQUENCE: 31
MVRKPIHADD AGAKSTEASK ERKGLWSPEE DERLFTHITY HGVSTWSSVA QLAGKIQFLQ     60
TDRDSRSGKS CRLRWLNYLR PDLKKEPISK REEETIISLQ QSLGNRWSTI AARMPGRTDN    120
EIKNYWNSRI RKRLNAAASR AAGCGDGGDS AAEPSGAAAA GGKEDSANAA PPPAAQPTPI    180
PARFPVFGCQ LPDGAGGGIS SPGSGKSPQS STTASMRQNA GDESDASDGG GGDSDMVHFL    240
SFDDLDYPGD LLIDVPGAMD AWESQLCYAN PMMSSLC                            277
```

```
SEQ ID NO: 32           moltype = AA  length = 273
FEATURE                 Location/Qualifiers
source                  1..273
                        mol_type = protein
                        organism = Zea mays
SEQUENCE: 32
MGRRACCAKE GVKRGAWTAK EDDTLAAYVK AHGEGKWREV PQKAGLRRCG KSCRLRWLNY    60
LRPNIKRGNI SYDEEDLIVR LHKLLGNRWS LIAGRLPGRT DNEIKNYWNS TLGRRAGAGA   120
GAGGSRVVFA PDTGSHATPA AAGSREMTGG QKGAAPRADL GSPGSAAVVW APKAARCTGG   180
LFFHRRDTHT PHAGGTETPT PMMAGGAGGE ARSSDDCSSA ASVSVSPLVG SSQHDPCFSG   240
DGNGDWMDDV RALASFLESD EEWLRCHTAE QLV                                273

SEQ ID NO: 33           moltype = AA  length = 674
FEATURE                 Location/Qualifiers
source                  1..674
                        mol_type = protein
                        organism = Zea mays
SEQUENCE: 33
MAAGGSGGEA AQKALQSVAQ STGWTYSLLW RLCPRQGALV WAEGYYNGAI RTRKTTMTTV    60
RQPAGAEDAG DEETALRRSR QLKELYDSLA AGEAAYDGGG GVGDPQQQHQ QQVAVVPPPR   120
RPVAALAPED LTETEWFYLM CASYCFPPAV GLPGEAFVRR AHVWLCGANK ADSKVFSRAI   180
LARTVACIPV DDGVLEIGTT EKVEEDIFLI QHVRNIFVDQ HGAHIMPTTL SGYSTSTPTT   240
QLNHQPFQTK TGISLNLGDE HNSEMEDDDD GRIDLENNTE NDSTRRHLPQ DASVGNELET   300
LNAESSGPML IANLTAQDEY CPLHRFHSED LSSKYLQSSG AEDQAAVAEN AHYIKTVLTI   360
LRFNACRQTQ AASSNIAKTY LALSKNSPFS KWNWKRKGIS SMLIPEGTQQ RMLKSVLLGA   420
PSSSSHRTSS SAPETRGDDG EGTSRSRRGP VPSQTELSAS HVLKERRRRE KLNEGFAMLR   480
SLVPFMDRAS ILGDTIEYVK QLRRRIQELE SRARLVGSNQ KTTMAQPPPP AASTEERGRR   540
QTSGGYLARA GTCSRAAEAS GNSNLGEEPP AAAASDTDTE VQVSIIGSDA LLELRCPHRE   600
GLLLRVMQAL HQELRLEITY VQASSAGDVL LAKLRAKVKE VHGRRSSTTE VKRAIHLIVS   660
SDWNWICEKN PCVA                                                    674

SEQ ID NO: 34           moltype = AA  length = 274
FEATURE                 Location/Qualifiers
source                  1..274
                        mol_type = protein
                        organism = Solanum lycopersicum
SEQUENCE: 34
MNSTSMSSLG VRKGSWTDEE DFLLRKCIDK YGEGKWHLVP IRAGLNRCRK SCRLRWLNYL    60
RPHIKRGDFE QDEVDLILRL HKLLGNRWSL IAGRLPGRTA NDVKNYWNTN LLRKLNTTKI   120
VPREKINNKC GEISTKIEII KPQRRKYFSS TMKNVTNNNV ILDEEEHCKE IISEKQTPDA   180
SMDNVDPWWI NLLENCNDDI EEDEEVVINY EKTLTSLLHE EISPPLNIGE GNSMQQGQIS   240
HENWGEFSLN LPPMQQGVQN DDFSAEIDLW NLLD                               274

SEQ ID NO: 35           moltype = AA  length = 237
FEATURE                 Location/Qualifiers
source                  1..237
                        mol_type = protein
                        organism = Glycine max
SEQUENCE: 35
MEGSSGVRKG TWSQIEDDLL KACVQLYGEG NWHLVPKRAG LNRCRKSCRL RWLNYLKPNI    60
KRGDFSEDEI DMMIRLHKLL GNRWSLIAGR LPGRTSNDVK NYWNTYARRK LHSHKKDNNI   120
EKQARAKTTV KPHEVIKPVP RALTKTSPRL QGKFINSSEV GVSHEEGATS ISGSGNWWET   180
FLDDKEDIEE GNNNKCFFGG EDGALDLWGE ELNSIACDFL TQGETWSDFL LDLGLGD      237

SEQ ID NO: 36           moltype = DNA  length = 3000
FEATURE                 Location/Qualifiers
source                  1..3000
                        mol_type = other DNA
                        organism = Zea mays
SEQUENCE: 36
aaactcccgc tttatattag tagaggttgt ttggattgat gcagctgcaa tccataaaga    60
caaaaaaaaa acactttaga aaaagtagaa gtcgatagag atatgaccat gcttttttgt   120
caacttaaac ttttgggggt tatttgaata ctgtatgcat gttaggtacg attgccatgt   180
atttctccac aattaggtca gttttttcta cacatgttct acatatatta gatatcttat   240
cacgaagact acagaacgac cacaagctga aattgaaggc tattttgtca tgtgtataaa   300
tgtatatttc aaaaaattaa taaaattact acctccattc atataaatat atgacaccgt   360
taactttttt tctaaaactt tggccattca tcttattcaa aaaatttaat gtgttatcat   420
ttattttatt gtggtttgtt ttatcactta agattgtttt agtgtgactt gaaattttat   480
atttcaaat aaatattttg aataagacaa gtgggtaaag ttttagaaaa aatcaacggg   540
taatataata taacgtgaag ctaacaaaag ttcagcgaca ataatgctag ttctagtagt   600
gtatatatac actatgtagt aatatatata tatatatata tatatatata tatatatgaa   660
gccctgtgct tctaataact tggcgaaagc tctgacctga tgttgtcagc cggttcaatc   720
gcaccaggtc cgaagctgct ataaaagaag ctccatatct ctaggggttta gcttttagcga   780
cgtcgatagt tacgccccca ccccgagag gcatatgcgg ctgatctggg gggcacgct    840
cgcgacggcg gatccctgag gctagcgcac gacgatggcc ctcctgaggc gcgcacggtg   900
gcgaggtggg agcggttgcg gcatcggatc ccgagggcac gcacgcgacg gttgccccat   960
gagatgtgca cgacggtgag gtggcatcga ccgcgacggt ggatcctggg gggcacgagc  1020
gcgacagggt ctccctgcga tgcacgtggc agcgacccct tgagttgcgt acgacggtga  1080
```

-continued

```
ggtgggagcg gcgatggcgg acttccctag gcgcgagcga atacggcagc ctccccctagg 1140
cacgaagtgg tggcgcatcc gagatgcgag gcgacggttc cgtagggcgg cggtcctatt 1200
tttatactat tttgtataca tattttttgtc aatgtcaata gttttttttacg acctataatt 1260
cagttatggc tccgcttcca tcttttttgcc tatttatgat atttctattc acattttatg 1320
caaatgatttt attgatttta tgcattatct catttactta atccaatgtg tattgggttc 1380
ctaccattta tgccatatgt ataagatata tttacgaccc acacatttac gcaacaaaat 1440
agaaatttag aaaaaggtaa ctgctataag aaatgaggtc atttgccacg attccataaa 1500
tctcgcgtat gccgatccat ttccttttca actcacattc ttgtcatact aaatttgtgc 1560
acatgcagta taaaatatat ttttacgcag tctactatag tgcataaata acttcatcgt 1620
gtagtataat tagtatcagt atatatcata aactggttgt aacgagcctt gatgcatgga 1680
tgttggagag atcctatatt tatggataaa ataaagcatt taaatcagat ttttttttgtt 1740
tccatgcatg ttttcggtat gaaatagatc gatgatttac acaaaaattc atacccattt 1800
acgctgtttt ggttcacgtt ttacgctaaa atccgtctga gctcctacgc acgattggct 1860
ccatattttc tgttcccata tacggtta cttccggctc cgttggcgcg ctaattacgg 1920
tggtgtgtgg acccacataa acgaaccaat gaaaagtttg ttgccgctct ccagttatgc 1980
aagtctgaac cattaaatat gctagcataa acacgagtag gaaccaacta cccgaccagc 2040
aaacacgacg ctggcccact ttcgtccatc ccaactcgac cccactacgt gtgcactttc 2100
tgtttacgca aaacataaca catgtttaca catgcataaa cgtgccccac aatcgcgcga 2160
acacacgcaa cccactggcc caatctaacc acgtgcgtga ccaccatcct gatgtgcgtg 2220
accactaagg cttcccatga ctatcggaag gccagagctt ccgttataaa taaataaata 2280
aataaataaa tatatatata tatatatata tatatatata tatatatata tattagcagt 2340
cgaataagca cttgtgtaat taatattgat gtgctgccaa tgctgtcgtt tagtctggcc 2400
ttgtagcgta ggatttggat ttccacggcg cgtagaattc tacgtacgta tagaattttg 2460
tggatgatac cgcagccaat cacgccgcct accgttgcgt tactgcctaa cttaatttgg 2520
aggacatggt tggtttgtgc acgaagcttc atattagagg taattaattt tgtcataata 2580
atttcagcat actagtacag aaaacatatt tgttgttggt atttttttta tatttctact 2640
ggcgcgcgcg cgcttttatt tattaaccgc caaagaacaa aatttatagg tcaggaaata 2700
tttttaattt tactgttgca tcctacacag gaaattaact gtctgaaata ggtcgggaaa 2760
ggaaagaaag gaacagccca atctcaatgt cacccaaaac tggcgatatg atcgattcaa 2820
gggtaattttt gtcattcctt catccccgta ttggccgtat acttttcttc tcccggcagc 2880
tataaatatc gcatgcatcc tccctaaact cctccacact acaaacgcat taagctctta 2940
gctagcccta gccacgtacc cacacatcgt agacaacgca attagctagg aatagcatcc 3000
```

```
SEQ ID NO: 37       moltype = DNA   length = 3000
FEATURE             Location/Qualifiers
source              1..3000
                    mol_type = other DNA
                    organism = Zea mays
SEQUENCE: 37
gttaaatgtg acctacggtt ggatcatgat ctaatggatc agatggtttg cttgcacgct 60
tgcacagaag gactgcttgc atagcagtcg ttgccgatga tgaacactga aatcatggta 120
acatgggtga aacggaacgc gaagctcaac tgctagatga gcgaggagaa tgatgcacct 180
acaaaccgat ccccgctctt ccttgtggtg aatggagatg gcaattccaa gcgttgtctc 240
gctcgggtca ctgggtcgat gaaaccacgg gtctccgaga gctcaccact tcggaagggg 300
ttcgctggat gggagagagg ccatgacccc tcttgcgctt tgccatttca attgcctcga 360
gttttcgttt attgggtttt ttgtttgtta ggtctgaact ctaaaccagc tagtagcagg 420
ttcatagttg agaccaaata cttttccttt gtccagggtt catgtatgtc tactgtattt 480
ggttcatgtc ttctgaatct tcgtcttctg tagctttgcg agtgccttaa tttctgtctt 540
tgagatcttg agaagcgagc ccacaaggaa gcctttagcg caaatatagt aacttgctat 600
aagaaaggct caatgctgag ttggaggaga gagaagagca gatagaggag acgcggactg 660
ttattatagc aggcttagac atgagaaaaa aactttgtga gggagacacg tgaatcatac 720
aactatacta ctctattaag aacataatgt ggacacctgg tgctaccacg gcttcaccct 780
cgcattgtca ctctgggcct gtcccaccca cccgccctcg gcgtcatgcc ctatgggccc 840
cacttctcgc acccgcgcag cgctctctca gttactgcca tgtggacctc cagcgcccat 900
gcagctactg cgtctgccca acacccgacc ccacccaccc agctaccaca ccacgcaaaa 960
aatagtgcag agtgagcact cgaacccacg ccctctgctt ctgaaaattg gggccaccaa 1020
accacatacc ttagtgttag aaataaaaat attatatttg aatgaatatc tcaatacttta 1080
tttatatgac tagcgagttg ctcgtgcttt gctatggttg ttatatatca tataaataga 1140
tattgagata tttatttaaa tataattatt gtttaattct atatactaag tactttgta 1200
tctggtggtt agtcccaaat ttctgcagcg ggagggcatg agttcgagtg cttgatctgc 1260
actattttttt atgtaggtgg ggtcgggtgc tggacaggcg cagtagcgca cggagcgcgt 1320
ggggcgggtg cgaagggtga agtcgtggta gtatgaggtg tctacattag gttcttaata 1380
gaatagtata aatatataac aaccatagca aagtacgaac acttgactag ttaataatga 1440
agaactaatt attatacaaa tgtgctaaga ggttggctgc aagccatctt agcccccgagc 1500
aagttagtgc ttgctaaatc agtagttttg tactacaagg agcatgtgtt agttttttatt 1560
tatgtactga ttgatgcaag tggacgcaaa cgtccaggca attggtatac ttcagcgaat 1620
catgcagcct tagctggtga tacatcagat ttccattcaa tgcgtatctc cacgaatctc 1680
tacacaaagg catcgttttct tatcgttgaa gaagttgtca tgtccctctta agtgtgttgt 1740
gtctcgcgtc gtcctcggtc aaagttggta gcctgaaacc agaacttgta tccaatagca 1800
ggctgcaggc ctagctcttt agtatatact acccttaggc ctagtttgaa actttgaga 1860
ttagagtgtt tgaagggat tggagaggtt gtaaatcttc gatagatcaa atactctctc 1920
aatacatctc aatccacttc aatcccactt attactagag tacctaaact aggcctcagt 1980
tatcaaatat ttgtcaccca ctaattcaat tttgaagtaa aacgcgacaa attaaaaaac 2040
agagggagta taatcaattg aatcgaaaca gtccaacata gctgctgtcc tttccttttta 2100
ctcctgtcac tgtaactaat aagaacagag aaagtgaagg cccacgccca caaactgcgc 2160
agctagatcg accaaacaag agcatttgt tctttttttc cgcggtaact ttgataaagt 2220
ccggttaagc caacatagca tttgaagtca actgtaggtt gggccgttgg ggtagacatg 2280
tatctagcct ctcatttgta tcttctgaa gtgggccaac acgatgtgct tgcaagatta 2340
gtcgtttctc tgagctgttg ccagacgttc aaatgacaag ttggagagac taccaggtgc 2400
```

-continued

```
aagattagca atttgtttgg agagactacc aggtgcaaga ttacaagttg gagagactac  2460
caggttcaaa tgacaagttg gagagactac aagttgccag acgttcaaat gacaagattt  2520
ggttgcgttg gaaattggaa tgaggatgtt ataaccttca gagcttgttt gggagcaatt  2580
aatggactta tatttagtcc cctcaacctc aatccactc cgtatccatt gacaaatgaa  2640
ccaagggtca gctgctgagg agcacattca gttacagttt gatgagcatc cttcaattca  2700
atctagatct ctgaccttat ctgctacgtt cagacttggt agagagaaaa ggtcaactgt  2760
tcaacgttca gcgccgtcta ttttctttg agaacactta atattaataa tgtaacagaa  2820
ttgacgttgg ccggccgta gagatata agtaccccga ctctcttctg atgtccacct  2880
ccaccaatcc aaccaaccat tggccattgc agagaagaga ttactttaag aatgggctac  2940
tcgaagcgca ttgcactggt acttgtagcg gctgttgtag cgctccacgt ccatgtcccg  3000
```

SEQ ID NO: 38           moltype = DNA   length = 3000
FEATURE                 Location/Qualifiers
source                  1..3000
                        mol_type = other DNA
                        organism = Zea mays
SEQUENCE: 38
```
ggaaaccaca cgcccacctt caatcacggc gcagacttcc taaacaaccg ccacctcgtc   60
tcctccgcat cctctgcgtt tttcatttct cctcggcgac tgggaggcga gcgaagttga  120
cctcgatgcg caacggaatc ttcttcggca gcgggttcga ttgatattgc atttcgccgc  180
cacttcctct agttgcggag tcggctgaca gttccatcgc tggtatgttt tctcggtcca  240
ccgcccctcc catagttgat attcgttcgc tagtgttaat actcggctgg tgtcgtctcc  300
cggagatttc cccttttgta gtatgtaaac cgatccattt catagtttat ccgcgttggg  360
gttttcaaag atgtttacta acattgcaag cgacctcgtt caattcgcca ttttcctgt  420
agcatctttc agtgacctag tctgctcatg ggatttgaag agccaatgag gtcggcgatg  480
ccaaactcat gtctcttaag tttgagagag ataactgaat ttttgccatg gctatgacag  540
ctttgcaaat tttcaagttg tttcattcgg tctatctcaa catgcccaca ctccagcctg  600
gcccggcgag cgagcacgtt acacactagt ctccttctcc taacttggta gcagatatat  660
tttgagtcca cctttaagt tggccaaagt ctcccttaac tagcaatgtg ggattaaccc  720
tgtaagggca tgtacaatcc catttaatat gaggtctctt gagggctctc tagagggtta  780
aatgaaaaaa atacaagaga cggactcttc gcgaagagct cgtctctaca tgactctcca  840
tacacatggt ctcttaagtg tatttatgat ccaaaggctt gggattgtat catgatgtct  900
cttgtatcta gaaaatcgat ctagcatctc taggttgtac aagcatattc ataaggtgc  960
ctcaaaatag tgcctcaaaa gttgaataaa ctacatcatt taaagtgtt aggacactaa 1020
aaataaattc agcttcaatg tatttaagga aataaaatac attattagga aagaaaatgt 1080
tgagcatgat gttgaaaaca aggataaggc actaatatgg ggtaggat atttggatca 1140
cttcatgtga tgtgcctat atattttttt aataaatatt tatgaaatag gacattgtta 1200
gagctgtttt tttatgagtt tagccttatg ttttaagata taacatttaa tacgaccat 1260
aaaatattaa ttgtattaaa tgagatggtc atgtcgtctt tcctaccgca agaccggctc 1320
catggcctcg gatgagggga tacgatgatg cagccgtgac gaacggaaga agaatgatgc 1380
aaacagagac agaaataaat ccactactag ctagtagatg ctactagtag tggtggaata 1440
taatacatac aaagcatggg ggtccaatcc gttagcaccc cggcccgcac caagaattcc 1500
acgtacgtat gcgtcattcg tcaacacaag ctgcgctaca tctccctgcc cgtaggcgta 1560
cgcaagggct ggctgccggg gattaataaa tacgatagcg cgcccatgtg gatatacata 1620
gatcatatag agagagaaga agaagaagaa cacaagatgc atggccggct gctagcggga 1680
tcctgcgctg tccctagctt gaagaagatc gaagaactcg ctgctgtacc gcatgcaggt 1740
agagcgaaga atttccatgc aggtagtagg gatagaattt gatgggctgg caaccctagt 1800
agcaaataaa aacaggccgg gacaggcaga tcaggggcac acgtacgcgc gcatgcatgc 1860
gatagcgatg caatggaatg caacgtaccc tgactactac ctagctaaag aaaagaaaag 1920
aacacaaagt acacacgagg aaaaacgagg ccggccggcg aacgggcggg cgggcttcca 1980
cttccacaat gcaacccgcc agttcccgcc cggacgacgg gggaacttg ttgttggata 2040
gcgtcgtgat cggagaatga tgccatcggt ctcccgtgga aaatggcgag gagatcgacg 2100
acgtgttccg ccggctgctg cgccggagac ggagactgat gtgtagacgc catgcgaccc 2160
gtgcaactta accggctgag accccgccg gccgtacatc gtaccgtacg taccctagct 2220
aggtcgtttt atcgacgtga caaggaagaa cgaactccca tatatacatg caggggatat 2280
atatatat atatatat agaacacata tatgcttgta tctatacaca gtagaagaat 2340
aatgttgttg tatatttaat agttaatcca cgatcttaag agtatgatat ccctgtatgt 2400
ggttttctat ataatacaaa tgccggtatt ttagaaaatc atggcaatca gctggtacgt 2460
gtacgtacac gcacgccgga aatttaaaaa aaaaaacaga gagagagcct gcgcagctga 2520
cacgcgcggg cttcttccac gtccgtcccg cggacttctt agcttgcttg cgtcgtcgtc 2580
gtcgatcggg atcagacgtc gaggtcgagc accgtagacc gccattattg tctccgtgga 2640
aaacgtacgt aggacgacga cgtacgacgt gtgtgccagg ctctgcggcg ccggagggggt 2700
gacacgaccc catgcatgca acttgatcca gatgccgcc ttatagctgt ggcgatcgag 2760
tgtggctagt gctagtagtc aacccggctg gccgcccgcc cgccgaacgg tgcaacacac 2820
accacgtcca catgcatgaa tataatgcgt ctttttttgga gtctctctgg acgcgggaaa 2880
cgtaccaggc tggcaactct gggaggccga ggcgaggcga ggctcatcag acctcggatg 2940
ggacgtgcgt gtatgcgtct tgtgtgtata taaaggggag ggggtgttcg ttgtatccaa 3000
```

SEQ ID NO: 39           moltype = DNA   length = 2193
FEATURE                 Location/Qualifiers
source                  1..2193
                        mol_type = other DNA
                        organism = Zea mays
SEQUENCE: 39
```
ataacaacac caaaaataag agcaccggag gacatagtat atggcccccg gtagtttctt   60
aaagggctag tttgaaagcc acgaaatcga agaaaatttg gagcggctaa aattctctct  120
ttattcaaaa ttaaaattaa ataaagaaag aattttagcc ccttcaattc tctatggatt  180
ttagactctc aaactagacc taaaatattt acttgttttt gtagaaattt tggctcgtct  240
tcacaatgct atttcgccgc catttctctc cgccaaacag gtcaaaaaaa gtgttgctac  300
```

```
atgtacaact ttattgatag acttacaaac gattagggtc atctaatggc tcataatata   360
ttagttcaga ataagagtca atgacagcca tataatttta aactaaaatt atttaagaac   420
cataatttaa tgtaaaaaat atatttgaat catgatccat tatcgctcta gttatagctg   480
aaatatttt  ccaaaacaaa agtgcatccg gcgaggagct ccttaattcg tgctcgcagt   540
gggtgctgct gcctagagtt caaagttggg gcatcatgct tgtagcttga gcgaccctt   600
tgtggtgtca aggagaagtt cgatggtgat tttatattga atgattggtg taatagtgca   660
aagagtaggt cacactacct gttagtgctc ttgtaccacg atgctcattg gttgcactat   720
aaaatcacag tcgaaggaac aagtgtgaca tttcctaaga ttgtgttgga aaatggatta   780
tgggtataaa aggaatgata tagagagtgt tcggtttata gagactaatt ttagtccaga   840
tattttattc tattttagtt tctaaattag taatattttc ggaaagtttc cgtgttggat   900
aatttagtaa ctaaaataaa atagaataaa atagagggac taaaaatata tattttata   960
ctactctatt aagaacctaa tgtggacgtc tagtgctacc acgtcttcac cctccgcggc  1020
ctgccccacg cgccccgcct cggcgctgtg ccctgtgtac cccacaccca gcgtccgtgc  1080
aaccagctac tacgcctgcc cagcatctga ccccacccgt gtggctactt gtctatcaca  1140
ttgtgcaaaa ataatgcag  aacgagcact taaactcata accctgctc  cagaaattta  1200
tcttagtatt tagaattaaa gaataattat atttaaataa atattttaat agtagcaacc  1260
gtagtaaagc acgatcaact ggctattatc taaaaaccaa acatcctgta atttgagaga  1320
gagagagaga atgggccgca ttacattgca ttgcagcgga tggacctggc cgccctcacg  1380
aggctgactc gcacgtgctc ctcacacctc ttgtcttggg ccgaaacaaa ggtaggcgag  1440
gacgcacgca gcgcagtcaa ccagatgatc tcccattctc catcttccaa catctgaaga  1500
ggggttccaa attctgaagc cgatggggac gcagagcgaa ggctgcgacg gaagctggca  1560
tgccccgtcc ccacgccgcc acgcgcgatc gcgaccccga agcaggctca cgaatcgcag  1620
gccggggagc gcgagccgac gcccgctgat catcaggctc aagaatagca agacatccct  1680
cccctaacca aacggggcag gggtccggtc agctcggcca ggaattccac gagcccgtcc  1740
aacgcgcgcc tttgtattct acgtgctatt catgcagcgt ccggcgccac aggccgcgat  1800
cggcggagga ccttctcgcc gcgcatgcat ctatctcagc ggccgccggc cgccgccggg  1860
ccgcgtgttt tgtgttgtgt gttaggccag ccgggatcgc gaccgccgtt gccatcctcg  1920
cgcatacggc catggcgtac tagctgtatc ccaatcccca actacgtacg tgcagtatag  1980
aaactagaga aaaatggctg tgtacgtaga cgtagtggtg gaaacttggg ggagaaaaaa  2040
caagaaccga tccatcgtca acgaccggcc ggggacttgc tggatggcta tgatcgtgtg  2100
gcctgcccaa ctggatagtg gccgccttgg aacggcctgc actgcctaca gctctacctg  2160
gctataaata tggccgcgat gcctcggtga att                                2193

SEQ ID NO: 40           moltype = DNA  length = 3000
FEATURE                 Location/Qualifiers
source                  1..3000
                        mol_type = other DNA
                        organism = Zea mays
SEQUENCE: 40
taaataggcc atctgcctga ctaactaggc acaactaat  tcggtaacta acttatttgg    60
aaaccaatcc gaccaactag gcaacaacta attaggcaat tacttatttg gtaaccaatc   120
cctctaccat taaggcctat caatttagcc atcaatctag ccattttccg tagtggtgcc   180
ttccttgtac gcactgctgt tctcgcccac cgtgtacgcc cgcgcctcag ctctcctagt   240
gtcgtgggcc cgctgttggc gtgcataggt gcgacccccc atgacatgaa tacacattaa   300
aaatctattg gtggatattg cctgaaatta ggcattggtt tctacaccgt ttcagtagtt   360
tatcgcactc tatggtaaga ttcaagagtc ttatccacgt gccagctttg aatctattat   420
tacaacgcct actttggtag ttcaaaccaa gcacctaaga agaagaaaca aaaactcatg   480
attgtgctag caaacaaatg tccactaaga atgtatacac ttcctggaac ttacatgaat   540
attggggaac gtgcttgtaa acatgaacca gttttttcat atataggagt aataaacgga   600
gttgtctttt gaaatatagg actctaacac caaaaatctt ctctaacaga ggtcttaatt   660
cataaaaatt catcaaatta tagaactcga gctctcatat cgtaaatata ggacctcata   720
tgctagagtc ctatccttat tttatagatt agtcataaca ttttatttcc taaatattat   780
gatatatttc gtaaataatg atgtggagcc caatattgga gctgcaaatg tttccctgga   840
ctaaacactt caaatcaagt cctattttaa ttttaggac  tgaagtatac ttcttattca   900
agatactctg acatcttgat actcagtaac ctcaaaacga aataagtttt ttttaagata   960
taaaaggtc  taagtatgaa ctaaagtaaa aaaaacaaaa atacgtgttt atatttactg  1020
taatttaatt aagatattaa ttataaaata tgttttcata gtatatccat ttgagacata  1080
agtattaatt atatttctg  taaacctatt taaattattt tataactcaa tacaaatcta  1140
gaactatatt atgttgaatt atagaaatac aagaaaagaa ataagaaaga gaaaaacata  1200
gcaacacggg gaaccaaaca aaatgctccg ctgctctctc tctcctttct actccgcac   1260
ggatggtaaa gagtggggag cgagcgagag caggggaaggg gagaagcaag caagacggga  1320
gcagagcata gtttcataac cccattgctg gccatcgcct agccgcccga gaaatcagtc  1380
cccaatctct cgcccacaaa atccctagg  tcccgtttat ttaattttat tttaaggaat  1440
taaaatctta ctaatggaat tactattat  ttttagaata cgacattcaa caactttcta  1500
aagttatcat ataagcctat ctcaaattta tgagtcgaaa gatggaaatt gattttataa  1560
atttacatgc tgtttttca  atacacaatt tatagaacac tcttttactt gctttgttat  1620
aacataaatg tagtatataa ttatctctca tataatttaa gataatatac aaatatacta  1680
catataaa   tatataaact taattagttt tgtctaaatt ataattatta aaatggaatt  1740
caattccaac aaaagaaaca ggccctaggg atttgtagat aaccccagtg tcgccccgta  1800
tttgtactac tcgcacgcga cgacaagcat tgctatttca tctcctaggg atgatccaca  1860
aaacagagac cgttggatat gattgaggga ggagggagga gataaatgga acgatcgtga  1920
gtattgattt taatggtgga agatgactgg agttaatttg ttgcgtggat ctagtgttgt  1980
tttaaggggg tgtttggttt ctagggacta attttttagtc tctacatttt attccacttt  2040
agttacaaaa ttatcaaata tagaaactaa aacttttattt tagtttctat atttgtcaat  2100
ttatatacta aaatggaaca aaataaaggg actaaacatt agtccctaga aaccaaacac  2160
ctcctaagtg gtaaatata  cagggtaga  gattcaaaat cgagacgtca tggttttcaa  2220
taggatgcat ccctggcttg cctattgcct caatggaatg tagatgcatt ggaccccgtt  2280
cccatagcga tatggtttag attttttttt tgtctgaata tgctgcagtg atgtgatttt  2340
ttttttgtatt tttactgatt aacgttaact aactttacgg attcagaagc ttgccctcga  2400
```

```
ttattaaatg aagggccggc tgttttagct gatgcaaaca taaacggaga tgaatatgga 2460
tggtcgtaga gaattaccgt ggaggagatg ctcttttagg actatagttg ggtcatccac 2520
ctaagggctt gttcggttag ctctcaatcc atgtggattg agtgggattg gatgggttta 2580
aaacccaaac aagtcaaact tcttctcatt tttttccaat cccatccaat ccatgtgttt 2640
tgggaataac cgaacaagcc ctaatcaatc agattggagc tgacaggcta caatgtctga 2700
tagtgcatga atccctcgga atacattcgt tcccctgttt tgctgcccag ctggttgcga 2760
ccccgcctac cgctgcaccc tgtttctcat gaattcgacc gacagcacac aaggaacgac 2820
caactctgcg ttgaatgtac ctctctctga ctcgtgtact cgtgtatgcc aaaccaagtt 2880
gctgatgcgt catgcaatct ctctctatat atatggagag agagaccagc agaaaacata 2940
gaacttgcga attcggtatt gagaatttgc gataccgatc tgggagaaga gaagggcgtc 3000
```

SEQ ID NO: 41        moltype = DNA   length = 3000
FEATURE              Location/Qualifiers
source               1..3000
                     mol_type = other DNA
                     organism = Zea mays
SEQUENCE: 41
```
aactagtttt ggcgcacata tgagatgtat ctagatttat cctgaaatcc agatgtgaca  60
ctgtcacaag gtgatttaag gctcgaccac caaacctctc caggtatcat actctatgta 120
tccattcgtg ttccccgcat cttggacagg tgttatgtcg tccgcaatgc cacactggca 180
acacgatttg ctctatcatg ttattacgct attggtgtcc acaggtgtca gccaccataa 240
tagctaatta cccgactttt tcggtctctc gatcaagacc caacactcgt ccttcaccgt 300
ttctggtacc gacacaaacc cacataacat tcacctttga tgtataccat catctctgaa 360
ctccacgact gcacacaaca agtaattaaa gagacatgtt gcacaaatac actcacgcct 420
ctgtctatac gactcaattc aagacattcc gcttattgac aatcattgtg ttcgcatcgt 480
ttagtgaggg atggatgatg tggcagttac tcgtgacttc tcgtgacttc gctcaaattc 540
aaaagaaaaa aaaatcgata ctcagttggg acatccgatc cacacaaatt aagcagcttt 600
cttaccagcc gagcaactcg tgtcgcatca aggtgaaaac tgacgtaagc aactgccaca 660
tcattcctta gtttacaaat cgaatgagtt aagcaattaa acaacaacgc aatcgtgata 720
tgatcgagtt tcttcttttt tttaagaaat tacaacatca ttatcaattc atcgatcaca 780
cgcctaccgt cctttatttc ccattggtgc acgttcatgc aatcatacac gcaaactttg 840
atcggactcg tacatatacg attacgcatt aaaagaaat ggcatcatcg ttatatcaat 900
tgtcatgtgt atcattaaag gggtgtttgg ttttaggga ctaatttta gttcgtcaat 960
attatttaat tttaatttca aaattgctaa atacgaaaac taaaataaag tttcaatttt 1020
cgtatttagt aatttaagga ctaaaataga ttaaaacata tatagcgact aaaaattagt 1080
ctctaaaaat caaatactcc ctaactctct gcctaacttg ccacacttg cctagctttt 1140
ctgcctaagg ttagttcttc aatttgaacg actaatctta ggcaaaatgt ggcgtattta 1200
gccacgaacc aaacatgccc tatgttaata ctagtaatct acgttttct gttagcattc 1260
aatgacatat aatataatat gcatgggtgc agatacaata ttatccgccg cgaatggcgg 1320
gaaaataacg gtcggacagg tcctcatttc caaagtcacc ggtgactttt ccacaccaca 1380
tgtgttatgt gtagttgtgt gttgtactgt gctgtggaaa ttctacgtgc aagcatccta 1440
tttcttcgta ccagacgttt taaccttcaa cacgcgccgt agaaatacgt cttatatctc 1500
tagtaggata tccgtagaat catataagct cttgactatc tcccatcat aaaggatttg 1560
aagaacacct agcctgtatt taaccttaat tataatggga tgtatagttg tatttaaata 1620
tattttgatc acaaattaat taaaagtgtg tttgtttgga attataatct atccagatta 1680
tataatctaa cttattttga actaacactt agttcaaaat aatttagatt atataatctg 1740
gtcagattat aattccaaac aaaaatgata tctaagtata tcgtatttta taaataatttt 1800
ccgaggcccc ttttcctgtc tgatgaagat cgctgaggct gaacatgaaa tgacagcagg 1860
tttcttatt ggccaagtcc cttgagaaaa cctaatggta aacaattagt cttctagaac 1920
cctagcgaac cttgtacgcg ttaagaaacg gattggtcaa gccagccgag atcatatgaa 1980
gtagatcttc cgatagtaag gaggtgtttg gtttgaggaa tcatttcatc caaaatgtag 2040
tgatgcatca tgggtccatt cctcaaattt ggtgggatga cctcattcct catattagta 2100
ctaactaaat aactataagg aatgaggtga tgatggatca actcaatcca ttccacaaac 2160
caaacaaaaa agtgaggagt gagaagacga tggactagta cattcctcaa accaaacagc 2220
ttataaagtt caaaactaga gttgagaata aaaactataa tatgcatgag cattaatctc 2280
ggtctcaagt tttatctgga taaagagtcc atattagtcc tggttgtggt tattacgaca 2340
aaatgtggat cctttatcaa ttggaactaa ttaagggatt tcacatgtc agttccgaag 2400
aaaagcgttc tattcaccta ctatgtaggt gaggtaaaaa aaactactct gctaataata 2460
cttcattcct tctttttat ttttcatatt ttaattttgaa aataaattaa ggataccaa 2520
tatttaagaa tagatgtagt atatgagatg acgggttcaa gccttccaag ccaattttcc 2580
tgctagtgtt ctctagaatg ccgtgccgt ccattttgta cctcctgctc ccagagtcta 2640
gtaaacgaaa tccatgttta tccgaaaact ttcctgccga tcctatactg ttactcgcta 2700
atttattttt aaactaaacc acgataaata aaaaaacgg atgaagtata tgctatccaa 2760
taatccgtg gaaattcttg gctcccttgg aagatcttga aggcgccaac attgaccgtg 2820
accatgccaa gtgcctacct tctgcaaatt atgctatata tcttgcttgg acttgcccct 2880
atatacgatt ataaatacca tggccagcca ccactcgcca catctcatgc acgccgatca 2940
cacattggac ttgcactggt gcttgctcat aattactagt tcatcagcaa acaacaaaca 3000
```

SEQ ID NO: 42        moltype = DNA   length = 3000
FEATURE              Location/Qualifiers
source               1..3000
                     mol_type = other DNA
                     organism = Zea mays
SEQUENCE: 42
```
cacgcgggct tgaggaggcg aggggcgaag cgggagtggt tgcgggcttg cggcggttgc  60
gaggcaaaga gcgagcacac gagcgtgggc agcatccgac gcacgatgcg atgtggacgg 120
ttgagattgg tgaaaggcag aacggtagaa ccagagagac agactacact tactatctta 180
ataattagta gagatttgta tagactagtc gcataaaata gttaacaata catccaaact 240
cttctgaaat tttgactttt ttaatttggg agttctgatt tggatttagg aagcccttat 300
```

```
agtgcagacg agcagcagat gatcattttt tcctacttct taacttagta atttaatagc    360
cctcgttttt attatagtat tgaactgaat ataatcttcg tatattacta gtgtgactgt    420
ggcctcagcg aaaggaacat tttcaaagct aaaaatatcc aagaattatt atgtcaacaa    480
atggtccctat aaactgactt cttttcggct gcgcaaatga tgtcactagg ctaagatggt    540
cctggaaaac gatccggttt tccgatgtta ctgattgttg cggttcatat ataagaccat    600
atttgtttag gcttttctta gcttctagtc atcaaaagct gttgtaaacg gtcaaatgct    660
ccagcttttt agtccgcttg tataataatc actttgataa taatttctac tacttattaa    720
ggctgcaaga gtagcatgtc attccgtgtt ctgtcattca cattccttgt tctgcctttc    780
tcattccctc ctcccccacac aactcattcc aatgttctgt cattctcatt ctcattccca    840
cgtacagtcc acgtctaagc tcattccaat gttctgtcat tctcattccc acgtacagtc    900
cacgtctagc taaaacctca caaagctcat tcctatgttc tactattttc attctcattt    960
ccacgtacag tccacgtcta gctaaaatta aaaaacacaa atgctagtgt gactatggcc   1020
tcagcgtaag gaacctttc aaagctaaaa ctatccaaga attattatgt caacaaatgg   1080
tcctataaac tgacttcttt tcggctgcgc aaatgatgtc actgggctaa gatggtcctg   1140
gaaaacgatt cggttttccg atgttactga ttgttagtcc gcttgtataa taatcacttt   1200
gataataatc tctactactt attaagcctg caagagtagc atgctgccat tctcattctc   1260
attcccatgt acagtccacg tctagctaaa attaaaaaac acaataaacc caaagggat    1320
ttgaacccac gacctcttag gcaaatgcat acaatagcca ccactacacc acatctgtgt   1380
ttatgtctac atctatgaca gcaaaaacat ctactacatc tctacgcaag cccacctgct   1440
acccttgcac aatgcgcagt agtagataag tatcaccgag attcttgaat tatatttttg   1500
gatggaggga gtaatattta aagaagagcc ttgcaagcaa tatcttttgt ttgaataatg   1560
ttttcaactt aattttttt tgcatgtgtg gtatttttc tccgtaatat ttttccatg    1620
gatctaactt atgagtcatt ttcataaatc aacgccaagg atgaatccat gtttcttgcc   1680
tgaaaacccc aaacaaacaa cactagcagg aggcgctcgc gttggcgtcg ctcatcgacg   1740
acaagaaaaa gcttgacgac tgctagttcg acctctcgaa gcagtcctac atggccgcat   1800
gagccgctgt gtatgacaag ctccgacgca gtcgccgctt ggacgcggtc tagagccgct   1860
gcatcgcgtt gtccatcgtc aaacagggg acctcatga cgttgtcatt gtcggcgact   1920
ctcggattgt tctgggcacc tcatccaatg acggtgtcat cacatcgtcc aactcatcgt   1980
acatctgaag cccaacttgc catgtaagtc gctactgtcc gaccatgaat tcgtgcgctg   2040
ggacgacagt cgttgctgac gttgtgtgag tgtcctcgaa catgatgtat gtagaggagt   2100
agcgcatcca gtggtgcaac ggccaggtgt actacactgc tgatgagccc gaggtgcact   2160
tcgtctggca gcacagccaa gagtcatcgg tactcgccat gtcgcgcgcg ttcgacatct   2220
actatatcat ggactgtggc gtcatctcgg tgccagaggt gacgtagagg aggaccgaca   2280
gcaatgatca gtttgtaatc ttcgtcaccg tcggggtagc ttttatgctg tgcctttaat   2340
tctcttcgca aacacacact tattttttg gtttgagcaa gcgcgtatgg tggtgtgtgt   2400
gcctgatgac tgacgatgta cgagggaatt tcttccgaca ggcgcgggac gtgctctcca   2460
atcatgagac tatagaaatt gtgtcatata tcgaagtctg cataaaagct gatggttgca   2520
atgtagtggt gaaaacaacta aattaaaata acaaaattta tgtatgggca agatcataaa   2580
tggattatga aacattttct aataacagaa taacacattt tatatataag ttactgtagt   2640
attatatgtc ttcttgtaat gcacgagcac tcatctagta atttaaaatc aacataaatc   2700
gatcgagttg ccacgagagt agaaaaccgt cacttttttag actctaaacc ttttgaccac   2760
ttcacgatac taatatcctt ttgacaacca gatttttctcc aaacataggc ataatatggt   2820
atgatatcgc ttaggagctt cctgactgct tctcttgcat gctgcgacacc ggcagcgacg   2880
ggctctcacc caactagtct gcgtagcgta ggtaagcgac ggcgacacgc cgttcttccc   2940
ctgccgttga ccaaatacat ttcgtcttct agcaccttct cgtttctctc ctcctcgacc   3000

SEQ ID NO: 43        moltype = DNA   length = 3000
FEATURE              Location/Qualifiers
source               1..3000
                     mol_type = other DNA
                     organism = Zea mays
SEQUENCE: 43
cattgcccac ttgagatgcc tgcgctccaa attcaacaat ataccaaata ctttcgtgga     60
gtgaggttag atgttgtctc attttatcac tccatataca ataatcttca ccatcaaagt    120
atggtggttt gcctaaggga atggaaagta aaggagcacg ttttaaaata cgacgatagt    180
gaagagggat cttactatac ttcttacgct cttggcgctt cgaagatgtt gactcgacgc    240
cggaggttga gggtgtggaa gaatcggtct cgtagtagac caccttcttc atctactttt    300
tcttcttgtc gcccttcttg tgtgacttga tggagccggc ggattcatct ttttcttcct    360
tgtgcttgtg gccggcctcc tttgacggag acttttcttt attcttcttt cctgaagatc    420
cgggctttcc cgcggtgatc aactcccttt tggtgtgttc tcccaacatc atttcgagtt    480
gttaaactct aatgaagcac cagacttga taccaattga aagtcgccta gagggggtg    540
aatagacaaa acctataaat tataaacttt gaacacatac ttcacctagg ttaggatta    600
gaaacatata ataatgaata cagagtgtgg aggagagttc ttcttgctat gagttgctca    660
atcaatgcgg ataactttgg gagcgaagtc aaaagattgt aagcaagaga acttagaag    720
aggagagagc aggaatcaaa tcgtgaggtg aagatcaaca caaattaaca caacgatttg    780
tttctcgagg ttcggttcca atgaatctac tcctcgttta ggaggccacg aaggccgggt    840
cttttcaac cctttccctc tctcaatcga tcacatagac cgattaagtg cttcttctta    900
atcttaagga tcacaaagac cccgcaagga tcaccacaca cttaggtgtc tcttgctagc    960
tttacaagtc acttagagag tttagaagga gatgaagaa gcacgattaa aaagccaagc   1020
aacaagagca acaagagcaa caatgaaat acgaataaca ctctcttaag tcactaatca   1080
cttatcttaa ttgtggcact tgagtagatt ggaagctttg aatgtgtctt ggaatgaatt   1140
tcttgctctt gtattgaatg tggatgtatt gaatgcttgg gtgtgctgaa tggaggtggt   1200
tgtggttgta tttatagccc tcaccacaat tatagtcgtt ggacagaaag caacggcttt   1260
ctgtcgatgg gcacaccaga cagtccggtg cgcaccgtgc atggcactgt tcattgtccg   1320
gtgcctgcca cgttacccga ccgttggcgt ctgtagcagt cgaccgttgg atccgcctgc   1380
tcttgtggcg caccggacag tccggtgca catcttacag tccggtgcga cctgctttct   1440
ctgacagttt ctgaccttcc gatcattggc agttgcagtg gcagtcgatc gttggcccct   1500
ctgcggtgaa gtcgaccgtt ggcgtgtggc tcatcggaca gtccggtgca catggacag   1560
tctggtgaat tatagccgcg gagcactgag ttttttccga gagtgaccta ttcgtcggc   1620
```

```
gcgtcagcct gggcatcgga cagtccggtg caccacaagc tggtgcaagt atgactcgcc    1680
ccatatttag aaacgaccca atggtccatt ttacttacag atgtatatga actttatgta    1740
tctgagaaaa gatcaactag gcaaactagt tagtctataa gttttatgat ggtcgtcaaa    1800
caccaaaata tattatggaa ttacaagcta tcagcaaaag taggatcgat tactcaaaat    1860
gcaattcaaa gattttcgac ctcttctttt tttgtttagt ttgttggttt actttggcac    1920
tacctccatt atcgaatatt tttcgtccgc tagttcgttt ttaaactaaa acatgacaaa    1980
taaaaataaa aatgaacgga gggagtacat catagtcttc tatgtgtctt agctatatat    2040
gttttattgt tgagacatat ggtatccctt tgtaataact ggcgatgcaa tctgaatcta    2100
ttagaggaaa gtaccggcga agaaagtaca ttagctcttc caacaattat ctttcctcgg    2160
tctgtcgggc ccggctacgg cctgcacaga tggactgggc ttgggctagc acgacacagt    2220
gaagttcatg ttgtttaatt tctttaattt agtaagttat agattttata ttattgtgat    2280
agttggactt tatgtgatca aatgatgtta gcattgttta atctctttaa tttagtaagc    2340
tatagacttt acgtagttgt aatatttga ttttatgtgg tcaaatatat aggccgggat    2400
tagaccggca cgacccaacg aaagcacagc gtgatttagg gtcgggctgt gtcactatgt    2460
ttacacttcg gattggcacg gcacatccta aaaaaattta gacttattg acctgaaccc    2520
gtttgggaga agcacgatag gctcacgtca ggctggcccg gtccgaccca attaacagca    2580
ctagtctcgg ctatatgatt tattgttgag acatgtggta tcccttttgta ataactggcg    2640
atgcaatctg aatttattag aagaaagtac cggcgaagaa agtccgttag ctcttgcaac    2700
aattatcttt ccttggtcaa aagtcaagac cgaaccatgg acaaaccgac ttactacaat    2760
gacgattctg gtccaagatc caaaatgcat ggtcattagc attatcaggt gagcatgtgg    2820
ccaccagcaa ttcaagcctg acttagttga cttcgaattc ggagaaaagc gtgcatttca    2880
gcgtaggcgc tgcagcacat agcagtattc cagacgatca caatcacatg gccagcgtcc    2940
agcagcagca gcactgcagc agtgtacgta tataaaggga ccagaacctg ccgtccgctt    3000
```

SEQ ID NO: 44         moltype = DNA  length = 3000
FEATURE              Location/Qualifiers
source               1..3000
                       mol_type = other DNA
                       organism = Zea mays
SEQUENCE: 44

```
gcagcagcac gaggcagagc aggcagcgca gcagcaggcg gcgcctcagg acgacgacca      60
gcagcagcag gacgacgacg accagcagca ggacgcctca ggttcaggcg gctctagttc     120
gaggagcatc tacctgcgag gccccgcgag tctcccgcct tgtcccatac ttcgggacag     180
acggccgttg attcggccgg aaggggagag gtatgtaact ttatgttctt cattcttgtt     240
catattatgt gttcaaaatc ataatataaa ctaatacttt ttatttatca cttggacagg     300
tcttggacgt ttttggatta tgctgggggt catcgtcgcc cccccaacaa catcctcggc     360
ctgctgtgca gggaacactt ccctggactt gtggagtacg ccggagtgac gggcccagcc     420
ttcaccttcg accactacgc cgtcgccccc gatgcagtaa accgggacgg cagggaattc     480
aataacaagg cggagcgggt gaagcaagag ctgtgggtaa gtcttagtat aatataaaat     540
atgtcacatt cgttgcaaat tcttgaaata atgtatggat acatcgtttt tgtatgcagg     600
atttcttcag atgcgatgct ggatacgagg ctagggcgga tgtggtggcc accacgtgct     660
gtaagaagct cgtcgtggac atgcactatg aggcccgcat ccaggccatc atcacctacc     720
acggctccgt ccttggggag aaggtgacca aacctcaagc ccgaaccatg tcgttgacca     780
gggagcagta cctgcaggta aagtcatgca tgtttggtac aagtactcca tgcatgaatt     840
ttattttatc ttctgatatg cactttatgt gtttactttg caggtgattc cacattggtg     900
cgccgcacat cctctctgct gggagcagat ggtggatagg tggtgttcgg ctgagtggga     960
cgaggcgcac gcagctagcc gggaacggcg tttgcagatg caaggccccct cgcaccacca    1020
aggcagccgg agcctgggcc aatatgccga agcatgggta cgccacccttt tttatttaga    1080
tatatagcac taagttagat attatttcta actatctcgt tggttttcgt tgcagtcggc    1140
gtcacatggt ggcagacctt gttccacctt ctcggcctat gctatggccc ataagggtaa    1200
ggcgacgtcc gacgtcacct acaacccaga tgaccgggcc gaggcctaca ccaacccgc     1260
cgtctacagc cgcctccatg actacaccgc catggcgcag gaggtccatg gcccagacta    1320
tgatccgagc accgagccta tcgacccccga tgtgctcatg agggtcggag gaggcaagag    1380
acatgggcgg tactggattg ccgacggggc aatcgactcg tcctccactc ccactctgtc    1440
tcaggtgaga gcaaggagca cgggctagag cccagccatt cgacctcggc acgacagctc    1500
acatcatcgc atacagcaac tcgaggttag tgattctata actcgtcctt cctttagtta    1560
tatatcagt ctttgagtta ctataacgtt ggcttgtaat attacagacc caactagaag     1620
agatggaggc gaggataatg gcggagcggg cggcggctga tcagaggatg gcggagatat    1680
tccagtacat gtagagcctt ggcgcgcac agggcatcgc tccgccacct ccattgttcc    1740
ccccagttga ccctactctc ttccacactc ctatgagtat caaaattgta gttagatgtt    1800
tgtaatgcat ctggtataac acatgctatc tcttctctgt gcagggccaa tctggggcgg    1860
catccaacaa ccctccggaa gggttcagcc caacgcaacc ccggcaaac cgcccacctc    1920
catgagtcat tgttttagac ttcagaactt atgtataata cttatgtttc tgtttgatac    1980
ttatgtgaga gcttgcgacg tttgagactt atgtttgat ttaatacttg tgttgaacac    2040
ttatgtttgt gatggatatt tatgtttgtg gtcacggttt tatgtttgtg ttggctattt    2100
atgtctgtga tgatatctgt gatgtatata tgtgatatat atgtgatatc ttctgtttat    2160
gtggatggaa aacaaaaaac aaataaaaaa ggtacatact ggtcactttg ccgagtgtaa    2220
cactcggcaa aggggctctt tgccgagtgt ctgggtcata acactcggca aagagcacag    2280
acctgggcac cggcttaggt tctttgccga gtgttatgtt gctggcactc ggcaaagagg    2340
tcggctttgc cgagtgccaa ttgggacact cggcaaagag cctgacacgg gaccctcccc    2400
tggcgggcta tttgccgagt gtcccaactg acactcggca aagaaggcgg ctttgccgag    2460
tgctgccagg aggacactcg gcaaagatat cttcgttgcc gagtatcacc gttgacactc    2520
ggcaaagccg ccgtctccgt caaccggcgc cgtaacggtc gcttttcttt gccgagtgct    2580
acctgcacct cggcaaagat atttgccgat gcactgtttg ccgacctgtc tttgccgagt    2640
gttacactcg gcaaagcctt tgccgagtgt ttttaaggct tcgccgagtg cttccggcac    2700
tcggcgaagc tattgattcc ggtagtgcta gtcgcgtttt ctattcatat tctactgatg    2760
agttcaggaa aaagcagatc gagataacct tcgtttcagc tctttacggt gcacgccgcc    2820
gtgtctagct ctagcagtaa ttgctaggaa cgaagcaagc ataggtatg gccagcacgc     2880
acaggttgac catggctggc tttaggtagg tcgctcgtag tttcgtgtag gtggatagct    2940
```

```
agctcaatga caatataacg agtataataa atagcgttgt ccgcccaccg gaacaatggc 3000

SEQ ID NO: 45            moltype = DNA   length = 3000
FEATURE                  Location/Qualifiers
source                   1..3000
                         mol_type = other DNA
                         organism = Zea mays
SEQUENCE: 45
caccggacat gtccggtgtg caccggaatg tccggtgcac catacgacag tcagccccac 60
caaacggcta gtttggtggt tggggctata ataccccca accacccacc atttatagca 120
tccaagtttt cacacttcca accacttaca agatctaggc attcaattct agacacactc 180
aagagatcaa atcctctccc aaattccaca caaagcttta gtgactagtg agagagattt 240
gcttgtgttc tttcgagctc ttgcgcttgg attgcttttct tctttcttgc gatcaaattc 300
acttgtaatt gaggcaagag acaccaatct tgtggtggtc cttgtaggaa ctttgtgttc 360
caagtgattg agaagagaaa gctcactcgg ttcgagggac cgtttgagag agggaaaggg 420
ttgaaagaga cccggtcttt gtgaccacct caacggggag taggtttgtg aaaaccgaac 480
ctcggtaaaa caaatccttg tgtctcaccg ctttactcgt ttgcgatttg tttttacgcc 540
ctctcgcgga ctcgtttata tttctaacgc taacccggct tgtagttgtg attatttttg 600
agaatttcag tttcgcccta ttcaccccc ccatctaggc gactatcagt cgtcaatctc 660
gcgcagacca cagaagccga tctccacgcc cgctagcgcg attcggcccg ccggagccaa 720
tctccacatc tgccagtcgg gagaagggtg agaagggtg gggatccggg ccgctgcgcg 780
gggggtgaag aaggggatga cgggggtgcg ggccggagga agaggcgtct ggtgtccatca 840
cggagaggat ggaaggggc acggctatgg agatccgata atggcggcgt cgatggcgtg 900
gggagggtg gggcggagga gagggaggcg tgcgtcgcgg agaggatctc gggcatgcgt 960
cgcggagagg atttcagagg agacagtggc agaactgtgc accataggat gtgaacgcc 1020
tacactaata tcttaaagag tagtatagat aactatatag taacattataa atgaccacaa 1080
caaacaaaat tacataatct acgaataata taagaaaaca atgtatacct gagatcgcgg 1140
acgagtcaag ctaacggtgg caaaggtcga gttggacgga cacctatgtt caaaaaaaat 1200
agtactgtca gtaaaaaatt cagcagcacc tcccctatac agtgtggttt ctaaaacttg 1260
caaagaaaca acaacacgat ggctgccatg cacactaaca aacacagaaa actgcatgat 1320
agctacgtaa taaacaataa gctgaccata tgataaacaa tgtgctaaat aatatgctaa 1380
atatatgcta actatatact cactaacttt tcgccatcta atatactaac aatatgctaa 1440
caatttacga actatataat cactaactat atggttaggt aaacaaaatg ctaaccatat 1500
actaactata tactcactaa cttttcctcca tatactaaca aatgtgataa gtaattaaaa 1560
aattaaaaaa gacttgactc gctgcgccgg cggcggagtg gctgggtggc tcacgcgcgg 1620
tggcccgatg ctgtgccgg gcggagtggc cggacggcgc ggtggcggcg agcacggcgt 1680
ggccgacggt gatagagctc gacggggaga gaaagaccag cgggaagaga gaacgatgcg 1740
cgggagatat ttttgttccg agctcggtgc taagatctac gacgccgagc tcgggccacg 1800
tcgacgccac gtcggccctc gctagcgagc gctgcagcta actcggtgcc aagatctata 1860
gcgtgagttg tgttagctca gtgccacgtc tcttggcgcc aagcaaaggg cctaaaactg 1920
ctattaagta ttctaagggt ctaaacgtga atattttca taaataggc taaaatacaa 1980
aaaaaatcag gaggttcgct gtgctgcgaa cagaggtgcg agcgaatata ataggatgtt 2040
tgtgtagtaa taagctagtg tattatcttc ttaatcctta cttttttatt tggtttgtga 2100
aatagaatga gggcacgttt ggtttgatgg actaaagatt agtccctcca ttttagtctc 2160
atttaatcct taaattgcca aacggtggga ctaaaacaga gacgactaaa ctgttttagt 2220
ctctagtccc taaagggatg actaaaaggg actaaactat ataaattcca cttttttacc 2280
cctctttat ttcagttgca ctaatgtagt gagaatgcca aaggggtattt cagtcctctt 2340
atgattcatt taatatgttt tgaatacttt tagtccctat aaccaaacaa ggtagagact 2400
aaactttaga ctcttaatta aattttagtt catggactaa aggaaccaaa caagccctga 2460
gtcgatccta aaccatctca tctcattcct tatagttagt tagtttgtta gttaacacta 2520
atataagaaa tgcggtcacc tactaaagct gagcaataga ctcatgatgc acaacatcgc 2580
tgaatgtcgt cagttcaaac tttacacgtt cgtaacagaa atacagataa gaatgcatct 2640
tatccgtttg acttcaactg cattttagac tagacagcat gcacgaattg accattccat 2700
gaggtccttt gatctgtaca atatataaat gcacctaaca gaatcaaagt tgcctcaacg 2760
ctatgcatgt cctgttcgtg gaattctatt gaactcatac gtagaaaaga ttggcatgcc 2820
ggccatattt tcgtgcaacg ggactatttt tccaagcata ctggagaaaa ttcatgcct 2880
ctccactatt aatagccccc acatatttgc agtatagcat ccacaaatta aactcacgca 2940
cacacacaat taggtcacat acacacatcc cggctgcctc cctaggtagc agcttctaca 3000

SEQ ID NO: 46            moltype = DNA   length = 3000
FEATURE                  Location/Qualifiers
source                   1..3000
                         mol_type = other DNA
                         organism = Zea mays
SEQUENCE: 46
aaagataaca ctgatgtttc cctaagcaac atccttaagc caacttttgg gagtctattg 60
accaattgac catcaggagt ttaaagacta tatgaagaag ctagagaggt ggtacctctc 120
gctctttaga ataaatcgcc actagaaggt cgtctagaaa agggaagtaa acttcgcttc 180
cttgacagcc tcgctatagc cccactataa gtaagaccat gtcaatattc aatctattaa 240
gaattatttt gatgaccgaa ttgaacttat ggtggagtgt cttgataaga tagagcgtgc 300
aatagaaaaa aatcatatgt ctaaatttcc gtcgtataaa ttgggcacta aaacagccac 360
gccaaacaca tcgataacat atgggttttc tcagtccgaa caatattatg gtaatgtcaa 420
tgacctcata tccagggcaa acactgccgc catcttcact gtatggtagg tcgactctga 480
gcatgtcaac acaatccgag cacgacctcg gagtgttcga cctctgttga accacccaac 540
actttctgcc agactgtccg agccacatcg agcctgccac atggctcgaa ggtgatgcct 600
agcacaaccg gacaacccgg gtataaccag cacaaccgga caaccgagt ataacctcgg 660
accatccggt ccctccccgg tatatgctgg acagtccaaa gccacaccga gccgtccaca 720
tgactcacag gtgatgcctg agataaccgg acaattcaag cataatcctg gaccgttccg 780
taccttcagg gatcgtctgg ccacatagag cagactgttc gggaacatct acgcagaaca 840
```

```
agatgctgcc cacaacacac aattttttccc acccatctta gcagcactac tctctctcac   900
ctacaataca tcaaagccac aacattccac cacctatgca tgagtcaata ttttttggtc   960
ccttgggagc cagagaaatt caacctaata gtgggatgca ttgcctgtat tcctcagggg  1020
cctatatcgg atgccacctt taatagttct agtgcaaaag gtcgacatga ggataacgag  1080
acaccgagc cccatgtttc aaggaccgat gggttaccat cgaccactat agataaagtt  1140
caggaagaaa taaccgaact atttcaagat aaattaggtg ttagtgtatc tggtccagga  1200
caatcgtccc atacctccg gggactattg tgccgaattt acccaaattc tcaggtaaag  1260
gcagtagaag cactcatgag cacatgtgtc aattcctagc acaattaggg gacttgaccg  1320
acacagaagc ttgtcgtgtt cacatgttct cattacccct tactcgcact tcattcgctt  1380
ggtatgatac cttgcctcct aactcgatga gttcctagga tgatctagag cataagtttc  1440
atgaacactt tttctctcgg gattacgagt tagatttagc tgatatggca ttgctccagt  1500
aagggggatta tcaatcgatt aatgattata tccggaggtt ccagaatact agaaactgac  1560
gttttcaaat ctagggcgta tataagcaac tagcagggtt ggctttcaat gggatgcgtc  1620
catacttgaa agaaaaatta tatggcaccc aattctattc tctaactcag ttgcatcagc  1680
ggactttggc ttgcaaaagc cgaagcaaag aactatctcg tcatcatgac gttagtagct  1740
cagataacga gtcgaaagag ttacatgtca ctgagcttat ttggcctatt aaggccaaac  1800
ttttcgcttg ctcttccctg cagtcagttc aaaggaatcg acaaggagaa gctaagttca  1860
catttaattt agctaattgt gacaagatat ttgatgaatt atttaaaagc agcaccatta  1920
aattgtttca caattccgtc gatagaggaa ttgaaacgac gtgcttggca tggctccttt  1980
tcttatgcca gtaataattg taatatcttt catcgacaaa tacaatcgaa tataaatgaa  2040
tgccaattga gatttctaga aaagtagatt gacatgcaac ccttccctat caacatagtg  2100
gatttggtgg gtaataaagt cttggttggg tcagatgtgg ccgataaaga tgaaggcaag  2160
aacaatgtca ttggcgatcc tcgcacgcca agtcagttac aaggagtggg tacttgaaag  2220
gctctgaaca agagaatgac taataagact caaggcccta gagggcaaac acgaccggat  2280
acccgattac gatcacatgt cttgtgtacg caggacggtc cggacctaa ggccgatcag  2340
tctaagaatg accaaaagca acaacgacct cagaccttta gaccatgaca tctagaagaa  2400
ggtatatgca agcaaaatac atctaaagca tctgactgaa tcgttagtgc tagcccttct  2460
tttgaacaac ttcttctaa gtatatgaat aagaaggtcg tttcacacaa ttgatcgaca  2520
aaacgatcaa tatcatccac aacgaggaag caatccatgc aagggcaaaa gccgaataaa  2580
tcggcccagg aagtggtgca accaatgtcg cctactcatc cgctctagga atgtcgtgtt  2640
actttccacc agtctactca tcgatgatgt tttatcctgc taacatgtga aaaagtgatga  2700
cgatgaatcc gtattacaca ggggcggacg cagagggagg caaagtgggt catagccacc  2760
tcaattttta tgatatttta tatatcatga cgtgcagtct ctttgcaacc ccagccacat  2820
taattaatag actccaccga cgagcgacga gtgatggtac cggccgccgg cccaggccaa  2880
cccaagtgga aaaggccgac gactcccgga cgtctcatcc tcaccggacg ccaccaaccc  2940
ccgcaatctc cagacgtacg agccgcctat ttaaagcccct cagtcgtgcca ctctcatggc  3000

SEQ ID NO: 47        moltype = DNA  length = 3000
FEATURE              Location/Qualifiers
source               1..3000
                     mol_type = other DNA
                     organism = Zea mays
SEQUENCE: 47
ggctcgcccc catggcccac aacacggtcc ggtggcaggc cgagcggagc ttcgagttcg    60
agcagcagca gcagcagcgg gtcgtgtcgg agcggagcgt gctgctgctg cagacgttgt   120
acttcaccga ccgggagaag acggaggcga cggtctgcga gctgctcgtc ggcctgaact   180
acatctgccg gtacgagcgg cagcagaacg cctttgctcg ctgccctage agtctcggct   240
tggatgattg tgtggagtgg caagtccagt agagccgaaa gccaaggtca ggcactcagg   300
cctctgctct ggtccgtagt gtatacaaca agtgatgtga ttcagcgaag ggtacctgtg   360
atttggtttt gcttgttttc tcttcccttt tttcttctac gttgttctcg gcgcattttg   420
cataggagct catcgtctgt tgttagatga aatgtagagg tttgtcgact cgaaagacgt   480
tcgctttaac tccctgctct gcataattaa tcttgtagaa tccttgtgtg aagcaacctg   540
aaaactggtt tggtacttag agcctctttg tttcagctta tagattatat aatctggatt   600
ataatttaaa ttatacattc tagattataa tctacacatg tacctatttg gtagtctaca   660
catgtaactg gatgaaatcg tgaataaaatt acttgttctt cttcaggtac gcaattactt   720
gtgttgaatt aggtttcagg ttacttcaaa tatatttgtt atcatgatta gtaaacaatg   780
ctaacagctc atgttcatat tctagaatgg caagcaaatg gtacacgagg gagtattgac   840
agttctagcg tcagtagcat attcatcaca ggtgttattc acttgggagt tttatgcata   900
ttgaatctct gtcattgtgc atcatagcct catggggttg tcgtattgtt gtagcgcttt   960
ctaacttact cataataaca acttatata tcatttacat tgttttttg ttgtctagct  1020
gattataagt ttgtagcaaa attttttttg tttgtccatt tacgtggggc agcaggctgc  1080
tgcgctcttg ggagagcagc ccgtctacca cgccgtacag cgtaccattg gctgcgggc   1140
tgccatgccc ccagtgtcgc tgcccggcaa ggaggctggg tatttggaga gtatcggcga  1200
agcatcatgg ctcccgacga agcagaggct gcgaccgagc cgctggagct tgctggggca  1260
gcctgatgct ggcggcggct gctgctgggg gcagcggca gagctcatga tcgtcgagac  1320
ctttgataac atattggtaa gagacacgtt ccctatactg acgatatgtt tccgttgcaa  1380
cgcacgagca cccacctagt agtagatata aaaagcaaaa gaacgaggaa cgtttgaatt  1440
ggcatggcac tgaaaaaacg caccgtcgtt cacaagtgct gcaccgaaga cagtgacatg  1500
tttgaacgac cgaaccttt tttttgttt tgccccccac tcaaacgttt gaatgatagt  1560
gtatgatcgg agacaacagg caattctaat ctcaagttca gttgatcggt ggataacatg  1620
acagacaccc accgagacga ttggttggtg gcgtgctaaa ctgctaagca gtgggcgctg  1680
gtgcgactta ctgttccctc gggctcgggg gctcggcag ctagtagtag tgcaggtgca  1740
gcttttgagaa gacaaggcgg cccacgcacg gcgctctcca gtctctcttt gccatggtca  1800
gcaaaggcga gctgccaca gagacttta cttttctccg caccaccacct  1860
gcgatatgtg gaggcaggca gctgtttagt tggcagtccc agtccgtcac agcgtgagat  1920
cagtcaatgg gctagattaa ttaatccaat ggttttattt attttgctaaa ctttctagaa  1980
gcagccgcga cttggcgtgg aatactgttt cgtcgccgcg ttttccatgt ctcgctgtcc  2040
tacgcttccg ctactccaga agacgttttg tgttccgtct ttcctcaatc ttcaagtagt  2100
aagtgcgagc cgtagcgcat gttcgcttcc cggcgtgccc atccagatcc aggccgcgca  2160
```

```
cacgtgtgcg tggagtatcc ttctgctcac gacttgagta ctgaccggtg ggaccgctca   2220
cagtcaaagc gtgaagcatt cctttccgt tcgccggtg ggaccgatca ggtaggtggt    2280
gtcgctgaca tggctggcct gcctacttac ttattagtta ttaccaggcg ctgtttgtg   2340
ccgcggctag tagctgcctc cctcctcct cgctctgtcc gctgatcgct gcataggaat  2400
aataaatagt ttggtcgtgt ttcgtccaga ctagaaaaga gaaagaaaga aaaacagatc  2460
atgtactgcg cttactgtct tcgagatggc cacaaaatca acggagatta tgtaacgata  2520
aaatactcgg tccttgccac taattaagcc acgtacgtag ctgcacgttt cgcccgcagt  2580
ttagcagtca catcaaacaa ctccaactca aacatatact ctcttctatt ttttttttcct 2640
cgaatacgta aatagtttac gccagcataa ccacgtacaa aatatttgag cacataaaca  2700
gcatgcttct gatcaatgct ctatagatag gctacaagaa ttagctctac agatagcata  2760
acaaacatat tcctttcaaa ctgagccaaa attttgacct gtctaaaaca acgtgcaacc  2820
gccactagcc aatgacacca gcgactcttg agtctctgaa gcttccaagc aaccatcacc  2880
cagcagaaaa cgagccaata attaacggga caatgcaaaa ggctgggcgt caccgtccca  2940
agtcacgttc ccactgacca gtacatataa gtgtgtcccc gcgcacgctc cagggttcac  3000

SEQ ID NO: 48         moltype = DNA  length = 1274
FEATURE               Location/Qualifiers
source                1..1274
                      mol_type = other DNA
                      organism = Zea mays
SEQUENCE: 48
gacgacggag cttgatcgac gagagagcga gcgcgatggg gaggagggcg tgctgcgcga   60
aggaaggcgt taagagaggg gcgtggacga gcaaggagga cgatgccttg gccgcctacg  120
tcaaggccca tggcgaaggc aaatggaggg aagtgcccca gaaagccggt aaaattagct  180
agtcttttta tttcattttg ggatcatata tataccaaga caagatcgga ggacgatcac  240
gtgtgtgggt gcaggtttgc gtcggtgcgg caagagctgc ggctgcgt ggctgaacta   300
cctccggccc aacatcaggc gcggcaacat ctcctacgac gaggaggatc tcatgatcat  360
ccgcctccac aggctcctcg gcaacaggtc ggtgcagtgg ccagtggtgg gctagcttat  420
tacacgagct gacgacgagg cgatcgagca tctgctgcga attcatctgt tccggttccg  480
gtgtcgccgt gcatgtgaga gtgagctcat atgtacatgc gtgttggcac gcaggtggtc  540
gctgattgca ggcaggctgc ctggccgaac agacaatgaa atcaagaact actggaacag  600
cacgctgggc cggagggcag gcgccggcgc cggcgctgga ggcagcaggg tcgtcatcgc  660
gccggacacc ggctcgcacg ccaccccggc cgcgacgtcg ggcagcggcg agaccggcca  720
gaagggcgcc gctcctcgcg cggaccctga ctcagccggg acgacgacga cctcggcggc  780
gcggtgtggg gcgcccaagg ccgtgcggtg cacgggcgga ctcttcttct tccaccggga  840
cacgacgccg gcgcacgcgg gcgagacggc gacgccaatg gccggaggag gattaggagg  900
agaagcaggg tcgtcggaag attgcagctc agccggcgtcg gtatcgcctc tcgtcggaag  960
ccaggacgag ccgtgcttct ccggcgacgg tgactgcgac tggatggacg acgtgagggc 1020
cctgcgtcg tttctcgagt ccgacgagga ctggctccgc tgtcagacgg ccgggcagct 1080
tgcgtagaca acaagtacac gtacggagag gagaatattt acagtcatgc gtatgtatag 1140
attttttcat ctgatcccaa cagaaatacg tatgaaagta ctcttagttc ttttttattt 1200
atcatatttt agtttataaa ttaattaacg tacgacaaat attaagacgc cgcctttcca 1260
tgcctacgcg cgcg                                                   1274

SEQ ID NO: 49         moltype = DNA  length = 9309
FEATURE               Location/Qualifiers
source                1..9309
                      mol_type = other DNA
                      organism = Zea mays
SEQUENCE: 49
gtggcatatc tgtaggcatc taccccgtct tcgtcgtccg ctcctcacta gctaccaaga   60
ggtcgccatt attgccaaca tagagtgtac gtggatgtct atatatatgc ctacttgcac  120
ccatatggca taggcgttcg atcccttag gcgcggaggag agctcctccg gttcttctct  180
accccttcgca tggaagttct tgcattgctt cgttgcttct ctagtttctt ccttctacgt  240
cttttccagca tacgcatgcc cctcgtccgc cggttcacga gcgatcgtct gatgatcagt  300
agataataag caatataata ctgatctaga atcgagttgt tgtactcttc gcagataggt  360
tcgttccttc acatagaagc gagtacgaca tacagaccac acagtatcag ctggcacaaa  420
acgaaaatgg ttacttgcaa attgcatgca cgagctagaa ttatattctt ctaatcttct  480
tcgttgactt tctggcttca gcaggcgcgt gatggcgctt tcagcttccc gagttcagca  540
ggcggaagaa ctgctgcaac gacctgctga gaggcagctg atgaggagcc agcttgctgc  600
agccgccagg agcatcaact ggagctacgc cctcttctgg tccatttcag acactcaacc  660
agggtaaatt aaagtcttat taattatgta cagttgatat ttggttggca gttttctgta  720
gttttgctga atgatgatca tcgtcgcatc atttgcctga gcttttatag atcccaggct  780
cccagcgcat acatatcaaa taaagagcat ttacttaaaa tttttttgc agaaaaggct  840
tgagcctttt tgtttgcaat gatgtcgcca ggttttatat ccaatttagt taatgatagt  900
actttgctac tgttcaatct cgatttaaga gagtactgga ccgattttca aatcatgcgt  960
cctgtgtggc cgcgtgtgtt ctcttctctc tacggcttgt tcggttattc ccatttcaca 1020
tgaattaaat tatattgaaa aaaaattaag aaaaaaatta atttacttga aatttaaact 1080
catatactct cactaaatcc acatagattg gaagataacc gaataagccc tacgtggtca 1140
attaaactct cctttcttg ccgttgtagt tgtagctata tgcagtgtta ccattaccaa  1200
gcccggaaac tccatttttt tatttttcca cttgtaatac cacagttatg agctgaaact 1260
atgcaagtag actagtagag tgtacgtatg agcaaccgga aactaaaccc atttattatt 1320
aggctttgct atgacctatg atactcctag ctaattatag accgtcaatc tagatagaca 1380
ttttttagt ttgataaata gagaaataag caaagtttta ggtaaatgtc taccaattgg 1440
atctaacatg catgcaaccg cacggggcat gcgtctgcat gtctggtcc tttttttaaa  1500
aggtatgtat gcttggttcc taacgtgaca agtggtggtc ttttcattaa ttgttctatg 1560
tgcagctgta atttatgtat ctaaacgtga actgtattgt ttttttacaa atgcgtgaca 1620
aaagtagaag tgtgttttag ttatttattt aaattcgaat gtgaaagtgt tgggtaacga 1680
gaacatcggt acggtctaga tcgtgtttgg tatttaaact attatttgct tgctttcgtg 1740
```

```
atcatcccag cgtagtagtt ttgtgactta actaggccct gtttggtccc tttagactaa   1800
agattagttc tatcctattt ggttctagag actaaaacta ttcaaaacac attaaatgaa   1860
tcaataaagg actaaatacc ccttagcatt ctcccgctat tagtgcaact gaaataaatg   1920
agtagcaaaa tgtggaattt atatgattta gtccatttta gtcacccttt gagggaccag   1980
agacaaaaac agtttagtcc caattttagc ctcatcgttt ggcaatttag tgaataaatg   2040
gtactaaaat aggactcaaa ccaaacggga cctcatcagt attttgcaaa tgtatgttca   2100
taagggaatg ctactcagtc aatagctttt gacattgatt tattagattc gtaccaccat   2160
atatgtgttc tcacgagagt aattattaac ttagcaagat ccattgttat tctatctctc   2220
tagaaaattc ttcttttcaca ttttgtagca aataacagtg attctgttct tctttgatga   2280
aactaataaa tactcaacaa caacaaaata taaaaggtga ggcccatcca gataacataa   2340
gcttgtgaaa atctagtaca cttagagttt tccaaagtat ttcctgctaa tacttatatt   2400
tcaatattat gctaatatga ataataacga ctcatagaca tgtgttccat aagtagatta   2460
aaataacata gataaagtcc tgttgcaata aagctgacgg atgcacaaca catctagcaa   2520
taaagatcga tgtcgcatgc aataaaaaaa gagcactaat tatctgtcgg catatctatt   2580
ttgttttaaa tatctaggct ggctcgacca aagaacccaa atgggtcttt tatcctaaat   2640
atagagaatc aaatggttct ctacgctctc caacagcgcc ctctaaacga tcctctaaat   2700
ttagagaacg ctgctggatt tctgtgtat agggtttctc taaacagtcc tctatccatt   2760
tgaatacttt aaaataatcgg tctaacaaaa ctaaaatatg tacaatatat ttgagagtgt   2820
gacaaatacg tatatacaaa aaaaataaaa atatctctaa tataggtatt tgagtataga   2880
ggacgtaatt tagaggatgt tgttggagag aaggagata tagaggacag aatcttttag   2940
agaagactgt aaagaacgga tatagaggat gtatatagca gtgcgtttgg atgttgaaat   3000
ttagactcgg aattcagaat tggaattgac aaacccgaat tctggtgttt ggatggtcac   3060
agtatttgaa attggaaatc caccaaattc cagccggtat tcaactctac acacgcctcc   3120
actctccaat tccgaccctc caccctctga tttgctcgga attgaactgg atttggtatt   3180
ggatccgatt tccaaagcca ggctgatttg gtattggatc caattcaatt ccaccatctc   3240
caattccaac atccaaacgg agcatagagg atattgctgg agacagtaag gctctactcg   3300
ctccaggtct aaattataat ttgtttagga cgacacggtc tcaaacaatt tagttttgac   3360
tattttctg ctataatata aatgaattat taatatattt atattttgt aaaaaatatt   3420
tttaagacaa attggtgcat gtgactacta ggtttcaaac taaataacaa aacagttatt   3480
tatttatact caatgtttta taagtttgac tcaaattttg tccaaaatga cttatagttt   3540
agacccgagg ggagtaggtg ctaataagaa atcatgttgt tggtggaaaa atctacgcag   3600
aggggaaaaa ctgagaaatt aagatatggt tttatcattt cacccacctt ttaaagttag   3660
acttttaatc taatggacaa aaggtgatat atttcattat cataagattt caacgcacac   3720
gtgtgtgtat aaaaatctac acgtcattat cattaagata gaatagtttt ataacaaaca   3780
acatgttcct cacgagcccc cctccccaa aaaacaaaaa aaaaggtcta cagtgcccgt   3840
tgttggggct ggaacgtcct gacacacggg atttaatttt gatattacat aaataattga   3900
caatggacga accaacctac aaagtagggg cggatctagg ggtgtttgtc ggggtcagct   3960
aatcccgata aaatttatat atcctttaga aaaacatcgt taaagttcaa aaactttata   4020
tcatatagca aatctgatct tactgacccg acaatatttt tagctagatt catcactgct   4080
acaaagtggg attgtgtctg tgatgtgttt gtgaattgtg agctccaatt ccgatgtcca   4140
gaaaaaagtg gttccaacac tcgaagcatt ccacctagcc tcgtagagct tcataggctg   4200
tgtccacact acaacagata gtatatatat atatatatat atatatatat atatatatat   4260
atatatatat atatatatat atatatatat atatatatat atatatgac gggtaaaata   4320
ttattttaca ggagcggata cagggttatg ggtcaagcca cctgatccat ggactaggac   4380
gtgatcaata tatctatgta taacttaatt gtatttagat taaaatacat tacaactcca   4440
gtagattaaa tagatgggtc tggggacgtg actaaatcct ggattcgtcg tgctattttg   4500
tactatctat attagtattt tttatatagt aaagtttaaa ataatagata agattggaga   4560
gcatctagaa ctagcttata tgccttcttt ttcgtcgtac ttagcataga cagacctgtg   4620
gctagaatcc gttgtatgat tagggtgtta cctcgcttga aagcgggcac tctagagagg   4680
ctcttggcaa gggtggatcc aggcccttt tgtggtgtcct acggcactaa tgaatttagt   4740
aattttcatt agaatgtatg tttggtagca cttaaatgag ttgatgattt tataatttaa   4800
tggagatgac atcaataatt attttgtcta gatacgctta tggctcttgg ctgctaaaag   4860
cttgctccgc agcgggaaaa acattcttta taggatatag caactagag caactccaac   4920
agactaaaaa tggtgtactc ggtaaaagaa aagaaaataa cgacaaaagc atgttccaac   4980
agactcgcca tcttcttcgc ctcttcatct cgctcggcat tagcttcact ccgctcggta   5040
tctttgccga ggttgtggca ctcgccatct ctccactccc gctctccgct accatgcttc   5100
gtgcgcgctc tccgtccccc gctgccacgg tttgctcgtg ctctccggcc atcgagctct   5160
ctcgatctcg acagcatcta cgtgtgcttt ttctcgagca tctcccagta ccggtgcctg   5220
ctctaggcgt tcatggtggt cggcaagttt ttggagcgca tcgtccaaat ggctcgaatg   5280
tcctcaaggt acttgttgaa atgtcaaaaa caagttatt ttgtctgcta ccttttcctc   5340
cgtacgtgag tacgtgaccc ttccatcaca tccactggtc agctctcgtt gcaactgtgg   5400
cggtggaaga agaggtgagg agcggagatg accagttttc ctacgtttg tttgggcaga   5460
aagacgagtt ggaggaggga agaaaataag atttagagag tctgttggtt tatcttaccg   5520
tttgagaagc tttctatttt ttagagacct cataaaagtc taaatttagc taagattata   5580
cctagacttt tggagttgct cttaggtggc tccagagttg caaatctcgc tcgggaagga   5640
gcgagaaggt ccggtgcgag ataaaaaacc ggccggtcca gttttgtgta tttcggttta   5700
gaatttgaaa aatatagagt caaactttgg tcaacgaaac ggttttctaa aattccaaaa   5760
caaaaatgga atccctgggt ggctcacaaa ttagcggga ggttggcctt ctgcagcagc   5820
gcttggagaa gaagttgtca aggtggagga gtcattggcc agggatttgg gaatccgttg   5880
tgagctcgtc gaccacactg aagcctagcc tgctgactgg taggtggtag cctcctctgt   5940
agtaaccggg gcctaatctt ccggccgggt tctggctgag acggacggct cctctgtagt   6000
aacgtcggcg gctgccgtgt ggagccagat catagcagac gtccatggct gcaaccgcaa   6060
gcccctccc tctctccgca ctggggttca cgaaaccact caaaccagtg tccctgaggc   6120
cgcggtgcac aaaccgac ggatgatctc aaaaccgtgt tgagggatgg gtgcagtcga   6180
gaaggtcatc aaataaaaga aaacatatct ggtgcacata aagagtttat gtacatggtg   6240
cacatattaa atcatcaccg ctcatttag atctaacgtc tttagttgtt tggtatattt   6300
tgctaagcac atcctctaat gtggtggtgt gtattggtgg aagtgctat ttgtaaattg   6360
aatgatcaac aagaaacgtt atatctaaaa tgagtggtga tgatttaata tgtgcatcat   6420
atgcattaat cttttcatgtg catcagatat gtccaccaaa taaaagacag atgtggccta   6480
```

```
actcacgacg agagtaaaat atggtcgttg cagggtgctg acgtggacgg acggggttcta 6540
caacggcgag gtgaagacgc ggaagatctc caactccgtg gagctgacat ccgaccacct 6600
cgtcatgcag aggagcgacc agctccggga gctctacgag gccctgctgt cgggcgaggg 6660
cgaccgccgc gctgcgcctg cgcggccggc cggctcgctg tcgccggagg acctcgggga 6720
caccgagtgg tattacgtgg tctccatgac ctacgcctcc cggccaggcc aagggtaatc 6780
gatcgattcg tttttttttt cgtgacgccc tttagtttgt tcttgctggc ctttctcctc 6840
tcggtgtctg tcgtcactcg ggtgcattgc atgcatgcgt cgccacaggt tgcccggcag 6900
gagtttcgcg agcgacgagc atgtctggct gtgcaacgcg cacctcgccg gcagcaaagc 6960
cttccccgc gcgctcctgg ccaaggtatg cacgtttctc acttgttctt tctgacgtg 7020
tactgttgcc ttccgtacgt gcatggtttt cactagtcgg ttgcgatctt tgttgaaatc 7080
gtgaactacg tgcatgcgtg aacgaccttg tcgtacctcc ctccggtcaa gcagagcgcg 7140
tccattcagg taattaaaaa gcgatttcca tgcttcgtct cgtctgaaac acatgtcact 7200
tcagagttct gactggggtc gtgcttgatt tctgcagtca atcctctgca tcccggttat 7260
gggcggcgtg cttgagcttg gtacaactga cacggtatgt tcagctcgag cttccgaatt 7320
aaatggccag ccgagcttcg tctcctgacg atcaggtacg tactagtatt taaccaaaac 7380
tgtaaatgcc attgccaggt gccggaggcc ccggacttgg tcagccgagc aaccgcggct 7440
ttctgggagc cgcagtgccc gacgtactcg gaagagccga gctccagccc gtcaggacga 7500
gcaaacgaga ccggcgaggc cgcagcagac gacggccagt ttgcgttcga ggaactcgac 7560
cacaataatg gcatggacat agaggcgatg accgccgccg ggggacacgg gcaggaggag 7620
gagctaagac taagagaagc cgaggccctg tcagacgacg caagcctgga gcacatcacc 7680
aaggagatcg aggagttcta cagcctctgc gacgaaatgg acctgcaggc gctaccacta 7740
ccgctagagg acggctggac ggtggacgcg tccaatttcg aggtccctg ctcttcccg 7800
cagccagcgc cgcctccggt ggacagggct accgctaacg tcgccgccga cgcctcaagg 7860
gcacccgtct acggctctcg cgcgacgagt tcatggcctt ggacgaggtc ctcgcagcag 7920
tcgtcgtgct ccgacgacgc ggcgcccgca gcagtagtgc cggccatcga ggagccgcag 7980
agattgctga agaaagtggt ggccggccga ggtgcttggg agagctgtgg cggcgcgag 8040
ggagcagcac aggaaatgag tggcactggc accaagaacc acgtcatgtc ggagcgaaag 8100
cgacgagaga agctcaacga gatgttcctc gtcctcaagt cactgcttcc gtccattcac 8160
agggtaatga acaagatacg taccatcgac ttttcatttt ttaaaatcctt tcgtcgtgtt 8220
gatttgaaaa cttaattgga gacaattttt tccccccaatt tggcaggtga acaaagcgtc 8280
gatcctcgcc gaaacgatag cctacctcaa ggagcttcag agaagggtgc aagagctgga 8340
gtccagtagg gaacctgcgt cgcgcccatc cgaaacgacg acaaggctaa taacaaggcc 8400
ctcccgtggc aataatgaga gtgtgaggaa ggaggtctgc gcgggctcca agaggaagag 8460
cccagagctc ggcagagacg acgtggacgg ccccccggtc ctcatcatgg acgccggcac 8520
cagcaacgtc accgtcaccg tctcggacaa ggacgtgctc ctggaggtga agtgccgggtg 8580
ggaggagctc ctgatgacgc gagtgttcga cgccatcaag agcctccatt tggacgtcct 8640
ctcggttcag gcttcagcgc cagatggctt catgggctt aagatacgag ctcaggtata 8700
tatccacacagc aaaactaagag acatgcatgg cgattgcaat actgctctgg ttaattagac 8760
tctttggttg gagagtttgt ttttactga gcgggtttgtt taacttatat gctcaattct 8820
tatgcagttt gctggctccg gtgccgtcgt gccctggatg atcagcgagg ctcttcgcaa 8880
agctataggg aagcggtgaa ggggcagctg gaaatttgga catcgacggg catggaaggc 8940
ttcatgggat cgaagcaaag atgtatttct tgtttctttta gataacagac atgaatcgga 9000
cctctatatc aacaattata ttggcatgaa tacttagact ccagccctta acacgtagaa 9060
actcaaaaaa agaagaaagg aagctaaaga ctaagcgtaa ggtatatttg gaagtaaatt 9120
gttttatag tttctaagca atcccatggt ttataggaat gctagagtgt ttatttatgg 9180
cataaggtgt ttggttgcat tcataaaaac tatattttca aagtcatagc attctagata 9240
catgatattt ttgtaatatt ggaaactaca ctccaacgca aagttttat gacatggcta 9300
acttttgtc                                                          9309
```

SEQ ID NO: 50        moltype = DNA  length = 4458
FEATURE               Location/Qualifiers
source                1..4458
                       mol_type = other DNA
                       organism = Zea mays
SEQUENCE: 50

```
taccgatcta gaatcgagtt gttgtactct ctctgtccct tttgtgcagc tataactagc 60
taggttcctt cgcatagagc ctctctacag agtacagact agctagcagt gtcaggcacg 120
aaatggaaat ggctacttcc aaattgcacg agctggaatt atatactctt ctgatcttct 180
tcaccgtctc tttatagcgt gatatgcgtt tctggcttct tgctgcgtg aaggattagt 240
aaggcgcgtg atggcgctct cagcttgccc ggctcaggaa gaactgctgc agcctgctgg 300
gaggccgttg aggaagcagc ttgctgcagc cgcgaggagc atcaactgga gctattccct 360
cttctggtcc atttcaagca ctcaacgacc acggtaaatt gaagtcctga taatctataa 420
tctgtctggc agttttctac aactctgatg aatgatcctc acatcgtttg cctgatacat 480
acataccgca tacatatgaa ataaagaaag tcggatcccg tgatgcgatt gtagttatcg 540
cttttccgca aaatggttgc ttttttgaatc tgcattcgtt tttttttcca catcttcttc 600
cttctcccga gtcccgacaa cgcaaccgcg cgccgcctgc cgcccatcgc ccgccttgg 660
ccggcgagaa actcagccta ctaccagcc ggcgaccttct ttccccctc ctctcaccgc 720
cgtcgtggcc gtgctcgccc ccgctctaac ctggctggcc cgctccgct gccacctgct 780
caggcggtgt catcgccgcc tccacctcac ccgcgtcttt ctcgtcctca ccctctctga 840
ctccgggcgc atcatcatat gatattctga tgcaaagaaa aaggtggacc atataaggta 900
aggacaagag aaaatatggt tgcagggtgc tgacgtggac ggacgggttc tacaatggcg 960
aggtgaagac gcgtaagatc tcccactccg tggagctgac agccgaccag ctgctcatgc 1020
agaggagcga gcagctccgg gagctctacg aggcccctcca gtccggcgag tgcgaccgcc 1080
gcgcggccg gcggtgggc tcgtcgtcgc cggaggacct cggggacacc gagtggtact 1140
acgtgatctg catgacctac gccttcctgc ctggccaagg gtaaccgatc gatgacaaca 1200
tctttttttc cccaatctg ttcgtgaccg gctctgtctg ccatggcgtt gcgttctgcc 1260
acagcttgcc cggcaggagt tccgcgagca acgagcatgt ctggctgtgc aacgcgcacc 1320
tcgccggcag caaggacttc ccccgcgcgc tcctggccaa ggtatatatg caatatgcat 1380
gcattcgccg tgtgtcttgt tattattgcc tttcatgcat gtcttgttat tattttttc 1440
```

```
attgtgccta attctcctgg tactgtttca aacatctaaa actaatagct aaaacatctc   1500
caacaaggtg actaaataca acattattta aagtgtttag ggtgttaaaa acaaattaca   1560
ctctctaaca gttaaatcct aaattatgta ttttattgta gtaagtaaat tacattattt   1620
ggaaagaaaa tgtcgagcta gggtgtaata tatttgggtc actccatggt gtgtcctata   1680
tttttatta aaaattataa aatataacat tgttagagct gtttatatg agttgagccc     1740
tatatttcaa tatagtgcac cgattttagg catggttgga gatattctta gcacctaatt   1800
agctaagagg tttagaaccc atcatctaat tgttagttat accctaaaa taactactag    1860
ttgttagctg ctaagctaaa atcagctaac aacttaggat ctgtttgcaa gagctctggc   1920
ttgcctgaaa atagctatag ctctaaagcc atttcacata tcgtttggca gaaacgactt   1980
atctagagcc agagccattt ctctatatta aagggcccct ttggctggct ctttaggcgg   2040
cttcgacttg ggctcattgt gaagccatac caaacggtca taaaaaacgg cttctcgtcg   2100
gaagtccctc gaggagctag agctgttttt gtgtcgactc ccccttcatt tcctgatat    2160
agcattaaaa acaaacacaa aagaagttgt tgccaaacg aattgtacaa cggctccggc    2220
tcctccaaac aagctaaaga gccagaggag ccagagccga aactgttta agaggaacta    2280
ccaaatggag ccaaagtgtt agagccagag ccggtgaagc tactatttgt ggcttcttct   2340
atgtagtaca aaaatagcta tagctttttag gtactttttg caataagtcg tataaaaaag   2400
tatttgacag gactttagct tttctaaag agaagccaga gcttttatta ggcccgctcc    2460
tactattctt aaaacggctt cggctctggc tcctctgagg tcttggcttt tctagaggag   2520
ccaaagccgt tttgcaattc atttggcaaa acaacttctc acgagggaaac ggtggcagag   2580
actgtaattt cgttaaacat tatttgtgtg cggatagaag gaaccggtag aagcttgttt   2640
tctcgtgctt cggctcccaa tatcaaaacg actctcgctt tttgatggct ctcagtgagg   2700
agccgttttt tttaaaacgg tttggtacgg cttcacgaag agctagaaaa tgggtcacgg   2760
agaaagccct gccaaagagg cacttagtcg ctagaggatg ccaaataagc ttccttgcca   2820
aatgagtttt tattatttga ctaactatta actttagagg tttaaaatag agcgggaacc   2880
aacctactgt aaattgcatt gccaggtgcc ggaggacccg gacttgatca accgagcaac   2940
cgcagccttt cgggagccgc aatgtccgat atactccgaa cagccgagct ccaacccgtc   3000
agcagacgaa accggcgagg ccgcagacat agctgtgttc gagggcctcg atcacaatgc   3060
catggacatg gagaccgcag gcatagctgt gttcgagggc ctcgatcaca atgccatgga   3120
catggagacg gtgactgccg ccgccggag acacggaacc ggacaggagc taggagaagc    3180
cgacagcccg tcaaatgcaa gcctggagca catcaccaag gggatcgacg agttctacaa   3240
cctctgcgag gaaatggacg tgcagccgct agaggatgcc tggataatgg acgggtctaa   3300
tttcgaagtc ccctcgtcag cgctcccggt ggatggctca agcgcacccg ctgatggctc   3360
tcgcgcgacc agtttcgtgg cttggacgag gtcatcgcag tcctgctccg gtgaagcggc   3420
ggctgtgccg gtcatcgaag agccgcagaa attgctgaag aaagcggtgg ccggcggcgg   3480
tgcttgggcg aacacgaact gcggtgcgcg gggcaacgag gtaacagccc aggaaaacgg   3540
cgccaagaac cacgtcatgt tagagcgaaa gcgccgggag aagctcaacg agatgttcct   3600
cgttctcaag tcgttggttc cctccattca caaggtaacg cggcagaaca aaccatcaaa   3660
aaaatttaca cttccgtatt gattttaaaa ataaataaat ggcaggtgga caaagcatcc   3720
atcctgccgg aaactatagc ctacctaaag gagcttcaac gaagggtaca agaactggaa   3780
tccaggaggc aaggtggcag tgggtgtgtc agcaagaaag tctgtgtggg ctccaactcc   3840
aagaggaaga gcccagagtt cgccggtggc gcgaaggagc acccctgggt cctccccatg   3900
gacggtacca gcaacgtcac cgtcaccgtc tctgacaggg acgtgctcct ggaggtgcaa   3960
tgcctgtggg agaagtcct gatgacacgg gtgttcgacg ccatcaagag cctccatttg    4020
gacgctctct cggttcaggc ttcggcacta gatggcttca tgaggctcaa gataggagct   4080
caggtatcgc accagctaat aattaagcca tggcgattgc aagctctggt ggctagcagt   4140
tttgcaactc agccttgact tcttggttcg tgctcgtttt actgacgctg ttgtttctgt   4200
tcatattctt atgcagtttg caggctccgg cgcgtcgtg cccgaatga tcagccaatc     4260
tcttcgtaaa gctataggga agcgatgaaa gggcgctaca tgtgaagctt aattaatgga   4320
agcaaacttg tatttcttgt gcaaaagctt actatatatt tctgcaaaac ctggtgtgcc   4380
ttgttttgat tttcagtcgc caattgtgcc cttgtttta tcaagtgatg atctacacta    4440
tatatatgga atatttga                                                 4458

SEQ ID NO: 51          moltype = DNA  length = 10551
FEATURE                Location/Qualifiers
misc_feature           994..1093
                       note = n is a, c, g, or t
misc_feature           5670..5769
                       note = n is a, c, g, or t
source                 1..10551
                       mol_type = other DNA
                       organism = Zea mays
SEQUENCE: 51
cacagcacac acactggaaa gtgcaagctg tagtgagacc tgcgcgactg ccagcgtgta    60
tccgcgcggc aaggagcgta gcgcgcggtc gtccgcccgc acggccacca actcccttgg   120
acgcacgcgc gcgcgcgacc agctgctaac cgtcgcaag tagtagtgcg acttcgccgc    180
cggccgggat cgctagctcg atcgatcggg ggaccacat acgactccgg tgtggccagc    240
ggcggccggg ccggggaacg cacgtgctgc gagcgagcga gggcagacgc tagctgttgc   300
cgggagctag ccggcgcgcg atggggaggg cgccgtgctg cgagaaggtg gggctcaagc   360
gagggaggtg gacggcggaa gaggaccagt tacttgccaa ctacattgcg gagcacggg    420
aggggtcctg gaggtcgctg cccaagaatg caggtaaacc aaagccggcc gcgcgccatg   480
catcgccacg tagcatcaat ctccgatcca tgcatatatg agcttcttct tcgtcgccgt   540
cgtcgttctt agctagttag gacgcgcatg caggcctgct ccggtgcggc aagagctgcc   600
ggctccggtg gatcaactac cttcgggcgg acgtcaagag ggggaacatc tccaaggagg   660
aagaagacat aatcatcaag ctcccacgcca ccctcggcca caggtaacaa taagcgcgtc   720
ctaatctcaa cgctgatcac tgtgcatccg actagagagt agtagtacta ctacttcctt   780
cctttatgca tgggagtcaa tgcacgcagt cccaaaaaac ttggtatacg tacttcctcc   840
ttcacacgaa gaacggaaat ctagtccaac aaatatcaact ttgatcaagg cattcatata   900
tattatgaaa tatattttat aagaaacttc cataaatata taaatgttga tagtactata   960
aatatagttg atgagaggac gaatcctag acgnnnnnnn nnnnnnnnnn nnnnnnnnnn   1020
```

```
nnnnnnnnnn nnnnnnnnnn nnnnnnnnnn nnnnnnnnnn nnnnnnnnnn nnnnnnnnnn   1080
nnnnnnnnnn nnnagtctga tgaatcagct tgattcgtac agtactctac tgtctgatgc   1140
aacttgatcg acaatttggt gcaacgaact agctcactca ttgatcgcgc cgctcacgac   1200
gcgcgtatat aggccgtagt aatcatgtgc cggcgtgtgt ttatatatgg cgctaaatgt   1260
acgcatcgtt cgcgaaggac gatgggcccc cgatagatct cgccgtacgt ccacagccgc   1320
gcctctcacc gtccgcagtg tcaacgttaa ggcgggggaa atcattaggg agggccggcg   1380
tgggcccgtc attaatccca ctgtgtgcca cggacaggga cccctctatg atcagatcaa   1440
ggcaacaggg aagctagcca atgcgcgctt gcacagtac cggccggcgg tgatggcgag    1500
gcagcaaagc gaaatggaca ggacgccaac caacgccatg gactgtgcgt gcgtcaagaa   1560
gaccgtgacc tgtccgctcg gcagcaggca ggctctgcca tgcgacgcga gttcgctccc   1620
agcgctagct agcttgaatg aagagcgagt gttggaccag attattgtcg tttctttcgc   1680
gtggtcctct cactctcact ctccgctagc cgctgacgac tcacagctag ctagtaatta   1740
gttaagctgc tttcacaaac catgtttcca tgactgtgtg gcaccgctag ctctcgcaac   1800
accatgtggg ttgtagttgt aggagcaata gcgcatatct atcattatat tacggcgcta   1860
cagtggcatg cattgcacga gggattattg tttaatcatc tattctctcc cgtgtcctgt   1920
ttgatagctc gccagttttg ttagatgatt tcttcagcga cttctaatct atcagtttgg   1980
gttttttttc tctatcttgt tcttccttcc atttactgta catatcagtt tgggttgtag   2040
atggtagaaa taaagtctga gcaccgaaga agctccatcg tccttgaatg gtgtggtgag   2100
accgtgagac gatgctgtcg acgaatcgca tgctttgtg tgctgtttat atatttttt     2160
caaagatttt tctgtactgt aagatatacg ctactcattg atcatattgg ttctcctaaa   2220
tttacggcaa accaaatcag tttaatttaa tgaaaacccg ttgttaataa atgccatgac   2280
attgttttt tgggtattat aaatactatg accagtatat tttatccaag ttcagtcaaa    2340
atcaggggcg gatccacaat gtgggcaaag taggccatgg cgccaccta atttttggaa    2400
ctgtttatac ctacctttta tatatactat aaaataaaaa ataaggta tatgcgacta     2460
aattagataa acaccgggtc caccacatca taccatcgac taacccacaa gatctagccc   2520
atcatcttag gtcacgacct atatcgaata aaacacagaa tgagaaaggc atcaaccgca   2580
cgtttgtagc atccaacccc gcttagcgc tcgtcctagc gttgtgcccg ctgtccaatt    2640
gacgtccaac agtcagttca tcatcgttgg ccgcccaccc aaccgtcatc gccagctgtc   2700
aggacactgt cgctagcttg ctgctcgtct tcctgcctcc actcggccac ggccccgcac   2760
tagagtgcaa gctgccacaa ccacaagatt gatggtttaa tggtgttttc gatgttttt    2820
ctatatagtt ttgtcttta cttacattga tgcttaccta atacttttc ttctaattgt     2880
agattgaatt ttcatcgat gatttggcgt cgctaaaaag attttcgata tccacattat    2940
tttataatag tcatgatatt acaacttaat ttcatgctat taccaaaaaa ccacttatag   3000
tttagcattt tttcttgtga tttctttatt acggattggc ctcacctgga ctttcgtccc   3060
gccactggtc aaaatcaaag aagttgcttg ggaaaaaata ggttaaacaa aactgatgga   3120
gcaaaaaaaa ccctgcattt tatggagtgg aaggtgtgtg tgtatatgca cgcatgacgc   3180
tatcacagta ctgctcagta gtagcttct aatcttccct tagttgcaca aatctttgag    3240
cacgagaaag tgcctagatc atttccctcgt gctgctgctt ttcgtcttag agatgaaatg   3300
taacgaatat atgacggatc agcttagaga gtgtttgatt tctaaagatt aattttttagc   3360
ctatctattt tatttttttt tagtccttaa attgtcaaat acagaaacta aaattagtcc   3420
atataaacca aacaccccct agtttagac ctcattacca cataatagcg aagctagatt     3480
ataattgaga gggtgtattt agtcttgtgg gtagataaga actttttcta ggagtgcata   3540
tatagtgaaa ttgtgactga atttatagaa atttatttt acagggtgca tttgcatcca   3600
cagttagcaa cctatttcgc ccctcttgcc acatatgcga agtcataaga agtggcgagc    3660
atcatcgagc ctgtttggtt cattttttc ttaccagttg tttaaaagaa tttggctgca     3720
gagagaatat gagtattgtg aggattatgt gcggaggaag attaatgtgt ctataggtt     3780
aacaatctag aaagtgatag attcctacta ttgcaacgtc cgaccgattt tgtgtttatg   3840
ttgattttgt tggatgattt ttaccaaatc gattttatata gaagtggact aaaaattgaa   3900
tatttgactg tctgtaccag attttggtag ccaaaatcta aaaaaaaggc cgaaacaaac    3960
atcacatcat gccatgttgg cgccatgcat gctcgtgcac gtggcctcgg aaatcacacg   4020
catctgactg gacagtaaac ttacacacgc agcacgccct tttggctgct gccacacgta   4080
cgggcaactt cagagacaca tgctgagcca gtgactgaca aggaccggac tgatagtagt   4140
gtagtaaagt agcactgctc aatgctgagg caagcgtgcg tagagcccgc gtgtacataa   4200
acatactaca gcacatcgat cggagggacc agatggccat attgttttca gccatgtctc   4260
tattaattta ggcctatag atttgtattag ctcaatagct ccggctcttt ctcacatata    4320
tgcattgtag taatatgcac cattctagca ctatagcaac actactcttt ataggagtc    4380
ctctctctct ctcttctctc ttctctcttc tcttctctct cttctctctt ctctctcttt   4440
tgtctttcgc tgatgaaacc atcttttttgg acattatcac tacagtagct aaacagtgat   4500
aaagccgatc gggaccccata ccatgcatag aaaaaaagga cattagccta ctattgctag   4560
gcgcgcctct attccagcag cgtgtgcccc tacatcattt aattcttat ttagtactgt     4620
gtacgtgtat ggtatacggt gtcttaactc tcaaccgatc ggggcagcta tcgaaattat    4680
aagatcaagt ttaataatat agtcaaccgc tggttataag taaggaacct tatagtctac   4740
ttcttagtct atctgtgtag tagttagctc tttactatta atttatgatt tacattagcc    4800
tatccgtgta gtggttagct cttcactatt aatttataat ttgcatgtct ttctcacaaa   4860
aaaagtttt agttctgtgt ctaagcccg acttttaagtt tgcagtccga ttctgctctc     4920
tctctcatca atctcaatat ttgctctaag atttcagtaa tgtggtgagc atatagagca   4980
ggcaattgtt actacactac tctatactcc tatgaatgag aactaaattt tcctcggagt   5040
aacccttat tggctgtgct gactgttcta ctctgtgct taagatcttt ttcccttgct     5100
ttggtttgtg ttggcatcaa tcaccaaaaa gggggagatt gaaagggaat taggcttaca   5160
cctatttcct aattgatttt ggtggttgaa ttgcccaaca caataattg gactaactag     5220
tttgctctag attatatgtt ctacaggtgt caaaggttca tctacaacta tactaaatcg   5280
actgtccgaa ataccgtaga ttattccgga caggagaagc ttttggaaa aataggccaa     5340
gcgcggaccg tccgggccct tgcggcggac cgtccgcaac accaggatga ccctcggaca   5400
gaaccaatgc aaaaactaa gtctacacta caggaccgtc gaaggaaaaa gcaaggaccg   5460
tccaagacct cgcgcggacc gtccggcctc aggcgcggac cgtccggtag gtgaggaacc   5520
gaaaacccga agtgacggg ttcggaaaaa tgaattatag cgtcctgcg gaccgtccgg     5580
ggtgcacgac cggaccgtcc gcgactggct ttatctgaca tctgacaaca cattaaatgc   5640
aatatagcca ttactgctga acgttgccgn nnnnnnnnn nnnnnnnnnn nnnnnnnnnn     5700
nnnnnnnnnn nnnnnnnnnn nnnnnnnnnn nnnnnnnnnn nnnnnnnnnn nnnnnnnnnn   5760
```

```
nnnnnnnnna ctctgatgat atcagcttga ttcgtttttg tgagaaagac atgcaaatta   5820
taaattaata gtgaagagct aaccactaca cggataggct aatgtaaatc ataaattaat   5880
agtaaagagc taactactac acagatagac taagaagtag actataaggt tccttactta   5940
taaccagcgg ttgactatat tattaaactt gatcttataa tttcgatagc tgccccgatc   6000
ggttgagagt taagacaccg tataccatac acgtacacag tactaaataa agaattaaat   6060
gatgtagggg cacacgctgc tggaatagag gcgcgcgcag caatagtagg ctaatgtcct   6120
ttttttctat gcatggtatg ggtcccgatc ggctttatca ctgtttagct actgtagtga   6180
taatgtccaa aaagatggtt tcatcagcga aagacaaaag agagagaaga gagaagagag   6240
aagagagaag agaagagaga gaagagagag agagagagag agagactcct ataaagagta   6300
gtgttgctat agtgctagaa tggtgcatat tactacagtg catatatgtg agaaagagcc   6360
ggagctattg agctaataca atctataggg cctaaattaa tagagacatg gctgaaaaca   6420
atatggccat ctggtccctc cgatcgatgt gctgtagtat gtttatgtac acgcgggctc   6480
tacgcacgct tgctctagca ttgagcagtg ctactttact acactactat cagtccggtc   6540
cttgtcagtc actggctcag catgtgtctc tgaagttgcc cgtacgtgtg gcagcagcca   6600
aaagggcgtg ctgcgtgtgt aagtttactg tccagtcaga tgcgtgtgat ttccgaggcc   6660
acgtgcacga gcatgcatgg cgccaacatg gcatgatgtg atgtttgttt cggccttttt   6720
tttagatttt ggctaccaaa atctggtaca gacagtcaaa tattcaattt ttagtccact   6780
tctataaaaa tcgatttggt aaaaatcatc caacaaaatc aacataaaca caaaatcggt   6840
cggacgttgc aatagtagga atctatcact ttctagattg ttaaccctat agacacatta   6900
atcttcctcc gcacataatc ctcacaatac tcatattctc tctgcagcca aattctttta   6960
aaaaactggt aagaaaaaag atgaaccaaa caggctcgat gatgctcgcc acttcttatg   7020
acttcgcata tgtggcaaga ggggcgaaat aggttgctaa ctgtggatgc aaatgcaccc   7080
tgtaaaatac aatttctata aattcagtca caatttcact atatatgcac tcctagaaaa   7140
agttcttatc tacccacaag actaaataca ccctctcaat tataatctag cttcgctatt   7200
atgtggtaat gaggtctaaa actaggggt gtttggttta tatggactaa ttttagtttc   7260
tgtatttgac aatttaagga ctaaaataaa ataaaataga taggctaaaa attaatcttt   7320
agaaaccaaa cactctctaa gctgatccgt catatatattcg ttacatttca tctctaaagac   7380
gaaaagcagc agcacgagga aatgatctag gcacttctc gtgctcaaag atttgtgcaa   7440
ctaagggaag attagaaagc tactactgag cagtactgtg atagcgtcat gcgtgcatat   7500
acacacacac cttccactcc ataaaatgca gggtttttt tgctccatca gttttgttta   7560
acctattttt tcccaagcaa cttctttgat tttgaccagt ggcgggacga aagtccaggt   7620
gaggccaatc cgtaataaag aaatcacaag aaaaaatgct aaactataag tggttttttg   7680
gtaatagcat gaaattaagt tgtaatatca tgactattat aaaataatgt ggatatcgaa   7740
aatcttttta gcgacgccaa atcatcgata gaaaattcaa tctacaatta gaagaaaaag   7800
tattaggtaa gcatcaatgt aagtaaaaga caaaactata tagaaaaaac atcgaaaaca   7860
ccattaaacc atcaatcttg tggttgtggc agcttgcact ctagtgcggg gccgtggccg   7920
agtggaggca ggaagacgag cagcaagcta gcgacagtgt cctgacagct ggcgatgacg   7980
gttgggtggg cggccaacga tgatgaactg acggttggac gtcaattgga cagcgggcac   8040
aacgctagga cgagcgctaa gcgggggttg gatgctacaa acgtgcggtt gatgccttc   8100
tcattctgtg ttttattcga tataggtcgt gacctaagat gatgggctag atcttgtggg   8160
ttagtcgatg gtatgatgtg gtggaccccgg tgtttatcta atttagtcgc atataccttta   8220
tatttttat tttatagtat atataaaagg taggtataaa cagttccaaa aattaaggtg   8280
gcgccatggc ctactttgcc cacattgtgg atccgcctt gattttgact gaacttggat   8340
aaaatatact ggtcatagta tttataatac ccaaaaaaac aatgtcatgg catttattaa   8400
caacgggttt tcattaaatt aaactgattt ggtttgccgt aaatttagga gaaccaatat   8460
gatcaatgag tagcgtatat cttacagtac agaaaaatct ttgaaaaaaa tatataaaca   8520
gcacacaaaa gcatgcgatt cgtcgacaga atcgtctcaca ggtctcacca caccattcaa   8580
ggacgatgga gcttcttcgg tgctcagact ttatttctac catctacaac ccaaactgat   8640
atgtacagta aatggaagga agaacaagat agagaaaaaa aacccaaact gatagattag   8700
aagtcgctga agaaatcatc taacaaaact ggcgagctat caaacaggac acgggagaga   8760
atagatgatt aaacaataat ccctcgtgca atgcatgcca ctgtagcgcc gtaatataat   8820
gatagatatg cgctattgct cctacaacta caacccacat ggtgttgcga gagctagcgg   8880
tgccacacag tcatgaaaac atggtttgtg aaagcagctt aactaattac tagctagctg   8940
tgagtcgtca gcggctagcg gagagtgaga gtgagaggac cacgcgaaag aaacgacaat   9000
aatctggtcc aacactcgct cttcattcaa gctagctagc gctgggagcg aactcgctcg   9060
gcatggcaga gcctgcctgc tgccgagcgg acaggtcacg gtcttcttga cgcacgcaca   9120
gtccatggcg ttggttggcg tcctgtccat ttcgctttgc tgcctcgcca tcaccgccgg   9180
ccggtactgt gcaaagcgcg cattggctag cttccctgtt gccttgatct gatcatagag   9240
gggtccctgt ccgtggcaca cagtgggatt aatgacgggc ccacgtcggc cctccctaat   9300
gatttccccc gccttaacgt tgacactgcg gacggtgaga ggcgcggctg tggacgtacg   9360
gcgagatcta tcgggggccc atcgtccttc gcgaacgatg cgtacattta gcgtcatata   9420
taaacacacg ccggcacatg attactacgg cctatatacg cgcgtcgtga gcggcgcgat   9480
caatgagtga gctagttcgt tgcaccaaat tgtcgatcaa gttgcatcag acagtagagt   9540
actgtatact ctctctatat atatactccc tccgtttctt ttttttattt tgtcgctgga   9600
tagtgcaatt ttacactatc ctgcgacaaa taaaaagaaa cggagggagt atgtactagg   9660
caggctaaga aacacgatag ataccacgca ttcggttctc attacgaagc tgcagctgcc   9720
caaccagcag cgatgatcac gtacgctcac catcctgcgt ccttgcggtt taaattaatt   9780
acgtatgtat ccgcatccgc atgcaggtgg tccctgatcg ccagccacct ccccggccga   9840
acagacaacg agatcaagaa ctactggaac tcgcacctca gccggcagat ccacacgtac   9900
cgccggaaat acaccgccgg gcctgacgac accgccatcg ccatcgacat gagcaagctg   9960
cagagcgccg acaggcggcg cggcggcagg accccgggcc ggcgccgaa ggctagcgcc   10020
agcaggacca agcaggcgga cgccgatcag cccggcggcg aggcgaaagg cccggccgcg   10080
gcggcgtcga gcccgcggca cagcgacgtg gtgaacccgg gcccgaacca gcccaacagc   10140
agcagcgcac ggccgaggag gaggggcccg gacgcgcggc ggcgcggcac ggccgatacg   10200
ccgtgggtgc tggagccgat agagctcggg gacctagtct gggggaggc cgacagcgag   10260
atggacgccc tgatgcctat cgggcccggc ggccacgact cggctgccct cgaagggctt   10320
ggcgcggtcg gctgcgaggc ccaggtggac gacctgttcg acatgactg ggatggcttc   10380
gcggcccatc tgtggggcgg gccggagcag gacgagcaca gcgcgcagct gcggcaggcc   10440
gccgagccgc tggaagttgc tgctgctgct gctgctgcga cggcggcccg cacccgggc   10500
```

-continued

```
gatcgcgagc tggaggcgtt cgagacttgg ctcctgtccg actcgttctg a          10551

SEQ ID NO: 52           moltype = DNA  length = 919
FEATURE                 Location/Qualifiers
source                  1..919
                        mol_type = other DNA
                        organism = Zea mays
SEQUENCE: 52
atggtgcgga agccgatcca cgctgacgac gccggcgcta agagcacgga ggcgagcaag   60
gagaggaagg ggttgtggtc gccggaggag gacgagcggc tcttcaccca catcacctac  120
cacgcgtct ccacctggag ctccgtcgcg cagctagcag gcaagattca gttcttgcaa   180
accgatcggg actctcggta cctgattcta tttcagctat cggacagcac aacgcggtat  240
gattaatctc ttcttaaatg ctgaatgcac aggcctgcgg aggagcggca agagctgccg  300
gctgcggtgg ctgaactacc tgcgcccgga cctcaagaag gagcccatct ccaagcgcga  360
ggaggagacc atcatctccc tgcagcagtc gctcggcaac cggtggtcga ctatcgcggc  420
gaggatgcca gcaggacgg acaacgagat caagaactac tggaactccc gcatcaggaa   480
gcgcctcaac gccgccgcct ccagagctgc aggctgcggc gacggcggtg acagcgcggc  540
cgagccatcg ggggccgcgg ccgcggggag aaaggaggat tcggccaacg ctgcgcgcc   600
gccagcggcc cagcctacgc ccatcccggc gcggttcccg gtcttcgggt gccagctgcc  660
cgacggagcc ggcggcggca tttcgtctcc cggcagcggc aagagtccac agtcgtcgac  720
tactgcgagt atgcggcaga acgcgggtga cgagagcgat gcgagcgacg gtgcggtgg   780
cgacagcgac atggtccatt tcctctcgtt cgatgatctg gattatcccg gggatttgct  840
cattgatgtg ccgggcgcca tggacgcgtg ggagagccaa ctgtgctatg cgaatccgat  900
gatgagctcg ctctgttga                                               919

SEQ ID NO: 53           moltype = DNA  length = 1082
FEATURE                 Location/Qualifiers
source                  1..1082
                        mol_type = other DNA
                        organism = Zea mays
SEQUENCE: 53
atgggcagga gggcgtgctg cgccaaggaa ggggtgaaga gaggggcgtg gacggccaag   60
gaagacgata ccttggccgc ctacgtcaag gcccacggcg aaggcaaatg gagggaggtg  120
ccccagaaag ccggtaaata aattgattag cttttcttgc agatttcgtt ttgggatcat  180
atcatatata tatatatata tatatatacc aagacaagat cgacgacgac gcggctgatg  240
gtgtgtgtgc aggtttgcgt cggtgcggca agagctgccg gctgcggtgg ctgaactacc  300
tccggcccaa catcaagcgc ggcaacatct cctacgacga ggaggatctc atcgtccggc  360
tccacaagct cctcggcaac aggttacatg agctgacgac gagcagccat ctgctacgaa  420
ttcatcagtt ccggtgttgg ccgtgagata gagtgatcga gctcatgttt gtctctactc  480
cttttacatac gtgatacgta cgtacgtacg tgttggcatg caggtggtcg ctgattgcag  540
gcaggctgcc gggccgaaca gacaatgaaa tcaagaacta ctggaacagc acgctgggcc  600
ggagggccgg cgccggcgcc ggtgccggcg gcagcagggt cgtcttcgcg ccggacaccg  660
gctccgacgc caccccggcg gcggcgggga gccgcgaggt gacggcggc cagaagggcg   720
ccgctcctcg cgcggacctc ggctcgccgg gctccgcagc agtagtgtgg gcgcccaagg  780
cggcgcggtg cacgggcggg ctcttcttcc accggcggga cacgcacacg ccgcacgcgg  840
gcgggacgga gacgccgacg ccaatgatgg ccggtggtgc aggaggagaa gcacggtcgt  900
cggacgactg cagctcggcg gcgtcggtat ctgtatctcc cctcgtagga agcagccagc  960
acgaccgtg cttctccggc gacggcaacg gcgactggat ggacgacgtg agggccctgg   1020
cgtcgtttct cgagtccgac gaggagtggc tccgctgtca cacggccgag cagcttgtgt  1080
ag                                                                 1082

SEQ ID NO: 54           moltype = DNA  length = 5928
FEATURE                 Location/Qualifiers
source                  1..5928
                        mol_type = other DNA
                        organism = Zea mays
SEQUENCE: 54
atggcggccg gcggcagcgg aggcgaggcc gcgcagaagg cgctgcagtc ggtggcgcag   60
agcagggggt ggacgtacag cctcctctgg cgcctctgcc cgcgcaaggg gtacgccttc  120
ttcctgcctg ctgctccatc gccgtcccaa ctctcgtcct tgctaaagcg ctgtctgact  180
aaccgatctg atcacgcatg catgcatggc cctgctcatc agcgcgctgg tctgggcgga  240
gggctactac aacggcgcca tcaggacgcg caagacgacg atgacgacag tgcgtcagcc  300
ggcgggcgcg gaggacgccg gggacgagga gacgcgctg cgccgcagcc ggcagctcaa   360
ggagctctac gactcgctgg cggcgggga ggccgcttac gctggtggtg gaggagtcgg   420
cgacccacag cagcagcacc agcagcaggt ggcggtggtg ccgccgcctc gccggcccgt  480
cgccgcgctg gcgcccgagg acctgacgga acggagtgg ttctacctca tgtgcgcctc   540
ctactgcttc cctcctgccg tcgggtaaac cggctatagc ctatatacat acatgctttg  600
ctttgcatgc tacctcacgt atctacagaa tgaagcacag cacagcacag cacagggaac  660
gaacgatcga gctcaaggtc tccacgtgta agatatgcaa ataaatagac cggctctcta  720
tgctgttcta tatttactaa tactttttt tcctcatgca tgttgtttca caggtgatga   780
tgaaccaaat gttcgttcct tctaataagc accgcatgta ccaacgatcc tctaaatatt  840
gaccctgttt gtttgggcaa ttttagtttt ttggcaataa aaagctgccg cggattagca  900
aacgtccag ctttttcagtc tgtttctata aaaatcgcta aaaaccattc aaaatcaaca   960
taaatacata atcgatcgag tcgtcacgat aaattccatc gctatctaga tcttgaaccc  1020
tttgaaccat tcatttcc tccgcacgta atcccacgt actcagatct ttcccacagc    1080
cagattctct ctacaaccag attctcaaaa aaactgatca gaaaaaactg aaccaaacaa  1140
acccattatt gtccttgctg gcgagctaaa tcttaccagt aaactattat acaaaaaggc  1200
catcatgaaa aattaccgga acacatgttt ttttggcgac attattgttt ttcttaccaa  1260
gtaaactcct aagataatta ttatttccac ctttttttgag ctattatata tacgtacatg  1320
```

```
acattcaaaa acagttgtcc cgtcctattt tatttactct aatgtctctt catattacta      1380
tagagcccgt ttcttagttt gacattatca tatatcgtct aattcgttat tcgcatcgtc      1440
ttatcctgaa ccaccgcgtg caattgactt tgtgcgagct tctatttggt tgtctatacg      1500
cgagagacac gggttgcata tgtggatgca aaacaagata ttttaaggct atttagttgc      1560
atccactcat actgccaaaa ttggctacc tagccgacca ggctcgcatc cgcctggttt       1620
gttgtgctca accatccaat cagccggata gctgatgcag catgcatcaa tgaattatcg      1680
aatgtcaaag cacaaacatt taatttcata taacaaacag ataatgttct tttttttcgtt    1740
gttgtaacaa gagagaagct tccatgtata agtcatatac atgtgtagtg cttccacgtt      1800
tcaggttgcc cggggaggcg tttgtaagga gagctcatgt gtggctatgt ggtgcaaaca      1860
aagctgacag caaggttgtc tcaagagcaa ttctcgctag ggtacgtacg cataccgtct      1920
ccattctctt ctatctcttt ttttttttaa aaaaatgttt ggtacttc tagtcgcaaa        1980
tatacttggc acattcaata acatcatact gtgcccatg tgttgtgaat tgtgatgcaa       2040
caaaattagt tttactatcg tttttttga aacatagcac ctgtagatta ttaaccctct       2100
cttacataaa atgtgaaaga atatataata gagatgctat tgtatatgcag gctcttcctc    2160
gttcgaacag attttggacg ggctgtcaca tctatatttc aatagaaaat atatatatat     2220
ttgttaaaat tgcacccaca agactatgca aaaaaaaaaa ctgaacaaag tcaaagcact      2280
ttttgaccct agctagtgag tagtttgcag tgtgtgaaaa ttatagtgat tttagaaaaa     2340
ggataaattt gaaaagaaat aaccttaatg aacatatacc tattctattt caaattataa     2400
ttcgttctgt cttttctaga tatataacct tattatgtat ttagatatat agtctatatc    2460
tagatataca ataaaagtat tatatctaaa aaaacttaaa acatcctata gtttagaacg     2520
gagggagtag ttagctacgc atgacaaaat ataagcttat gattgtagtt gaacttaaaa    2580
acattgtttt cctttcaaga tatgagtatg aagctcaaat aattgtttat cgatatccaa    2640
aagtattatt ccccttcttg ccccatgata gagaattgaa ggtactaact aattctccat     2700
ttattacgct tttcatgtgg aacatcaaaa atgttggtgg caacaaatat cagagtgcag    2760
gtatacaggt attaaaattc acctctaaaa ctacttttt atatggtttt tattgtataa      2820
gccttaagaa gtactgtttt gccattcaat gctagctaaa gtaaaatcac ttctagcatc    2880
acaacaacgt tttagcaaat aagtaagtct tcatttgcat tgaacttata ctatttttcaa    2940
tattcagcaa ttgcatgacg tacttctact aaatattgag tctcgctcag gcatacgatg    3000
gatgtgcgta tgtgttgact ttgatcttaa taatgcagac agtagcatgc attccagtcg    3060
acgatggtgt cctggaaatt ggaactacag aaaaggtcag tagtgagtta attatgcatt    3120
ttagaaatta cagtcgtcaa tccctcatct gttaatgttc tacaaaactg atcatacaat    3180
aatacttaca taaattcaat tagtattttc gataataaaa ttaataaatc aaacatcaat    3240
tatatatata tatatgga gatgtcgaa acaataggg atctaacaaa tctattaata        3300
agtttcaggt agaagaagac atttcttaa ttcaacatgt taggaacatc ttcgtggatc      3360
aacatggcgc ccacataatg cctaccaccc tctcagggta ttcaacttcc accccaacca     3420
cacagcttaa tcatcagcca ttccagacaa aaacaggaat cagtctcaat ctaggagacg     3480
agcataatag tgaaatggaa gatgatgacg acggcaggat tgatttagag aacaatactg     3540
aaaatgattc aacaaggcgg catttgccac aggacgccaa tgtaggcaat gagctggaaa     3600
cgctcaatgc agagagcagt gggccgatgc tgattgctaa tctgacagcg caggatgaat    3660
attgtccgtt gcatcgtttt cacagtgaag acctaagcag taaataccta cagtcatcag    3720
gtaacatgga cctgtgtaca tattattaat tagccttgca gtaaataatt tcaaactccc    3780
tgttcgctac cttccaacat tatataatcc agcttatata ttatatatct atttacagat    3840
tatcataatc tatgcatcta gattatataa ttcaactaat aatctgtgt gtttgtttgt    3900
ctcttaactt atttcagcta gattatataa tttggagggt aaacaaacat gtcctaaaat    3960
taaagtagct aacttattat ttttgatgat gtgttaagtc taggagtaat ttatttggtg   4020
catttagtga ttgatatgga tgtgggatga tttggttagg tagattttgc aaagtttaaa    4080
ctggtagatt atatagatat acaaattgaa aaaggaaatt ctaaaaggtg tacgaactat    4140
atatggagat gtgataatcc atcatgatac tagctaatac tataatctga aaaataaaca    4200
acttagatat tgtgtgacga tagtggaata cagatatctt ctatagttct atcagatttt    4260
tttattcaaa acaaacatta catttttcca ccctctattt actctctatg aatccatttg    4320
ctcgatcttc cttccagggg cagaagatca agcagcagta gcggaaaacg cacactacat    4380
caaaacggtc cttacaatcc tacggttcaa cgcgtgccgg caaacgcaag cagcctcctc    4440
aaacatcgcc aaaacctacc tggcactctc caagaactcg ccattctcaa aatgaaactg    4500
gaagcgcaaa ggaataagca gcatgttgat ccctgagggc acccagcaga ggatgctcaa    4560
gagcgtcctg ctcggtgctc ctagcagcag cagtcaccgg acgtcgtcct cagcacctga    4620
gacgaggggt gacgatggcg aaggcacgag ccggtctcgg agaggtccgg tgccgtccca    4680
gacagagctg agcgccagcc atgtcctcaa ggagcggcgg cggagggaga agctcaacga    4740
agggttcgcc atgctccggt ccttggtgcc gttcgtcaca aaggtgcgtg tgcgtgcgtc    4800
gtatttaaat gcaagacaaa ctcgtgtagc atctccaaca atgcctcaaa ctagtgtctc    4860
aaattgaaat atagggctcc acacaggaaa aactactcca acagtgcccc atttcataaa    4920
attttgtcaa aaaactatag gtcactctct caagtgactc aaatatacta caccgtagtg    4980
ggctgccctg taatatagat ttgaacttta ctgttggagc ggggtgtttt attgatgccc    5040
taaattctat aaaatatact cattttcaaa ttatatagca tttttatagg tcaacttgtt    5100
ggagatgctc tgacgggcta acagcagcct acatgctaca gcaacagcaa ctcttttgt     5160
ttgtctctcc tattcgcacc gcagatggac agggcgtcga tcctgggcga cacgatcgag    5220
tacgtgaagc agctacggag gcgtatccag gagctgagt cacgagtccg gctgttggc      5280
agcaaccaga agacgacgat ggcgcagccg ccgccgcctg cagcctcaac ggaggagaga    5340
ggtcgtcgtc aaaaccagcgg cggttacctc gctcgcgcag gtacatgcag cagagcagcg   5400
gaggcgagcg gcaacagcaa cctcggggag gagcctccgg cggcggcggc gagcgacacc    5460
gacacgagg tgcaggtgtc catcatcggg agcgacgcgc tgctggagct ccggtgcccg     5520
cacagggaag ggctcctgct ccgggtcatg caggcgttgc accaggagct ccggctggag    5580
atccctacg tccaggcctc ctcagctggc gacgtgctac ttgcaaagct gcgtgcaaag    5640
gttagcgcca tggaatggaa gtatcatgga aaatgctgtt tcgatctgcg attctttttc    5700
tattctcttg ttgggacaca gaagacagat tgatttcagg tgtgcttctg aatgctcaag    5760
tgttcttgga ttgctgctg caggtgaagg aggtgcatgg caggagaagc agcaccactg    5820
aagtgaagag agcaattcac ctcatcgttt catcagactg gaactggata tgcgagaaga    5880
atccatgtgt agcatagtat taaatacata tacagactat atgggccg                 5928

SEQ ID NO: 55    moltype = DNA    length = 3398
```

```
FEATURE              Location/Qualifiers
source               1..3398
                     mol_type = other DNA
                     organism = Zea mays
SEQUENCE: 55
cacaccacag ctcccacaca cagcaggcag cagctcgatc gctagctcct ccgaaccgga   60
aagccaagcc cgctttggcg atcgtgcttg cttgcttggt tccttcaatt cctgccggag  120
ccagcgagag ctagctgctg ctgtcgcgtg gtagacgtcg tcttgccagc gagagcctag  180
ctcgatcggt ctctctggta caacgtaggg agaaagatcg aggggagag gacgacgacg   240
atggccagcg cgaccgtgac cgtggaggag gtgaggaagg cccagcgcgc caccggcccc  300
gccaccgtgc tggcgatcgg caccgccacg cccgccaact gcgtgtacca ggccgactac  360
ccggactact acttccggat caccaagagc gagcacctca ccgacctcaa ggagaaattc  420
aagaggatgt gtgagtgccc ggcctcgatt atatatctag ctcactctct ctcgcccgt   480
ctccatccct cgctcgctcg ctagcttgaa gaacatacac tcacgtcacg tcgtcgtcgt  540
ctcctgctac ctgcttaatt gtttcacgtc gtcggtaggt ctcgggcgac gactactagc  600
tgacgacgga cgatgctagc tagctgctgc ctcgtgcgca gcagcttcca cgtattaatt  660
ttctccgtcc cctcgcgcca tgcacaaaga catgaatatt tttactaacc cacgtagtct  720
attgtctctc ctgggtaaac actcgtgggt tagttactat ctagctacta cttatctgaa  780
tattttact agcagtggga gaacagaaag ctaatagact acggtcgatc gtacgtgtcg   840
tctcttcgtt taattttaa cagattccaa aaacttctcc atcatgaa tatatatact    900
ctatgttgcg atccggatag agagagaata taactgcaat aaactccttg ttgttgagat  960
atgtatatgc tgcttgctgc tacacaattg ctactaccta ggcagtcgta cgttacaaca 1020
acaacaaaca gcagcaaaac ttgtgtgtgc accatgaaac cccgtgttc catgattttt  1080
gggggcgcag gtttagcatg gacactagct aggctaggct aggatatgtt ttgggtaggg 1140
tccatatata tataccagct gctaacgagc gagtaacaca cacgtacgca cgcacgcacg 1200
cattctagct cggccgatac cgtacagaca tgaaaaaaaa gaaggtgcgt ggtcaacgcc 1260
gcctggccgt gcccgtacca acaactaaca caaacgtttt cattttcttg gggtgaaaaa 1320
aaaagagaga gaagtgagaa cgagacgtaa agcaggcgtc tgtgcacggg agtgaagaga 1380
taatacagct tttgtgcccc tgtcacgggc tgttaggtgt gcaacacaaa tggcacgtcg 1440
aggcgtcttt tgccgccggc ctctgctagt tcttccatca ctgttgcaca ctgaccactc 1500
aagaaacccg ctctaattaa gctgttgacc tcttcttctt cttctagcgc gcgctagctg 1560
atgagtagct agcgcaccag agtccagagg tggtagcagt agaaacagga ttctttcgt  1620
ggacgtcgat gtgccatgct agctgccatc gtccccactg cacggggcag acagggaccc 1680
cgtgccgtcc catcgactcg actacctcag gcctgcagct agcgcaactc gtatagagag 1740
atggaatagt actccatcag cacggcattc ccacaccact tggattttgt cgacctgacc 1800
ggcaagcaac tagcccctc ctgttccatc aatcgaattg acgtagcaac tagctgcctt  1860
gacgtccgtg ctcgggcatg gccagtacac atacggccgg ccgtacggt tgttttaat   1920
tgggccggtt tgattttgac gtgcatgcag gcgacaagtc gatgatccgg aagcgttaca 1980
tgcacctgac ggagagttc ctggcggaga acccgagcat gtgcgcgtac atggcgcgct  2040
cgctggacgc gcggcaggac gtggtggtgg tggaggtgcc gaagctgggg aaggcggcgg 2100
cgcagaaggc gatcaaggag tggggggcagc caaagtcgcg gatcacgcac ctggtgttct 2160
gcaccacgtc cggggtggac atgccgggcg ccgactacca gctgaccaag gcgctgggcc 2220
tgcgccctc cgtgaaccgc ctcatgatgt accagcaggg gtgcttcgcg gacggcaagg 2280
tgctgcgcgt ggccaaggac ctcgcggaga caaccgcgg cgcgcggtg ctggtggtgt   2340
gctccgagat cacggccgtc acgttccgcg gcccctccga gtcgcacctc gactcgctcg 2400
tgggccaggc gctgttcggc gacggcgcgg cggccgtggt cgtgggcgcc gacccggacg 2460
accgcgtcga gcgcccgctc ttccagtcg tctccgccgc ccagaccatc ctgcccgact  2520
cggagggcgc catcgacggc cacctccgcg aggtggggct caccttccac ctgctcaagg 2580
acgtgcctgg cctcatctcc aagaacatcg gccgcgcgct ggacgacgcg ttcaagccgc 2640
tcggcatctc cgactggaac tccatcttct gggtggcgca ccccggcggg cccgccatcc 2700
tcgaccaggt ggaggccaag gtcggggctgg acaaggccag gatgcgcgcc acccgccacg 2760
tcctctccga gtacggcaac atgtccagcg cctgcgtcct cttcatcctc gacgagatgc 2820
gcaagcgctc cgccgaggac ggacaggcca ccacgggcga gggcctcgac tggggcgtcc 2880
tcttcggctt cggcccggga ctcaccgtcg agaccgtcgt gctccacagc gtccccatca 2940
ccaccggagc ggccaccgcc tgattcatcg attcatcaac gatcaaattc ctccctctc  3000
cgatccaatt cgtcgtcgtc tcgttcgtca ttattttacg tcgtccgtcc gcaaataatg 3060
tgctctctgc tataattgtc gtgtgtagta gtaagtagct gttactattt tccatgtac  3120
tgtcagtcgc acaatcatca tatataatta atatctctat atatgcattt catgcaagac 3180
cagggtagag ctagcttgag gagaagaccc ttatcgttgt cacttagca tgcatggggt  3240
ggtgaggtat tgggtatacc tgtgtaaagac aagcttggct ggtttaatta tatattttt  3300
ttaaaaaaa atctgtttga tacaaaaata cacctgtaa tgtgcatggt gacggcaaat   3360
tgaccgccat tttcagtgca cctaaagctg tattggat                         3398

SEQ ID NO: 56         moltype = DNA   length = 3986
FEATURE              Location/Qualifiers
source               1..3986
                     mol_type = other DNA
                     organism = Zea mays
SEQUENCE: 56
cgagaactag ccatacccac gcgacccaac taactactaa agcaccccgt ggcggccctt   60
gcgcccgtcc aactcaccta acccgaccgc gcggctatat aagcaccgca ccccggcggg 120
cctcctctgc cattaagact agctaactag cgtgaaagag ctcctccgac gactactagc 180
tctcgcttgc tccgacgacc cctgccggcc gcctctggta caacgtacga gaggaagaga 240
gacgatcgat ggccggcgcc accgtgaccg tggacgaggt gaggaagggc cagcgcgcga 300
ccggccccgc caccgtgctg gccatcggga cggcgacgcc cgccaactgc gtgtaccagg 360
ccgactaccc ggactactac ttccggatca ccaagagcga ccacctcacc gacctcaagg 420
agaagttcaa gaggatgtgt gagtatctct actacccta ccctaccta ccctacctac   480
tatcgtcgtc cacgctcgct ctacgcatca aaaccgcaag agcttgcttc gttcagcacg 540
tcgtcgtcat cgtcgtcgtc cacacaccgt ctcccgctcg ctctcttgtt tcttcttctc 600
```

```
gtcgacgatc gaccacgcac gcatgctgca tggcgttata acgtcgtact agactctata  660
gcttgacaat gacgaccacc gtacagtact gcagtggaga tcgagcgatg catgactacg  720
gtctcgctcg tctcttgctt caaaattccg cacttattat tgcaccacta gtcttcttcc  780
tactctgttg acgacgacag aagcagacat gcatgcatgc atgcactcac gcagccaaa   840
tatttaatcc ttaatcagct aggaccacat gtccaggtag agaagaatta gctagagaga  900
ttgccccggg tacggtagca aattaaacca cgcacgcact agaattagcc aacaaacggt  960
ttgttagcta gggcacatgc agtacgtaca acctatatta tataaattac tcgtatctta 1020
attaagtggt gtttgaagga gacaagtgaa gaaaaaaaac acgacgtagc acactagcat 1080
ggttctaata tacgatttca tccatacaac ccacgtacat gagacatgtc ttaagtgttc 1140
tagtgaatta atatataaga tacaaggctc agcactggta cagagaagct ctatacagtc 1200
ggttctgaac acatttgcat tagcgttttt cagatccgct agttctacgg gccagtagaa 1260
aaaaaattgt acaaattcgt ggctccgttg aagtcgcaag tcgtgatatt tttcgcggaa 1320
aattcgcggc cggttggaat ctaacccaca aaaaaccact ccctcacgcg aagcctcctc 1380
taccacttca cctatatgac gtgccttgta tctatattgc agttttgttg cccacgtaga 1440
acaaattcga gtataaattg actacttgag gctatgaacg aatccaaacg aaaaaagttg 1500
ttaactacaa agtttcgtaa cttttgaagt tatataactt ttatcttgat accttctttt 1560
ccatgcgagg tcgtttgcaa aatttgcatt ttgcatttga caaattcgaa tgcattttt  1620
gagagacgag atgaatttcaa ataaaaaaag tttcaatta taaagttcca taacttttga 1680
agatctacaa attttatgt tggtggtttt accatccgat gtcgtttgaa aaactaaaaa 1740
aattaaggat gaaaatgttt tctagtggct gttttttta aaaaaaattg ccactacaaa 1800
tagtactggc ggttgataat caaattcatt tgcaaaaaat caaatcccac cgcgtgcttt 1860
gaactctttt ctgctagtgt agataccta gactatatgt gatatataac catgaactgg 1920
atacgtgaca caaacagca caaacttgtg tgcaccacac atgcataaaa accccgtgtt 1980
cctggaattc cgggggccat cgacgagcac gcgacaagcg tgcattctag ctagctagct 2040
agctagccca ataccggccg tacggagttc atggaatgt gatgaagtgg aggagggtca 2100
acaacggccg tgcgtgcatg ccggcacag cacacgtacg gatcatcttg aaaataataa 2160
caaaaaagtg taagttgaat aataacagac tgttagtagc aagcatggta ataataataa 2220
gtcaaggcgc gtctactagt tgctagctac tcctagctag ttgacggcct gctgctgatc 2280
caaccttccc aaaaaaatt aaaaataatc aggccttgtt aatctcttgg tactagtaac 2340
aaacaaatct tagaaatcta atcaaacttt aatgccggag gagacaaact ggtgctacac 2400
ttatttgctt cttttcgtgg acggcgacgg gccgggccgg cctacgtgct atatactacg 2460
cgtacttgca tgcttgtagc ccaagaatat gttgggctca gggcccacag ggcagacagc 2520
aacggcatgc cggccgatcc gccatcgtca aggcaacggt gctcctagct aattccattg 2580
catggcatgg ccatggcatc cgtgcaggcg acaagtcgat gatccggaag cggtacatgc 2640
acctgacgga ggagttcctg tcggagaacc cgagcatgtg cgcgtacatc gcgccgtcgc 2700
tggacgcgcg gcaggacgtg gtggtgacgg aggtgccgaa gctggggaag gcggcggcgc 2760
agaaggcgat caaggagtgg gggcagccca agtcgcggat cacgcacctg gtgttctgca 2820
ccacgtcggg ggtggacatg ccgggcgccg actaccagct gaccaaggcg ctggggctgc 2880
gcccgtccgt gaaccgcctg atgatgtacc agcagggtg cttcgcgggc ggcacggtcg 2940
tgcgcgtggc caaggacctg gcggagaaca accgcggggc gagggtcctg tggtgtgct  3000
cggagatcac ggccgtgacg ttccgcgggc cgtccgagtc gcacctggac tcgctcgtgg 3060
ggcaggcgct gttcggcgac ggcgcggcgg ccgtcgtggt gggcgccgac ccggacgggc 3120
gggtcgagcg cccgctgttc cagctcgtgt cggcggccga gaccatcctg ccgactcgg  3180
agggcgccat cgacgccac ctccgcgagg tggggctgac gttccacctg ctcaaggacg 3240
tgcccgggct catctccaag aacatcgagc gcgcgctgga ggacgcgttc gagccgctcg 3300
gcatctccga ctggaactcc atcttctggg tggcgcaccc cggcggggcc gccatcctgg 3360
accaggtgga ggccagggtc gggcgggaca aggccaggat gaacgccacc cgccacgtcc 3420
tctccgagta cggcaacatg tccagcgcct gcgtgtctct catcctggac gagatgcgca 3480
agcgctccgc cgaggacggc caggccacca ccggcgaggg gctcgactgg ggcgtcctct 3540
tcggcttcgg cccgggcctc accgtcgaga ccgtcgtgct ccacagcgtc cccatccaca 3600
ccggagcgcc caccgccgcc tgagtcgtcc atctatcctc gcgatcgctc cagacatgaa 3660
cgacccgacc tacgaataat gtatctgcgt aattaattac tatctgtctt gtgtcctagt 3720
agctgtttta aaaccccttaa ttaattttat tatgggcgag ctagctcaag agtggagtca 3780
taaaaccgca tggatggtga ggtattgtat agtacctgtg taagacaagc ttggctggtt 3840
ttttatttt atattttaat ctgtttgctc aagacaaaac aaaaaaaaaa atgaattgtt 3900
gagctgtcat taatttgcag tgcaccagct caagttggtt gtactcctat cctatgtatg 3960
aaatgaaatc ccttctagta gtatct                                      3986

SEQ ID NO: 57        moltype = DNA  length = 1529
FEATURE              Location/Qualifiers
source               1..1529
                     mol_type = other DNA
                     organism = Zea mays
SEQUENCE: 57
cccacagcta accctccgtg cccttctctg gcgggccgtc cccgcatatt tatcgcaaca   60
accccggcct gccaagtgcc acaaccgtag cctgtagctt catccgttgc gctgctcccg  120
gttccatcgc gcggtgcgga atttaacatg gccgtgccgg aggtggtggt cgacggcgtc  180
gtcttcccgc cggtggcccg cccgccgggc tccgccggct cgcacttcct cggcggcgca  240
ggtgcgtcgc gttgcgtttt gagggtccat tcccgtgcgc agtctgtctc tagttccgtc  300
agtacaaggg agggtacaa ctgtagttgg tggcgcagag tatggcatgg cagcttccgg  360
ttgacctgac ccttcttggg cttggcccgc cgcgcgtgca ggcgtgcgag gcctcgagat  420
cggaggcaac ttcatcaagt tcacggccat cggcgtgtac ctggaggacg cggccgtgcc  480
cgcgctggcc aagaagtggg gcggcaagac ggccgacgag ctcgcctccg acgccgcctt  540
cttccgcgac gtcgtcacgg gtgagtgaga ggttctcgcc cgtgagtgat ggtcaacagt  600
caacactgct gatggtgttg tgtcattgtg tgccgtgcg tgtgtgtgcg cgtcaggcga  660
cttcgagaag ttcacgaggg tgacgatgat cctcccgctg acgggcgagc agtacgcgga  720
gaaagtgacg gagaactgcg tggcgttctg gaaggccgcc ggcctgtaca cggacgccga  780
gggcgtcgcc gtggagaagt tcaggggaggt gttcaagcca gagactttcg cgccgggcgc  840
ctccatcctc ttcacgcact cgcccgccgg agtcctcacc gtgagtacca atctgctgtc  900
```

```
cccgatcttt ctctctttc atttccgtct actctcaagc tgctgctgct ccgatccgat  960
ccgatccgtc ccgttccatc caggtcgcct tctccaagga ctcgtcggtg ccagcggccg 1020
gcggcgtggc gatcgagaac aagcgcctct gcgaggccgt gctggagtcc atcatcgggg 1080
agcgcggcgt gtcgccggcc gcgaagctga gcctcgccgc gagggtgtcg gagctcctcg 1140
ccaaggagac cgccgcgccc gccgacgcgc cgcaggccgg gcccgtctcc atcaccgcct 1200
gaggcgagga gcggcgggc gagcgaacga accgcgagga gaaagaaagc aaccagacgg 1260
ttgggcggca cggcgtctca cacctgccgc ctgcgcttgc gtgctccgga ccggagagat 1320
gccgcgcggg tgcagtgcag ccgtcgcgtc atgtctgtcc gcgctctggc gtcgtgttcc 1380
tgcctttctg gtcgcgtagt tgtcttgtgt tcgctgttgg tcgttctggg taacatttga 1440
ataaaacaag cggatttgtt gcacttgcac ggttgcaccc tctaattccc cagcatgtgt 1500
ggatcaattg actctcagcc agagacttt                                  1529

SEQ ID NO: 58       moltype = DNA  length = 1650
FEATURE             Location/Qualifiers
source              1..1650
                    mol_type = other DNA
                    organism = Zea mays
SEQUENCE: 58
aacaaggccg tagcccgcag cttcgtctgt tacgctacgt ccggttcccc accgcgccgt   60
gtgaaaaaaa tggctgtgcc ggaggtggtg gtggacggcg tcgtcttccc gccggcggcc  120
cgcccgccgg gctccgcggg ctcgcatttc ctcggcggcg caggtgcgtt gcgtcccgg   180
tccagtccag gttccattcc acttctgtgc cagttcgttc gctcgtctct agtttcttgt  240
acgtagtcgt cgtagcacaa gggagaggga acgtgccgga gtatgtcgtg tcagagcttc  300
cggttgacct ctgtcttggc gcgcgcgcgt gcgtgtgca ggcgtgcgtg gcctcgagat   360
cggaggcaac ttcgtcaagt tcacggccat cggcgtgtac ctggaggacg cggccgtgcc  420
ggcgctggcg aggaagtggg ccggcaagac ggccggcgac ctcgcgtcg acgccgcctt   480
cttccgcgac gtcgtcacgg gtgagtgagt actgtagtac tacagacgac tacagagtct  540
gaagaaggtg cctcgttgtc gttgtcgttc ttgcgcgtgg cgtgatggtc gtcaacgctg  600
ccgcctgtaa agttgccgct ttgtggacgt ctctgtgtgt gtgtttgtct ctcaggcggc  660
ttcgagaagt ttcgcgcggg gtgacgatga tccgcccgct cacgggcgag cagtacgcgg  720
ggaaagtggc ggagaactgc gtggcgtact ggaaggcggc cggcctgtac acggacgccg  780
agggcgtcgc cgtggagaag ttcaagcagg tgttcaagcc ccatacgttc ccgccgggag  840
cctccatcca cttcacgcac tcgccgcgcg gagtcctcac cgtgagttca gttcatttcc  900
gtgcgacgaa atgagaacgt atcttgtgcg caaggagcgt tggtgctccc atgagcaaaa  960
tcaatccaga ccacaccctc cacatccaac ggtgctgtca cagggggtt tgtaaaatgt  1020
tctttgcaac tctgtacatt ttacaaaaac ccccctgacgc agcaccgttg gatgtggagg 1080
gtgtggtctg gattgattct gctcatggga gcagtagggc tccttgctca taagatacgg  1140
tgtccgacga aataggatgg tgacacgtac gtactcagta ctcacgctgc tgttctgctc  1200
cgatccgctc catccaggtc gccttctcca gggactcgtc ggtgccggtt gccggcggcg  1260
tggcgatcga caacaagctt ctcgcgagg ccgtgctgga gtccatcatc ggggagcacg   1320
gcgtgtcgcc ggccgcgaag ctgagcctcg gcgagggt gtcggagctc ctgaccaaag    1380
ggaccgccgc agccgcagcc gcgctgcggg cggagcccgt ctcggttacc gcctgagcgg  1440
tccagcgaac cgcgaggaga aagagaaccg atcaagcaat cacgtctgcc gcccttgcgg  1500
gctcctgctc cgaacagatg ccacgacgga cggtgacgct gtcgcgtctg tttgcgctgt  1560
ggcgttggcg tcgtgtctct gcctttctgg ccgcatgtgt tcgcgtggt aacatttgaa   1620
taaaagaaaa cgcagatttg tttgcactgc                                  1650

SEQ ID NO: 59       moltype = DNA  length = 4088
FEATURE             Location/Qualifiers
source              1..4088
                    mol_type = other DNA
                    organism = Zea mays
SEQUENCE: 59
cgaaaccgcc accaagctgc ttgcttacgg cctagtttca cctcccccat tcccttggaa   60
ttggatttgc tcccgaatcc ggcgaggaag cgaccggcac tccacgccac gccgcggcgc  120
ccaaggaagg gaagcttggg gccctaggcc tcgtctccat ccccgccgca gccggcgcga  180
ggcggcgcgg cacgagcacg acggtcacca tcagccaccg cgcgatcccg ggggacggcc  240
aggccaggtt cggcgctttt ggtttgcgga atcgcggtcc gagcaacgaa tgcgggatct  300
gttgcggtcg tgtggaagga gtggggtttg tttggagatt tgggcatttg gttgcctggt  360
gctgcgcggt gaggctgggc ggcgctacga ttggcgcct ctgcggggtt ggtgctgtat  420
gaatgtgaat cctgggggcc aatagcgaga tcgtcgcgtt ctgatgctaa tttgggatgt  480
ttgggatcag gggttcgggg ctttgtagtt tttctgtaac cgggtgagat ttcgggtgct  540
cttttcaagct cgtttgcgag gcactaattc tgatcgagtt agaacaccat agcagataga  600
tcatcactgt tttgctttgt ttaccttga ggtcgcggtt tttttttcca gggatagtt   660
tgagaagagc aatttaggat ctagtttgag aagctcaacc ttttatattg caattttgat  720
gcgattttga ttagtatctt ttcatatttta ttcatttaaa tgtttgtgag acgattaat   780
agtgctgcta aggtctacat acagattctg ctgtaaaata gtatgcccag gggggaaaat  840
ctgtgtaagc atgtatgcaa ttgacatatt acttctttgt gtcctgattc gcttttgttg  900
ctccaattgg cagattccac aacgttttac tcttattaaa ctcccaact tcgtctaagg   960
aagcaagtga tttcattatg aaagactggt ctatttctc caaacttgat cacaatggag  1020
gttaccttcc caggttccca atggactctc caatatctca tgatattggg ttacgattgg  1080
tatcgcaagt cggaaactta gttgagtgtt catttcaaca tccaaggcat atatgtgcta  1140
cggggagtgg agctgttcag gaagcattca gctgtttcaa caagtttgct ggagcttttct 1200
atttctggtt ttctagagca tcgaatccta agttattcca aaggctatca gcagctgcag  1260
gctcaagttc aagagcttgt cggtcacaca taaagcaagt gacctcttgc ttgcagcatt  1320
tacctggact ggagtttggt tcacaattaa gagaagatca tgctgtacaa gtgcttttag  1380
caaggccttg aagcgcaact tttggacgcc tgtggacaga ggtggaggag cggcatgcct  1440
gcaacatcct tatgctggct gctgctactg taattccacc atttgaaaac atgtatgagt  1500
tcgtcacatg ctgtttctg agctgacaga acttacttt gccatttgtt ttaacttt    1560
```

```
tttattttttt gctttgttaa tattttttttt attcgtggac aagatcacca aagatgctgg  1620
ctgcgtcaat ggcactaaga aaagatcgtg gaaacataga gcctactgaa cagtcttatt  1680
cagaggaaaa ccgtccaggt tgtgcgtgtg ttgctgtgcc aagagtactc ttaccagaag  1740
atgcaacgga accaacaact ggcatcaagt tccccactgt actcgaagac aattccaatc  1800
tgactacaga ggtccttttt caagcatgct tctgtgaatt tttgttttat gggccaaatat  1860
tttttctcca tatttgaaca ccacatgctc tacagattat ctataatgtt gatgcttcta  1920
ggtacactgc ctccacttga tacatgtatc tgatggttaa aaattggcag gtccttgttg  1980
gaatgggttt tagaagcatg cgaataatga gggtcaaaaa tctgaatctt tatgcctttg  2040
gattatgtga gtaaagtaaa atttgtcgtg tttactgtta tttatgattt gtgaattgat  2100
aacaggtagt tactgcttaa ttattgcctt ttggttactt accgtgggggg cagtcttttcc  2160
cctaccggcc gagttttat tatgttatat tggcatattc tcagatatac aacctgattc  2220
tgtctgcaag aagctgggtc caaagtacgc ttatattcca gatgctgagt taaaggatca  2280
cccagatttc tatgaagatc ttctgaggtg tgcgatgcct attgatcatt tatgtgtctt  2340
cacgaattct gttattaaga gcaagttcaa taatataacc cataatgggga ttatgatgtt  2400
gccatgtcac atatcatagc caactaaaag cctacttata ttataaccct ctcatgatat  2460
aagctatata tttaatattt gctttatctc ttcctctcac aaagtgtctt ggagtttgtg  2520
agcagtctac ttttagctgg ctactagtga ccagtccgct ttctttctca ctccatttct  2580
cttttttttcg cgtcaccata aatctgacat gacatctcct gcagtcggtc tatgtcacct  2640
tattatactt gctctaaaga ccttcccaaa attctggcca ttacctagcc agtcaaccct  2700
ttacacggaa acactcgtgt cagcttaggc ccacatttta aagaaatgct aggaaatgtt  2760
ggtatcatta aaagggaaa aagtgttgtg tatagaacac ttctcagggc ctgcaattgt  2820
ttgagaacca tttaatcatt tatagtgcta tttatttcgt gaggttctga tgctgcatag  2880
gatttgacac tgcaaagttt cctgccattt tcccttatg tgcatcctag ttgcctatga  2940
tgctaacaaa cttccaatct tttccaggga aaatattgat atgactgtta ggctagtagt  3000
aagctacaat ggtctcagca ttggcacagt tcgagagtaa gcgttctttt ctttatttgg  3060
ttcaaatatg ttagtatcta tgcaaagtta atcatttgtc tcaacatgct ttccagtgga  3120
tttgagaagt ctcttggctt ccggttcaa aaggtatttg ctgtttattc agcaattatt  3180
tcatcctttc ctaaccatat aggcctaagt gagcttttta tgtatacatc attgaaccag  3240
atgaatccta atactgatta tggttgcttg aagacttttg gttcttgttt tagtgaagac  3300
attcgtatac ctgctgtaag tttcaatgtt atgtctgagc tacataactt tgcgcatttg  3360
gtgtgagaag ttaaaagtca atgcaactgc agggtacaaa gattgacttc cggcaaacat  3420
ctgatggcca gctaataact gaaagttagt accatatagc ttatttcttt ccacatgctt  3480
tagtttcttg tctccactac aatgtcttga ctaaaaacat ccgtgtgcag ttgatggcaa  3540
acaaattggc actgtccaga gcaaagatct ttgcagtaag tcagagtgtc aaagatactg  3600
agtatttat gcattttatt tagagtttac taatcattaa ttcttattaa atcatgtatt  3660
tatgaacagg agccttcttc gatatgtata ttggtgaccc cccagtttca gtggagacta  3720
aacaagacat tgcgcaaaat gtggctggac tcataagaag atgctaggga aacgggaaaa  3780
ctaaatcgaa gaacctggaa ttatttcatt catctataca aggagaggac atataaacag  3840
aaaggaagcc aggagaggat cgattgtatt tatagtggta gactgtcttt gtaagctata  3900
aacataaagc atatgcttgg caaaggcctc catgcctttc atatggtttg gcatctttgc  3960
catttcctgg ctgctggcg tgctgtatca tgtcgacaaa tatatgatac agtaaaaagt  4020
tgtacaacaa gagcatgttt ctgtgcccca agtgaaaaat gacggggttc agctttgttc  4080
atacagat                                                            4088

SEQ ID NO: 60           moltype = DNA  length = 15155
FEATURE                 Location/Qualifiers
source                  1..15155
                        mol_type = other DNA
                        organism = Zea mays
SEQUENCE: 60
acagctctcg tcacgacaga taaggccatg tgcatccttc gccactcacc agcgctctcc   60
agtccacttc acttcatccc tgatcggcga tcgcgtcgag cgagcagcgc tataacgcac  120
gatgaacttg gcgtccgtcg ttccctgcgc gcaggcattc ctcgcgttaa tgactcccgc  180
cgctggctcc caccgtcggg tccacacgca tgcggcggcc tccaagagcg gattggcctg  240
ccgcgtcgcg cgcagcgggg gcacccggtg gctgccggtc tcctgtgcag gcgggggcgg  300
tgcaggttag ggtccgtgtg acttgtctat ttatgtttgc tgcaagtttt ggttcccaat  360
tttccttcca gttcgaactt gaggtagaaa aattagattc gagtagttgg tgatgcagca  420
tgggaggaat ttgcttggtg aggggcttgg agtactcttg gggagatag gcgttcgctt  480
catgcttatc caacagagtg agtcatcaaa tcagatctaa gttcttgaat aaactggtac  540
aatttccagt ggtctccaatt ctttcatcta cgatgagcac taatagttga gaaagaacat  600
gccaattcat atcccggttc atacctgctc ccgatatcta ttatcgagga tacttgctct  660
tttacacgac gggtaacagc agttctcatc ctctcttatg gattctactt gcttctgttc  720
catgtttagc atcgctggcc cgagtgttat tcctgttgtc caaatctttt gagccttact  780
gctacagggt gtgctgaact ttgattctat ccatcataat caaaaagggg aaaaggtgat  840
gtctgcactt tctagtttct ggaaaagaac tctttatgct gtcctttatt atgaaataag  900
tgtaggttga aactcatata tttagttttt tgccactaag attaactgtg tgggaagtta  960
ttatttggaa tatttaaatt catggaaat taaaataaac aaataaaact tatttactca 1020
ctaggaaaat cattttttagg gtgttacatc agtagatcca tacagaacaa tccggtaagg 1080
agaagcagca atactgggtg cagttgcatt agggtttgtt gaacaaaggt ttccagtagt 1140
agtttgcaat ccccaggcag aaaatatggt ggaatagcaa ctgatctgca actagcttat 1200
cagccactat tgggaatccc accggcgaac ctgcaggttg tcactgggga gagcacct   1260
gcagcgctct atgtgtagcc aaagaatgta aggatgcagc ttggtccaca gtagtaaaac 1320
caaactttgt tggcactaaa aaacaagtgg attgagcagc ttgaaaagga gaattattca 1380
gcttcctcta ttgtgctgaa ctgacttctg aagcactatt tttgctgca agtgcagtta 1440
taaggaaagg tgttactgct atgcattggt gctggacctc atgatgaagc attgtgctca 1500
ttctgtttag gttctgaact tttgtgtttc tttcacaggc agtgaagacc attattgtca 1560
gtcttgtctt gtgccccatt gctataatca tcttttttcat tgggatcaat ctcaataggt 1620
gggatggctt gtataaattc gtcaacctct aaagtgaaag ttatgtcata acccaccttg 1680
atcagtggta cacgggaatt gttccatatt caacactgtg catgtcaaca tcttgggctg 1740
```

```
caccaaccac aattcccact acccaaaaag ctaggtgctg gcgccaagca aagagcttgc   1800
ctgaaatatg gatctggatg accaagtgca atagaaatag ttttagggtg gagaaatgat   1860
tgggactgat acctgatcta tattttccc ttttgtgtgc acacatctta gctagcaatg   1920
catgtatttt ataaacttc tgttgctcct taatatcagg ttggtcgtac cacagtcaaa   1980
tctacagaag acctgattct tggcgttccc ttgataactg tcaatctgtt ggacttgtac   2040
ttaagtctca tgtatacaca attatacata tgaatatgtt gtaagttgtg attagtcgat   2100
taggagtctt acattgaaaa ttttacatcc agtcatctag ctgcaaagct tgctatctta   2160
gcttttgaag ctttagaaaa aagattgtta gataaactgt ctgtcccaag ttcgcttgtc   2220
atgatatatt ttttcttca aatgtgtttg agtttttct ctagaatatt tactattaca   2280
atgactcaac ccatctttct ctgtagttgg tgacactttt gttactgagg acactacaaa   2340
tgtgatgttt cctcgggaag taacagttcc aggctataca cacccattgg ttgcagttgg   2400
cacaggtatt tttcactgtc atgtcactgt caaactaaat tccatattgt tctgtcacca   2460
tttttcgta ctggcttttg tggttgagtt ggtctgtgat aacagagggt ttaagttcag   2520
ggtggaaacg agccgagcag tacgtaatgg aaaatagcat cttctagctg taggctgtag   2580
catttgaacg attcaatgag ataataagcc atccagcatg atccaagcac catcaccagt   2640
ccagactcca agtccatagt gcaacataaa acaaaacaga acaacatatg acttgaacaa   2700
aacagagcaa tccagctgta ggcctgtagc acttgataac atccaaacat ccagcaccag   2760
gagcttgctg ctctagcaga ccagcagcat gcaaaaaaca tccaaggtat aagatcagca   2820
gcttgcttgc tgctctagca ccagcagcct gattgcactt gcatagttgc acctgaacaa   2880
gaaaacgacc acacataagc atcttactag ccataaataa gtattgaata aaagtaataa   2940
attgcaatgt atattaccag ttgctctcca caaaacttat tggaaacgaa agtctccata   3000
tcatcctcat catgtacttg ttgaaaaaac ttacaaactt caatcaaaat ctgaaaaaaa   3060
tgagaaacca tctctaagaa atagtaaaat accaacttac cacatatgtc atgcttccat   3120
catcttggct gataaagaag agaagacaac atgagtctca aatcaaatca ttatatctaa   3180
aattgtaaga tctctaaatg tggtgataaa atctagttac cattaccact taccaacatc   3240
cctaatcagg tctcacggaa aacaaataat tttggcactg aacttcgcag gaaaaagtag   3300
catctacttg gccgattagg tctcacaaaa gaaacatgtt cacacataag actatgcgag   3360
ggacaacttg catgaactgt gagcaggttg gtttgaatca atagataaac taaatgggtt   3420
agctactcca tagtcctcca ctggtacggt acgcgaacgt ggtagtggta cttactggct   3480
agtggcggag gccggacgcg agtggcagta gccgacagat gaggcctaca ggctgcttct   3540
tgcggatgat ggaggtcgga ggaggctgat ggaagatgt cggaggaggc cgacctgaca   3600
cgcgagcgcg acgacggagg tcggactcgg aggggtcagc gacgtaggcg caggcgcgta   3660
gcgccgcaag cctgcaacgg tgtgaagcta cggtggcggg tggcgggcga cgtgacgatg   3720
tcagtggaac gggcgaacgt tgaacaatgt tattcagttg tgcgtgtgcc tgtgcctgat   3780
aaaattaggg tttaaggatt taggtgacct ggctgctctt attgggcctc aacacgcgca   3840
tctgggttgg gccgttggca ttccatttct gctattgggc cgttgccaag ttctggaacc   3900
atgtatcgcc atgatcgagg cacaatacat gaggaaccct tggatggcac tgacattgac   3960
cctataactt gcagatcatc atgccccggt tttgcttcat catcctgttt gtagtgttta   4020
gcaatctctc ttgtagtgtt tggacacttg acaatgtctc cataccacc tgctaaatgt   4080
tgtttcaccc tcttgattcc tccttttatc tgtttggggg cacaaagcac attgaatcag   4140
ctcttgcttt cctgcctcaa cataatatgc atatttccat cctagatcat ttgactttgg   4200
ccttcgtgac tgatctttta gtggatcata ggattcatta ctttgacggc caggcagtga   4260
ctcactattg gttgccattg aaattattca gagcctaaca cattgattca gtgtgattgt   4320
gagaaaatgc caagtgctaa ctgctgggtg cagagcagct gagtaggatg atgcaacct   4380
tgattcataa tctcagatgg ccagatcact taccaaacag agcatgcagt gggtgattc   4440
attgtcttca ctcttgccca ggaagtctgg aacttgatgt ttgcaagtga cgttggctgc   4500
tagaggagct ggcgagcgac attagaggtg ttcgacgctg gaggagggag gcgggcgctc   4560
gagcgctgga ggaggcggtc aacgctattg cggagcgtca tggtggcgtc gtgtcggacc   4620
tgatgacgct ggacgaggga ggaggggcgg aggagaggag ggaggcagtc gaggttggac   4680
ggctggacgc tggagcgggt ggtgctagag gagaggaggg agccgtgcgg cgatgctagt   4740
aggcaatgga cggctggagc aggggcgggt gatgctggag gagaggaggg taggtgggaa   4800
tggataactg gagctgacga cattggagta gaggagggat gcgggcgacg acgctagcag   4860
gagctagagg agaggaggga ggcagacgac gctgcactgg gaggagactg tcttgaccta   4920
gtattttttg ggcctttaag aggcccaata acataaaacg ttataaatgc atctaaagcg   4980
tccaaaaacg tttaaaaggc gcgaaatgga cgtttaaacg tgtttcacga atgttctacg   5040
tgatttggtt aaaacgtctg gacgttctac actttaatca cattttagcg tttaatcaca   5100
tttcttgcca ggttcgtcat gatggctatg gtgatatatt tagctatggc ggttgagctt   5160
ccaccttggg cacttaaggc ttggataagg tgagatgtgt ttttctatag agaaggcgta   5220
aagatgctag aggtggttac tatctgcttg ctttggccaa agcgatgaga ccctcgattt   5280
gggaggtttg gggatccatg acctcaagat gctatcctgg tctttgagaa ttaggtgact   5340
ttggtgaagg aaaacgcaac cagataagcc atgtgcaact tttccgattc agatcaatag   5400
ccatgtttag agcctctttg atgcagctat ggagtctgtg gtgggagatg gatgcaacac   5460
tcttctagac agataattgg ctacatgcca agtcaattgc ttggttggca ccttatatca   5520
tggggcggt ttccagaagg ttcgaatcca agctagct ctgtgaggct ttgcaagatc   5580
agaggaacgc taagtgtgac ggccctggct gaatttctag acgtgctcgg tgttctggag   5640
gatgtgaatt gactaaagat actcatgaca cccacagatg taagtttgca gcttctggac   5700
agtactctgc aaagtccgct tatgaaacct tacttcattg gatcaacttt tttctaggac   5760
tgggatatac tatggaagag ttgggcaccg agaaagtgtc aattcttatg gctagctctc   5820
catgatcaat gctggacagt agacacggtg acaaggagga atttgtccca tccagagtgc   5880
tttgttttat gtgatcaaga agaggagaat atccatcact tgttgattag atgtgtcttc   5940
tctagacaac ctggttccac ttccttatgt ctattggcct ggccatcctc gcgccacaag   6000
ggcaggataa tagttttggt gggtggtggg tcaagatcga caaatgggag ccttcaacct   6060
taaaaaggtg tgaattcctt ggtaatccta ggctcttgga ttatttggaa acaaagagat   6120
gagatattt tcaatgggac cacaatgagt atccaaagga tcttgcccg gattgaggag   6180
gctcatctgt ggtgtcttgt aggagccaaa gagctagccc gcctaccgtg agcactgcta   6240
gcctcttaag tgtttgggga tgtttgggga ctccgctgct gccagtggga tgtttgggga   6300
ggcggggctg gaggttgtgg ggtggggct accccaggga gtgcggctcc cggtgttgtg   6360
gttccggtcg gggttcctca gtcgactgga ggccgaatcc tgagcctctc tgtccacatc   6420
catctctctt ccttccgttc ggccggttgg tgactggatc cgtgcggcaa gacgtgtggt   6480
```

```
gggggtccc ctggcaaaag ccatgctcgc ttgcgggtgg acggcagtta cgcctgtggg    6540
cgctgctcct acccttttgt gggtgccgtc catggaatct ctgtcccatc gtgtggatgt    6600
cctcgtctcg gtcgtctcag ggttttgtcg tgtggatgtc atgctgggtt ggtgcgtcgg    6660
tggatgacag aaagtggcaa cgtgtgtcgg cttcgtgggg tgacatcggt ggtggctatc    6720
cctgcagccc tctccatggt actggcgatc gcagctactc ctgtgggtct tcggaggaaa    6780
ctttgtctga attatcctag acgggcggca attcggcgtt gttctccttc cttgaaggca    6840
ctgtccagaa gaccttcatt ttgcgtggtt gtcggcaaag tggaggcctt tcgtcattcc    6900
gcttgtctcg gtggtgtttg ggcctttgtc gctccgggca tctgcttgct cccggtgctc    6960
ggcgctatgg cttcaagctc gttggtgaag aatcggagct gcctcgcatg gggtgtgtcg    7020
aggcttggca acgatgcgc accgcaggct tcacccatgt gtgtcggtgt ttgggtgtag    7080
acgtcatcga gttcctttgg ccatgtgctg cccgtcttgg gaagtcggaa ctgctcgtac    7140
attgtgttga gcttggcaac gatgattcta gatggggttt gtgtgtgggg ctaccgttgg    7200
tagtgtttct agtcctacca gggatctgcc gaagggagta tgggtgaggg gaggtgccat    7260
gtggggccgg acctacaaca gacttaggcg cgcccgcgac gtaggcgatg cgtccgagcg    7320
cacagaccac aagggggcac caatagccag gggctgatta ggagtcgatt tggataagtc    7380
tagagaataa gatttagatg agagaattga ggagagttag ttagttagat aagtccaaga    7440
ttagatgaga gttttttagga agagtttggtt agcaacaggg ctatatgtaa gccgcatggc    7500
agcaaggaat aatcaagtaa tttgttaccct gtttaattcc ctctctaccag tttctaacaa    7560
gcctgcgaca gaggtgatta acctcgccgg agaagacgga ccaagactac aatctccgta    7620
gtcgagagcc agctaccccta gggactgacg cccttgacaa cctggtatcg cgatcccgac    7680
gatcctccta cgctcgcaca tcctgccccac taccagccgc cgcccactct ccaccattcg    7740
ccgcctcggt gacattgccg ggacacctcg gtaccatggg ggagacctc aagtccacct    7800
tggaaacact catggccaac atgcagacac tacagtccgt tgtccaggcg aatgttgtag    7860
caatccaggc cctggccgat cgctcatcat cgtcctccaa cgggtctcgc tcgaacatgg    7920
gcgaacacca tactgatcgt tcaccgcggt tccagaaaat ggattttccc cgttacgacg    7980
acaagtccaa ccctcatctt catcagccac tgcgaatcgt actttcatca gcagcgcatc    8040
atggaggaag aaaaggtttg gatggcctca tacaacctgg aggaaggcgc tcagatgtgg    8100
tacatccaaa tccagcagga cgagggcgg attcccacat ggcgccgttt caaggtcctc    8160
ctcaacctcc gctacgggtc gctgctctgt tctgccccgc tgtttgaact cgccgactcc    8220
cggcgcacag gtacggtcac cgaataccag gaccgttttcc aggcacttct acctcgggcg    8280
gggccactgc aggagatcta gagggtgcag ctgttcatgg gcgggctggg acctccgctc    8340
agccacactg tgcgcatcca caacccgcag tcgctcgcgg ttgccatgag tctggcgcga    8400
cagatcgagt aaatggagct gtccacgccg gccttcacca atgttgcgcg ccacgccatt    8460
ctgccgaccc ctccaccacg cctccctgcg gccacagacc accgggcagc tacaccaact    8520
gccacggtgg tcgggcaacc ggtgaagcgt ctatcacgac cggacgcagga ggagcgccgt    8580
cgtttgggcc tgcgcttcaa ctacaacaag aaatatatgt gggggcacaa ccgcacttgc    8640
aagcgactct tctacgtcca tggcgtggac atcgacgaca ccactgaggc agagactcat    8700
gtcttctccc tgcacgcatt ggcaggcgtc cgcttcggcg acaccatgca ggtcgccgtc    8760
aagttgggag cctcccctct tctggcgttc cttgactcca ggttgaccca tgacttcatc    8820
tccgagtccg cagccagacg taccggcctg cctctccaaa gccagccgtg acttacgggg    8880
actgtgcgca atgcgaacg cgtcacctgc gttccgaatt caccatccac gacgcaacct    8940
tccacaccga tttgttttgtg atgacccctta caggttttga catggtgttg ggcactcgct    9000
ggctggcac gttggggccg gtcctctagg attttgcagc ccggaaactg acgttctatc    9060
ggcagggcca accaatttgc gccaccatcc ttactggacg agctacttgc gcccttcgcc    9120
ggcgtcttct ctgaaccacg ggggcttcca ccgatacgct cccacgacca cgcatcactc    9180
tcgtccacgg ctcggagccg gtcgcggtgc gcccctaccg ctacccagcg tcccacaagg    9240
atgagctgga gcgacagtgc actgccatgc tcgagcaagg gctcgttcgc cggagctcct    9300
tggcgttctc ctcactcgtc atccttgtta agaaaccaga tggctcgtgg aggttttgcg    9360
tcgattaccg cgccttgaac gccatcgctg tcaaggatgc ttttcccatc cccgtcgtgg    9420
acgagctcct cgatgaactc cacggcgcca agttcttcac caaacttgac ctgcgtgcgg    9480
gctatcatca agtccgcatg cgtccagctg acatcaacaa gacgacgttc cgtacccacg    9540
acaacttcta cgaatttcta gtgatgtcgt tcggcctgtg caatgcgccg cgacgttcc    9600
aggcattaat gatgatgtgc tacgactgtt cctgcgccgt ttcgtgctgg tattttttac    9660
gacatttga tctaaatgcg tcatgggtgg accatcttcg acgtcttcgg gccatcctca    9720
cggtgctgca gcaacacctc ctcttcgcca agcgctccaa atgcacgttc ggtgagcgct    9780
ccatcgccta tctggggcac gtcatctccg acgccggcgt cgccatggat cccgccaagg    9840
tgcaggcggt ggctgattgg cccaaacccc ggcccgcgcg ggctacacgg gggttcttgg    9900
gtcttgcggg ctactaccgc aagttcgtcc acgactacgg catgattgcg gccccactga    9960
ccgcgatgtt gaagaaggac gacttcatgt ggaacgacgc cgccgccgcg gcttccacgg    10020
ccctcaaagt cgcggtgaac tccgctccag tcttggcgct tcccgacttc acgcgcccgt    10080
tcgtggtgga gtgcgatgca tcaacctacg ggctacgact ttggggcggt attgacccag    10140
gacaagcacc ccattgcata cttcagccgg ccgatggctc cctggcaccg atccctagct    10200
gcctatgagc gggaactcat cggtcttgtg caagccattc gacattggcg gccgtacttg    10260
tggggccggc gtttcacggt gtggacagac cactacattc ttaaattct acttgatcaa    10320
cgcctcgcca cgatcccgca acatcattgg gtcgacaatt ttcttggctt cgacttcgcc    10380
gtcgaatata aacccgacgc cctcaacatg tggtggatg ccctctcccg tcgcgacaca    10440
ggaggctaac agaggcacgg ttctcgttat ctccgcaccg cgcttcgact tcatcacacg    10500
tctccacgac gtttaggcct gcgaggagtt ggctgcggga tctcgatcgg ccccatgggc    10560
tctcactgac gacttggtga cctatgacgg tcggctgtac gtgccaccga catcgtcgct    10620
cctacaggag ctggtggcgg cagtacatga gtacggccac aaaggggtgc agcgcacctt    10680
gcatcgtctt cgccgagact ttcacttccc cgacatgcgt cgcgtgcgcg tcgttcagga    10740
ttttgtgcgc tttcgccaca tgccaaaggt acaaatcgga gcacctacat ccagcgggcc    10800
tccttccgct acccgtacca acagctgcct gggcgggcat tggcttcgtg gaagcactgc    10860
cacgtgttcg gggcaagtcg gtcatcctca cggtggtgga tcgcttcagc aagtactgcc    10920
acttcattcc gcttgcccat ccatatttgg cggaatcagt ggccaggcg ttcttcaccg    10980
acattgtccg ctgggatgcc gcagtccatg gtgtccgatc gggatcctgt gttcacctcg    11040
acgtttggaa aggagttgat gcgccttatg ggtgccaagc tgcacatgac ttcgacattc    11100
catccacagt ccgacggcca aacagaggct gctaaccgtg ttattaccat gtacctccac    11160
tgttttatag gtgatcgtcc ccgccattgg ctccgatgat taccatgggc tgagtacacg    11220
```

```
tacaacactg cctaccagtc gtccctacga gatacgccct ttagggtggt ctatggccgg  11280
gatcctccgt ccatccggtc gtatgagcct ggagatatgc gagtggccgc tgtggccaag  11340
acgatggaag aacgagaaga gttcttggtc gatgtgcggt acagactgga gcaagcacaa  11400
gctgttcaga agctccacta tgacaaacac caccgccagg tctcctatga agtgggcgac  11460
tgggtcctgc tccgccttcg acaccaccca gttgcctccc tgtcaccggc ggtccaaggc  11520
aagttgcagc caaggtactt cgggccctac cgcatctcca agctcatcaa cgacgtcgtt  11580
gttcgtctgg agttcccacc tcgcgccaag ctccacgacg tctttcattt gggcctgctg  11640
aagaagtgag tgggcgcccc tgcagcagct ccgccatcgc tgcccaacat tcatcatggc  11700
gcggtagagc cggaaccaga cctacgcgcc cgcatggctc gaggcgtccg tcaagtgcta  11760
gtccattgga agggccaatc tgcgtcatca acaacatggg aggacttgga ctgattccac  11820
gataagtacc ccgactttca gctcgaggac gagctgggtc tcgaggggg agggatgtca  11880
tgtgggccg gacctacaac agacttaggc gcgcctgcga cgtgcgcagg gcggccgagc  11940
gcacagacca caagggggcg ccaacagcca ggggctgatt aggagtcgat ttggataagt  12000
ccagagaata agatttagat gagagaattg aggagagtta gttagttaga taagtccaag  12060
attagatgag agttttaagg aagagttggt tagcaatagg gctatatgta agccacatgg  12120
cagcaaggaa taatcaagta atttgctacc tgtttaattc cctcttccca gtttctaaca  12180
agcctgcggt agaggtgatt aacctcgccg agaagacga ccgagactac aatctccgta  12240
gttgagactt agctacccta ggggcgacg cccttgatag gaggagcaag ccgggctact  12300
gcctagaggt ggtgctggtg gctgcctctt gggcgtcgta gtcacaggga acgacgcaca  12360
gggatgtgga ttccagctcc cgtgaggaag ctggcagaag atatctgcta ttgcttgcct  12420
tctcttgatt acaaagtcct aattatatag gcctaaggcc aaccgaccac tctacaatac  12480
taagagactt atccaactaa actactccat aatattagga gataaattgc taagacttat  12540
ccaactaaac tgattactta tctcctgatc tcttgtgcct accctggtgg gtctagtcgc  12600
cttctagtac accaggccgg tcataacaac tgttgtatgg gttgtttgag ggggccttt  12660
gccggtttct ctgtcgtgca ctttgtgtag gttttgggcc cagttgttcc ttaaaactgg  12720
tccaattcta ttcttcttaa ttgagaagca tagctcctgc cattacgcta aaaaaattga  12780
agtatttcag gaactcaaca agccactttg ctagtctcct gaggttacta cagccagggc  12840
accatagttc gagccttggt agacacgata ctaactattt gccttcaata aaagctaaga  12900
tgagttgaaa cttgaaacta acaaaaaaat cgaagtattt tggaaagcat ttttgtgcg  12960
catatgttat gctgggatgg taatgccagt gctgtgctgc atcaggattc aggtgccata  13020
ttggcgctgc tggaacctga ggtggatcgg tgcagcaagg agcccaaaat actaaatagt  13080
ttctcaagct agtttgatta ggtttgttgg attgcttaac cagttaaacc tcacttaggg  13140
tatcaagctt atttggtaga atagatgagc tctaactaaa aggaaactcc ataatggcat  13200
attcttaaga aactaggaaa gaagtcagaa gcctcctttc attttttgata gtcatctctc  13260
tcttttggcca agctgactca agctaaaatt tgtagggaaa acccaatagc agccagggaa  13320
acctcaaagt taaatattgt tctcctggta tcaggagtgc aagatagata tataagtaaa  13380
attatgtttt cggacttaat tttaatgtct attattaatc atagttcgca aattgactt  13440
tagctcactt ttaggttaca gagaaaagtt ttttgtcaaa gtatatgctg ccgcgttcta  13500
tgtagattac tcacttcgcc ttgatactga gcaatgaaa gcaaagactg gtattgagag  13560
ctttgacagt tcctctgttt tcgactccat ttttaagggt aagacataac tatcaattcc  13620
aaatttaagg aatcgtaata tgtgctaata tcacaagttt attttgcagc accggttgtg  13680
aaatcattga gtataattct tgttagagcc gttgatggca agacctttgt gaatgctcta  13740
aatgatgtca ttgcccgcca aataaaaaac ccaaacgccg aggaagaatc ttccctgtca  13800
accttgcaga atacctttct tgggcgcaat ctcaaacagg gaacaagcat atacttaact  13860
tggcttgaac ccaaaagaat gctggtcagt cactgtcaat actgtgaatc ttatgaatct  13920
tcgatgctgt ttcatccctc aaagttgaat attgatttta taaactattt agaaataaca  13980
aacttatccc acaatgaata cgcttccatc gtacaagaac tagcaatgct tctttagga  14040
catgatactc caaggttgct cactttttc tgtactgata cttctgtcag atcattagcc  14100
aatgtgctgc atttcgtggt aatgaggcta atgccgtcac ctcaacata gaaaacagtg  14160
gaattcaaac agtaaagatg gcagtagagg gggttagatt gtataggatt aaatggaagt  14220
gacctgccaa cttctctccg tcatgtaaat ttgcctacat tacctggaga ataaaagctg  14280
gcatgcattg accatttctt gttttagttc actagtggca caagaactga caacttgcac  14340
aaataagaaa aggcacacac agacacagtg tgacaccttt tttatccaaa gaaaaaaaaa  14400
acaaaatatg tacttactac taggatgaa atcttattgg tttaactgac tagagcaaac  14460
ttttctgaat tgtagacctt aaagctttag ttgaggttga caagaagctt gaattgcatc  14520
aaagattga cagtaaagct ggaattctgt ttgttagcca gatttccttt tatctactga  14580
tggatttatt caaatttga atattaac attaaatttt attttgttag ttacggaaca  14640
gaatgatcat tgcattctgg aaaaattaa caagtttgtg cataaataaa agtataaaaaa  14700
gggggcttgt agagatttac gtagagaggg agctcaattt gaatgctgtt aacttttatt  14760
gtgtagatct ccatttcgga agatgaagat ccacgtcaag ttgatgcaga gatcaaatct  14820
gctactgtta attatgctct atatgatggc ttctttggta aatccacagt gtgcccttct  14880
ttaagatcat ctacagccca gttgctggac gcgcttctgc ttgcgaagtg acaaaccagt  14940
cgtggttcca tatcaatggt tacgagtggt tattcccttc tcccttgttt tcccgaggga  15000
acacaggacg ggctaggtgt ccataatcat aagtcccata aaggaaatta atttaattat  15060
tatagagttc atatgtaaca tttttgtcgt ccctgatgaa atatggtgaa tttgtcacgc  15120
ccctatgctg atattatgat tggcagattg cttta              15155
```

SEQ ID NO: 61     moltype = DNA   length = 15155
FEATURE             Location/Qualifiers
source              1..15155
                     mol_type = other DNA
                     organism = Zea mays
SEQUENCE: 61

```
acagctctcg tcacgacaga taaggccatg tgcatccttc gccactcacc agcgctctcc    60
agtccacttc acttcatccc tgatcggcga tcgcgtcgag cgagcagcgc tataacgcac   120
gatgaacttg gcgtccgtcg ttccctgcgc gcaggcattc ctcgcgttaa tgactcccgc   180
cgctggctcc caccgtcggg tccacacgca tgcggcggcc tccaagagcg gattggcctg   240
ccgcgtcgcg cgcagcgggg gcaccccgtg gctgccggtc tcctgtgcag ccggggcgg   300
tgcaggttag ggtccgtgtg acttgtctat ttatgtttgc tgcaagtttt ggttcccaat   360
```

```
tttccttcca gttcgaactt gaggtagaaa aattagattc gagtagttgg tgatgcagca   420
tgggaggaat ttgcttggtg aggggcttgg agtactcttg ggggagatag gcgttcgctt   480
catgcttatc aacagagtg agtcatcaaa tcagatctaa gttcttgaat aaactggtgc   540
aatttccagt ggtctcaatt ctttcatcta cgatgagcac taatagttga gaagaacat   600
gccaattcat atcccggttc atacctgctc ccgatatcta ttatcgagga tacttgctct   660
tttacacgac gggtaacagc agttctcatc ctctccttatg gattctactt gcttctgttc   720
catgttagc atcgctggcc cgagtgttat tcctgttgtc caaaatcttt gagccttact   780
gctacagggt gtgctgaact ttgattctat ccatcataat caaaaggggg aaaaggtgat   840
gtctgcactt tctagtttct ggaaaagaac tcttttatgct gtcctttatt atgaaataag   900
tgtaggttga aactcatata tttagttttt tgccactaag attaactgtg tgggaagtta   960
ttatttggaa tatttaaatt catgggaaat taaaataaac aaataaaact tatttactca  1020
ctaggaaaat catttttagg gtgttacatc agtagatcca tacagaacaa tccggtaagg  1080
agaagcagca atactgggtg cagttgcatt agggtttgtt gaacaaaggt ttccagtagt  1140
agtttgcaat ccccaggcag aaaatatggt ggaatagcaa ctgatctgca actagcttat  1200
cagccactat tgggaatccc accggcgaac ctgcaggttg tcactgggga gagagccct  1260
gcagcgctct atgtgtagcc aaagaatgta aggatgcagc ttggtccaca gtagtaaaac  1320
caaactttgt tggcactaaa aaacaagtgg attgagcagc ttgaaaagga gaattattca  1380
gcttcctcta ttgtgctgaa ctgacttctg aagcactatt ttttgctgca agtgcagtta  1440
taaggaaagg tgttactgct atgcattggt gctggacctc atgatgaagc attgtgctca  1500
ttctgtttag gttctgaact tttgtgtttc tttcacaggc agtgaagacc attattgtca  1560
gtcttgtctt gtgccccatt gctataatca tcttttttcat tgggatcaat ctcaataggt  1620
gggatgcctt gtataaaattc gtcaacctct aaagtgaaaa ttatgtcata acccaccttg  1680
atcagtggta cacggaatt gttccatatt caacactgtg catgtcaaca tcttgggctg  1740
caccaaccac aattcccact accccaaaaag ctaggtgctg cgccaagca aagagcttgc  1800
ctgaaatatg gatctggatg accaagtgca atagaaatag ttttagggtg gagaaatgat  1860
tgggactgat acctgatcta tattttttccc tttttgtgtgc acacatctta gctagcaatg  1920
catgtatttt atataaactttc tgttgctcct taatatcagg ttggtcgtac cacagtcaaa  1980
tctacagaag acctgattct tggcgttccc ttgataactg tcaatctgtt ggacttgtac  2040
ttaagtctca tgtatacaca attatacata tgaatatgtt gtaagttgtg attagtcgat  2100
taggagtctt acattgaaaa tttttacatcc agtcatctag ctgcaaagct tgctatctta  2160
gcttttgaag ctttagaaaa aagattgtta gataaactgt ctgtcccaag ttcgcttgtc  2220
atgatatatt ttttcttca aatgtgtttg agtttttct ctagaatatt tactattaca  2280
atgactcaac ccatctttct ctgtagttgg tgacactttt gttactgagg acactacaaa  2340
tgtgatgttt cctcgggaag taacagttcc aggctataca cacccattgg ttgcagttgg  2400
cacaggtatt tttcactgtc atgtcactgt caaactaaat tccatattgt tctgtcacca  2460
tttttttcgta ctggcttttg tggttgagtt ggtctgtgat aacagagggt ttaagttcag  2520
ggtggaaacg agccgagcag tacgtaatgg aaaatagcat cttctagctg taggctgtag  2580
catttgaacg attcaatgag ataataagcc atccagcatg atccaagcac catcaccagt  2640
ccagactcca agtccatagt gcaacataaa acaaaacaga acaacatatg acttgaacaa  2700
aacagagcaa tccagctgta ggcctgtagc acttgataac atccaaacat ccagcaccag  2760
gagcttgctg ctctagcaga ccagcagcat gcaaaaaaca tccaaggtat aagatcagca  2820
gcttgcttgc tgctctagca ccagcagcct gattgcactt gcatagttgc acctgaacaa  2880
gaaaacgacc acacataagc atcttactag ccataaataa gtattgaata aaagtaataa  2940
attgcaatgt atattaccag ttgctctcca caaaacttat tggaaacgaa agtctccata  3000
tcatcctcat catgtacttg ttgaaaaaac ttacaaactt caatcaaaat ctgaaaaaaa  3060
tgagaaacca tctctaagaa atagtaaaat accaacttac cacatatgtc atgcttccat  3120
catcttggct gataaagaag agaagacaat agagtctca aatcaaatca ttatatctaa  3180
aattgtaaga tctctaaatg tggtgataaa atctagttac cattaccact taccaacatc  3240
cctaatcagg tctcacggaa aacaaataat tttggcactg aacttcgcag gaaaaagtag  3300
catctacttg gccgattagg tctcacaaaa gaaacatgtt cacacataag actatgcgag  3360
ggacaacttg catgaactgt gagcaggttg gtttgaatca atagataaac taaatgggtt  3420
agctactcca tagtcctcca ctggtacggt acgcgaacgt ggtagtggta cttactggct  3480
agtggcggag gccggacgcg agtggcagta gccgacagat gaggcctacg ggctgcttct  3540
tgcggatgat ggaggtcgga ggaggctgat ggaagatgtt cggaggaggc cgacctgaca  3600
cgcgagcgcg acgacggagg tcggactcgg aggggtcagc gacgtaggca caggcgcgta  3660
gcgccgcaag cctgcaacgg tgtgaagcta cggtggcggg tggcgggcga cgtgacgatg  3720
tcagtggaac gggcgaacgt tgaacaatgt tattcagttg tgcgtgtgcc tgtgcctgat  3780
aaaattaggg tttaaggatt taggtgacct ggctgctctt attgggcctc aacacgcgca  3840
tctgggttgg gccgttggca ttccatttct gctattgggc cgttgccaag ttctggaacc  3900
atgtatcgcc atgatcgagg cacaatacat gaggaaccct ttgatggcac tgacattgac  3960
cctataactt gcagatcatc atgccccggt tttgcttcat catcctgttt gtagtgttta  4020
gcaatctctc ttgtagtgtt tggacacttg acaatgtctc cataccccacc tgctaaatgt  4080
tgtttcaccc tcttgattcc tccttttatc tgtttggggg cacaaagcac attgaatcag  4140
ctctttgcttt cctgcctcaa cataaatagc atattttccat cctagatcat ttgacttttgg  4200
ccttcgtgac tgatctttta gtggatcata ggattcatta ctttgacggc caggcagtga  4260
ctcactattg gttgccattg aaattattca gagcctaaaa cattgattca gtgtgattgt  4320
gagaaaatgc caagtgctaa ctgctgggtg cagagcagct gagtaggatg atgacaacct  4380
tgattcataa tctcagatgg ccagatcact taccaaacag agcatgcagt tgggtgattc  4440
attgtcttca ctccttgccca ggaagtctgg aacttgatgt ttgcaagtga cgttggctgc  4500
tagaggagct ggcgagcgac attagaggtg ttcgacgctg gaggagggag gcgggcgctc  4560
gagcgctgga ggaggcggtc aacgctattg cggagcgtca tggtggcgtc gtgtcggacc  4620
tgatgacgct ggacgaggga ggaggggcgg aggagaggag ggaggcagtc gaggttggac  4680
ggctggacgc tggagcgggt ggtgctagag gagaggaggg agccgtgcgg cgatgctagt  4740
aggcaatgga cggctggagc aggggcgggt gatgctggag ggaggggga taggtggaga  4800
tggataactg gagctgacga cattggagta gaggagggat gcgggcgacg acgctagcag  4860
gagctagagg agaggaggga ggcagacgac gctgcactgg gaggagactg tcttgaccta  4920
gtatttttg ggcctttaag aggcccaata acataaaacg ttataaatgc atctaaagcg  4980
tccaaaaacg tttaaaggc gcgaaatgga cgttaaacg tgtttcacga atgttctacg  5040
tgatttggtt aaaacgtctg gacgttctac actttaatca cattttagcg tttaatcaca  5100
```

```
tttcttgcca ggttcgtcat gatggctatg gtgatatatt tagctatggc ggttgagctt   5160
ccaccttggg cacttaaggc ttggataagg tgagatgtgg ttttctatag agaaggcgta   5220
aagatgctag aggtggttac tatctgcttg cttggcccaa agcgatgaga ccctcgattt   5280
gggaggtttg gggatccatg acctcaagat gctatcctgg tctttgagaa ttaggtgact   5340
ttggtgaagg aaaacgcaac cagataagcc atgtgcaact tttccgattc agatcaatag   5400
ccatgtttag agcctctttg atgcagctat ggagtctgtg gtgggagatg gatgcaacac   5460
tcttctagac agataattgg ctacatggca agtcaattgc ttggttggca ccttatatca   5520
tgggggcggt ttccagaagg ttcgaatcca agcgtactgt ctgtgaggct ttgcaagatc   5580
agaggaacgc taagtgtgac ggccctggct gaatttctag acgtgctcgg tgttctggag   5640
gatgtgaatt gactaaagat actcatgaca cccacagatg taagtttgca gcttcttgga   5700
agtactctgc aaagtccgct tatgaaacct tacttcattg gatcaacttt tttctaggac   5760
tgggatatac tatggaagag ttgggcaccg agaaagtgtc aattcttatg ctagctctc    5820
catgatcaat gctggacagt agacacggtg acaaggagga atttgtccca tccagagtgc   5880
tttgttttat gtgatcaaga agaggagaat atccatcact tgttgattag atgtgtcttc   5940
tctagacaac ctggttccac ttccttatgt ctattggcct ggccatcctc gcgccacaag   6000
ggcaggataa tagttttggt gggtggtggg tcaagatcga caaatgggag ccttcaacct   6060
taaaaaggtg tgaattcctt ggtaatccta ggctcttgga ttatttggaa acaaagagat   6120
gagatagttt tcaatgggac cacaatgagt atccaaagga ctcttgcccg gattgaggag   6180
gctcatctgt ggtgtcttgt aggagccaaa gagctagccc gcctaccgt agcactgcta    6240
gcctcttaag tgtttgggga tgtttgggga ctccgctgct gccagtggga tgtttggga    6300
ggcggggctg gaggttgtgg ggtgggggct acccagga gtgcggctcc cggtgttgtg     6360
gttccgtcg gggttcctca gtcgactgga ggccgaatct tgagcctctc tgtccacatc   6420
catctctctt ccttccgttc ggccggttgg tgactggatc cgtgcggcaa gacgtgtggt   6480
gggggtccc ctggcaaaag ccatgctcgc ttgcgggtgg acggcagtta cgcctgtggg    6540
cgctgctcct acccttttgt gggtgccgtc catgaatctc ctgtcccatc gtgtggatgt   6600
cctcgtctcg gtcgtctcag ggttttgtcg tgtggatgtc atgctgggtt ggtcgtcgg    6660
tggatgacag aaagtggcaa cgtgtgtcgg cttcgtgggg tgacatcggt ggtggctatc   6720
cctgcagccc tctccatggt actggcgatc gcagctactc tactgggtct tcggaggaaa   6780
ctttgtctga attatcctag acgggcggca attcggcgtt gtttctcctt cttgaaggca   6840
ctgtccagaa gaccttcatt ttgcgtggtt gtcggcaaag tggaggcctt tcgtcattcc   6900
gcttgtctcg gtggtgtttg ggcctttgtc gctccgggca tctgcttgct cccggtgctc   6960
ggcgctatgg cttcaagctc gttggtgaag aatcggagct gcctcgcatg gggtgtgtcg   7020
aggcttggca acgatggcgc accgcaggct tcacccatgt gtgtcggtgt ttgggtgtag   7080
acgtcatcga gttcctttgg ccatgtgctg cccgtcttgg gaagtcggaa ctgctcgtac   7140
attgtgttga gcttggcaac gatgattcta gatggggttt gtgtgtgggg ctaccgttgg   7200
tagtgttttct agtcctacca gggatctgcc gaagggagta tgggtgaggg gaggtgccat   7260
gtggggccgg acctacaaca gacttaggcg cgcccgcgac gtgcgtaggg cgtccgagcg   7320
cacagaccac aaggggcac caatagccag gggctgatta ggagtcgatt tggataagtc    7380
tagagaataa gatttagatg agagaattga ggagagttag ttagttagat aagtccaaga   7440
ttagatgaga gttttttagga agagttggtt agcaacaggg ctatatgtaa gccgcatggc   7500
agcaaggaat aatcaagtaa tttgttacct gtttaattcc ctcttaccag tttctaacaa   7560
gcctgcgaca gaggtgatta acctcgccgg agaagacgga ccaagactac aatctccgta   7620
gtcgagagcc agctaccccta gggactgacg ccccttgacaa cctggtatcg cgatcccgac   7680
gatcctccta cgctcgcaca tcctcgccac taccagccgc cgcccactct ccaccattcg   7740
ccgcctcggt gacattgccg cccgccaccg gtaccatggg ggacgacctc aagtccacct   7800
tggaaacact catggccaac atgcagacac tacagtccgt tgtccaggcg aatgttgtag   7860
caatccaggc cctggccgat cgctcatcat cgtcctccaa cgggtctcgc tcgaacatgg   7920
gcgaacacca tactgatcgt tcaccgcggt tccagaaaat ggattttccc cgttacgacg   7980
acaagtccaa ccctcatctt catcagccac tgcgaatcgt actttcatca gcagcgcatc   8040
atggaggaag aaaaggtttg gatggcctca tacaacctgg aggaaggcgc tcagatgtgg   8100
tacatccaaa tccagcagga cgagggcgca atttcccacat ggcgccgttt caaggtcctc   8160
ctcaacctcc gctacgggtc gctgctctgt tctgccccgc tgtttgaact cgccgactcc   8220
cggcgcacag gtacggtcac cgaataccag gaccgtttcc aggcacttct acctcgggcc   8280
gggccactgc aggagatcta gagggtgcag ctgttcatgg gcgggctggg acctccgctc   8340
agccacactg tgcgcatcca caacccgcag tcgctcgcgg ttgccatgag tctggcgcga   8400
cagatcgagt aaaatggagct gtccacgccg gccttcacca atgttgcgcg ccacgccatt   8460
ctgccgaccc ctccaccacg cctccctgcg gccacagcag accgggcagc tacaccaact   8520
gccacgtgtg tcgggcaacc ggtgaagcgt ctatcacgac cggagcagga ggagcgccgt   8580
cgtttgggcc tgcgcttcaa ctacaacaag aaatatatgt ggggggcacaa ccgcacttgc   8640
aagcgactct tctacgtcca tggcgtggac atcgacgaca ccactgaggc agagactcat   8700
gtcttctccc tgcacgcatt ggcaggcgtc gcttcggcg acaccatgca ggtcgccgtc     8760
aagttgggag cctccctct tctggcgttc cttgactcca ggttaccca tgacttcatc      8820
tccgagtccg cagccagacg taccggcctg cctctccaaa gccagccgtg acttacgggg   8880
actgtgcgga atgcgaacg cgtcacctgc gttccgaatt caccatccac gacgcaacct    8940
tccacaccga tttgtttgtg atgacccctta caggttttga catggtgttg ggcactcgtc   9000
ggctggccac gttggggccg gtcctctagg attttggcgc ccggaaactg acgttctatc   9060
ggcagggcca accaatttgc gccaccatcc ttactgacg agctacttgc gcccttcgcc    9120
ggcgtcttct ctgaaccacg ggggcttcca ccgatacgct cccacgacca cgcatcactc   9180
tcgtccacgg ctcggagccg gtccggtgc gccccgaacg ctacccagcg tcccacaagg    9240
atgagctgga gcgacagtgc actgccatgc tcgagcaagg gctcgttcgc cggagctcct   9300
tggcgttctc ctcactcgtc atccttgtta agaaaccaga tggctcgtgg aggttttgcg   9360
tcgattaccg cgccttgaac gccatcgctg tcaaggatgc ttttcccatc cccgtcgtgg   9420
acgagctcct cgatgaactc cacggcgcca agttcttcac caaacttgac ctgcgtgcgg   9480
gctatcatca agtccgcatg cgtccagctg acatcaacaa gacgacgttc cgtacccacg   9540
acaacttcta cgaatttcta gtgatgtcgt tcggcctgtg caatgcgccg cgcgacgttcc   9600
aggcattaat gatgatgtgc tacgactgtt cctcgcgcgt ttcgtgctgg tattttttac   9660
gacatttgga tctaaatgcg tcatgggtgg accatcttcg acgtcttcgg gccatcctca   9720
cggtgctgca gcaacacctc ctcttcgcca agcgctccaa atgcacgttc ggtgagcgct   9780
ccatcgccta tctggggcac gtcatctccg acgccggcgt cgccatggat cccgccaagg   9840
```

```
tgcaggcggt ggctgattgg cccaaacccc ggcccgcgcg ggctatacgg gggttcttgg    9900
gtcttgcggg ctactaccgc aagttcgtcc acgactacgg catgattgcg gccccactga    9960
ccgcgatgtt gaagaaggac gacttcatgt ggaacgacgc cgccgccgcg gctttccagg   10020
ccctcaaagt cgcggtgaac tccgctccag tcttggcgct tcccgacttc acgcgcccgt   10080
tcgtggtgga gtgcgatgca tcaacctacg ggctacgact ttggggcggt attgacccag   10140
gacaagcacc ccattgcata cttcagccgg ccgatggctc cctggcaccg atccctagct   10200
gcctatgagc gggaactcat cggtcttgtg caagccattc gacattggcg gccgtacttg   10260
tggggccgga gtttcacggt gtggacagac cactacatcc ttaaatttct acttgatcaa   10320
cgcctcgcca cgatcccgca acatcattgg gtcgacaatt ttcttggctt cgacttcgcc   10380
gtcgaatata aacccgacgc cctcaacatg gtggtggatg ccctctcccg tcgcgacaca   10440
ggaggctaac agaggcacgg ttctcgttat ctccgcaccg cgcttcgact tcatcacacg   10500
tctccacgac gtttaggcct gcgaggagtt ggctgcggga tctcgatcgg ccccatgggc   10560
tctcactgac gacttggtga cctatgacgg tcggctgtac gtgccaccga catcgtcgct   10620
cctacaggag ctggtggcgg cagtacatga gtacggccac aaagggggtgc agcgcacctt   10680
gcatcgtctt cgccgagact ttcacttccc cgacatgcgt cgcgtgcgcg tcgttcagga   10740
ttttgtgcgc tttcgccaca tgccaaaggt acaaatcgga gcacctacat ccagcgggcc   10800
tccttccgct acccgtacca acagctgcct gggcgggcat tggcttcgtg gaagcactgc   10860
cacgtgttcg gggcaagtcg gtcatcctca cggtggtgga tcgcttcagc aagtactgcc   10920
acttcattcc gcttgcccat ccatatttgg cggaatcagt ggcccaggcg ttcttcaccg   10980
acattgtccg ctgggatgcc gcagtccatg gtgtccgatc gggatcctgt gttcacctcg   11040
acgttttgga aggagttgat gcgccttatg ggtgccaagc tgcacatgac ttcgacattc   11100
catccacagt ccgacggcca aacagaggct gctaaccgta ttattaccat gtacctccac   11160
tgttttatag gtgatcgtcc ccgccattgg ctccgatgat taccatgggc tgagtacacg   11220
tacaacactg cctaccagtc gtccctacga gatacgccct ttagggtggt ctatggccgg   11280
gatcctccgt ccatccggtc gtatgagcct ggagatatgc gagtggccgc tgtggccaag   11340
acgatggaag aacgagaaga gttcttggtc gatgtgcggt acagactgga gcaagcacaa   11400
gctgttcaga agctccacta tgacaaacac caccgccagg tctcctatga agtgggcgac   11460
tgggtcctgc tccgccttcg acaccaccca gttgcctccc tgtcaccggc ggtccaaggc   11520
aagttgcagc caaggtactt cgggccctac cgcatctcca agctcatcaa cgacgtcgtt   11580
gttcgtctgg agttcccacc tcgcgccaag ctccacgacg tctttcattt gggcctgctg   11640
aagaagtgag tgggcgcccc tgcagcagct ccgccatcgc tgcccaacat tcatcatgcc   11700
gcggtagagc cggaaccaga cctacgcgcc cgcatggctc gaggcgtccg tcaagtgcta   11760
gtccattgga agggccaatc tgcgtcatca acaacatggg aggacttgga ctgattccac   11820
gataagtacc ccgactttca gctcgaggac gagctgggtc tcgaggggggg agggatgtca   11880
tgtggggccg gacctacaac agacttaggc gcgcctgcga cgtgcgcagg gcggccgagc   11940
gcacagacca caaggggggcg ccaacagcca ggggctgatt aggagtcgat ttggataagt   12000
ccagagaata agatttagat gagagaattg aggagagtta gttagttaga taagtccaag   12060
attagatgag agttttttagg aagagttggt tagcaatagg gctatatgta agccacatgg   12120
cagcaaggaa taatcaagta atttgctacc tgtttaattc cctcttccca gtttctaaca   12180
agcctgcggt agaggtgatt aacctcgccg gagaagacga ccgagactac aatctccgta   12240
gttgagggcc agctacccta ggggctgacg cccttgatag gaggagcaag ccgggctact   12300
gcctagaggt ggtgctggtg gctgcctctt gggcgtcgta gtcacaggga acgacgcaca   12360
gggatgtgga ttccagctcc cgtgaggaag ctggcagaag atatctgcta ttgcttgcct   12420
tctcttgatt acaaagtcct aattatatag gcctaaggcc aaccgaccac tctacaatac   12480
taagagactt atccaactaa actactccat aatattagga gataaattgc taagacttat   12540
ccaactaaac tgattactta tctcctgatc tcttgtgcct accctggtgg gtctagtcgc   12600
cttctagtac accaggccgg tcataacaac tgttgtatgg gttgtttgag ggggcctttt   12660
gccggtttct ctgtcgtgca ctttgtgtag gttttgggcc cagttgttcc ttaaaactgg   12720
tccaattcta ttcttcttaa ttgagaagca tagctcctgc cattacgcta aaaaaattga   12780
agtatttcag gaactcaaca agccactttg ctagtctcct gaggttacta cagccagggc   12840
accatagttc gagccttggt agacacgata ctaactattt gccttcaata aaagctaaga   12900
tgagttgaaa cttgaaacta acaaaaaaat cgaagtattt tggaaagcat ttttttgtgcg   12960
catatgttat gctgggatgg taatgccagt gctgtgctgc atcaggattc aggtgccata   13020
ttggcgctgc tggaacctga ggtggatcgg tgcagcaagg agcccaaaat actaaatagt   13080
ttctcaagct agtttgatta ggtttgttgg attgcttaac cagttaaacc tcacttaggg   13140
tatcaagctt atttggtaga atagatgagc tctaactaaa aggaaactcc ataatgcat   13200
attcttaaga aactaggaaa gaagtcagaa gcctcctttc atttttgata gtcatctctc   13260
tctttggcca agctgactca agctaaaatt tgtagggaaa acccaatagc agccagggaa   13320
acctcaaagt taaatattgt tctcctggta tcaggagtgc aagataagata tataagtaaa   13380
attatgttt cggacttaat tttaatgtct attattaatc atagttcgca aattgacttt   13440
tagctcactt ttaggttaca gagaaaagtt ttttgtcaaa gtatatgctg ccgcgttcta   13500
tgtagattac tcacttcgcc ttgatactga gcaatgaaaa gcaagactg gtattgagag   13560
ctttgacagt tcctctgttt tcgactccat ttttaagggt aagacataac tatcaattcc   13620
aaatttaagg aatcgtaata tgtgctaata tcacaagttt attttgcagc accggttgtg   13680
aaatcattga gtataattct tgttagagcc gttgatggca agacctttgt gaatgctcta   13740
aatgatgtca ttgcccgcca aataaaaaac ccaaacgccg aggaagaatc ttccctgtca   13800
accttgcaga ataccttcct tgggcgcaat ctcaaacagg gaacaagcat atacttaact   13860
tggcttgaac ccaaaagaat gctggtcagt cactgtcaat actgtgaatc ttatgaatct   13920
tcgatgctgt ttcatccctc aaagttgaat attgattta taaactattt agaaataaca   13980
aacttatccc acaatgaata cgcttccatc gtacaagaaa tagcaatgct tctttaagga   14040
catgatactc caaggttgct cactttttt tgtactgata cttctgtcag atcattagcc   14100
aatgtgctgc atttcgtggt aatgaggcta atgccgtcac ctctaacata gaaacagtg   14160
gaattcaaac agtaaagatg gcagtagagg gggttagatt gtataggatt aaatggaagt   14220
gacctgccaa cttctctccg tcatgtaaat ttgcctacat tacctggaga ataaaagctg   14280
gcatgcattg accattttctt gttttagttc actagtggca caagaactga caacttgcac   14340
aaataagaaa aggcacacac agacacagtg tgacacctt tttatccaaa gaaaaaaaaa   14400
acaaaatatg tacttactac taggatgaaa atcttattgg tttaactgac tagagcaaac   14460
ttttctgaat tgtagacctt aaagctttag ttgaggttga caagaagctt gaattgcatc   14520
aaagatttga cagtaaagct ggaattctgt ttgttagcca gatttccttt tatctactga   14580
```

```
tggatttatt caaattttga atattttaac attaaatttt attttgttag ttacggaaca  14640
gaatgatcat tgcattctgg aaaaaattaa caagttgtgt cataaataaa agtataaaaa  14700
gggggcttgt agagatttac gtagagaggg agctcaattt gaatgctgtt aactttatt   14760
gtgtagatct ccatttcgga agatgaagat ccacgtcaag ttgatgcaga gatcaaatct  14820
gctactgtta attatgctct atatgatggc ttctttggta aatccacagt gtgcccttct  14880
ttaagatcat ctacagccca gttgctggac gcgcttctgc ttgcgaagtg acaaaccagt  14940
cgtggttcca tatcaatggt tacgagtggt tattcccttc tcccttgttt tcccgaggga  15000
acacaggacg ggctaggtgt ccataatcat aagtcccata aaggaaatta atttaattat  15060
tatagagttc atatgtaaca ttttttgtcgt ccctgatgaa atatggtgaa tttgtcacgc  15120
ccctatgctg atattatgat tggcagattg cttta                             15155
```

| | | |
|---|---|---|
| SEQ ID NO: 62 | moltype = DNA  length = 1458 | |
| FEATURE | Location/Qualifiers | |
| source | 1..1458 | |
| | mol_type = other DNA | |
| | organism = Zea mays | |

SEQUENCE: 62

```
atgacgacgg gggcgacgtc caggtgcccg agagatatct cagcaaggat cccagcagcg   60
cggaggaggt cgtcgtcgta gccggcgacg acagcgcctg cagggcgatt cctgtcatcg  120
atctccgtag cccgtaggtt gctcgatccg gagtcatcgg aggaggagac cgccaagctg  180
gcgtctgcct gcctcgactg gggcttcttc caggtacgag tacgttcttg aggtggtcgg  240
atcatttgct gcttgtgttg tatatcaacc atgagccggc ggccggtccg gcctgtgctg  300
ctgtgcagct aatcaaccat ggaattccgg acgaggtgac cggaaacctg atgaacgacg  360
tggctgggtt cttcgggcag ccgctggacg ccaagaagga atgcgcgcag caggccgaca  420
gcctcgaagg atacgggcag gccttcgtgg tgtcagagga ccagaagctg gactgggccg  480
acatgctctt cctcatcgtg cagccgaggg aggccaggga cacgcgcttc tggccgacgc  540
gccccgcgtc cttcggggac tccgtggact cctactccct ggaagcttcg aggctagcgt  600
accgcctgct ggagctcatg gccagggggcg tcggggccgc cgaccggcg tcgctaagac  660
gcgtgttcga ggggcagacg cagggcatgc gggtgaacta ctaccgccg tgccggcggg  720
cggcggaccg ggtgctgggc ctgtcgccac acaccgacgc gtccggcctg acgctgctg   780
tgcaggccag caacgcgcgtg cagggcctgc aggtcaggaa ggacggcagg tggttcgccg  840
tggacgccat cgacgcgcc ctcgtcgtca acgtcggcga cttcttgag gtacgtacgt     900
gctgtcagtt ttgtgtggat tctatgtggc tgatgtatat cgatcgtctt gtgtccgttt   960
tgcagatcct gagtaatgga aaattcacca gcgttgagca cagggccgtg gtacacccca  1020
ccagagagag aatgtcggcg gcgctgttcc tgtaccctcg ccagaacatg agggttggcc  1080
cattgccgga gttcgtggaat ggcggtaatg agccggtatgg atcaacggat tatgaggaat  1140
ttatgaagca ttactttgca acgaagcttg acggaaggaa gcacctagac agattgaagt  1200
tggagcagta ggcagtagct atctctaccg tatctatctc gctggaggga ccaataaata  1260
attttttctat gcgataaaata cttcgtcctc aagcacctag agagcagata taaataatgt  1320
tctccagctt tgattcgcaa aaatgcgca tgattcaaaa tgtgttatga taggatagga   1380
tcgactcggt ccatgaccga gacggtcaag atcaacccta acattctctc catttaatct  1440
catactcatt ttcttata                                                1458
```

| | | |
|---|---|---|
| SEQ ID NO: 63 | moltype = DNA  length = 1991 | |
| FEATURE | Location/Qualifiers | |
| source | 1..1991 | |
| | mol_type = other DNA | |
| | organism = Zea mays | |

SEQUENCE: 63

```
accagtcaaa caacgccaag cgcgcctccc gtgaacccag cggcccgtca agtcaaagca   60
tggacgtgcc gctcccgctg ctgctcggct ccgtggccgt ttccctcgtc gtgtggtgcc  120
ttctgctccg ccgcggcggg gccgggaagg ggaagcggcc gctgccgcc ggtccccggg   180
gctggccggt gctgggcaac ctgccgcagg tcggcgccaa gccgcaccac accatgtgtg  240
ctatggcgcg ggagtacggc ccgctgttcc ggctccggtt cggcagcgcc gaggtggtgg  300
tggccgcgtc ggcgcggggt gcggcccagt tcctgcgcac ccacgacgcc aacttcagca  360
accgccgcc caactccggg gccgagcacg tggcgtacaa ctaccaggac ctggtgttcca  420
cccgtacgg ctcccggtgg cgcgcgctac ggaagctgtg cgcgctccac ctcttctccg   480
ccaaggccct ggacgacctg cgcggcgtca gagagggcga ggtagcgctc atggtgaggg  540
agctccgccg gcagggagag cgaggacggg ccgccgtggc gctgggcag gtggccaacg  600
tctgcgcgac caacacgctg gcccggggcga ccgtggccg ccgtgttc gccgtcgacg  660
gaggggaggg cgccagggag ttcaaggaga tggtggtgga gctgatgcag ctcgccgggg  720
tcttcaacgt cggggacttc gtgccggcgc tcgcgtggct cgaccgcag ggcgtggtcg   780
gcaggatgaa gcggctgcac cgcaggtacg acgacatgat gaacgggatc atcagggaga  840
ggaagccgc cgaggaaggc aaggacctgc tcagcgtgct gctggccaga atgcgggagg   900
agcagccgct agcggagggc gacgacacta ggttcaacga gactgacatc aaggcacttc  960
tcctggtaag cttaccttc ccgtacgagc gcaacgactg ccggcagtga cggggacatg  1020
ctttgtactg taccttttatt gcaaattgca attgaccccg tccgtcgtg ctggggagtt   1080
ggagttttgg gtcttgttttt tcacatggaa cggaaatact ttctgtggcc atatcgtgac  1140
aacagaacct cttcacggct gggacggaca cgacatccga cgacgtggg tgggcgctgg  1200
ccgagctgat ccggcatccg gacgtgctca ggaaggccca gcaggagctc gacgccgtcg  1260
tcggccgcga ccgcctcgtc tccgagtcgg acctcccgcg cctcacgtac ctcacggcgg  1320
tgatcaagga gacgttccgt ctgcacccgt ccacgccgct gtcgctgccc cgcgtcgccg  1380
ccgaggagtg cgaggtggac gggttccgca tcccgccgg caccacgctg ctggtgaacg  1440
tgtgggcag cgcccgagac ccggcggcgt ggggcgtgc tctcgagttc cggcccgccc  1500
gcttcctccc gggcggctcg cacgcggag tcgatgtcaa agggagcgac ttcgagctca  1560
tcccgttcgg cgcggccgg agaatctgcg cgggcctcag ctgggtctg cggatggtca  1620
cgctcatgac ggccacgctg gtgcacgccc tggactggga cctcgccgac ggcatgaccg  1680
cggacaagct ggacatggag gaggcctacg ggctcaccct gcagcgcgcc gtgccgttaa  1740
tggtccgccc agcacccaga ctgctgccgt ctgcttacgc agagtagaaa tcgatgctcg  1800
```

```
ccggccatcc atgccgtccg tatgcatgga tgcatggtca aataaataag cgttgtacgt 1860
gggtatcagt gtcacaaact cacaatgtgt atcatgtatt gcttcgtcag tggcgtgtgt 1920
aagcgtccga ttttttttg tattttattc ttttccaga aaaaaatcgc cgttgaaatc 1980
gcataacaaa a                                                     1991

SEQ ID NO: 64           moltype = DNA  length = 1849
FEATURE                 Location/Qualifiers
source                  1..1849
                        mol_type = other DNA
                        organism = Zea mays
SEQUENCE: 64
atctgctaac tgtgatcacc aaagttgtgc tgatacgatg tgcaattctc gctctttctt  60
ctctagaatg ttcctgccga tgctttataa agaaggttg gtcagcatat cgatctctgc  120
cagtgtctag ctgagaacat ggtgacctca agcaaggca aggtatgtgt aaccggggcc  180
tcaggctttg ttgcctcttg gcttatcaaa cggctcctcg agtctggata tcatgtggta  240
gggactgtca gggacccagg tatttgcgaa atatcattac tttcgtatca gtcctcttta  300
ttacattaat aattcttgat taccaatttt tttctttt ttttgtaacc ccacaaggaa  360
atcaccaaaa aacagcccac cttttggaaat tacctgcaag taaagagagg ctgcaaatcg  420
tgcgagctga tctgttggaa gaagggagct cgacagcgc cgtgatggcc tgtgagggtg  480
tattccacac tgcatccccc gtcctcgcta aaccagactc tactagcaag gcatgccatc  540
gccgcatata tgcatatc tggaccatcc atcctactgc agccttttct acggaagcgc  600
gttgcatcta ctagctaatt aagctgtttt tcatgcatgc atggtgcagg aggaaacgct  660
cgttcctgcg gtaacggta ctctgaacgt gctgagatcg tgcaagaaga acccttcct  720
gaaaagggtc gtccttacgt cttcgtcgtc tgcggtgagg atcagggacg acggccagtc  780
cagcagtaac atctcgctgg acgaaacggc atggagctcc gtgccactct gcgagaagat  840
gcatgtgaga tactgaacag tgtctactct ctgtcatcgt cgatctctca aaccgtgatc  900
tgaaaacacg catgcacacg tcgttgcggt gtcgtccctt gctttgttgt tcacccgaag  960
ctatggtatg ccctagccaa ggtatttgca gagaaagcgg cgtgggagtt cgccaaggag  1020
aacggcatcg accttgtgac tgtcctcccg tcgttcgtga tcgggcccag tttgtcccac  1080
gagctatgcg ttaccgcttc agacgtccta ggcctattcc aaggtactca ttcgtacgtg  1140
ttctggtttt cgtatgttaa atagatgact ggaaacaaga ggtatatata tatatata  1200
tatatatt ctctgttccc aggcgacacg gcaaggttca gctcgtacgg aagaatggga  1260
tacgtccaca tcgacgacgt tgcgagcagc cacatcctgg tgtacgaggc ccccaggcc  1320
gccgggaggt acctgtgcag ctcagtggtg ctggacaacg acgagctggt ctcctcgctc  1380
gcgaaacgct acccgatatt cccatacc cggaggtcag tcgtcgtcgc gtcgtctgga  1440
tgtgcgtgcc atttaagat ctctgaacgg agagccgtgt gcatggtccg ttctgctgca  1500
ggctgaacag cccctacggc aagcagtcgt accagctgaa cacgtcgaag ctgcagggcc  1560
tgggcttcaa gttcagaggg gtgcaggaga tgttcgacga ctgcgtacag tcgctcaaag  1620
accagggaca cctgctggag tgcccctgt gaactgcgat ggggtgcctc cgcctgtgaa  1680
cgcgccggtt gggttgcgtc ccgaacccgc tgttaattcg ttttttttc ttcaataatt  1740
ccacgtcatg tcacggtgtc ctcgcgcaga ctgctactgt cagggcgtca tagctcacgg  1800
gctctccggc tacatgaata aaaatgtcac gtcgtcatt tgctttgcc              1849

SEQ ID NO: 65           moltype = DNA  length = 1911
FEATURE                 Location/Qualifiers
source                  1..1911
                        mol_type = other DNA
                        organism = Zea mays
SEQUENCE: 65
gccaactctc cacctgccca accgagtcac caaaaaggg tgacacacta gccatactgg  60
gtacttcaat gtgcacaata taaactagct gggatcaaat acaggagcac ctcgagtctg  120
agagaatggc taacactgct aagggtaagg tctgtgtcac tggggcgtct ggtttcatcg  180
cctcctggct cgtcaagcgg cttcttgagt ctgggtacca tgtcctgggt acagtcagag  240
acccaggtca gtttcatctt attctgatga tgatctgaat taaaatacta gtaatacctg  300
ttgacggttt atgtccattt tcattacctg tcaaataact cactcctgaa agcaaagatg  360
tcttggtagg gaatggcaag aaagtagggc acctctgggg cctggaaggc gcaaaggaaa  420
ggctgcagct cgtgagagct gatctcttgg aggaagggag cttcgacgac gctgtgatgg  480
cttgcgaggg cgtcttccac accgcatcgc cgtcgtcac cggatctaat tccaaggcat  540
gctaaacacc aattctgttt ctcatatttg cagcttcagg aaaggcctgg acatatagcg  600
acctgaaaca tgttggtgcc acttggcagg aggagatgct tgattcagca ataaacggca  660
cgatgaacgt gctacgctcg tgcaagaaga acccatcgct caagagggtt gtcctgacat  720
cctcgtcgtc gacagtgagg atcaaggacg aagccgacct gccccctaac gtgctgctgg  780
acgaatcgtc gtggagctcc atcgagttct gcgaaagtct ccaggtgagc gtacggtcgt  840
cagaagagtg atttggaccg tacctgcgtg acaatgtgat gttcccgtgc tcccttagat  900
atggtacgcc gtcgcaaaga tcctcgccga gaaggcagcc tgggagttcg ccggagagca  960
caggatcgac ctcgtcaccg ttcttccgac cttcgttgtc ggacctactc tgtctcctga  1020
gctcggccc accgcttctg atgtcctcgg cctgttccaa ggtacgtccg caaaagtttg  1080
tgcaagacca gagcccctctc gtcagtctca tagacctttg tctttgttgc aggagagacg  1140
gggaagttca cgacgtacgg gaggatgggg tacgtccaca tcgacgacgt gcgaggtgc  1200
cacatgctgg cgtacgaggc cgcgggcgcc cgagggaggt acatctgcag cgcggcggtg  1260
ctggactgcg gcgacctcgc cgccctgctc gcgcggcggt tccagcgta ccccgtcccg  1320
aggagcctgc cccgcgccta cggcgagcag tcgtacggct tcgacacgtc caaggcccgc  1380
gcgctggggc tggcggaatt caaggcgtc gaggagatgt tcgacgacgc cgtcgcctcg  1440
ttcataggcc atggccatct ccccgccgc gaggaacgct gttccgcgta gcctcttgg  1500
ctgaaactac atgaatgaac gtatcatgta ctaattaaat tatttaatac ttttaactag  1560
catctaatca tgccgtttag tctttatcag tgtgttttat tttatagtt atattatat  1620
taatactttt aactagcatt taattatctg atgtgatgga ctaaaattta gtcggttaga  1680
accaaaccga ccctaaatct tgtcgtaacc agtagaaaga ttatcccatg gatcgtacgg  1740
gtctatttgg ccttttggtgg tctaagctag ttgaaatact cgtctgctcg tttgaattct  1800
```

```
tttatgagcg gagttgacat ctcagctcgg tttattaata agccagctcg caagctaaac   1860
gagctatcac atttcagcaa aatagaaata tatgtgtatc atttacgtag c            1911

SEQ ID NO: 66              moltype = DNA   length = 2263
FEATURE                    Location/Qualifiers
source                     1..2263
                           mol_type = other DNA
                           organism = Zea mays
SEQUENCE: 66
cctagctcta gtctagaata aaacatctat ctatctttat ctatctatct atctatttgt     60
tgaacagggg ccccccggaa actagctagc taggatgcca acagcagagg cgacgacgcc    120
cgtgccgccg gagctgtcct ccgggcaagg gcggacggtt tgcgtgaccg gagctggagg    180
gttcattgcc tcctggctcg tcaagcgcct cctggagaag ggctacacag tccgcggcac    240
ggtcaggaac cctggtgcgt ggcttaacga tgatgatcct gctgtgctgt gcgcgtcgtc    300
gacttgcaaa atatgtaacg aataaccctc tctgcattta attgttgtcc aattatttga    360
cagtggatcc aaagaacgac cacctgaggt cccttgacgg cgccgacgac cgcctcgtcc    420
tcctccgcgc cgacctgctg gacccagaga gccttgccga ggccttctcc ggctgtgacg    480
gcgtcttcca cgccgcctcc ccggtcaccg atgaccctgt aagacattat tagagtatag    540
tatatatata tatgtatttc ttgtcgatcg tcgacaagca gcgattagca cacgacgacg    600
atggcatgcc gcatgcatgc aggagatgat gatcgagcca gcgatccggg gcacgcgcta    660
cgtgatggcg gcggcggcag acgccggagt gaagcgcgtc gtgttcacgt cctccatcgg    720
caccgtgtac atgaacccct accgtgaccc cagcaagcct ggtgacgaca cctgctggag    780
cgacctcgag tattgcaaga cacccaggt acgcgtacac gcatgcaagg gtgatgcgtc    840
atgcgtgcag tgcatatcca tccaagtccc tgtatgtatg tacctcgttt ttttgctttg    900
aagcgagcta gcagaatgag acagctaatg atatatatag agtcctagtt actacgaaag    960
agtaagatat tagtgagtcg aagatataga cgacggccga tgcttttgtg gtcgcgcact   1020
tgtcaatcct caccaaccac aaccatgcat gcatgaaaaa gggaaagagc gacgttgaca   1080
tgtgaactac acaccacgcg cgcgcctggg gtgatcaggt ttcttggtcg tctaggcacc   1140
atcagttacc aaccagctag caggccattc ttctccgcca tctctaactg ctcctaatta   1200
ctttcgtgcc tataccta ctactactac tgctatttct gactgcaccc agagaaacca   1260
tatatatata ttgacatgaa aaacatctat ctgaaaacca caaataatca atatatattt   1320
atttatatga taacatctat atattacggg tgcgtgcgtg cgtgcgtgca tatgcagaac   1380
tggtactgct acgccaagac ggtggcggag cagggcgcgt gggaggtggc gcggaagcga   1440
gggctggacc tggtggtggt gaacccggtg ctggtgctgg gccgctgct gcagccgacg   1500
gtgaacgcca gcacggacca cgtgatgaag tacctgacgg ggtcggccac gacctacgtg   1560
aacgcggcgc aggcgtacgt gcacgtcagg gacgtggccg aggcgcacgt ccgggtgtac   1620
gaggcgcccc acgcgcacgg ccgctacatc tgcgccgaga gcaccctgca ccgcggcgac   1680
ctctgccgcg tcctcgccaa gctcttcccg gagtaccccg taccaccaa gtgcaaggac   1740
caggttaacc ctccggttgt aggatacaag ttcaccaacc agcgcctcaa ggatctggga   1800
atggacttcg tgccggtcct ccagtgcctc tacgagacgg tcaccagcct ccaggagaaa   1860
ggcatgctgc ccgtgcttcc gacaaaacac gaccatgcat gaccaactcg gcaaatcatg   1920
atcatatcga tcccatcctt gacgatacta gctgctgcta ccacgcatat catatcatat   1980
atacgata tatagtgg attcatataa ttgaccttat tatatatat atatatatat   2040
atatatatat atatatatat atatatatat atatatatat atatatatat atatatatat   2100
atatatatat atatatatat atatataata tgtgtgtgtg tgtgtgttat tagtgtgtac   2160
aattaaatgg caactctaat gggtgcatgc atctgcatgc atgctttcct gacaagtgcc   2220
acacatgcct gcaatgtatc tctttggacg aatatttata tac                    2263

SEQ ID NO: 67              moltype = DNA   length = 1119
FEATURE                    Location/Qualifiers
source                     1..1119
                           mol_type = other DNA
                           organism = Zea mays
SEQUENCE: 67
atggggggcg agacgcacct gagcgtgcag gagctggcgg cgtcgctggg cgcgctaccg     60
ccggagttcg tgcggtctga gcaggaccag ccggggcgcga ccacgtaccg cggggccgcc   120
gtgccggacg cgccggtgat cgacatatcg gagcccgggt tcggcgcgcg catgccgca    180
gccgccaggg agtgggggct gttccaggtg gtgaaccacg gcgtgccctc agcggcggtg   240
gcggagctcc agcgcgtcgg gcgggccttc ttcgcgcttc cgacggagga gaaggagcgc   300
tacgccatgg acccggcgtc cggcaagatc gagggctacg gcaccaagct gcagagggac   360
ctcgagggca agaagacgtg gaacgacttc ttcttccacg tcgtcgcgcc gccggagaag   420
gtggaccacg ccgtctggcc ccggagcctc gccgggtaca gggaggccaa cgaggagtac   480
tgccgccaca tgcagcgcct gacgcgcgag ctgttcgagc acctcgcgct ggggctgggg   540
ctccacgggg gcgccatggc ggaggcgttc ggcgagacg gcctggtgtt cctgcagaag   600
atcaacttct acccgccgtg cccgcagccg gagctcacgc tcggcgtcgc ccgcacacc    660
gacatgagca cgctcaccgt cctcgtgccc aacgaggtgc aggggctcca ggtcttcaaa   720
gatggtcaat ggtacgaggc caagtacgtg cccgacgcac tcatcgtcca tcggcgat    780
cagatcgagg caagcgacct acgtagcatc ttttttttt cattctattg tgttgtgatg   840
atcttgctcc ctcaagtatt tctttgatgt cggacaacta ctaactggta cgaaccgatc   900
gagcagattt tcagcaacgg ggcatacaag gcggtgctgc accgtacgac ggtgaacaag   960
gagaagacgc ggatgtcatg gccgatgttc gtggagccgc cggggagct cgtcgtcggg   1020
ccgcacccca agctggtcac ggaggagagc ccggccaagt acaaggccaa gaagtacaag   1080
gactaccagc actgcaagat caacaagctc cccatgtaa                         1119

SEQ ID NO: 68              moltype = DNA   length = 1096
FEATURE                    Location/Qualifiers
source                     1..1096
                           mol_type = other DNA
                           organism = Zea mays
```

```
SEQUENCE: 68
atgggggcg   agacgcacct   gagcgtgcag   gagctggcgg   cgtcgctggg   cgcgctaccg    60
ccggagttcg  tgcggtctga   gcaggaccag   ccgggcgcga   ccacgtaccg   cggggccgcc   120
gtgccggacg  cgccggtgat   cgacatgtcg   gagcccgggt   tcggcgcgcg   catggccgca   180
gccgccaggg  agtggggct    gttccaggtg   gtgaaccacg   gcgtgccctc   agcggcggtg   240
gcggagctcc  agcgcgtcgg   gcgggccttc   ttcgcgcttc   cgacggagga   gaaggagcgc   300
tacgccatgg  acccggcgtc   cggcaagatc   gagggctacg   gcaccaagct   gcagagggac   360
ctcgagggca  agaagacgtg   gaacgacttc   ttcttccacg   tcgtcgcgcc   gccggagaag   420
gtggaccacg  ccgtctggcc   ccggagcctc   gccgggtaca   gggaggccaa   cgaggagtac   480
tgccgccaca  tgcagcgcct   gacgcgcgag   ctgttcgagc   acctctcgct   ggggctgggg   540
ctccacggga  gcgccatggc   ggaggcgttc   ggcggagacg   gcctggtgtt   cctgcagaag   600
atcaacttct  acccgcgtg    cccgcagccg   gagctcacgc   tcggcgtcgc   gccgcacacc   660
gacatgagca  cgctcaccgt   cctcgtgccc   aacgaggtgc   aggggctcca   ggtcttcaaa   720
gatggtcaat  ggtacgaggc   caagtacgtg   cccgacgcac   tcatcgtcca   tatcggcgat   780
cagatcgagg  caagcgacct   acgtagcatc   tttttttttc   tttctattgt   gttgtgatga   840
tcttgctccc  ctcaagtatt   tctttgatgt   cccgatcgag   tagatttca    gcaacggggc   900
atacaaggcg  gtgctgcacc   gtacgacggt   gaacaaggaa   aagacgcgga   tgtcatggcc   960
gatgttcgtg  gagccgccgg   gggagctcgt   cgtcgggccg   caccccaagc   tggtcacgga  1020
ggagagcccg  gccaagtaca   aggccaagaa   gtacaaggac   taccagcact   gcaagatcaa  1080
caagctcccc  atgtaa                                                          1096

SEQ ID NO: 69          moltype = DNA  length = 3676
FEATURE                Location/Qualifiers
source                 1..3676
                       mol_type = other DNA
                       organism = Zea mays
SEQUENCE: 69
aattagttcc  tcgatcgatt   atcaccagca   tctcacttcg   ttcagatata   tatagcaagt    60
ctaagtctta  gttttgctt    ttggaacatc   tctctaattt   cacgattgag   cgtacgtgcg   120
cacaaacaaa  caaacaaaca   aacaatatat   gggttcttcc   aatgatgtca   cggcgattcc   180
tctaatcggt  aagattttac   tgaccctct    aacacatctt   atataaattt   tcatatattg   240
tatatataact tcatgtgacc   acccttgatt   tagtgaacta   gctgcttgtt   acaaattttg   300
agtttcttct  tttccttta    ttttgtagtt   tctctttgct   acatttttctc  cgatcctcct   360
ttttgaagga  ttatggtaca   ctataggaag   cttcgcagtt   tatttcagcc   aaaaatcctc   420
atcgaaaaaa  taaaataggc   tgaaaaaaat   aagggatggc   cacaaaaaag   gctcgtgtgc   480
atatttttc   atccgttgaa   aataatacag   tttgtttct    actactttct   tttgccactg   540
aatataaattt ctttattga    aaatataaat   tagtaaaaaa   ccatagtttt   cgacgatttt   600
cttggccaca  caaattacta   tatgatttct   tataaaaata   aataagtgca   aataaagcat   660
gtaaaattct  aggcagaatc   acagaaaaat   tatacaatat   catataatta   catataacag   720
gttacaaatg  atattagtac   atggattcac   ataaactata   aaggaagtaa   gatgtccagt   780
aaaaggaaat  tggcaaaaat   gtctttcagt   aattgtttca   caccaatata   atgaatctcc   840
acacatgaac  tacatgcatg   gatgtagtag   ataacagatc   tgctatatca   tgttctgcta   900
tatcattagc  ttctcgaacc   atgttctgct   gctcggtgac   ttggcgatg    ccaaagagat   960
ctgtcgggaa  actgccattc   atatttacag   ccgggaaagc   agtgattatt   gtacataata  1020
gattagtagt  agcagtagat   atatgttagt   gtcatcacag   tgttaaaaaa   tgcacattag  1080
aaaatagcat  gccacatccc   aagataaata   gcctacttta   ttaactgaat   tttaattcca  1140
cgaaatgaag  agaaacaaac   agggccttag   tggtaagaga   atgtctgaag   atggattta   1200
tctttcatta  tcgaaaaaaa   aaatctcaat   gtcgatttgg   aaatatacgg   ttatcatttg  1260
tggtctgcca  tttgcttctt   tcttttgtct   tttattttcc   ccccattgtc   agatgttgcc  1320
ccacttgtca  aaaagattga   tgatccgac    atggcaaatg   ataaggattt   gctacgagtt  1380
gttctaacgt  tggactatgc   ttgcaaggag   gttggattct   tttatgtggt   aagcagtact  1440
catgtacact  gctgacgatt   tgcttgaaac   ttcgaagcaa   actggcacat   atgcttaatt  1500
tcacttgcaa  taatattaat   tctgatgttt   gaataaaaac   gaaaatgagt   taccaatata  1560
tatatatata  tatatatata   tatatatata   tatatatata   tatatatata   tatatatata  1620
tatatatata  tatatatata   tatatatata   tatatacaact gaactgctac   ttgttcagct  1680
gtatatcaac  tgaacttact   ttccttgtta   tgaatgaaaa   taacaaaagg   ctgaatatct  1740
aactgatgag  gtaactatat   atatatatat   atatatatat   atatatatat   atatatatat  1800
atatatatat  atatatatat   atatatatat   atatatatat   atatatatat   atatatatat  1860
atatatatat  atatatatat   atacttgtaa   taactcgtca   cgacaacaga   aaggccacgg  1920
catttgtgag  atgctaatga   gggaagtgag   ggatgtgtca   cacaaattct   ttcagcttcc  1980
acatgaggaa  aagatgaaga   ttaagatgac   acgtcaaagt   gggtataggt   gtgtgtgact  2040
tgtccaatat  ataatgtcct   tatgaggtcc   attatattat   attttgggt    gtcgaggccc  2100
ttctaaaatt  aaatgatcgt   tctttccaga   gggtatcaaa   agctaggaga   gaatgttacc  2160
aaggaaaaac  gtgatatgca   cgaagcagtc   aatgtgaaga   ccttttgtct   ctgtacttct  2220
cttctcatgt  tttaatttt    aattattgag   agctaaacta   acaagaagaa   tatatatatt  2280
gcagtgcttg  actcctattg   cacctggcaa   atacggagac   cttggtaaaa   cacttgaagg  2340
agacaatctg  tggtacgttt   ctaaattcct   gtttgtttc    tgtatcgtac   aattaaaatt  2400
tttaaatcgt  aagtatggtg   gtaccatgcc   aggcctgaat   accatcaaa    tttgaaggta  2460
gtgctggaaa  actatatcag   ccttgtcaaa   ggtcggtcca   cttcttgact   tactatatat  2520
aatatccatt  ctcctccgat   cctcttatta   tcacaataaa   ttaatgcaac   atgtagacga  2580
caattaaatt  gatctgtca    aggaagatca   tgcgaggtat   agcttggca    ttgggtgggc  2640
ctgctgatgc  ctttgaaagg   ggaatagcag   gagatccttag  ctgggctctc   aggctggtta  2700
gctaccctgt  ttcaagcagt   gatgagaaac   gcactgatga   tactgggatg   atgtacgtgt  2760
atatatatgt  cgttagttgt   tgtttacatt   tttttgtgt    ttgtatatata tatgctagct  2820
gcttacttgt  tcaacatttt   atttgtgttc   ggacggaagg   ggatcgcaca   cagactacgg  2880
ttagtgctgc  atctcttctc   ttcaacaagt   ttatttctgg   tcttgtttat   atatatagta  2940
tgcatgcatg  caggacttgt   tacactggtt   aaccaggatg   atgacatttg   tgcccttgag  3000
gtaacttaat  ttttttcttg   gttctgggtt   tctcttgtac   agtactctat   cactagatta  3060
atcattttt   tttctgacga   tgcaatttac   aggtccaaaa   tcgttccggt   gtgtggatac  3120
```

```
gtgccaaccc gattcctgaa acctttcttt gcaacatcgg tgacatgctc caggtttgtt    3180
tgttttgtat ccctattccc taggatggat ggataatgtt aattaatttc atttaggtct    3240
ggtcaaatgg aatttaccaa cccacagttc atagagtcat caacagctcc catcaacgcc    3300
gcgtttctgc tgtgtttttc tatgaggtac acatcatgca tgcatgcatg catgcataca    3360
gatcgattat catttcaatt catttcattt taattttttt aaacaatgct ggtgcagacc    3420
gattttgatg ctgccgtaga gcccgttgag ttgtgcgtgg agaaaacagg cggcgtcgcc    3480
aagtatgaca aggtcgtgta tggggagcgt ctggttcgga aggccttctg ctgctttggc    3540
catttatagg gctggagaat aagttatatt gctactgtga aaacaaaggg catactatat    3600
gcattgcaca cacaatgatc tgttgttaaa cctatgtgat atatattgtg aaataaagga    3660
acacttatta tatata                                                    3676
```

SEQ ID NO: 70         moltype = DNA   length = 1799
FEATURE               Location/Qualifiers
source                1..1799
                      mol_type = other DNA
                      organism = Zea mays
SEQUENCE: 70
```
gagcagcagc taaagaagca aagcaagtgt ctgctcactc agtcctgcgc aagagctcgc      60
tctcggagaa aaaaacgcgg gaggcgataa tggaggagg tgccggtgcg agcgagaaag      120
ggaaggtgct ggtcacgggg gcgtcgggct tcgtcggctc ctggctcgtc atgaagctcc      180
tccaggccgg ctacaccgtc cgggcgaccg tgcgcgatcc cggtgagttt gtctcgatcg      240
tcctcgtac gtcctcctcc tgcagccaaa tctgattcg ctccgtgtat atatgccgtg      300
tcctgatcgt cctgcagcga acgttgggaa gacgaagcca ttgatggacc ttcccggagc      360
aacggagcgc ctgtccatat ggaaagccga cctggcggag aaggcagct tccacgacgc      420
catcaggggc tgcaccggcg tcttccacgt cgccacgccc atggacttcc tgtccaaaga      480
ccctgaggta gatcagtctc tagctctggc tgcacaatta attagtctct cgatctctac      540
gtcttcactg cacatgcact gcacacatat actacatacg tatggtttcc attgcagaat      600
gaggtaatca agccgacggt ggaagggatg ataagcatca tgcgggcatg caaggaggcc      660
ggcaccgtgc ggcgcatcgt cttcacttcc tccgccggga cggtcaacct ggaggagcgg      720
cagaggcccg tctacgacga ggaaagctgg accgacgtca acttctgccg tcgcgtcaag      780
atgaccggat gggtacgtac gcagccactt gtcagcctg cgcctcatca attcaactga      840
acttcgacga cgacagtgtt tggtcaccat cagcccctgcc tgcggctgcg gcacatggcg      900
accgcgctga cgacaccttt tatttatgtc cacccccctg cagatgtact tcgtgtctaa      960
aaccctggcg gagaaggcgg ccctggccgta cgcggcggag cacggcctgg acctggtcac    1020
catcatcccg acgctcgtgg tcggcccgtt catcagccgc ccagcctcat                1080
caccgcgctg cgctcatca cggggaacgc gccccactac tcgatcctca agcaggtgca    1140
gctcatccac ctcgacgacc tctgcgacgc cgagatcttc ctcttcgaga acccggccgc    1200
ggccgggcgc tacgtctgct cctcgcacga cgtcaccatc cacggcctcg ccgccatgct    1260
cagggatagg taccccgagt acgacgtcc gcagaggttc ccccggatcc aggacgacct    1320
ccagccggtg cgcttctcgt ccaagaagct ccaggacctc gggttcacct tcaggtacaa    1380
gacgctggag gacatgttcg acgcgccat ccggacttgc caggagaagg gcctcatccc    1440
cctcgccact gccgccggag gggacggctt tgcctcggtg cgcgcacccg gcgagacgga    1500
ggcgacgatt ggcgcttaag caacaatcac ccggctctcc cgtcgtgatga tgctatcagc    1560
tatctatctc ttcgagctcc gctgccaata cggaacttac ttccatgttc aacgaattgt    1620
tttatcccct ggattacgta ttgtttttat gttttatacc caaacaacga atgtttctca    1680
gtatttact acagctagcc cctatagtag agattctatt atatgaataa gctatctgta    1740
gaggctctgg tgcaatatat atttcgagtt atttggatta ctagcataat tcaattttt    1799
```

SEQ ID NO: 71         moltype = DNA   length = 2839
FEATURE               Location/Qualifiers
source                1..2839
                      mol_type = other DNA
                      organism = Zea mays
SEQUENCE: 71
```
atatttaaaa attcaatatt tgtttgttta tgagtgtttg atgagtatat tgtacctctt      60
gtaaactgaa gcacacgatt aattctttgt taaagaatgc catgataata gtttgctata      120
aatgaaatta atgttaaatc aatttgttaa aaattatggt ttcttctgaa tttagttatt      180
gccgatagag aaaaaacatt gaaaaaatat ttagatcata tacggctgaa tttagttatt      240
gatgatctta tttgttatat tttatttgtt tgaggaatac acgcttattt tacttcaccc      300
tgtttgttac tttagtcact agattaaact tagtttaat cgctaaagta cctcgttgtg      360
ttcagtgact aaaccagact aaagagcatt aattgatgta ataatgact atgttgtcca      420
tattaattag tggatatttg ctgcaaaaag aaagtgaaga gggcaaataa ggtaaaaatc      480
ctactttaat ccctttttagc catcccttgg tgactaaaga attaaagttt agtcacaaca      540
ctttagtcac catatttaat tcttaggga ctaaaagtta ctaaacttta gtcaccccaa      600
actaaacggt accttagatc tatttatttg aggaatgcaa gtgtttgaat aactattcta      660
tttaaataag atctacctaa cgacgtacgg acatctaact agtatagaat taacgtacac      720
atgtattgat ttgagtgacc catggctgat tccagtgatc aacaataatc ctgccaagca      780
tcaagctaat cccaaggtgc cacggaatgg tctcgcccgc cgcgcgctgg cacatatacc      840
agcaggtgac cgtcggattg ggtggcgctt ggcacggaaa aaatttggt gcagcactgc      900
tgcaaaccag agtggtttgc agcccctcac aaaaaggagg atagacccca cctgcaggtc      960
cagcagataa cgtttagtt gtattattgt tgctgcgggt ggggtctatc ctctttttg     1020
tgaggggctg caaacactct ggtttgcagc agtgctgcac caaattttt tcccttggca    1080
cgtgttcggg tggtagctgg ctcctccatg caatgcctat gcctgtcgtc gcgatcgcaa    1140
ccaccagtca agacgaatgg caggcagcta agtagtcaac acaacaggc ttgtattgta    1200
tgtacagcaa tatatataca tctcgagaag ctcctagcag agatgcatcc atctcgacga    1260
cgatccatcc atcttaaagc aagcagagac atggagtcgt cgccgctgct gcagctgccg    1320
gcggcacgcg tggaggctct gagcctcagc ggcctcccg ccatcccgcc cgagtacgtc    1380
cgccccgccg acgagcgagc cggcctcggg gatgccttcg acctgcgcg cacccatgcc    1440
aacgaccaca ccgcgccgag gatccccgtc gtcgacatct ccccgttcct cgacagcagc    1500
```

```
agccagcagc agcagcggga cgaatgcgtg gaggccgtgc gtgccgccgc cgccgactgg   1560
ggcgtcatgc acatcgccgg ccacggcatc cccgccgagc tcatggaccg cctgcgcgcc   1620
gcaggaaccg ccttcttcgc cctccccgtc caggacaagg aggcctacgc caacgacccc   1680
gccgccggcc gcctgcaggg ctacggcagc cgcctcgcca ccaacacctg cgggcagcgc   1740
gagtgggagg actacctctt ccaccttgtg caccccgacg ggctcgccga ccacgcgctc   1800
tggcctgcgt acccgcccga ctacatcgcc gccaccgcg  acttcggccg ccgaacgcgg   1860
gacctggcct ccacgctgct cgccatcctc tccatgggcc tccttggcac agaccgtggc   1920
gacgcgctag agaaggcgct caccaccacc accaccagga cagcagctga cgacgacctc   1980
ctcctgcagc tcaagatcaa ctactacccg aggtgcccgc agccggagct ggccgtcggc   2040
gtggaggccc acacggacgt cagcgccctc tccttcatcc tccacaacgg cgtgccgggc   2100
ctgcaggtgc tccacggcgc ccgctggggt acgcgcgcc  acgagccggg caccatcatc   2160
gtccacgtgg gggacgccct ggagatcctc agcaacggcc gctacaccag cgtcctccac   2220
cgcggcctcg tcaaccggga ggccgtgcgc atctcctggg tcgtcttctg cgagccgcca   2280
ccagactccg tgctgctgca cccgctgccg gagcttgtca cggaaggcca ccccgcaagg   2340
ttcacgccgc gcacattcaa gcagcacctg gatcgcaagc ttttcaagaa gaaacagcag   2400
cacaaagcaa aagcagagga agaggatggc ggcaatggtg accaccaccg ccacgagccg   2460
ccgccgcaga ccaactgatg ggctgcacat gtctttccat ccgcccacgc atatcttctc   2520
tcgcgaaatt aataaggatc catcagcatt ttccatatat ttatattagt ttcatgctcc   2580
tacgttacta cgagaaaaaa aatagtatct atgatatata aaatccatgt gttaaaatat   2640
tactgtaaca ctaatattat atatgttgtt acgaaatcaa tataataaaa taatttgata   2700
taccaaaaca ctaattatta ttctataatt ttgttagcgt aactaaaagt taagatttat   2760
atactttaaa agatatataa gattgtacca tcactagtaa aaaaataaac aataccaata   2820
ttttataaaa tatgagtat                                                2839

SEQ ID NO: 72          moltype = DNA   length = 1624
FEATURE                Location/Qualifiers
source                 1..1624
                       mol_type = other DNA
                       organism = Zea mays
SEQUENCE: 72
agaggtggat gaggagcaca agcagcaagg tcaactcagg cctccgcaag ctagctcaaa     60
gaaaaacgaa atgagggatg tggtggcaaa gcgggaggcg atgaagggag gcgcgagctc    120
gaaagggccg gtggtggtca cggggcgtc  gggcttcgtc ggctcctggc tcgtcatgaa    180
gcttctccag gccggctaca ccgtccgggc gaccgtcgc  gaccccggtg agctgtctcg    240
ttctgcgtcg tcgcaggtgc gtgcagggca tccaaaccg  tagcagcaga atttttgattt   300
gctccgtgac ggtgtccttc cagagaacgt tgggaagacg aagccattgc tggaccttcc    360
aggagcaacg gagcgcctgt ccatatggaa agccgacctg gcagacgaag acagcttcga    420
cgaagccatc aggggctgca ccggcgtctt ccacgtcgcc acaccaccg  acttcgagtc    480
caaagaccct gaggtaaata aacgtgcctc tgttcaattt gtcatgagt  caacgtcatt    540
gcagttgcac gtacatacgg ccgctcccgt tacagaatga ggtgatcaag ccgacggtgg    600
aagggatgat ccgcatcttg cgagcctgca aggaggccgg caccgtgcgc cgcatcgtct    660
tcacttcctc cgctgggacg tctgcgtcg  aggagcggca gcggcccgtc tacgaccacg    720
acaactggag cgacgtcgac ttctgccgcc gcgtcaagat gaccggatgg gtacgtagcg    780
acttctctgc ccagcggccc aattcaaccg aacttcgtcg ctcgtcggtc gtggacatgg    840
acatggacct tgaccgcgct gagaaacacg tttaattatg tccacccggc agatgtactt    900
cgtgtctaaa tccctggcgg agaaggcggc cgtggcgtac gcggcggagc acggcctgga    960
cctcgtcagc gtcatcccga cgctcgtgct cggcccgttc ctcacgcgcg ccatgccgcc   1020
cagcctcgtc accgcgctgg cgctcgtcac ggggaacgag gcccactact cgatcctgaa   1080
gcaggtgcag ttcgtccacc tcgacgacct ctgcgacgcc gagatcttcc tcttcgagca   1140
cccggccgcc gccggacgct acgtctgctc ctcgcacgac gccaccatcc acggcctcgc   1200
cgccatgctc agggataggt accccgagta tgacatcccc cagaagctcc gcgggatcga   1260
ggacgaactg cagctcgtgc acttctcgtc caagaagctc ctagaccatg gcttcacttt   1320
caggtacacg tgtgaggaca tgttcgacgc cggcatccgg acgtgccggg agaagggcct   1380
catcccgctc gccacggccg gaggggtcgg ctctgcctca ctgcgcacac ccggcgagac   1440
cgcgagcgga atgtgacgaa tggcgcttag acaataatcg cttgtttcaa gaaaaatcac   1500
tacaacttgc ctctacagta gaaatcctac gaataagcta tatgtagagg ctgtgatgta   1560
atattattgt tttcctgcaa caactcaaaa cacatctgtt cccaaatcaa acagaacttc   1620
ttat                                                                1624

SEQ ID NO: 73          moltype = DNA   length = 1635
FEATURE                Location/Qualifiers
source                 1..1635
                       mol_type = other DNA
                       organism = Zea mays
SEQUENCE: 73
atggctccgc cgccggcaat gcagagccca ggagagctaa cgacggcgc  ctacgacgcg     60
ccgcacatcc tattcatccc gagcgccggc ataggacacc tgaccccgt  cttccgcgtc    120
atcgccggct tctcgagccg gggcatcgac gtctccgtcg tgacgtgct  gccaccgtg     180
tctgccgcca agactgacta cttcaacggc tccttcgtga actacccgc  cgtccgagcc    240
gtcgacatgc acctattgcc gctggacgcc tccgaattca cgagagagga cccgttcttc    300
ctccggtggg aggccctgcg ccgctccgtc cacctcctcc gccccatcat cactaacgcc    360
gcgccgcgca tcacggccat catcaccgac atcaccctga cctcctgcgt catccccatc    420
gccaaggagc tggacgtccc gtgccacgtc ctcttcccca gccgccac  catgctctcg     480
ctcaacgctc actaccaagt ctatctcgag aagctcaagg gtggaccgga gccgggcgtg    540
atcggcgacg ccgtcgacat ccccggcgtg ttccgcatgc cgcgctcgc  cctcccgccg    600
gcgctcctcg acgtgaacaa gctcttcacg aagcagttca tcgacaacgg cagagcgatc    660
gtcaaagccg acgcgtcct  cgtcaacacg ttcgacgccg tggagccggc accgctggca    720
gccctgagag gcgcaagat  cgtcccgggg tacccgccgg tgtacaccat cggcccactc    780
aagtcgcacg ccacgaaagc gggcgacaag ccaggtgacg cgttgcttga cgaatggcta    840
```

```
ggtaagcagc gagcgcgatc tgtggtgtac gtggcgttcg gcaaccgcag cgctgccagg  900
ctggaccaga tccgggagat cgccgccggg ctggaggaca gtggctatcc tttcctgtgg  960
gtgctcaaga ccacgaaggt ggaccggagg acgacgccg agctggcgga ggtgcttgga  1020
gacggatacc ttgagcgcgt gaaagggcgc ggcatcgtga ccaaggggtg ggtggagcag  1080
gaggacgtgc tgaaacaccc ggctgtgggc atgttcgtga gccacgcgcg gtggaactcg  1140
gcgctggagg cgtcgtccgc cggcgtgccg ctgctggtgt ggccgcagct cggcgaccac  1200
cgcgtgaacg cgatggcggc agtgagggca ggcatcgggg cgtgggcgga gcactggagc  1260
tgggacgggg aggacacgct ggtgaccagg caggagatcg ccgacaaggt gaaggaggtt  1320
atggccgacg ggaagttgag ggcgagcgtg gcggtggccc gcgaggaggc cgcaaaggcc  1380
gtcgcggagg gcggcacgag ttaccgtaac atgcatgact tcatcgccaa gcttaaggga  1440
ggagcttgag gcttgaggag atgatgttac gaacgcaaca atcatgcact gcacgtccat  1500
tcccaccatt ccgacgagtg aagtgactgc tgttacactc agccgtacca ctttggttct  1560
gggttttcat ttcatgttca tgtgtcttct actactatat acaagcatat tcagtgtctt  1620
atgtgaacta aagat  1635

SEQ ID NO: 74           moltype = DNA  length = 1807
FEATURE                 Location/Qualifiers
source                  1..1807
                        mol_type = other DNA
                        organism = Zea mays
SEQUENCE: 74
gcagaacttc gccgccgtcg cctttctcag tttctcctgg gagcttgcct gtgtcgaaca   60
tggcggtggc tgcgacgacg gtgctggaca tcgcggagct ctccttctcc gacttagtcg  120
ccctcctatc tcccgagact cttgctgacg acggccgctg ccgacgtgtt gtggacaccg  180
tcgcaaccga gctcggccga ggtgggtccg ggttgctggc tatcgacgga gtgccgcgcg  240
tgggcgccct ccggcgacga ctcctcccct tggcccgacg cgtcgccctc atggatcacc  300
tgacccgctc ccaactcctc aaggtacccc tgcacctccc ctttcgatct cgttgatgtt  360
gaaactacag tgtgccttga tatatttccg tcgattattt cagaagcacg gtttgggcag  420
cgacgttcct ttgaagaagc tcgatcggtc cgtatcctcg ttcgcgcagc ttctaaggca  480
ttcaggtgaa ctcgtcttgc tagagtcggt gaacaacaat ggttcaatt cttctgatag  540
ggtacaggat tgtaaccaat ccgaggatgt taatgatgat gatgatgctg atgatatgga  600
taatctgggt gacctcatta aggagcttgg tttgtacatg atggagcttg gaatcttgat  660
tgcacgagct tgcgatattg tcatcggtag aggtcagcta agcagagca tcactgactt  720
tgggacagca aaggctaggc tcattcacta ccactctgag ctggataaca ttgtgatcga  780
ggataacaat gcaaagagga aaggttcggc aagtaaagtg gcagtacaac cttaccagtc  840
atgctctgga aataggtccg ggtcagtgtg cccgtgctgt attaagtcag aagatgggac  900
tactgtaatg gcaatagaag aaaataattc taatgatgcc tcgattcagg gtcaggctgc  960
tgaaatttcc ctgttaaacc tatggcagga atggcactat gactatgaa tcttcactgt  1020
tttaacagca ccgttgttca tgagctctc tgaggatgaa aaaagtttgg tcaatctgga  1080
atatcatcct cctgatggcc acacacacct acagttatgc aatggaagga agatattctc  1140
tgttagatgc tctcctggaga gcttcattgt tcaagttgga gaggcagcag acatcttgtc  1200
ccaagggaaa ttgaaatcta cacttcatgc tgtgagtaga cctcgagtt ccacagacat  1260
cagccgtgag acttttgttg tcttcctaca gccctcgtgg gacaaatttt tagcttatcc  1320
tggttactct ttagatgctg aaggtgaacc cattcttagc aagcagactt caatcatcag  1380
tgatggatca gcagggcctt gtaatgaaga tgcatttatg caagaaattc tgaaaaaagt  1440
tccacctcta tcatcaaggc taaagaagg gatgacattt gcagaatttt ctcgtcagac  1500
aacaaaacag tattatggtg gcaatggcat ccaacagaac aattgagcac ttgcaataca  1560
atggcaatgc atgtagcaca caatgaactg atgtattgac ttacattttg atactgattt  1620
ggatgcacaa aactaaagca tcctggcaaa caatgcatac ggctgatcct ccttgatgac  1680
taagttttgc aattgtttgt tgggaatagt cccacattgt gagttgtggg tggcaaaca  1740
tgatttatat ggttgaggtt ataaccttct aataggctaa cttttggtg agtattgaat  1800
caacaga                                                             1807

SEQ ID NO: 75           moltype = DNA  length = 4135
FEATURE                 Location/Qualifiers
source                  1..4135
                        mol_type = other DNA
                        organism = Zea mays
SEQUENCE: 75
atggtacgct gtacgacgtg gtagacgggc tgctctccca agagcgcagc agcctgctgc   60
cccacgtaaa tggacaaaca aaaaaatta ttgctacaaa cttatgatca gctagataat  120
aaaaaaacaa tgtaaatgat atataaagtt gttattatga gtaagttaga aagcgctaca  180
acaatacgac aaccccatga gaccatgatg cacaataaca gagattcaat atgcataaaa  240
ctcccaagtg aacaacgcct gtgatgaatc tgctactgac gctagagctg tcaatgctct  300
ccgtgcacca tttgcttgcc attctagaat atgaacatga gcacttagtc cttaacttta  360
gccaactttg gaccgtacag gatccaaaca gggtcttagt tagaagcttc tagttttgttt  420
tgtgcacggt gataaacaat gataacacac cataagtaca aatgaaatcg tatccagaat  480
aaagttcaaa taaaagatgc tagaaaaaaa taaaaatcac tacgcaagaa gacaagatag  540
tagcatagaa gtaatgctca cgtcttcttt agtcactgtc ctcggaacat atccgacaaa  600
aagtttgaca tagttacttc tactatcatg atctggagga actttcaaga gtaatatcaa  660
tatttgacaa agaaatggta agagattaga attaaaatta ttttttccac ttaagctcaa  720
tcacatacaa cacttttcca tatggtcttc ctaccatgga atgataaatt caacattttt  780
tagcaatact gtcgcgatca catacatcac tgaatagttg ttgccaaaaa gtgcttttga  840
agactgtcgc gatcggaaat aatattggtc cgatcagtaa agactttgaa ttgagacaac  900
cagctttgaa gtcgagggtc actggttta gacaccttca taggtatata gcgttgtcca  960
ttagctactt agaccaactc cagcagcact ccacatgcgg ctccgtatcc cttttttgca  1020
cagcggagca cactattcat cagtccagca gtctccgtat ctgtctccct aaaacgcacg  1080
ccctgtacct gcactcccct tttccacggt ttctctctcc tctccgcagt tgactgcatg  1140
cgttcgcggc tgctcgcggg ccccagctgt catagactgc atgcggagtg caaatacgga  1200
```

```
gtctgctgga aacggggacg gatacggaga ggagagagaa actattggcc gtgctaaata   1260
cggatacgga gagggagtct gctggagttg gtcttaggct aataaaggtt gcaccatgac   1320
gattgcatca taaggaagat acgtactggg tgcaccatgg tacattagaa gcaccattgc   1380
gttggcactg tcagcagggc aattgagagc tattaatctg ctcaagtctg aattttcaga   1440
acaccaactg aacaagtcaa cttgtgcaaa gaaaatagat atccagatgc cccaaaccca   1500
aatcagaacc acctccttga aactaagtaa gtagctacca cgaagtgcat caagacagat   1560
caggtgattt ttctgttgga ttatccaggt ataactgaac atcaatcaat ctccagttac   1620
cttgtacaaa gcagcgacac gaactatgag aacagggaca caacctaga gatgtgtatg   1680
gtacccgaat atgtagagtg cgagcaccat atagctgaca gattgcatcg cgggaattag   1740
catgttaccg aagcaactga gacagaccag agtcatgcat gccattaaat tcatatgaga   1800
ataatgtgca tcatatgaat ttgaactggg ccatattgca aacatagaag gggtgatcct   1860
tgacaatatc tgcaacatct cactttggta ccctgcattt gaactcaatg ctggagtcca   1920
caggaagaga aatgtgtaca acaagcactc aaacagcgac tgtatagctc ccggtaatgc   1980
aatcctcaca tccgcagcaa tttccttagc tgcaactttg aacagggca tcaagtgctt   2040
actttcagat gggtctccat agttttcact ccatgagaac attatgaaag ccatgccaat   2100
cgctagaagg catgcaaccg catcaaattg aaccacatga ccaaaaccca agcctctttg   2160
gtcgtctgcc aaacacaaca caaactgaca ttttctccac aaagtgtact tcaactttgc   2220
cttcagatca ggttctagga ccgcaagata atgtgcacca gacttgttca gaggccagga   2280
tggcacatac ctgcttgcta gttgttcctc ttggacgaag tcaccttca tattaacggc   2340
ctcttcaagc aaagctgctt cagctggtgt aaggcattgt gctactctag cacagtcctc   2400
ttcagattgg cattgcatag tcctgaaata attacgagat ggggtggcca tggaattggt   2460
ctgactttaa cgccattagc cagtatcaca aactgcattg gttgacgctg aagtagcgct   2520
ttgaacaaaa agcaatgcct ctcaccagca gtatcttgga ggcccaaaca tagccaacct   2580
tcacgcaacc atattgtctt ttgttcccat ctcataggtt gtccttcgaa gttgaaaatg   2640
accacccttaa catcatctgc aattcctagt tcctttcgca ctgacgatct aaacctgtgc   2700
catcttctga ccaccagagg aacatcaatg acatcacgga aagttggcat ggggacagta   2760
tatgggagt tggagcagaa aatcgtaatg ggagtaatcc tccgctactt gccatacaag   2820
tgagcgatga tgatgtccag ctgctgcagc gtactccgtg aaaatgaagt tccagctttg   2880
cgccgtttca tcgaacacca cgtgagcatc caatgaggta gatgcaggct tgctcgcaac   2940
tgtcaccatg acgccgatgc gggccacgtc agtgagcatc gtagagaagt cgtacttcgt   3000
ggagggcagt tgccagctgg gcttgtccgt tcctagggaa gccatggcca ctccgacaca   3060
ggcagcagag ctcccacgcg cgcgggcggt ggcggtagtc agacacactg accacgggc   3120
acccgacggg caggggaatg gagcagagca taggatcatc cgcctggtgt ggtgacaagg   3180
aggagtggag taggtggact gcgccatctg cgcgggacca ctctgtcccg ccgacgagcc   3240
cgtcgtggac cttctcgcac gagtcgatcg cgcctccaag gaattcgcat gccgccttgg   3300
cctccagtag cgcgagcacc tcgccgatct cattgcggtt cggctcatcg tagcagtcgt   3360
agacgacagg aggaggagga gcaagtcgta gactccgact cctcagggag gttggagtat   3420
tagctgtcct tgatgtagtc cgagatcaca gatatgttgt agccgtttgg cttcgtcgcc   3480
tcctgctgat gcctggcgac atagttgctc cgtacgtcgc ggatgcttgg cgacataact   3540
gctccttggc acagaccgtg gcgacgcgct agagaaggcg ctcaccacca ccaccaccag   3600
gacagtagct gacgacgacc tcctcctgca gctcaagatc aactactacc cgaggtgccc   3660
gcagccggag ctggccgtcg gcgtggaggc ccacacggac gtcagcgccc tgtccttcat   3720
cctccacaac ggcgtgtcgg gtctgcaggt gctccacggc gccgcctggt tgacggccga   3780
ccacgagccg ggcaccatca tcgtcgacgt gggggggcgcc ctggagatcc tcagcaacgg   3840
ccgctacatc agcgtcctcc acagcggcct cgtcaaccgg gaggtcgtgc gcatctcctg   3900
ggtcgtcttc tgtgagccgc caccggactc cgtgctgctg caccccgctgc cggagttcgt   3960
cacggaaggc cacccccgcaa ggttcacgcc gcgcacattc aagcagcccg tggatcgcaa   4020
gcttttcaag aagaaacagc agcacaaagc acaagcagag gaagagaatg gcgcgcaatgg   4080
tgaccaccac caccacgagc tggcgatgga cgctagatcg ctagtgctat tgtag        4135

SEQ ID NO: 76           moltype = DNA  length = 4379
FEATURE                 Location/Qualifiers
source                  1..4379
                        mol_type = other DNA
                        organism = Zea mays
SEQUENCE: 76
gctgcgcgcg gcggcaggga agggacgata tagatacaca cagatggcgg actgcatgca     60
ggagtggccg gagcccgtcg tccgcgtgca ggcgctggcc gagagcggcc tgtccgtcat    120
cccgcgctgc tacgtcaagc cgccgtgcga ccgccccgc gtgtcccggg cggcggcaac    180
gacagtccag gagaccacgg agccctcgga catgagcatt ccggtcgtcg atctcggcga    240
gctgctggcg gcggacgcg gcgccgcgt caccgaggcc gtccgcgccg cgtgccggga    300
gtggggcttc ttccaggtgg tcggccacgg ggtgcgcccc gagctgttgc gcgcggcgcg    360
ggaggcctgg cgcggcttct tccgccgccc gctcgcggag aggcagcgct acgccaactc    420
gccccgcacg tacgagggct acgggagccg cctcggccgg cagaagggcg ccgccctcga    480
ctggggcgac tacttcttcc tccacctcgc gccggaggcg gccaagagca cgcccaagtt    540
ctggccggcc gtgccggca actgcaagta cgcccactc caaatttcgt acccttcttc    600
ttggaaaaaa atttgttgca gtccggctgc aaaccaggct gtttgcagcc cctcacaaaa    660
aggaggatag gtcccacccg caggtaaata atacaactaa acgttatct ggtggacctg    720
caggtggggc ctatccacct ttttgtgagg ggctgcaaat agcctggttt cgagccggc    780
tgcaacaaat tttagcgtgc cttcccatca tgcatgtgca tgcatttaga gctgtggcga    840
tgttgttatg tactaggtaa tcaacacgag gctagctccg attccatccc gtttggaaca    900
catgcatgaa ataatttctg gctatcgagg agaattgaac tgttcttatg aaactttcat    960
taattatgtg taggagtact atataaggtg ctgctacata gaccccccgg ccctaggaa   1020
gagtgggcta gcttgagttt gattgaaccc tgcaagcttt gagattcacc ttttcttctg   1080
tttgggcata tgcctatatg gaagaaaag tgaatctcaa agtttcacag ttcaacatt   1140
tagatgatgc tatatatagt tcatatgatt atatggcttt gttttttgtg tatatattaa   1200
atacaatatg tttaaacaag agtgtgtaga aaaggatgt ccttggcaaa aaatgtttt   1260
ttatcagtga catactgcga aaactacaca gctatattta attgttctat ccttaatgaa   1320
cacatatttta ggattaatga tgttttacca gagagaacga cagtgcactg actgttagga   1380
```

```
aatagattaa cgtaactgtc cctgccatg catgccgtac ttctccagca accattacat    1440
cttgttccct agtcattggg tggagccggc ctaaaatgca tagataacac ttttaagtac    1500
tccatagaaa acaagtcccg ccgtagcaat gactcagcgt ccaaatacaa cacgtgcatg    1560
aaaaatggaa agtaggtcca tggtgctttc atgcatgcaa aatgcctaga gagccacagc    1620
gcaacgcatg cagctggtca agaattccaa agctatgggg gtaggcgagt agcacggcac    1680
cgggacgtgc tgctgctaaa tcataaaagg ggtgtccctg tcgttgtaga cctcgttcct    1740
agcacgcttc tactcctgca tgcatgccaa gtgccaaatt ggctgtgctg ggactgcccg    1800
ttgctgcagt aaaaaaccgg cacatacacg tggtcgaagg acaagattac tgttagttac    1860
tgacatgcac gtacgtacaa cagtatagct agtagctagc ggctcatgta ctgtattgat    1920
gtgtatacat catgtgcgtg tatatatgct atatacaggg aggtgtccga ggagtacgga    1980
cgcgaggtgg tgcggctgtg cgagctgctg atgcgggtga tgtcagtgag cctagggctg    2040
gacgaggcgc accttcagcg ggcgttcggc ggggcgggct gctgcggcgc caccctgcgc    2100
gccaactact acccgcggtg cccgcagccg gacctgacgc tgggcctctc cgcgcactcg    2160
gacccgggcg tcctcaccgc cctcctcgcg gacgagcacg tccgcggcct gcaggtccgc    2220
cgtagcgccg gcgactgggt cgacgtcgcg cccgtccgcg acgccttcat cgtcaacgtc    2280
ggcgaccaag tccaggtaat atagcaacca acatcgttcc agctaattaa gctaggtata    2340
catcttgtgc atgttggctg tatcgtccct actctctact atagctagcg tgcccgatcg    2400
cgcgtcgtcc acagctcgtc tagatgcgtg gcttcctgga gctacgtact agtcgatgtc    2460
gacgacagat ctctgtcacg tattgtacaa acgtgaagta tttggtcttg tggttggtcg    2520
gcactcctac acgcgtacag ctagttagtg cgctgccgct cgccttgcat cggttggaat    2580
ttaaaagaat cgatagctag ctgcatctct ggatagataa ctcgtgaatg attagtttta    2640
ttaaaaacac tttaaggaca aaaggatccg atcgatgaat cttatctgtg tatactatac    2700
gtcaggaaca gtcttaattc agctctgctt ataaaaaaaa cctgtattaa ttcagcaggt    2760
agttgactct gaaacaaact aatcgtcggt gtacgtgcat gctggaatca atactagata    2820
gatgctacta gctagtacta ctcctatatc agtactagct agtagtttgc atgagaacac    2880
atgcatgggc ggtgagccgg tgacgatcat cgatcgagca caatcttaag atttatcgtg    2940
cacaagcagc aaccgaggac agagttgcat gcatgttacc gtactgtacg gtgacaactg    3000
acgaatcgcg cgcaccacgc gcgaaagcac atgcacaggt gcacaagcca atcatcgtga    3060
tatcccacgt atatgttgca tgcaccggcg gccagccagc tggcagccgc taacaatatt    3120
tgcacctgtg tagttgtagg ctctgtgtag actgtagtac aactgtacaa gttagctaat    3180
cccctgctcc acatgcatga acagaattac tgttaggccc cgtttatttc gttggaattg    3240
aatttcattt taataattat aatttagaca aaactaatta agtttatata tttatatatc    3300
taatatattt gtatattatc ttaaatcata tgagagagat agttatatac tacattaatg    3360
ttatagcaaa gcaagtagaa aagtgtctta taagttgtac atcgaaaaaa tagcatgtaa    3420
atctatagaa tcaattttca tctctcacca tgtgaatttg agatagactt atatgataac    3480
tttagaaagt ggtgaaatgt cacattctaa aaaatagcat atttcattag taagatttta    3540
attcctcaaa atgaaagaaa acaaacgggg ccttaccgta attaataaac ttcaactaga    3600
agtaacagac caacgaccgt accgctgtat atctaatggt gtaagtatat atgtgtcaat    3660
gtatgcatgc atgctactgt ttacgtacgt aactccacct ttccttttga atacgaatgc    3720
tagatgcatg taactgtccg ttcatgcatg catcgaaaaa acctcgctca tatatagcta    3780
taattaatac tgcacactgag aatgttgaat tatttattca ctcatgcatg catggacaga    3840
taatgagcaa ctccgtgtac aagagcgtgg agcaccgggg ggtcgtgaac gccgaggagg    3900
agcgcatatc cctcgccatc ttctacaacc ccaagggcgg cgtccccatc tccccggcgg    3960
cggagctggt cacggccgcg aagctgccac cgctctaccc gacgatgacc ttcgacgagt    4020
acaggctcta cgtgaggagt aagggcgcca ggggcaaggc gcagatcgag gctctcaagg    4080
gccaggcatc accagaaaat taattaattc gccaccatgc acctgcagcc tacgtacatt    4140
aattacagta cgtacgtact agcttgctag ttaataacat atcgcgtgtg tatcctagct    4200
aatgcaatt gctaatataa tctgagtta gttggctaca tgctatgagt tggctggctc    4260
caccggcgga ccaagtataa tcttatctga aataacacat gcatgtgtaa gaccaaccta    4320
ctaccttcgg taccacttag tacatatata atgatcgcat gcatatatgc gcgtggtgc    4379
```

```
SEQ ID NO: 77           moltype = DNA   length = 4243
FEATURE                 Location/Qualifiers
source                  1..4243
                        mol_type = other DNA
                        organism = Zea mays
SEQUENCE: 77
cacacagcac agcaaaagaa cctgtgtgct agctgtggct gtgatcctgt cctcctctct     60
agctagtagc tatctccatg catcttcttt aattttgttc tcatctccga ttctcagata    120
tcctcttctc tggtctcttt atatatatct atctatctct gctccagctc cagatgatga    180
gatgagatgc tggcatcata tctatctttt gttgatctga tcccttagct tgctgttgat    240
atacatgcat gcataatatt attattagta gtaattccgt cgtcaggcca gcgttcgttg    300
ttcacgcttg gttcgccgtc gttgacaaat atcggcgaat tgaagcttta ggctgtgctc    360
agcagaatta gcaagtgcaa cgcgcagttg tcaagagcaa cccaacaagg aagatatatc    420
gaaggctgca gtgatcgatc gatcgatcga ggatggaagg cgcggcggct gggtggccgg    480
agccggtggt gagggtgcag tcgctgtcgg agagcgcgcg ggcgacgatc ccggcggggt    540
acgtgaagcc ggaggctgag cggccggcgt cggcggcggg cgaggaggag ggcggcggcg    600
ggatccccgt ggtggacctg tcgtcgccgg cgacggcgcg cgcggtgtcg gaggcgtgcc    660
gcgactgggg cttcttccag gccgtgaacc acggcgtgcc cggtgagctg ctgcggccgt    720
cgcgcggcgc gtggcgcggc ttcttccggc agcccatgga ggtgaagcag cggtacgcca    780
actcgccggc cacgtacgag gggtacggca gccggctggg cgtggaggct ggcgccctcc    840
tcgactgggg cgactactac ttcctccacg tccgccgcc ccacctctgc gacccgcgca    900
agtggcccca cctgccccc ggcctcaggt acattaacta ctacttgttt atttattttt    960
tattattata ttccatctga ggaggatcgg atcatcggag gagttgatgt acttacgagt   1020
ttacggcagg aagacgacgg aggagtacag ccgcgaggtg gagtgctgt cgggcggct    1080
gctggcggcc atgtcggcgg ggctgggcgt cggggaggcg cggctgcggg aggcgttcgg   1140
cggcgcggag ggcgccgggg tgtgcgtgcg cgtgaactac taccccgcggt gcccgcagcc   1200
ggagctcgcg ctggggctgt cgtccactcc gacccgggg gcatgaccg tgctcctcgc    1260
cgacgaccgc gtccgcggcc tccaggtgcg ccgccgcgg gcctgggtca ccgtcgaccc    1320
```

```
cgtgcccgac gccttcatcg tcaacgtcgg cgaccagatc caggtatgcg tattacaaac   1380
agacacagtc gttgacgcgt gtttggttca gggcttatta agtcacatgc atccctccct   1440
cgtggttgcc cgtgactaac cgtcgttgcc aagtgatggg ttagctagct agttgtgtaa   1500
acgtggcagc ctcacaaaag ccatcgttca tttcaccacg tacgacacgc acaccggccg   1560
tccctcagtt gttaactgat aattacgtat gtggccgaca ataataatcc acctggcccg   1620
taatgatggt agttagcttg gacgcacgca tgcccgtcgt gtcgagcgat gagttagctg   1680
gggataatga tctgcaggaa gacttgcgcg tacgcggggt ggatggatgg atggctaaag   1740
tatgcagaga gcagtagtgc gctactagtt agatgctaat attagctata tacagcagtt   1800
ctaaacaccc tcaactaatt cttaattgac ccacagctaa caactagttt atgaagcatt   1860
aaatatgttt tggacataga aaaaccatcg tgaacccttt gcattgagaa agggtaggtc   1920
tataagtagt gtgttcttga tgatgtgtta atataaatat cgtttataca aaggggggg   1980
ggggggggggg gggggggttg tcgccttgtc gggactggtc ttagctggct taacccacct   2040
acaatttatc agctggctaa ctaagctaac tactagttat aagagtatct ctccaagaga   2100
ctacttaact cacctaacaa ttcattagat atgttaattg gtttcctcac cggctaaact   2160
tttggctag ctaccctgaa tagccaaact aagatgatac atatagagag ctcaaaatga   2220
agaatcccctt gatgaagatg ctctaatggt tctaagcagg acctcaatta gctatccagt   2280
actagagaga acgacgagta ttaattagca ctctcgcata gtagtagtag agagaaagag   2340
agagagaaa atgatctgtt gtatctgatg atctcatggt cacgcgggcg atcaggatca   2400
gctgcacccg tccagtacgc acggccagga atttttactta ccccttttgga gggcacaagc   2460
actcacatca ttctggtggt gcttcgctac actagtgcta cccctgctag tactgcacta   2520
ctagagaagg aaagagcgcg tgcaggtgca gagcgcagca gctgagcagg cagcagcaaa   2580
aaagaaaaaa aagattccca tatcgctcgc gacccacggt ttgagaccgc acgcaccacg   2640
agaggtgagg tgattgatag cgtacctaac ctacttactc tactctaccc gtcgtgtggg   2700
cccttcacca agacgagttt ccaaaacggg catacgccca cgtcaggacc cagtcatcgc   2760
acacgcacac aacccaaacc gaggcccgtc tagtgtagtg tagtgggccc gcggccgcca   2820
tcaatggat ctgcgtccca tctcggcggg cgcgaggtga ggagaggagt cgtcgtcgac   2880
gacgacgagt agtctgcctc tgctccggcg ggccggacgg ccgcagtggt gtggtgtggt   2940
cgtcatggtt atgacaggga cgacaggcgc ccgtgggcct ggtggctgga cgacgatgca   3000
tatctccgat ccatgtgctg tgtgtgccca tcatcctgtt ggtacggttg gggggaacag   3060
gagcagagac agcaggcagg cacaggcagg gctcactcca ccggccaagc gagccaaatc   3120
tcggtcggaa tgaaacgtgc gtgtttgcta gccttttgct ttattagcac tcattatata   3180
tatatatata tatatatata tatatatata tatatatata tatatatata tatatatata   3240
tatatatata tatatatata tataactcaa tgcagaatgg attatccaga ccatgcctgc   3300
atgcgatgcg acgcaacatg ctagcacgtg cccgcgtagt atatattagc cacccaccca   3360
actgctggg gggcactctg cactctgcaa gtctgcatca gcatgcccat ggctggcgt   3420
gctgctagct gtcctgcact gcacgctggt gctgctgggc gcgcgcggcc accggccacc   3480
gccagccttc cctgctaccg acgcagcgcg tgcatgcaaa gcaaagcagt gcgagagaga   3540
ccatgtgtcg attaactgct tcctggtcct ggtccaggct tctgctcccc gggccacacg   3600
gggagctagc acagagacgc agcaagcacg tttttcaaaa tccacataagg ggcagggatc   3660
cgtccgcggc tgggcggcgt gcatgcagca cggcctcctt tgttgccccg atctctctgc   3720
tccggtccgg cctcccgatg tcgatgaaac tgatgtgata ggagtacatg catgcgcatg   3780
gtaatgatgc cgacaggttt catgtatttg ggacagatgg gtcagtcggc tggtggtgtt   3840
gcatgcgta ctcgtcccg accagcgcat gcacacgtac gtcgcgtcgc tccatgcatg   3900
cagtcctaat actactacgc atgtctctct ctgtgtgtgt gtgtacacgc aggtgctgac   3960
gaacgcgacg taccgcagcg tggagcaccg ggtggtggtg aacgccgccg acgagcgcct   4020
gtcggtggcg ctcttctaca accctaggag cgacctgccg ctggcgccca tgccggagct   4080
cgtctcgccg gaccgccccg cgctctactg ccccatgacc ttcgacgact accgcatgca   4140
catccgccgc aagggggcctc gcgggaagag ccaggtcgac tccctcaagg tcgccgacgc   4200
agtcgacgcc gacgccgacg ccgacggcag acggtgctac tag                    4243

SEQ ID NO: 78          moltype = DNA   length = 4274
FEATURE                Location/Qualifiers
source                 1..4274
                       mol_type = other DNA
                       organism = Zea mays
SEQUENCE: 78
atagcaagca aacccagctc gatcgcctct cgcactccgc gatccatctc tggcaatttt    60
ttttcctctc gaaattaaac gtctgttttcc atctctggct atatataccc ctcgttaggt   120
ctctcactcg ttaagccatc caaggagcga ggggtacaag caccaccgca g tctcagccct   180
ccgccctctc tctctctccc ttcaagaact actcgaggtc taattgtccc agtacgtctc   240
agctcgttcc ccttgcgaat ctctctactc gcttgcatgt gtcctagcaa atcaagctca   300
tcgttatata tattgctcga tcgatccagt ttttattggc acagcacgcg cccggccata   360
ccttacttac tgcatgcatc atgactcatg agtcctcgtc gtcgtcagtt gtcaccggca   420
ttcccatcca tgatcgtcgt agaccgatcc cctcgtcctcc cctcccacca tcaccccttgt   480
ttcttcgcgc gtcgaatgca tatgcagtca cctcggtact ttcctcgctc tcagctgctg   540
agccgaccgt taatttcttc actgttgcgc atgcacaggc ctgccgcgcg cgtcggcac   600
gccagaagga aggacgtacc agaggcacac aattcaaat ggcggactgc atgcaggagt   660
ggccggagcc cgtcgtccgc gtgcaggcgc tcgccgagag cgggctgtcc gtcatcccga   720
gctgctacgt caagccgccg tgcgaccgcc cggcccccg accatggcag   780
caccggcgcc ggcagtccat ccgaggaaga aggagcccag ctcggacgcc atcgccagca   840
ttccggtcgt cgacctcggc gagctgctgg ccgcagacgg cgccgtcgcc accgtcaccg   900
aggccgtcgc cgccgcgtgc cgggactggg gcttcttcca ggtggtcaac cacgggtgc   960
gccccgagct gatgcgcgcg gcgcgggagg cctggcgcgg cttcttccgc cgcccgcccg  1020
ccgagaagca ggctacgcc aactcgccgc gcacgtacga agcgcgatca  1080
gcgtccagag gggcgccgtc ctcgactggg gcgactactt cttcctccac ctcgcgccgg  1140
aggcggccaa gagcacgccc aggttctggc cggcccagcc cagcaactgc aagtacgtgt  1200
accttttcgat ttttttctact gttctgcgtg cttccagatg atcctaagct gatggttaat  1260
tgagctgtag cgcgtgccca tgtgcatgcc ttctagttca cataatcata cgtacttaat  1320
taactccgaa ttgtcaacct actagataga tagactaatt cgtgatgtgt ggacacgaac  1380
```

```
acacaattta ttttattccc aagtaagaca ttatcagtgt gttgtgcgta tatgattttt   1440
tttactcttt tgtagtttta ccagagctag atggccttca tacatgtatt acatactcct   1500
ctgtcctaaa ttaaaattcg ttttacctt ttattagatt catacaataa tatattctat    1560
atatatctag ttcataacca tctatattaa tatagacata aaaatataga gttaaaacaa   1620
ctactacttt agaaccgaga gagtaggata tatatatgtt tacacacgcg tagaaaaaaa   1680
aaagacgtgt ccttggcaaa gtttaaaata gtgttttagt gacatactgc gaaaactaca   1740
caacaaccat acttaattt ttctattctt attaatcaac acatatttct gttgaattga    1800
ttagctaggg tttggtgatg ttttgtgcta gctccgactg ttcggaaaca atagattaac   1860
gtaaaccgtc actgtccatg ccgtacttct ccaaccattg cgtggagcct agctaaaatg   1920
gtatagataa cacgtactcc atagctagaa aacaattaag ttccgccgta gtaataatac   1980
agatgactga gagcacctaa ataacaacac gtgcatgaaa acggaaagta ggtccatggt   2040
gctttcatgc aaaaaaaaaa tgactagaga gagccacagc tagctagcgc gcagcgcatg   2100
caggtctaca gtccaaagcc atggcagcac acggcactgt cgtgctcctt ccaaattgta   2160
agaggggtgt ccctgtcgta gtagaccttg ttcctacact agctagctgc atgcaaagtg   2220
ccaaattggc tggccgggct cgttgtgtat attgatgtgt gtgcattata ttatacaggg   2280
atgtgtcgga ggagtacggg cgcgaggtgg tgcggctgtg cgagctgctg atgcgggtgc   2340
tgtccgtgag cctagggctg gacgaggcgc acctccagcg ggcgttcggc ggggcggagt   2400
gcggcgccac cctgcgcgcc aactactacc cgcggtgccg gcagccggac ctgacgctgg   2460
gcctctccgc gcactcggac cccggcgccc tcaccgtcct cctcgcggac gtgctcgtcc   2520
gcggcctgca ggtccgccgc gccgccgccg acgactgggt caccgtgcag cccgtccgcg   2580
acgccttcat cgtcaacgtc ggcgaccaag tccaggtata ttatattata ttataaccac   2640
accaattaat accatcgcga ggatgatgac ccgcgctatc agagagccaa taattaaaag   2700
ctcaacatat agaagaaaat acttccagtt ccagatgcgt agctttctgg agctactata   2760
gtcaacggat taagatcgtg actgtcacgc gtacctacct gtacaaacgt gaagtatttg   2820
gtctcgcctt attagataga attttgtttg ggagcaacgg aagggatccg aggagttaaa   2880
atgccattac tatttaaaat taaaaatagc aaagaaacac atctggatga gtataatcac   2940
tgatgatgaa tgattaaatc tttaattagt attcaggtag ttgactctgg aacatatga   3000
ttgacgggcg cgcggtgata gatcatgcat cgggcataac gcgtataaat aatattagat   3060
ttttcgtgca gaagcagcta gctataccgt ggaaccagat agttgcattg catgcatgtt   3120
acgacggtgg caactggcaa ctaacgaatc gtacaacgca cacgaaagca catgcacaga   3180
caggtgcaca cgccgttgca cgtaccggta ccctctagca gtgttcgtac ctgtagactg   3240
ttgtacaagt aaccgtaatc ttcaaccagt agaccaacga ccgttatata gttaagcatg   3300
catgttactg tttacgtgca gtggtatatc ctttcgaata cgaatgttgc atgttactgt   3360
tcatgcatgc atatatagaa aaccccgctc agctttagct ttagctacaa tcccaaatcc   3420
caattccctc ccgatagata accacgatgt ataccagtat atatatatgc gtgttaggtc   3480
aaatgatttc tagaagtcta gaaccggtca ttagttgcct actatagcta aaggttgctg   3540
atgatgatct tgcatttcca ctgactcacc gacgacagat actgagcaac tccgtgtaca   3600
agagcgtgga gcaccgggtg gtcgtgaacg ccgaggagga gcgcatctcc ctcgcgctct   3660
tctacaaccc caagggcgac gtcccatcg ccccggccgc cgacgctggtg gcggccgcga   3720
gcctgccggc gctctacccg acgatgacct tcgacgagta caggctctac gtcaggaaca   3780
agggcgccag gggcaaggcg cagatcgagg ctctcaaggg ccaggaaca ccagaaagtc    3840
aattatagac gacgactagc tagctactag ctagtacgta gccaccactt gtctacgtac   3900
attacagtat atactagcta ctagctagtt aataaacaat tcgtcgtgt gtgtcctaat   3960
taatatgaca attgttaatc tggagttagt tcgttactat acgctgcgct ggctcccccg   4020
gcggacgacc catggataat ctgattgtaa ttgtaataac acgtgtaaga ccaacctact   4080
acctttggta ccactttcta ctcaaatatga tcgatcgcat gtatatatgt gtgttggtg   4140
cgatatacaa cctgattgga tggttgcacg tctatgtgca gtctggccgc gtcttagcta   4200
gctagatacg ataattttg agcgtatagg taaatgcagg ttaatagcat caaaatagtt   4260
tattttgctt atat                                                     4274

SEQ ID NO: 79          moltype = DNA  length = 1112
FEATURE                Location/Qualifiers
source                 1..1112
                       mol_type = other DNA
                       organism = Zea mays
SEQUENCE: 79
atggcgacac caccgcgcgc gctgctcgag cgcgtggcgg gcctagtcgg tgggcggcct     60
ccgcgccgac ggcttgagct cggcgagcgc gtcaagctcg gcgtagagcg tggcggtgac    120
gcggtcgagc ctgcgcacga gcggcacggc gtcggagcgg gatgcgacgg cggcgagcgt    180
gcccgcgtcg gcgcgttcgg ccaggaggtc ggcgtagacg tggccgaagc ccacgagcgc    240
cggggccgcg caccggtggc cgaggcgcga ggccaccgcc accacgcggt tcagcgcgtc    300
cagcttctcg acgagcgagc cagcctcggg gacgccttcg acctggcgcg cacccatgcc    360
aacaaccaca acgcgccgag gatctccgtc atcgacatct ccccttcct cgacagcagc    420
aaccagcagc agcagcggga cgagtgcgtg gaggtcgtgc ggccgccgc cgccgactgg    480
ggcatcatgc acatcgccgg ccacgacatc cccgccgagc tcaaggaccg cctgcgcgcc    540
gcaggaaccg ccttcttcgc cctccccgtc caggacaagg aggcctacac caacgaccct    600
gcctccgccc gcctgcaggg ctacggcagc cgtcttgccg ccaacgcctg cgggcagcgc    660
gagtgggagg actacctctt ccaccttgtg cacctgacg ggctcgccga ccgcgctctg    720
gccacgtac cctcccgact acgtcgccgc caccccgac tttgtcgcg cccgcccgat     780
tgcgacgttg gttagcgcgg gattgttggt cgcagcgcga ttggcggaat gatttggagg    840
ggggcgagcg tggttcgttt gcggacgggc ggggttggca ggcggagacg gcggcgtgga    900
ttccgggcg acagttgttg gcggcgtgga tttcgggcgg gcggaggtgg tggggggca    960
gtctacattg agctccttaat agttagtaga gataaatcat aaacacaaac tgactccaa    1020
atcatagaca cagatgatgt gatcgcaaag aaacaccaca tgtgggttgt aaaatttcaa    1080
atgttctggg tccttggtg taccagaact aa                                   1112

SEQ ID NO: 80          moltype = DNA  length = 1521
FEATURE                Location/Qualifiers
source                 1..1521
```

```
                        mol_type = other DNA
                        organism = Zea mays
SEQUENCE: 80
atggcgcccg ccgacggcga gtcctccccg ccgccgcacg tggccgtggt cgccttcccg    60
ttcagctccc acgcggcggt gctgctctcc atcgcgcggc ccctggctgc cgccgcggcg   120
ccgtccgggg ccacgctctc gttcctctcc accgcgtcct ccctcgcgca gctccgcaag   180
gccagcagcg cctccgccgg gcacgggctc ccggggaacc tgcgcttcgt cgaggtaccg   240
gacgcgcgc ccgcggccga ggagaccgtg ccggtgccgc ggcagatgca gctgttcatg    300
gaggccgcgg aggccggagg ggtgaaggcc tggctggagg cggcccgcgc cgcggcgggc   360
ggcgccaggg tgacctgcgt ggtgggcgac gcgttcgtgt ggcctgcggc ggacgcgggc   420
gcctccgcgg gggcgccgtg ggtgccggtg tggacggccg cgtcgtgcgc gctcctggcg   480
cacgtccgca ccgacgcgct ccgggaggac gtcggcgacc agggtgcgtt ggattctact   540
actacagtac tacttctctc ccttccttgt cccttcattg cgcgcgggtt tgatgagcga   600
atggctgttg catttccatc gttcgcagcc gcaaacaggg tggacgagcc actgatctcc   660
caccccgggcc tcgccagcta ccgcgtccgt gacctcccag acggcgtcgt ctccggcgac   720
ttcaactacg tcatcaacct cctcgtccac cgcatggggc agtgcctccc cgcgctctgcc   780
gccgccgtgc cactcaacac gttcccaggc ctggaccccgc ccgacgtcac cgcggcgctc    840
gcggagatcc tgcccaactg cgtcccgttc ggccctcacc acctcctcct cgccgaggac   900
gacgccgaca ccgccgcacc agccgacccg cacggctgcc tcgcctggct gggccgccaa   960
cccgcgcgcg cgtcgcgta cgtcagcttc ggcacggtgg cgtgcccgcg gcctgacgag  1020
ctccgcgagc tggcggccgg gctggaggcc tcggccgcgc cgttcctgtg gtcgctgcgc  1080
gaggactcgt ggacgctcct cccgccgggt tccttgacc gcgccgcggg caccgggtcc   1140
gggctcgtgg tgccctgggc gccgcaggtg gccgtgctgc gccacccttc cgtgggcgcg  1200
ttcgtgacgc acgccgggtg ggcgtcggtg ctggagggcg tgtccagcgg ggtgcccatg  1260
gcgtgccgcc ccttcttcgg cgaccagcgg atgaacgcgc ggtccgtggc gcacgtgtgg  1320
gggttcggcg ccgcgttcga gggcgccatg acgagccgcg gagtggccgc ggccgtggag  1380
gagctgctgc gcggggagga aggggcgcgg atgagggcaa gggccaagga gctgcaggcc  1440
ttggtggccg aggcgttcgg gccaggcggt gagtgcagga agaacttcga caggttcgtc  1500
gagatagtct gtcgcgcgtg a                                            1521

SEQ ID NO: 81           moltype = DNA  length = 420
FEATURE                 Location/Qualifiers
source                  1..420
                        mol_type = other DNA
                        organism = Zea mays
SEQUENCE: 81
atgggagcct tcatgacgca ctgcggctgg aactccgtgc tcgagtgcgt cgcggcgggc    60
ctgccgatgg tgtcgtgccc gcacttcacc gagcagttca tgaacgagaa gctcgtggtg   120
gatgtgctat gggtcggcgt gcctgtcggc gtcaaggcgtg ccgcgcagtg gggcgtggat   180
gcggagggtg tgctggcgac gaggcaggac gtggagaggg cggtggctgc ggtgatggac   240
tacgggagg agggctctgc cgccgggcag agggccgcca agctcggcag gaaggctcgg    300
gaagccgtgg tacacggtgg ctcatcgttc ggaacgtgg cgctgctcat acaacacgtc    360
cagcagcgag ccagcacttag aaatccatgg attgaaaaga agccgagcga ctgtagataa   420

SEQ ID NO: 82           moltype = DNA  length = 1763
FEATURE                 Location/Qualifiers
source                  1..1763
                        mol_type = other DNA
                        organism = Zea mays
SEQUENCE: 82
ctgtccgcca atcgaggtgc agctgcaatg gggtcgccgt tgccgcacgt cgccgtggtg    60
gcttttccct tcacctccca cgccccgaag gtcctgatgg tggcgcgcgc tctcgccacc   120
gcggcgcctt ccgccacctt ctccttcatt tccaccaccg actccctggc gcggctcccc   180
accggcgccg cgctgccccc gtcgaacctg cgcttcgtgg aggcgccgtc aggggagggg   240
gatgccgcgg ggatcccatc gtggcgccgc atggaactct tcctcgacgc cgcagaggat   300
ggtgggcttc ggcaggcgct tgaaacagcc cgcgccgcgg ctgcggcgc cgccgtgacc    360
tgcgtcgtcg gggacgcctt catgtccatg gccgcggacg ccggggtgcc ctgggtcgcg   420
gtctggacgg gaggccgtg cgcgctcctg gcgcacgtca tcggcgacac catccgcaag   480
gacatcggcg accacggtac gtaccgccact cccggtccgc cgccgttgaa tctatttgct   540
gcctgagctc gagctgctgc gctgcactct gcatctgtaa tggtggcaac acggctggtg   600
cagcggcgag ccgggccgat gagcctctgg cctcgtaccc tggcctcggg atgtaccgcg   660
tccgcgacct ccccttcggg gacgccgcg ccggcggcga catgtatcgc gtcatgacga   720
ccctcctcgg ccgcgtggcg gagcgcgtac ccgcgccgc caccgccgtc gcgctcaacg   780
cctccccggg cctcttccccg gaggacgtgt cggccgacgc cgccgggtcc aggccaact    840
gccttcccat ggggccctac cacctcctcc ccggcgccgc cgccgccgcc gccgcgctag   900
cagacgacgg cgaccgccac ggctgtcttg cctggctcgc ccggcgcgac gcgggcaccg   960
tcgcgtacgt cagcttcggc acggtcgccg cgctgccacc ggacgagctc cgcgagctgg  1020
cctccgggct cgaggacagc ggcgcgccgt tcctgtggtc gctgcgggag gacgcgtggg  1080
cgctgctgcc tccggagttc ctggagcgag ccaaggccgc agccgactcc aggctactgc  1140
tgccgtgggc gccgcaggcc gccgtgctgc ggcaccggc cgtgggcgcg ttcgtcacgc   1200
actccggctg ggggtccgtc gtcgagggca tggccgcgg cgtgcccatg gctgccgcc    1260
cattcttcgg cgaccagctg atgaatgcgc gtgcggtggc gcgcctgtgg tgcttcggca  1320
cggcgttcga cgaggacaag ccgatgacga ggggtggcgt ggcggcggcg gtggcgtcac  1380
tgctgacagg ggaggaaggg gcacggatga gggctacgac gcggacctg caagccaggg  1440
tggtcaaggc cttcgggcct gacggtggat ccgtcaacaa cttccacaaa tttgtcgaca  1500
cttgcctgac tgtagggaga gacatgcact tgaacgcccg tggtaatcat ccaatgtgaa  1560
acactaaaat aaatctacta gagcatggac agatctccaa catattggac ctctctcatc  1620
tttttgtttt acatattttt agttcaaaat aaattaacag atcataaaca ttctgtaaca  1680
gagatagtaa cacgttattg cctagcaata tctaagatta cttttttttca caataaaatac 1740
```

```
agtggcgccc attgtttgtt gct                                                    1763

SEQ ID NO: 83            moltype = DNA  length = 1377
FEATURE                  Location/Qualifiers
source                   1..1377
                         mol_type = other DNA
                         organism = Zea mays
SEQUENCE: 83
atgcacctgc tgatgctccc ttggctcgcc ttcggccaca tcgtgccgtt cgtgcagctg    60
gcgcggaggc tgctgtcctc cacctcctcc tccgtccgcg tcacgttcct cacggccgct   120
ggcaacgtcc cgcgcgtcga ggccatgctg tcctctccct cgtccaccgg cgaggcggcc   180
gtcgtcgtgc cgctgcgcct gccccacgtg ccggggctgc ccgaggacgc cgccagcacg   240
gcggacctct cgcccgaggg cgccgagctt cttaaggccg cgctggacgc tgcccggccg   300
caggtggccg cgctgctggc cgagctccgc ccggacgccg tgctgctcga cttcgccacc   360
ccgtgggccg ccgaggacgc cgcggcgctg ggcgccaagt cgctccggtt cagcgtcttc   420
tccgccgtcg caggcgccta cctctccgtc ccgcgcgcc gccccgacgc ggcgggccag   480
ctgccgtcgc cgcgcgacct catgtccgcc cctgccggct tccccggctc ctccccgctc   540
gccgccgccg gcgtcccggc gtaccaggca gccgacttca cctacatgtt caccagcttc   600
ggcggccagc cctgcgtcca cgaacgcgtg gtggccggca tccgggcctg cgacgggctc   660
gtgctcaaga cctgcgccga gatggagggt gcctacatcg actacctcgc cgcgcagttt   720
cgcaagcccg tgctcgtggc ggggccgctg gtgcctggcc cgccggcggg agatctcgac   780
gaccactggg ccacctggtt gtccgcgttc ccggacggcg cgtcgtctt cgcctcgttc   840
ggcagcgaga cgttcctgcc gccagccgcg gccacggagc tgctcctggg gctcgaggcc   900
acgggtcgcc cgttcctcgc cgtgctcaac tccccgacg gcgccgtccc gccgccgggg   960
ttcgcggaga gggtgtcggg gagagggctc gttcatgccg gtgggtgcc gcagcagcac   1020
atcctgcgcc accggagcgt ggggtgctac ctcacccacg ccggcttcag ctccgtcgtg   1080
gagggcctcg tcgccggctg ccgcctcgta ctgctgccca tgaagggcga ccagttcctc   1140
aacgcggcgc tgttcgcgcg cgagctccgc gtgggcgtgg aggtggcgcg ccgcgacgac   1200
gacggctggt cgggcgcca ggacgtgtgc gacgcgatcg ccgcagcggt ggcggacgtg   1260
gggaaagggg acgccaggaa gtgggccgac ttttttgacgg acgacggcgt gcaagggagg   1320
ttcgccgacg agttcgtccg gcagctcagg gagctcgtcg gcgcggcctc cagttga      1377

SEQ ID NO: 84            moltype = DNA  length = 3687
FEATURE                  Location/Qualifiers
source                   1..3687
                         mol_type = other DNA
                         organism = Zea mays
SEQUENCE: 84
cgacatctcg tgtctctgtt gggagctcct tcaacatctc gtctctctca tcctccgacg    60
ccatccgctc ccggcccggc cgagccgcgc gttgtgtatg gtacaaaccg caaaccttct   120
ctctctaatc gatgctggta cctgagaccg gttgcggaac tttgccgccc agcctcctgc   180
attgcgtatt tgcatgcttg gtgttcgctt gtttgtctgg caccagatcg ggtctgaagg   240
cgagaacgcc agacggccag ataatattgt ccttgtgatg ttctcattt cattaccgtc   300
cccgggtgat ccgaagttgg tctatttagc gtgacaatat attcaattta gtagcttaat   360
tgaacttgct ctagggtaaa ttggcctgtt tgctccctga tgtgcagatg aaaaaaaata   420
tacattatgc tccaccagat tttggtcatc ttcttgcaaa aggacagtat cctatgcgtt   480
gggatcttgg tgcatgtttt ctgatctcct tgctttatct atacatatta cgtccgttga   540
tttcattagt gaaatggtat cctatttttta gtaaaggaat gtgctcttct ctcctgtttt   600
gtgttgggat gattaagata ttatatatag tggtaacaga taaattacca gtagattcaa   660
ctaaatgcag cgttccttct ttcttgattg caaggatgtg cttagtaata tagcatgtgc   720
cacgctgatc tgagctctca attgtttgta cacgcacggt ggcatttgtc aacacgcttc   780
cagtttctgt gttgtaattg tttaatatga tatattttct catgcatata tggatccaca   840
caattattta tgaactgaca accaattgcg cccacgtgca catggaacta ttttcatggt   900
gctttggaaa tcgattcct gcttcttggc tgaatgtttc ttttctttt gcaatactaa   960
tttcaacttc ttatagttaa aaattttgtg tcgtgttccc attgtgtgac atgtaaatct   1020
tcatcattaa ctgcgaaaat taattagctt tgctctgttt gaatgcaatt catatctgca   1080
gcattagttt gatcttttcag catgttgtca gctctaatcc tgtttagtca ctttgctctt   1140
acaacaggat tccaaaagca atcatacagg ggctatggcg aggccttaca aacctaagaa   1200
tatcctcatt acaggagctg ctggttttat cgcctcccat gtcgcaatcc gcattaccaa   1260
gaagtacccc gattacaaga ttatcgtcct tgacaaactt gactactgct ctaatctgaa   1320
gaacctgctt cctgtgagct catcaccaaa cttcaagttt gtgaagggtg atattgcaag   1380
tgttgatctt gtcaacttcc ttcttgtcac agagaacatt gataccataa tgcacttcgc   1440
ggcccagaca catgtcgaca attcatttgg gaattcttc gaatttacca agaacaatat   1500
ttatggtaca catgtacttc ttgaggcctg caggattagt ggcagatca agaggttcat   1560
ccatgtcagc actgatgagg tctatgggga gactgacgag gatgcagttg ttggcaacca   1620
tgaagcatca cagctgcttc ctacaaaccc atatgcagcc accaaagcgg gagcggagat   1680
gcttgtaatg gcatatggga gatcctatgg actgccagtt atcactactc ggggaaacaa   1740
tgtctatggc ccaaatcagt tccctgagaa gcttatccca aagttcattc tcttggccat   1800
gagaggggag cccctcccta tccatgtgga tggagtcaat gtccgtagct acctctattg   1860
tgaggatgtt gcgaggcat ttgaggtcat tcttcatcat ggagaagttg acatgtttta   1920
taatattgga acaaaaaggg agaggacagt gcttgatgtg gcaaaagatg tttgcagact   1980
cttcaatctt gaacctgaca aagtcatcat gtttgtcgag aacagacctt taatgaccaa   2040
gaggtatttc ttgacgatg agaagctcaa gagccttgga tgggctgagc gcaccccatg   2100
ggaagaggtc ttaaaaaaga caatggaagtg gtatgtagaa aattctgatt attggggtga   2160
tgtttctggg gccttactgc ctcatccaag gacattgatg atgccagggt gcgaggggtc   2220
tgaggagatt aaaggaatac tcagccggtt taataacatt caaacaaagg tcggttcaac   2280
atcagataat gctccagaac cgcatgcctt caagttcttg atatatgcca ggacaggatg   2340
gatcggcgga cttcttggga aaatatgtga gaagaagga attccatatg aatatggaaa   2400
tggccgcttg caagagcgtt cttcactcgt cctagacatc caaactatta agccaacaca   2460
```

-continued

```
tgtcttcaat gccgctggtg tgactggaag gcccaatgtt gattggtgtg aatcgcacaa   2520
gccggacacc atccgtacca atgttgtggg caccttgaat ctagcagatg tatgtaggaa   2580
gcatggctta ttgatgatga actatgccac tgggtgcata tttgaatacg atgcacatca   2640
tcctgaaggg tcaggtatcg gcttcaaaga ggaagataca ccaaattta  ctggttcgtt   2700
ctactcgaag acgaaggcaa tggtaagtcg gtaaatgctt gttacccttg caactgttac   2760
ttttgtctca actcctaagt tgacatattt catgtttcga atagtgaaag aaacaagtgg   2820
ctattctttc ttgaaaaatg caggtcgagg agttattgaa ggagtatgag aacgtctgca   2880
ctctgcgagt tcggatgccg atatcctctg acctcagcaa cccgcggaac ttcgtgacaa   2940
agatcagccg ttacaacaag gtggtgaaca tccccaacag catgacgata ttggacgaac   3000
tcctgcccat ctcagtggag atggcgaaga ggaacctgcg gggcatctat aacttcacca   3060
accccggcgt cgtcagccac aacgagatcc tagagatgta caagcagtac atcgaccccta  3120
gcttcaagtg gacaaacttc accctcgagg agcaggcgaa ggtcatcgtt gctccgcgaa   3180
gcaacaacga gatggacgca accaagctga agaacgagtt ccccgagctg ctgtcgatca   3240
aggactcgtt gatcaagtac gtctttgagc ccaacagaa  ggtgcccaca gactgaagcc   3300
cgaagggctg gcacagctga taccgtacaa cacagcaacc attagtgtta gactatgtgt   3360
gtgggccagc actactttac ttttgggctg tcggtctatt agggttagag tcctgtgagt   3420
ctatatattg tacctcatct cttatacaat acatttttgg gctgtgagtc tatatattgt   3480
cgaacagcag aggaggtcga gggcgggct  gtccgcccaa atccacaccg ccgccgcttc   3540
tagggcaggt cgtcgtgacc tggacctccc ccgcacggac atcctgcgg  ccgctgacg    3600
cggccactaa gtgtgtttgg tttgatgtca aagtaggatg agtcgggggc gctatcgtcc   3660
cctcgatttt ttgggatcat gccgccc                                       3687

SEQ ID NO: 85         moltype = DNA  length = 1567
FEATURE               Location/Qualifiers
source                1..1567
                      mol_type = other DNA
                      organism = Zea mays
SEQUENCE: 85
agtctcgatg gccgccgccg actcctcccc gctccacatc gtcattttcc cttggctcgc     60
gttcggccac ttgatcccg  gcctcgagtt cgccgagcgc ctcgcagagc acggccagcg    120
cgtgtctttc gtctccaccc agggcatcct ccgcaggctc cgcccggtcg cgcccgcgtt    180
ggcctcgctc atcgacttgg tggccctccc gttcccgcgc attgacggcc tcccgatgg    240
cgccgaggcc actagcgacc tcccgcccgg cacggccgag ctccacgtgc aggccatgga    300
ccgcctcgcc ccggccttct ccggccttcct cggtgccgc  tgcgccgacg ggagcgaccg    360
caaggtggac tgggtgctcc tcgacaactt ccacgcgtcc atggcggacg tcgccagcga    420
gcacaaggtt ctggagatgg atatagtaca gcgcaatgaa attaaaatga taccctgca    480
ctgcagtaac ccccttccca tgtcctgcag gttccctgca tactgaacat gccctactcc    540
gcggcgacga cagaggattt cggcattcca gacccgtcgg ttctaccaat gttccggcca    600
tttgtggaga ccttcaagag atgcaaagtc atcgctgctc gtagcagctt cgagttggaa    660
ccggagtccc tgcctctcat gacaaagatc ctcgggaagc cggtcatccc cgtgggccta    720
cttcctccgg cgcccgccgg aggcaacacg cagcgcgacg acagcgcagc cctgtcgtgg    780
ctcgacgagc agccgtccaa gtccgttgtc tacgtcgcct cgggagcga  gtacccgatg    840
accgtcaagc agctgcacga gatcgcgcgc gggctggcc  tcgcccggac gcgcttcctc    900
tgggccctca agaggcctag cgtcgcccac cccgacgagg acctcctgcc gccaggtttc    960
gaggagcgca cgcgcggccg tggctccgtc gtcacgggct gggttcctca gaccagcata   1020
ctggggcatg gcgccgtcgc cgcgttcatg atgcactgcg gctggggctc caccatcgag   1080
gcgcttcagt acggccatcc tctggtcatg atgccagttc ctgtgacca  cctgtccacc   1140
gcgcgggtga tggagcagcg gaaggtcgga gtcaaggtgc ggaaggagaa gagtgacgaa   1200
gcgttccttg gtgacaacat cgccacagcg atacgggctg tcatgtgcga agaagagagc   1260
aagaggatct ttgtggccaa tgctaagagg atgcaggaga ttgtggcaga cgacgagtgc   1320
cacaagaggt acatagacga attcgttcag agcctgaaga cctacaagaa ctgaaacatg   1380
catgctgagt gcactcaggc agcatacttg gcaatggcat tggcgttaca caagtgatcc   1440
gctggactcc agctaatagt acgatgtatc ttattttgct gcaatatgta actttatcat   1500
tgtttggttg taaaaatatt tgaatttgtt tctcgtgaat tgcatgaaag ttattcatat   1560
ctatcat                                                             1567

SEQ ID NO: 86         moltype = DNA  length = 1790
FEATURE               Location/Qualifiers
source                1..1790
                      mol_type = other DNA
                      organism = Zea mays
SEQUENCE: 86
gagaagcatc ccagagaccc agacagcaag gaaccttgag cctgccggca actctaacga     60
cgacgatggc cgaaggggac ggtccaactc cagcccgcgg cgctcgcgtc gtgctgttcc    120
cactgccgtc ccagggccac ctcagcccga tgctgcacct cgccagcgcg ctccacgcgc    180
gggggctcgc agtcaccgtc ctccacacgg cgtacaacgc gccggacccc gcgcaccacc    240
cggggctagc cttcgtcgcc gtgcccgacg tcatcccgga ggccgtggcg cgacgacga    300
atggcatcgc gaagatcctc gccctgaacg ccgccatgga ggcgtcgggg cacgtccgcg    360
gcgcgctcgc gtcgctcctc ggaggaggag cgggcggaag gcggcgtgcc tgcctcatct    420
tcgactccac cctcttcgcc gcgcagaagg ccgcggctgg cctcgggctg cccacgctcg    480
tgctgcacac cggcagcgcc gccggcttcc gtctgttcag gtccgacacc tacaacatgc    540
tccacgacag gggctatctg ccagccacag gttcgtaaca aatgctgcca ctgccactga    600
tttcagaaat atctgcgctc gcatcgcagt gttcttgaca gagatcattc tgtcccgttt    660
cattatttca gagtccaacc tacacatgcc ggtaaaggag ctgcaagtgag tgcaagtgag    720
ggacctgttc gacccaagca agctcccaa  caaggaaatc gtgcagaaga tcttgggctg    780
cgccacggag agcacgacga actcgtccgg cgcaatcctc aacacgtttg aggctctcga    840
gtcccgcgag ctcgagatga tccgggacga acttgccgac agaggtatcc caccttcgc    900
cgtcggccg  cttcacaagc tcaccgccgc cccctccaac gatggcgccg acgagactag    960
tctactcagc caggaccgcg tctgcatgga gtggctagac gcacgggcc  ctggctccgt   1020
```

```
gctgtacgtg agcttcggca gtgttgttca tgtcaccgcg gacgagttgg tggagatcgc 1080
gtggggcttg gcgaacagcg gcgtgccgtt cctgttggtg gtccggcgtg gccttgtggt 1140
cggagtggac aagcaggagc tcccggacgg gttcatggcg gccgtggagg caggggcaa  1200
ggtgatcgag tgggcgccgc agcaggaggt gctagctcac ccggcagtcg gaggcttctg 1260
gactcacaac ggatggaact ccacgctgga gagtatctat gaggggtgc  ctatgctgtc 1320
gaggcccatc tttggagacc agttgccaac ggcaaggtac gtgtgcgacg tgtggaggat 1380
tggagtttg  ctggagggtg tgctggagcg cgggaggtg  gagaaggcca tcaagaagct 1440
gatgaagaa  gacgagggag ttggtatcag gggaagagcc aaggatttga aggagaaagt 1500
gcggatgtgc cttgagagca gtgggtcttc tcaacttgcc gtcgataagt tggtggatca 1560
catactttct ctttgagttt ttttttatca cacaaacact gtgttgtgtc tgttcatggt 1620
ttcaactcaa taaattaata actgctggtt tatgatacgc tggtggtttc gctttacatc 1680
attgttagat tgaaaaaggg cctgtggcga atttatgtcg gcctaaaaca accattgtaa 1740
ataaggttta gaccctcata aataattatt acatctgttt agacttattt            1790
```

SEQ ID NO: 87          moltype = DNA   length = 2197
FEATURE                Location/Qualifiers
source                 1..2197
                       mol_type = other DNA
                       organism = Zea mays
SEQUENCE: 87

```
gctcaagtca attcataaac tcacaatggc ggcaacggca taccccactg tggtgctcat 60
cccactatgc gtcccaggcc acctcgcgtc catgatcgaa gccggcaagc ggctgctcgg 120
cagaagccgc tgcccatgt  ccctcaccgt gctcatcacg cagatgacca tgtccgccaa 180
cctgatgtcc gacgtcgacg acatcatgcg acgggaagcc gactccggcc tggacatccg 240
cttcgtccac ctccccgccg tggagctccc caccgtccac cacggcctcg aggacttcat 300
gatgcgcttc atacagcttc acgcgacgca cgtcaaggag gccgtctccg gcatgctgtc 360
cccggtcgcc gcggtcgtgg tggactactt ctgcaccacc ctgttcgacg tcgcgcgcga 420
gctcgcgctg ccggcgtacg cctacatgcc gtccggcgcg tcgatggtcg cgctcatgct 480
gcggttaccg gcgctggacg gggaggtgtc cggggacttc gaggcgatgg aaggaacggt 540
cgatctgccc gggatccgc  cggtgccggc tcgtctcatg ccgtctccgg tgatgaggaa 600
ggacccgaac ttcgcgtggc tggtgtacca cggcaagcgc ttcatggagg ccgacggggt 660
catcgtgaac acggcggccg agctggagcg gtccatcctc gcggccatcg ccgacggcct 720
ctgcgtgcca agacgccgcg ctccggccgt ctacccgatc ggcccggtcc tgcctctcaa 780
gccgccgtcc gcgccccggcg acggcgagca ggtagtagca cagcggcacg agtcgtgag  840
gtggctcgac gcgcagcccc cagcgtccgt cgtgctgctc tgctttggga gcatgggcgg 900
cagcttcccg tcgcccaggt tccgagagat cgccgacggc ctcgagcgca gcgggcaccg 960
cttcctgtgg gtgctccgtg gcccgccacc gccggacggt tccaagtacc cgacggacgc 1020
caacgtccac gagctgctcc cggaagggtt cctggagagg acgaagggcc gaggcctcgt 1080
gtggccacg  tgggcgccgc agaaggacat cctcgccaac cccgccgtcg gcggcttcgt 1140
cacccactgc ggctgaaact ccatcctcga gagcctgtgg cacggcgtgc cgatggtgcc 1200
ctggccgcag ttcgcggagc agcacctgaa cgcgttcgag ctcgtggccg tcatgggcgt 1260
cgccgtcgcc atgcaggtgg acaggaagcg cggcaacttc gtcgaggcgg cggagctgga 1320
gcgcgcggtc cggtgcctga tgggcgggtc ggaggagaag gggaggaagg cgtgccggag 1380
ggccacggag gcgaaggccc tgagccggaa cggcgtggcc agcgcgggt  cgtcggacgt 1440
gtcggtgcag aaactggcgc gagagattt  gcacaagcac gacgacaagg ggtgtgccac 1500
cgcaagcggg gagagcatgg gcagcgtcgt cgttcccgca tctccggcca gaataatatg 1560
atccccgaa  cacggagaaa tcgccgtcgt ccacgaataa atcggaggcc gccatgcgat 1620
ccgtctggca ctgctcacgt tgtttggcat tgttcacaat cgccgtgtgc actgtagttt 1680
cttatccgca gtaactttac cattcgaaat aatgtagtat agcacgcgct gcttcttcct 1740
aagtccgtgt agcgtagccc gcgtgttcga gctagtttgt gttaagttga atgagttaat 1800
ggatgctagt tgtagtcttg tagtcttta  gtgaactaga gagtactgtg cgtgccggag 1860
atgatgaggt gtcgcaaatt gagtagtaca gaaattcttt cttctgggct ccttttggac 1920
aaagctagct tccttttctt tactaggaaa aggaggcgcg cttcgcggcg ccctacttcc 1980
atatacatta tatataaaca cagtgtagaa acacaaacac attgtagaaa cacaaacata 2040
ttgtaggata caatatgaca atataataca tatggcgcgg gcgcaggttc cacaactgtc 2100
tctaaaagac agcgtacatg cagttgcgaa acagtgttca gtacaacagt acataactct 2160
aacagtttac agctccatag actatacatg tacggtg                          2197
```

SEQ ID NO: 88          moltype = DNA   length = 1354
FEATURE                Location/Qualifiers
source                 1..1354
                       mol_type = other DNA
                       organism = Zea mays
SEQUENCE: 88

```
gcgtgataat tatgcttggc caggcaaagt ctgctggagt caccaagcaa gcacttacat 60
tgtgcaactg catgatgcag atattcccaa gaatgtcttt tcaagatttg atagaaaatg 120
cctatatgta ctaaaagaac gggcgcatca tcgtagccgt acataaacaa tgttattacg 180
aacacgtgct gttctgctct cgtgtaaggt ccagctacaa gcacgcgcgc cgcgcgcgag 240
ccgattttgg acgcaccaga accggttagc tcgcaccaag ccgcacgagc accgaccggt 300
caatgacacg actcgccagt cgccactacc ggctcccgtt taaattgccg gccgcatcaa 360
gctgagggct gaggcagaga tgccaacaga agtcacgtcg acaccagcca gccggccgga 420
ctgcagctcc tcgtcgtcga tgacggccgg gaccatgcgt gtgctaggcg ggaggtcag  480
cccgttcacg gcgcgggcgc gtctggcgct ggatctgcgc ggcgtggcgt acgagctcct 540
cgacgagccg ctggggccca agaaaagcga cgtgccaacc cgtctacgg             600
gaagatcccc gtgctgctcc tcccgacgg  ccgcgccata tgcgagtccg cagtcatcat 660
ccagtgcatc gaggacgtgg cgcgtggaag cggcggcgcc gaggctagca gctgctgct  720
gccgacgac  ccctacgagc gcgccatgca ccgcttctgg accgccttca tcgacgacaa 780
ggtgagcacc gagcagagca cggcagcaag tgtctttcct tcaaggtaac gtgcaacaaa 840
ctgccgtgcc tttctgcagt tttggccggc gctggatgcc gtctccctgg cgccgacccc 900
```

```
gggagcacgc gcgcaggccg tggaagacac ccgcgccgcg ctgagcctcc tggaggtggc      960
gttcaaggac cgcagcaacg gcagggcttt cttctccggt ggcgacgccg cgccaggcct     1020
cctggacctg gccctcggat gcttcctgcc ggcgctcagg gcctgcgaac ggctccacgg     1080
cctctcactc atcgacgcgt ccgcgacgcc gctgctggac gggtggagcc agcgcttcgc     1140
cgcgcaccct gcagccaagc gcgtcctgcc ggacacggag aaggtggtgc agttcacgag     1200
gttcctccag ggacagttca gggtccacgt gtcctaaatg atttagcgtc tccaaaagat     1260
tgtcaaaatc tccgtctaaa gtctgtttta gaaacttaaa tcactttcag gattctcgga     1320
aattgagaga aaaataaaat aacttttcac tcaa                                 1354

SEQ ID NO: 89           moltype = DNA   length = 1452
FEATURE                 Location/Qualifiers
source                  1..1452
                        mol_type = other DNA
                        organism = Zea mays
SEQUENCE: 89
atggcggcag caacggcaac tgcaactgca actgaggctg ccggccacca ccaggagcag       60
cagcagcgtt ccgcgtcgt cgacacggcc ctggtggcgc ctgcagctgc tcccgcactg      120
ccgccgcgct ccatcccgct caccttcttc gacgtcaagt ggctgcacct ccgcgccgtg      180
gagcgcgtcc tcttgtaccg cctctccccg gacgccgacg tccccgccat tctctccggt      240
ctcaggacct ccctctccca ggccctccgc gccttctacc cgatggccgg ccacgtccgc      300
atgccggcca ccaataaccg ccgccacgag ctgtgctacc gccccggcga cgccgtcccc      360
ttcaccaccg cggagtacaa cgtggacatc gaccacctca tcccgtcccc                 420
gtgcaggtgg cccagctcgc ccctctcgcg ccgcacctgc taagggccg cgccgtgctc      480
gccgtgcagg ccacgctgct gctcggccgc cggggcctcg cggtcggcgt caccgtccac      540
cacaccacct gcgacggcgc agggtccacg cacttcctcc acacatgggc cgccgccgca      600
gccgcaagag cagatgagca cggtcatctc gtcatccccc cgccccccgt catcgaccgg      660
gaactcatcc cggaccccag gggcctgtac gacgtgtacc tcagaagcat gccgccatg      720
gtgtcccagg acgactttga gttcgtgctg ggcaagcctc aggatcccgg cgaggacaag      780
gccctggcca cgttcacgct gtcccagcag cttctgcaga gcatcaagag cgcggtcgcc      840
cacgaggcgg cgccggcgtg catgtgacg ccgccccggt gctcgtcgat cctcgccacc       900
tacggcttca tctggtcctg ctactgccga gcccgagggg cggcggcgg ggcggcagag        960
aggagctact tcctcttctc cgtggaccag cgctctcgcc tgaagccggc cgccgtcccg     1020
gagaagtacc tgggcaactg ctgctgcccg gccatcgcga gggcgcgggc ggacgaggtg     1080
tccgccgggg gcatcgcggg gctgttcgcg gcgtgcgcg cggtggcgcg ggcgttggag      1140
gaggaggtgc gcgaggggc gcaggagcgg tgggacacgt gctgcgccgcg ggtgaaggag     1200
gccgcggcca aggggatgct gtccgtggcc ggatcgccca ggttccgcgt ctacgacctc     1260
gactttggat tcgccggcc ggagaaggtg gacatggtgt cggtggccaa gaccggcgcc      1320
atctccgtgc cggacgcgcg tgttggaggt ggaggcgtgg aggtgggtat ctctctgccg     1380
gtggcgtcgg gtgacatgga ccgcttccga cagagcgttg cagacgggat ggagtggctc     1440
cggttgctgt ga                                                         1452

SEQ ID NO: 90           moltype = DNA   length = 3965
FEATURE                 Location/Qualifiers
source                  1..3965
                        mol_type = other DNA
                        organism = Zea mays
SEQUENCE: 90
ggttttgctc cgctgctccc ccgccgcccc tgacaagtat aaccagccgc gtctcggcaa       60
aaagtcctcc gcgacagaga gcgtgcagcc agccaccgac cacccgcgca gcgcaggact      120
tggggagcaa gcaaggcgaa gcggcctgcc atggattcct tctcgtcctc gccgtcgtcg      180
tcaggtcccg gcgctaaccc ggacgttgtt atggaacaga tcaagacgca gctcgcacg      240
gcttacgcgc aggagtttct cgaggtcaaa tctctcgcaa cctttctctt cgttgacgcc      300
accttttgcta ttcgtaatat gtaatggatg gttagattgt ggttgctctg actgatggac      360
tgagattctt gatttctcat atgatacctc tgtttgcttg aggggagtga tctgggatc       420
attgtttttt tcttgtaatc attactactt tttattgtt agattgtatg gagcgattg       480
gcgcaatagc agtttagctc ttttttattg ttagattgta tggagcgatt gggcgcaata      540
gcagtttagc tattatggtt gcacttgcac tcagagaggg agaggagg agggagggag        600
gtgccctgtt atcaatgcga ggaaaaaaat gtcaagctct atgtttctat tgagcagctg      660
gcctctcatt taagctaagt actcaagata ttaattgggg gtgatttcat tggattgaaa      720
acctaattca cggtgaccct tgtttagggt aaaaatggtg aagtaatgct tatatgctgc      780
tgtagtgact attgatggta gccagagcta ggctgacatt taattgaaca agtaacagct      840
cctttctggt gcaattctag tcaatttttcc agttccctct cttttttctc gcagacattt      900
aacgacatta actaagtgca actactagcg catgctaaaa aaggcccaaa cagtcaccta      960
cagtcagaca taagcttatt gtttcaaccc cctagtctcc atagtctggc ctataggagg     1020
tggaccctca tgctgaacgg ggagccaatt ttcgtgacct ttctcggccg gggctctaat     1080
tgagcttctt cttaatataa taccgtgggg gcggtctttc cccttccag ccgagttttg      1140
tacttgccct ccctctaata tgttgatgtt ttgcatgttt tttgttttct aatacatact     1200
ttgcttaaat acattgtttt cttctaccaa ggttattaaa acgataaaac gttgaaacgt     1260
tcatgggtga gttttgact tttaaacgtt taaacaatgt tttaaacgtag ttttaaaacaa     1320
cacaggaaaa ataccaatat atcataattt gagacaataa cattaagtta aatatcaaaa     1380
caaagaggtt agtggcttac caaaacttca cccatgagcc ggattggacc ccaaaagtag     1440
ataacagact gaacccaaaa gtagctaatg gtctaaaacg catgaaacac tgcgttttac     1500
agtttagaac gccaaaacgc taaaacatga attcaatctc taattaaagt tttgtcgttt     1560
aaacgtttt ttaataacac tgcttctacc tctgctgcc tccattttt tatcctttgc       1620
tatattgaaa gccgataaag agttttgcag cattattttt actccatgct gtgtttttta     1680
tgccattgtt ttttttggaa tatgatattt ctttgttcgt attcaaagcc aataaggagt     1740
tttacaacat tcttttttata catgcttgga ttactagcta actatagctt atcggtagca     1800
tcctactcat gaagccccca ttagcataaa gcaaagactg aacaaattta catagatgtc     1860
cactcatcaa ccacactaac caccaacaat tgctacagat caaacaagtt taggaccggt     1920
```

-continued

```
cgccagtctc atggagtcca taacacaaaa tcattcatcc attgtagtgg tggcataatg    1980
agcagtgtct tccacttctg ccgaaacgat acccaagaga acaattggtt tgttaggaat    2040
ttaatttctt ttaaattgtc atccttattt ttcctgaacc gaaccttggc ccatttggcc    2100
acttccattc cagagaaacg acaacatttg gccatttcta ttccagagaa cggcaacatt    2160
tggtcactt  cattctagag aaacggcaat aggattatct ttacaagcag aagtacaaga    2220
gaagtgctgc gatgagatac taagctaaat ctaggaaccc tcatcatttg gctaacatat    2280
atgatatgcg gatacttcca aattctcgaa aattgatact cctcccttgt caggaaaaga    2340
tactcagaca tgtataggac gttttcatga tttaataaat aaaaatataa aatagttctg    2400
gtactttttgt tgacaccact tactcttaga ttagattctt tgcagacctc tgaatcctga    2460
acccttatta cctctatgaa cccacccact gcacgcaccc catttgttcc tgacaataca    2520
taggttcaaa taatcaggta tattctgaga cttattaaat caatagcgag caaatcaagt    2580
tgcagaataa cctttcaatc aacttctttt taatttttt  ttattataca ttatacatat    2640
accaccatat ctgaagtcct gtgtcatgat agtaccggat tgtccatcct tgactttggg    2700
taatgcatcc tgcgtgatga tttgggtcaa aataaattct agttcaacag gatggcaaag    2760
ctacaacaat aaccaaaatc agggagaata gcctaagctt tgatggtgtt aggtttcaat    2820
tccaattgac attttgttat gcatctttga aagtgctcac acaaaacctg gaaacaaaac    2880
aaaccccaa  gtattatgag atccaaaatt accgattgtc ccccaagtcc caatcggagg    2940
catttatcat tctgtgtgcc tttatccttt tgatatcagc ttggtttacc ttttggccat    3000
ggttgattct tcttcagctg tgttaataa  tggagtgaat gtattttttt ttgaggaaaa    3060
tgtatttttt tgttgaggcg gtgctttcag cctgaaacga tgacataaca agcagtatac    3120
atgcaattag ccaattatat tggaagtttc ttccttgttt ctgtgccacc agtattaatt    3180
tttcgccttg ggtcacgtgc aatgtgttga gcccgaacaa ttgactagtt cttctttggg    3240
ggtcacatga gcgaatttaa aaactattta gttgccttgg aagattcaca gccctgaggg    3300
gacaacacga tgtatctagg aaattgccag tctttttttcc acatgttgcc aagtttttat    3360
taaaaaacaa ataggatgat gctgattgcc tctacaaact taaataaaca aagattacac    3420
acgaaagcgc aaaaggatga atctaggaaa ttcctgccat ttcatatggt gaaatttctt    3480
aagctcacag gtggtgttga tctgtcttgc agaccgtcgg gaacaagtgc tttgaaaagt    3540
gcgtgaccaa gccaggatca agcttgagtg gaagcgagag cagctgcata tcacgttgtg    3600
ttgaccgcta cattgaggcc actggtattg tcagccgcgc attgttcact tcccagcgct    3660
aagatcacat gaataaggag atggtttcga agatcgctcg tgagagtaat gtcgccatga    3720
gttttttgac ttgtcggaat acaatgacat ttgatgcttg gttattcaaa aaaaaagtct    3780
gcctatagac tcaggtttct tgtacaccta tctgctttag taatagaaa  acgtgctcta    3840
tttaagtggc tctgatgtta atttatgctc atcatgtggt ttgtttcgct taatgttgta    3900
tgcttcttat gcctgtttgt tgcccaagcc ttatcgaata tcgtgaagga tgtgttgttg    3960
ttatt                                                                3965
```

MODIFIED PLANTS AND METHODS OF DETECTING PATHOGENIC DISEASE

CROSS REFERENCE TO RELATED APPLICATIONS

This application is a U.S. continuation of International Application Serial No. PCT/US2021/023631 filed Mar. 23, 2021, which claims priority to U.S. Provisional Patent Application No. 62/994,036 filed on Mar. 24, 2020, the disclosures of which are expressly incorporated herein.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 326 kilobytes xml file named "335004.xml", created on Sep. 21, 2022.

BACKGROUND OF THE DISCLOSURE

The global population is expected to reach 9.7 billion people by 2050. The resulting increase in food demand is estimated to be from 59% to 98%. To meet the growing food need, it is desirable to improve agricultural productivity. Losses in crop yield due to pathogen infections are estimated at between 20% and 40% (Fang, Y.; Ramasamy, R. P. Current and Prospective Methods for Plant Disease Detection. Biosensors 2015, 5, 537-561). When pathogens are detected early, farmers can intervene early with a crop protectant that maintains crop health and thereby minimize the impact of the pathogen. However, typically, disease symptoms manifest in plants one to six weeks after the initial infection, at which time significant damage to the crop yield already may have occurred. Consequently, there is a need for early detection of pathogen infection in order to improve crop yield.

Currently, there are at least three methods to detect plant diseases. First, a farmer or agronomist walks through a field and detects diseases by eye. This process is time-consuming and may be impossible if soil or weather conditions prevent it. Often only parts of the field are examined due to time constraints.

Second, drones or satellite pictures are used to monitor field crops for diseases. Although this method enables broader detection of a given field, and is independent of the soil conditions, it still does not allow for early detection of diseases. Significant numbers of plants must be damaged for drone or satellite images to allow the disease to be detected. Also, for a diseased plant to be noticed in such photographs, the plant disease generally must be well advanced, for example, to the point of yellowing the leaves. Additionally, numerous diseases occur under the canopy in humid areas near the bottom of the plant such that the initial signs of disease cannot be detected by overhead photography (Pangga, I. B., Hanan, J. and Chakraborty, S. (2011), Pathogen dynamics in a crop canopy and their evolution under changing climate. Plant Pathology, 60: 70-81. doi:10.1111/j.1365-3059.2010.02408.x). Current attempts to improve the accuracy of overhead photography for detecting plant diseases involve using hyperspectral imaging (Adão, T.; Hruška, J.; Pádua, L.; Bessa, J.; Peres, E.; Morais, R.; Sousa, J. J. Hyperspectral Imaging: A Review on UAV-Based Sensors, Data Processing and Applications for Agriculture and Forestry. Remote Sens. 2017, 9, 1110). Hyperspectral imaging enables increased detection of the spectral range. However, limitations to using hyperspectral cameras include high costs and complex data acquisition and analysis.

Third, disease modeling algorithms are used to predict plant disease onset and spread. However, disease modeling algorithms have limitations. For example, these algorithms often ignore the number and density of plants as the number of plants often changes within a single season (Nik J. Cunniffe, Britt Koskella, C. Jessica E. Metcalf, Stephen Parnell, Tim R. Gottwald, Christopher A. Gilligan, Thirteen challenges in modelling plant diseases, Epidemics, Volume 10, 2015, Pages 6-10, ISSN 1755-4365, https://doi.org/10.1016/j.epidem.2014.06.002). Additionally, it is challenging for algorithms to account for plants' spatial structure as host location data is expensive and difficult to collect (Nik J. Cunniffe, Britt Koskella, C. Jessica E. Metcalf, Stephen Parnell, Tim R. Gottwald, Christopher A. Gilligan, Thirteen challenges in modelling plant diseases, Epidemics, Volume 10, 2015, Pages 6-10, ISSN 1755-4365, https://doi.org/10.1016/j.epidem.2014.06.002). Disease modeling algorithms often are not a trustworthy method of detecting plant diseases.

In view of the difficulty in detecting pathogens early enough to avoid loss of yield, crops for human consumption may be preventively sprayed with pesticides regardless of disease presence, resulting in a substantial cost to the farmer that is wasted if no disease is present. For example, agronomists recommend that fungicides be sprayed on corn at tasseling, when the uppermost leaves have developed, to protect those leaves from damage. This practice is recommended despite actual conditions in the field, whether or not any disease is present, or if the onset of disease was earlier or later than average. In tomatoes, the presence of disease can destroy an entire crop and quickly bankrupt the farmer, so fungicides are sprayed on a schedule throughout the growing season every 7-10 days, regardless of disease presence. It is desirable to avoid the unnecessary use of pesticides and fungicides to reduce the environmental exposure to these products and reduce the costs to the farmers by providing a reliable, effective method for detecting pathogens in time for effective application of a crop-protective response.

Thus, a need exists for improved early detection and remote detection of plant disease manifestation to allow for early and accurate response, and yield improvement.

SUMMARY

The present disclosure is directed to methods and compositions for detecting pathogenic disease, pest infestation or other abiotic and biotic factors causing stress in plants. The methods utilize sentry plants that are planted adjacent to plants of the same species and of similar genetic background. In accordance with one embodiment the sentry plants produce a detectable signal (e.g. a detectable change in visible color) upon encountering stressful a condition caused by adverse environmental conditions, lack of water or nutrients, or contact with a pathogenic organism or a crop pest, providing a monitoring system for the early detection and rectification of the condition causing stress to the sentry plant and surrounding plants.

In one embodiment a modified plant cell is provided wherein the plant cell comprises a stress inducible regulatory element operably linked to a nucleic acid sequence encoding a signaling moiety, wherein the signaling moiety produces a signal detectable by an external detector. In one embodiment the inducible regulatory element is a pathogen inducible regulatory element and the signaling moiety is an anthocyanin pathway factor. In a further embodiment a plant comprising such cells is provided as a sentry plant for the detection of contact of the plant with a plant pest or pathogen, including contact with a fungus, a nematode or other insect pest, or contact with any molecule specific for a fungal, nematode or other insect pest. Contact of a modified plant cell with a plant pathogen associated molecule activates the pathogen inducible regulatory element resulting in an enhanced expression of an operably linked nucleic acid sequence encoding a signaling moiety. In one embodiment the signaling moiety is an anthocyanin pathway factor, wherein increased expression of the anthocyanin pathway factor ultimately produces an increased production of anthocyanins that alter the color of the plant cell. In accordance with one embodiment the regulatory element and the anthocyanin pathway factor are both endogenous/native to the plant cell, but are not naturally in a functional relationship, where the regulatory element is operably linked to the anthocyanin pathway factor in the modified plants and plant cells of the present disclosure. In one embodiment the anthocyanin pathway factor is a transcription factor that enhances production of anthocyanins, or alternatively the anthocyanin pathway factor is a rate limiting anthocyanin pathway enzyme.

In accordance with one embodiment a modified tomato plant or tomato plant part is provided wherein the cells of said tomato plant or plant part comprise a pathogen inducible regulatory element operably linked to a nucleic acid encoding an anthocyanin pathway factor, optionally wherein the pathway factor is anthocyanin transcription factor having an amino acid sequence at least 95% identical to SEQ ID NO: 34. In one embodiment the transcription factor of SEQ ID NO: 34 is operably linked to pathogen inducible promoter comprising a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9.

In accordance with one embodiment a modified corn plant is provided wherein plant cells of the corn plant comprise a pathogen inducible regulatory element operably linked to a nucleic acid sequence encoding an anthocyanin pathway factor, optionally wherein the pathway factor is anthocyanin transcription factor, having a sequence at least 95% identical to SEQ ID NO: 28. In one embodiment the transcription factor of SEQ ID NO: 28 is operably linked to pathogen inducible promoter comprising a sequence selected from the group consisting of SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 and SEQ ID NO: 47.

In one embodiment a monitoring system for determining when to apply fungicide or insecticide treatments to a field comprising a plurality of plants is provided. In one embodiment the system comprises:

a plurality of sentry plants comprising the modified plant cells disclosed herein, wherein said sentry plants comprise a pathogen inducible regulatory element operably linked to a nucleic acid sequence encoding an anthocyanin pathway factor; and a detection system comprising a remote device for monitoring said plants to detect any change in color in said sentry transgenic plants. In accordance with one embodiment the remote device of the detection system is capable of monitoring a field of plants comprising a sentry plant disclosed herein, and detecting a change in color of the sentry plants present in the field. In one embodiment the remote device is a camera that captures visual images. In one embodiment the remote device is mounted onto a mobile vehicle that can move around, through and/or over a field of crop plants. In accordance with one embodiment the remote device is a camera for taking still pictures or video, optionally streaming the collected data to a processor located at a central processing center. In one embodiment the camera is mounted on an unmanned vehicle, including for example a flying drone. The system can be further provided with software for analyzing the data produced by the remote device.

In one embodiment the detection system comprises
a wireless controller including a processor;
a memory storing a program and a communication unit; and
a remote device configured to detect color changes in said plants and to communicate with the wireless controller, wherein the program, when executed by the processor, analyzes data received from the remote device and produces a signal when the data indicates the presence of plants with an altered change in color and optionally, the location of said plants with an altered change in color.

In one embodiment a method of treating pathogen-infected plants is provided, wherein the method comprises the steps of:
planting a sentry plant in a field, wherein the sentry plant is a plant comprising modified cells as disclosed herein that comprise a modifying gene construct comprising a pathogen inducible regulatory element operably linked to a nucleic acid sequence encoding an anthocyanin pathway factor;
planting crop plants adjacent to said sentry plants wherein the crop plants lack the modifying gene construct;
monitoring the field comprising the sentry plants for alteration in color relative to the crop plants lacking said modifying gene construct;
applying an anti-pathogen treatment to the field in response the detection of an alteration in color in said sentry plants relative to the crop plants lacking the modifying gene construct.

DETAILED DESCRIPTION

Definitions

Figure 1:
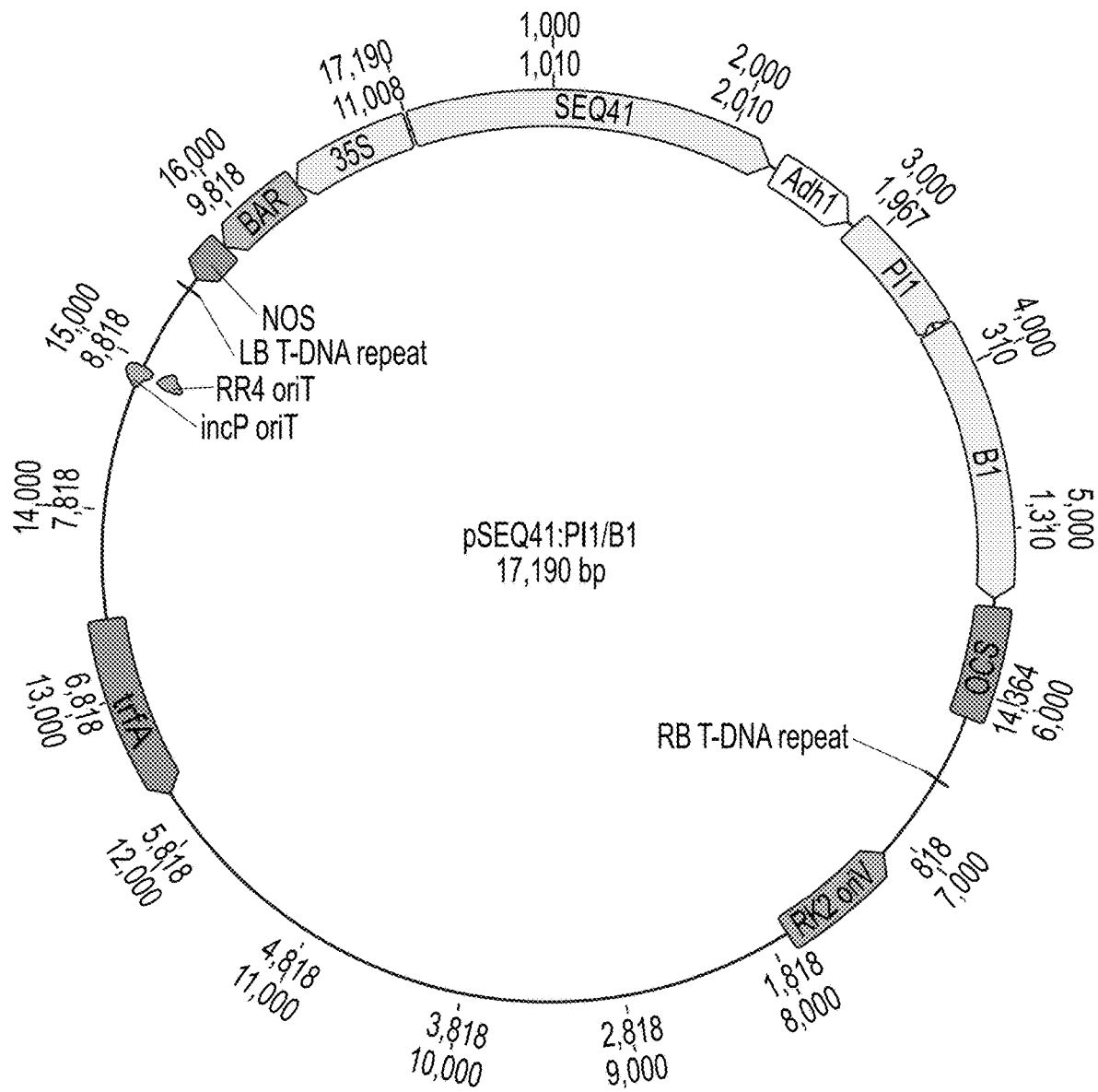
FIG. 1 is a schematic drawing of an expression vector comprising an pathogen inducible regulatory element operably linked to an anthocyanin pathway factor.

Unless defined otherwise, all technical and scientific terms used herein have the same meanings as commonly understood by one of ordinary skill in the art to which this invention belongs. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. In describing and claiming the invention, the following terminology will be used in accordance with the definitions set forth below.

As used herein "anthocyanins" are water-soluble vacuolar pigments that, depending on pH, may appear red, purple, blue or black. Typically, anthocyanins have the general structure

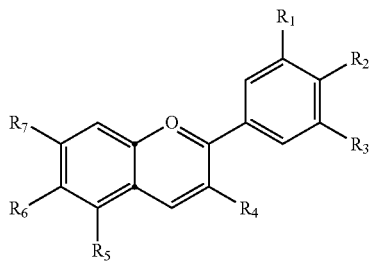

wherein $R_2$ is OH and $R_1$, $R_3$, $R_4$, $R_5$, $R_6$, and $R_7$ are independently selected from H, OH and $OCH_3$.

As used herein, the term "anthocyanin pathway factor" defines a nucleic acid or protein that participates directly or indirectly in the biosynthetic pathway that produces an anthocyanin. An increase in an anthocyanin pathway factor is associated with an increase in anthocyanin production.

A "trait" refers to a physiological, morphological, biochemical, or physical characteristic of a plant or particular plant material or cell. In some instances, this characteristic is visible to the human eye, such as the color of a plant or plant cells, or can be measured by biochemical techniques, such as detecting nucleic acid or protein content of seed or leaves, or by the detection of novel combinations of DNA sequences.

"Trait modification" defines a detectable difference in a characteristic in a plant. In some cases, the trait modification can be evaluated quantitatively. For example, the trait modification can entail at least about a 2% increase or decrease, or an even greater difference, in a trait, under a specified condition, as compared with a control or wild-type plant. It is known that there can be a natural variation in the modified trait. Therefore, the trait modification observed entails a change of the normal distribution and magnitude of the trait in the plants as compared to control or wild-type plants.

"Promoter" refers to a DNA sequence capable of controlling the transcription of a coding sequence or functional RNA. In general, a coding sequence is located 3' to a promoter sequence. Promoters that cause a gene to be transcribed in most cell types at most times are referred to herein as "constitutive promoters". Promoters that allow the selective transcription of a gene in specified cell types or in response to developmental or environmental cues are referred to herein as "inducible promoters."

As used herein a transcription factor is DNA binding moiety that targets specific DNA sequences and activates or represses gene expression of coding sequences operably linked to the DNA sequences that interact with the transcription factor. The transcription factor can be a DNA binding protein or nucleic acid (e.g., microRNA) or a combination thereof.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

A "host cell" is a cell which has been transformed or transfected, or is capable of transformation or transfection by an exogenous polynucleotide sequence. A host cell that has been transformed or transfected may be more specifically referred to as a "recombinant host cell".

A "non-natural modification" to a plant's genome includes all manner of recombinant and transgenic manipulation to the plant that results from human activity. For example, introgression of a desired trait by directed crossing of plants using traditional breeding techniques is a non-natural modification of the parental lines to produce a hybrid. Similarly, the directed insertion of a DNA sequence, whether the DNA sequence is foreign to the host cell (i.e., an exogenous sequence) or originally present at a different location of the host genome (i.e., an endogenous sequence) into a plant's genome to produce a recombinant plant is a non-natural modification of the original native plant. Non-natural modification also includes site directed gene editing (e.g., CRISP/Cas9 mediated editing) of a target gene.

In the context of the present disclosure a "modified plant" or "modified plant part" is a plant or plant part that comprises a non-natural modification to its genomic DNA.

"Transgenic" modification involves the insertion of foreign DNA into a host cell (i.e., insertion of DNA that is exogenous to the host cell) from an unrelated genus or species. A "transgenic plant" or "transgenic tomato," is a plant or tomato including one or more copies of an exogenous nucleic acid sequence (e.g., a transgene) inserted into a host cell's genome. The transgene may be the target gene of interest or another gene or nucleic acid sequence which regulates the expression and activity of the target gene. For example, a transgene may be a gene encoding a promoter sequence or a gene regulatory element.

"Cisgenic" involves the insertion of one or more gene of the same or a related species, or from a crossable donor. The introduction of specific alleles/genes present in the gene pool, without any DNA sequence change, into new varieties is termed "cisgenesis," and such processes accelerate the breeding of species with long reproduction cycles with no linkage drag. On the other hand, "intragenic" modifications involve the use of genetic elements from other plants from the same sexually compatible gene pool and, thus, the coding regions of genes are combined with promoters and terminators of different genes from the same sexually compatible gene pool. Kamle et al., "Current perspectives on genetically modified crops and detection methods," 3 Biotech. 2017 July; 7(3): 219.

As used herein a "cisgenic construct" is a recombinant nucleic acid sequence present in a cell, and optionally integrated into the cell's genome, wherein the recombinant nucleic acid sequence comprises an inducible regulatory element operably linked to a nucleic acid sequence that encodes a detectable marker, wherein the inducible regulatory element and detectable marker are both native to the plant but are not operably linked in the native cell.

As used herein an "inducible regulatory element" is a nucleic acid sequence that when operably linked to a gene will increase the expression of that gene in the presence of an inducer that specifically interacts with the inducible regulatory element. In one embodiment the inducible regulatory element is an inducible promoter.

As used herein a "stress inducible regulatory element" is a nucleic acid sequence that enhances the transcription of an operably linked gene when the host cell is subjected to stress due to the presence of an abiotic or biotic factor. For example inducible regulatory elements are known that are responsive to stress caused by fungi; bacteria; nematodes; parasites; viruses; insects; heat; water stress; nutrient stress; or phytoplasmal disease.

As used herein a "pathogen inducible regulatory element" is a nucleic acid sequence that enhances the transcription of an operably linked gene when the host cell is contacted with a pathogen or pathogen specific compound.

As used herein an "anthocyanin transcription factor" is a protein that binds to one or more promoters that encode products associated with anthocyanin production, wherein interaction of the transcription factor with a target promoter induces enhanced transcription of the associated gene products.

As used herein a "signaling moiety" is any gene product that can be detected, or causes the production of a detectable product, that is detectable in intact plant tissues, including for example the production of a signal in the electromagnetic spectrum. Typically, the signaling moiety is either a phenotypic marker or an agent that directly impacts the production of a phenotypic marker. For example the signaling moiety may produce a detectable change in pigmentation or a detectable change in emitted or reflected light from said plant.

As used herein, the term "plant" includes a whole plant, including angiosperms (monocotyledonous and dicotyledonous plants), gymnosperms, ferns and multicellular algae, as well as any descendant, cell, tissue, or part of a plant thereof.

The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants) and a plant protoplast. A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

The term "plant cell," as used herein, refers to protoplasts, gamete producing cells, and cells which regenerate into whole plants. The term "plant cell," as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues.

The term "protoplast," as used herein, refers to a plant cell that had its cell wall completely or partially removed, with the lipid bilayer membrane thereof naked, and thus includes protoplasts, which have their cell wall entirely removed, and spheroplasts, which have their cell wall only partially removed, but is not limited thereto. Typically, a protoplast is an isolated plant cell without cell walls which has the potency for regeneration into cell culture or a whole plant.

A polypeptide "substantially identical" to a comparative polypeptide varies from the comparative polypeptide, but has at least 80%, preferably at least 85%, more preferably at least 90%, and yet more preferably at least 95% sequence identity at the amino acid level over the complete amino acid sequence, and retains substantially the same biological function as the corresponding polypeptide to which comparison is made.

The term "substantial sequence homology" refers to DNA or RNA sequences that have de minimus sequence variations from, and retain substantially the same biological functions as the corresponding sequences to which comparison is made.

As used herein, "hybridizes under stringent conditions" is intended to describe conditions for hybridization and washing under which nucleotide sequences that are significantly identical or homologous to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chlorine/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 4×SSC plus 50% formamide at about 42-50° C.) followed by one or more washes in 0.3×SSC, at about 65-70° C. A preferred, non-limiting example of highly stringent hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM NaH2PO4, and 1.25 mM EDTA, pH 7.4) can be substituted for SSC (1×SSPE is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm (° C.)=2(# of A+T bases)+4(# of G+C bases). For hybrids between 18 and 49 base pairs in length, Tm (° C.)=81.5+16.6(log10[Na+])+0.41(% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to the hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS) chelating agents (e.g., EDTA), Ficoll, PVP and the like. When using nylon membranes, in particular, an additional preferred, non-limiting example of stringent hybridization conditions is hybridization in 0.25-0.5M NaH2PO4, 7% SDS at about 65° C., followed by one or more washed at 0.02M NaH2PO4, 1% SDS at 65° C., see e.g., Church and Gilbert (1984) Proc. Natl. Acad. Sci. USA 81: 1991-1995, (or alternatively 0.2×SSC, 1% SDS).

"Polynucleotide(s)" generally refers to any polyribonucleotide or polydeoxribonucleotide. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "isolated nucleic acid" used in the specification and claims means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene. Specifically excluded from this definition are nucleic acids present in mixtures of clones, e.g., as those occurring in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine, as described in a preceding definition.

As used herein, the term "operably linked" refers to two components that have been placed into a functional relationship with one another. The term, "operably linked," when used in reference to a regulatory sequence and a coding sequence, means that the regulatory sequence affects the expression of the linked coding sequence. "Regulatory sequences," "regulatory elements", or "control elements," refer to nucleic acid sequences that influence the timing and level/amount of transcription, RNA processing or stability, or translation of the associated coding sequence. Regulatory sequences may include promoters; translation leader sequences; 5' and 3' untranslated regions, introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule. Linking can be accomplished by ligation at convenient restriction sites. If such sites do not exist, synthetic oligonucleotide adaptors or linkers are used in accordance with conventional practice. However, elements need not be contiguous to be operably linked.

A "gene product" as defined herein is any product produced by the gene. For example the gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

The term "heterologous" is used for any combination of DNA sequences that is not normally found intimately associated in nature (e.g., a green fluorescent protein (GFP) reporter gene operably linked to a SV40 promoter). A "heterologous gene" shall refer to a gene not naturally present in a host cell (e.g., a luciferase gene present in a retinoblastoma cell line).

As used herein, the term "homolog" refers to a gene related to a second gene by descent from a common ancestral DNA sequence. The term, homolog, may apply to the relationship between genes separated by the event of speciation (i.e., orthologs) or to the relationship between genes separated by the event of genetic duplication (i.e., paralogs). "Orthologs" are genes in different species that evolved from a common ancestral gene by speciation. Normally, orthologs retain the same function in the course of evolution. Identification of orthologs is important for reliable prediction of gene function in newly sequenced genomes. "Paralogs" are genes related by duplication within a genome. Orthologs retain the same function in the course of evolution, whereas paralogs evolve new functions, even if these are related to the original one.

The nucleotides that occur in the various nucleotide sequences appearing herein have their usual single-letter designations (A, G, T, C or U) used routinely in the art. In the present specification and claims, references to Greek letters may either be written out as alpha, beta, etc. or the corresponding Greek letter symbols (e.g., α, β, etc.) may sometimes be used.

Nucleic acid constructs useful in the invention may be prepared in conventional ways, by isolating the desired genes from an appropriate host, by synthesizing all or a portion of the genes, or combinations thereof. Similarly, the regulatory signals, the transcriptional and translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various nucleic acids and/or fragments thereof may be combined, cloned, isolated and sequenced in accordance with conventional ways. After each manipulation, the DNA fragment or combination of fragments may be inserted into a cloning vector, the vector transformed into a cloning host, e.g. *Escherichia coli*, the cloning host grown up, lysed, the plasmid isolated and the fragment analyzed by restriction analysis, sequencing, combinations thereof, or the like.

Various vectors may be employed during the course of development of the construct and transformation of host cells. These vectors may include cloning vectors, expression vectors, and vectors providing for integration into the host or the use of bare DNA for transformation and integration. The cloning vector will be characterized, for the most part, by having a replication origin functional in the cloning host, a marker for selection of a host containing the cloning vector, may have one or more polylinkers, or additional sequences for insertion, selection, manipulation, ease of sequencing, excision, or the like. In addition, shuttle vectors may be employed, where the vector may have two or more origins of replication, which allows the vector to be replicated in more than one host, e.g. a prokaryotic host and a eukaryotic host.

Expression vectors will usually provide for insertion of a construct which includes the transcriptional and translational initiation region and termination region or the construct may lack one or both of the regulatory regions, which will be provided by the expression vector upon insertion of the sequence encoding the protein product. Thus, the construct may be inserted into a gene having functional transcriptional and translational regions, where the insertion is proximal to the 5'-terminus of the existing gene and the construct comes under the regulatory control of the existing regulatory regions. Normally, it would be desirable for the initiation codon to be 5' of the existing initiation codon, unless a fused product is acceptable, or the initiation codon is out of phase with the existing initiation codon. In other instances, expression vectors exist which have one or more restriction sites between the initiation and termination regulatory regions, so that the structural gene may be inserted at the restriction site(s) and be under the regulatory control of these regions.

"Pathogens" include, but are not limited to, viruses, bacteria, nematodes, fungi or insects. A "plant pathogen" refers to an organism (e.g., bacteria, virus, nematode, fungi or insect) that infects plants or plant components. Examples include molds, fungi and rot that typically use spores to infect plants or plant components (e.g., fruits, vegetables, grains, stems, roots). See, for example Agrios, Plant Pathology (AcademicPress, San Diego, Calif. (1988)).

As used herein the term "remote" means at a distance from a reference point. For example, a remote controlled device is located beyond physical contact of the controller of the device. A remote device is one that is capable of operating at a distance from, and independently of constant monitoring of, a human.

As used herein the term "optical device" includes any instrument that processes light waves, either to analyze and/or determine the characteristic properties of the detected light waves. An "optical detector" includes optical devices as well as biological detectors of light including the human eye. A "detectable signal" used in the context of a sentry plant is any signal that can be detected by an optical detector.

As used herein the term "unmanned" means without the physical presence of people in control.

As used herein a "sentry plant" is a plant that comprises non-natural modified plant cells wherein the genomic DNA of the non-natural modified plant cells has been modified to comprise one or more cisgenic constructs wherein a stress inducible regulatory element is operably linked to a nucleic acid sequence encoding a signaling moiety (e.g., an anthocyanin pathway factor).

Embodiments

In one embodiment the present disclosure is directed to a genetically modified plant that produces a detectable signal when the plant is subjected to stress, including stress caused by abiotic and biotic factors such as adverse environmental or nutrient conditions or the presence of plant pathogens, including insect pests. By placing such modified plants in proximity to crops, the modified plants can serve as a monitoring system for assessing the health of a crop and allow for early mitigation to alleviate any detected plant stresses. In one embodiment the modified plants disclosed herein can be used for the early detection of plant pathogens in a field of crops. In one embodiment, a modified plant is disclosed comprising a stress inducible regulatory element, optionally a pathogen inducible promoter, operably linked to a nucleic acid sequence encoding a signaling moiety. In this embodiment activation of the inducible regulatory element increases the expression of the signaling moiety and thereby produces a detectable signal in those plants comprising the inducible marker construct. The signaling moiety can be any compound that is detectable, or initiates the production of a signal that is detectable, by the human eye or by an optical device that scans the surface of a plant comprising the inducible marker construct (i.e. the nucleic acid comprising the inducible promoter operably linked to the signaling moiety). In one embodiment the signaling moiety is an anthocyanin pathway factor, wherein induction of the inducible regulatory element increases the production of the anthocyanin pathway factor resulting in a detectable change in anthocyanin levels in the plant. In one embodiment, the change in anthocyanin levels is detectable by spectral analysis of whole plants. In one embodiment, the spectral analysis is conducted in a spectrum that is visible to the human eye, including for example in wavelengths from about 380 to 740 nanometers.

In accordance with one embodiment a modified plant or plant part is provided comprising a cisgenic construct that produces a detectable signal upon insult to the plant. In accordance with one embodiment the cisgenic construct comprises a stress inducible regulatory element operably linked to a nucleic acid sequence encoding a signaling moiety, wherein both the inducible regulatory element and the signaling moiety encoding sequences are endogenous to the native plant or plant part, but are not operably linked in the native plant or plant part.

In one embodiment the cisgenic construct of the modified plants or plant parts disclosed herein is generated by inserting the stress inducible regulatory element into a genomic location comprising a nucleic acid sequence encoding a signaling moiety or by inserting the nucleic acid sequence encoding a signaling moiety into a genomic location comprising a stress inducible regulatory element wherein said insertion results in the operable linkage of the stress inducible regulatory element to the nucleic acid sequence encoding a signaling moiety. In one embodiment the cisgenic construct is prepared outside the plant or plant part as a recombinant sequence comprising a stress inducible regulatory element operably linked to a nucleic acid sequence encoding a signaling moiety, wherein both the inducible regulatory element and the signaling moiety encoding sequences are endogenous to the native plant or plant part, but are not operably linked in the native plant or plant part. The entire cisgenic construct is then introduced into plant cells to produce the signaling modified plants and plant parts of the present disclosure. In one embodiment the cisgenic construct is inserted into the genome of the plant cell, and a plant comprising such cells is generated.

In one embodiment a sentry plant is provided wherein the cells of the sentry plant comprise a cisgenic construct comprising a stress inducible regulatory element operably linked to a signaling moiety, optionally wherein the stress inducible regulatory element is a pathogen inducible regulatory element and said signaling moiety is an anthocyanin pathway factor. In accordance with one embodiment the anthocyanin pathway factor is a transcription factor that enhances production of anthocyanins, or the anthocyanin pathway factor is a rate limiting anthocyanin pathway enzyme. In one embodiment the anthocyanin pathway factor is a transcription factor that enhances production of anthocyanins, including but not limited to a transcription factor selected from the R2R3 MYB gene family or the bHLH gene family, optionally wherein the transcription factor is selected from the group consisting of C1, R, P11, and B1, or alleles of these genes, optionally wherein the transcription factors are P11, and B 1.

In one embodiment, the regulatory element and the anthocyanin pathway factor are both endogenous to the plant but are not operably linked to one another in the native plant. In one embodiment, the modified plant comprises a non-natural modification where a pathogen inducible regulatory element is operably linked to a nucleic acid sequence encoding an anthocyanin pathway factor. In one embodiment, the anthocyanin pathway factor is a transcription factor that binds to one or more promoters that encode products associated with anthocyanin production, wherein interaction of the transcription factor with those promoters induces enhanced transcription of the associated gene products. This allows the modified plant to produce a detectable color change in response to contact of the plant with a pathogen. This genetic modification and therefore response to a pathogen, is not present in non-modified plants.

In some embodiments, the change in color of a sentry plant induced by the presence of a plant pest or pathogen is further intensified or altered based on the level of exposure to the pathogen and/or progression of the disease state associated with the pathogen. In such an embodiment the color of the sentry plant not only indicates the presence of a pathogen but also indicates the level of disease progression or prevalence of the pathogen. In some embodiments, the inducible promoter is selected to be responsive only to the presence of pathogens and not other environmental stress factors. In this embodiment the sentry plant does not change color responsive to an environmental stressor other than a plant pathogen such as a fungus, bacterium, or insect pest.

In some embodiments, the plant is selected from the group consisting of woody, ornamental or decorative, crop or cereal, fruit or vegetable plant, and algae. In some embodiments, the plant is a crop or cereal plant. In one embodiment, the modified plant is selected from a group consisting of genuses *Acorus, Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea,* and *Zinnia*.

In one embodiment, the modified plant is selected from the group consisting of asparagus, field and sweet corn, barley, wheat, rice, sorghum, onion, pearl millet, rye, oats, tomato, tobacco, cotton, rapeseed, field beans, soybeans, peppers, lettuce, peas, alfalfa, clover, cole crops, cabbage, broccoli, cauliflower, brussel sprouts, radish, carrot, beets, eggplant, spinach, cucumber, squash, melons, cantaloupe, sunflowers, wheat, cauliflower, tomato, tobacco, corn, oats, rice, wild rice, rye, wheat, millet, sorghum, triticale, buckwheat flax, legumes, and soybeans. In one embodiment, the plant is ornamental. In one embodiment, the plant is a fruit. In one embodiment, the plant is vegetable. In one embodiment the modified plant is a corn or tomato plant.

In some embodiments, a pathogen inducible regulatory element for use in accordance with the present disclosure is a pathogen inducible promoter or an enhancer of a pathogen inducible promoter that is induced by the contact of a pathogen or a pathogen specific moiety with the host cell/plant. In accordance with one embodiment a modified plant is provided wherein said plant comprises a plurality of plant cells that comprise a pathogen inducible regulatory element operably linked to a nucleic acid sequence encoding an anthocyanin pathway factor, wherein contact of the modified plant with a pathogen or a pathogen associated compound moiety induces the pathogen inducible regulatory element resulting in enhanced transcription of the anthocyanin pathway factor. In some embodiments, the pathogen inducible regulatory element includes both a pathogen inducible promoter and an enhancer. In some embodiments, the pathogen inducible promoter is endogenous to the modified plant. In some embodiments, the enhancer is endogenous to the modified plant. In some embodiments, the pathogen inducible promoter is selected from a group consisting of pathogenesis-related (PR) gene and systemic acquired resistance (SAR) gene.

In one embodiment, the pathogen inducible regulatory element comprises a nucleic acid sequence selected from a group consisting of Pathogenesis-related protein 1a (Solyc01g106620; SEQ ID NO: 1), Osmotin-like protein (Solyc08g080660; SEQ ID NO: 2), Beta-1 3-glucanase (Solyc01g008620; SEQ ID NO: 3), Chitinase (Solyc04g072000; SEQ ID NO: 4), non-specific lipid-transfer protein-like protein (Solyc09g082270; SEQ ID NO: 5), Pti5 ethylene response factor (Solyc02g077370; SEQ ID NO: 6), plant cell wall protein S1TFR88 (Solyc01g095170; SEQ ID NO: 7), proteinase inhibitor II (Solyc03g020050; SEQ ID NO: 8) and PR-5× (Solyc08g080620; SEQ ID NO: 9) or selected from a nucleic acid sequence having at least 80%, 85%, 90%, 95% or 99% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 or SEQ ID NO: 9.

In some embodiments, the pathogen inducible regulatory element comprises a nucleic acid sequence selected from a group consisting of Subtilisin-like protease Sbt4a (SEQ ID NO: 10), beta(1,3)glucanase (SEQ ID NO: 11), CHI2 (chitinase 2; SEQ ID NO: 12), Pathogenesis-related protein-like protein (SEQ ID NO: 13), putative lipid-transfer protein DIR1 (SEQ ID NO: 14), Late elongated hypocotyl and circadian clock associated-1-like protein 1 (SEQ ID NO: 15), Short-chain dehydrogenase/reductase family protein (SEQ ID NO: 16), Major allergen Mal d 1 (SEQ ID NO: 17), Pectate lyase 1-27 (SEQ ID NO: 18), pollen proteins Ole e I-like (SEQ ID NO: 19), Phytoene synthase 1 (SEQ ID NO: 20), Acidic chitinase (SEQ ID NO: 21), S8-Rnase (SEQ ID NO: 22), Gty37 protein SEQ ID NO: 23), Glutathione S-transferase-like protein (SEQ ID NO: 24), Non-specific lipid-transfer protein (SEQ ID NO: 25) and S1PMT4, Polyol monosaccharide transporter 4 (SEQ ID NO: 26) or selected from a nucleic acid sequence having at least 80%, 85%, 90%, 95% or 99% sequence identity to SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26.

In some embodiments, the pathogen inducible regulatory element comprises a nucleic acid sequence selected from a group consisting of Zm00001d031157 (SEQ ID NO: 36), Zm00001d032947 (SEQ ID NO: 37), Zm00001d042140 (SEQ ID NO: 38), Zm00001d037656 (SEQ ID NO: 39), Zm00001d018738 (SEQ ID NO: 40), Zm00001d010870 (SEQ ID NO: 41), Zm00001d040245 (SEQ ID NO: 42), Zm00001d049288 (SEQ ID NO: 43), Zm00001d009296 (SEQ ID NO: 44), Zm00001d028815 (SEQ ID NO: 45), Zm00001d042143 (SEQ ID NO: 46), and Zm00001d038791 (SEQ ID NO: 47) or a sequence having at least 95% sequence identity to SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 or SEQ ID NO: 47.

In some embodiments, the modified plant comprises a nucleic acid sequence encoding an anthocyanin pathway factor. In some embodiments, the anthocyanin pathway factor is endogenous to the modified plant. In some embodiments, the anthocyanin pathway factor is a transcription factor that enhances production of anthocyanins or a rate limiting anthocyanin pathway enzyme. In some embodiments, the anthocyanin pathway factor comprises a transcription factor that enhances production of anthocyanins and a rate limiting anthocyanin pathway enzyme. In some embodiments, the transcription factor that enhances production of anthocyanins is endogenous to the modified plant. In some embodiments, the rate limiting anthocyanin pathway enzyme is endogenous to the modified plant.

In some embodiments, the transcription factor that enhances production of anthocyanins is selected from a group consisting of Alfin-like; AP2 (APETALA2) and ERE-BPs (ethylene-responsive element binding proteins); ARF; AUX/IAA; bHLH; bZIP; C2C2 (Zn); C2C2 (Co-like); C2C2 (Dof); C2C2 (GATA); C2C2 (YABBY); C2C2 (Zn); C3H-type; CCAAT; CCAAT HAP3; CCAAT HAP5; CPP (Zn); DRAPI; E2F/DP; GARP; GRAS; HMG-BOX; HOMEO BOX; HSF; Jumanji; LFY; LIM; MADS Box; MYB; NAC; NIN-like; Polycomb-like; RAV-like; SBP; TCP; TFIID; Transfactor; Trihelix; TUBBY; WRKY.

In some embodiments, the transcription factor that enhances production of anthocyanins is selected from the group consisting of nucleic acid sequences encoding genes having 95% sequence identity to ANT1 (SEQ ID NO: 34), C1 (SEQ ID NO: 48), R1 (SEQ ID NO: 49), B1 (SEQ ID NO: 50), P1 (SEQ ID NO: 51), MYB76 (SEQ ID NO: 52), in1 (SEQ ID NO: 54) and PL1 (SEQ ID NO: 53).

In accordance with one embodiment, a modified plant is provided wherein the plant comprises a pathogen inducible regulatory element operably linked to a anthocyanin transcription factor. In one embodiment the transcription factor is selected from the group consisting of anthocyanin1 transcription factor (ANT1; SEQ ID NO: 34), Zm00001d044975 (SEQ ID NO: 27), Zm00001d026147 (SEQ ID NO: 28), Zm00001d000236 (SEQ ID NO: 29), Zm00001d028842 (SEQ ID NO: 30), Zm00001d008695 (SEQ ID NO: 31), Zm00001d037118 (SEQ ID NO:33), Zm00001d019170 (SEQ ID NO: 33) and Glyma09g36990 (SEQ ID NO: 35). In some embodiments, the transcription factor that enhances production of anthocyanins is an anthocyanin transcription factor selected from a group consisting of sequences having at least 95% sequence identity to (SEQ ID NO: 27), (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34) and (SEQ ID NO: 35).

In accordance with one embodiment the modified plant is a tomato plant wherein plant cells of the tomato plant comprise a pathogen inducible regulatory element operably linked to an anthocyanin pathway factor, optionally wherein the transcription factor is anthocyanin transcription factor having an amino acid sequence at least 95% identical to SEQ ID NO: 34. In accordance with one embodiment the modified plant is a corn plant wherein plant cells of the corn plant comprise a pathogen inducible regulatory element operably linked to an anthocyanin pathway factor, optionally wherein the pathway factor is anthocyanin transcription factor, having a sequence at least 95% identical to SEQ ID NO: 28.

In some embodiments, a modified plant is provided wherein a pathogen inducible regulatory element is operably linked to a rate limiting anthocyanin pathway enzyme. In one embodiment the rate limiting anthocyanin pathway enzyme is selected from the group consisting of chalcone synthase, chalcone flavanone isomerase1, chalcone flavanone isomerase2, chalcone flavanone isomerase3, chalcone flavanone isomerase4, chalcone flavanone isomerase5, flavanone 3β-hydroxylase1, flavanone 3β-hydroxylase2, flavonoid 3'-hydroxylase, dihydroflavonol reductase1, dihydroflavonol 4-reductase, anthocyanin synthase, UDP-glucose flavonoid 3-O-glycosyltransferase, isoflavonoid synthase, flavonol synthase1, flavonol synthase2, cncr2 (cinnamoyl CoA reductase2), CCR4, dihydroflavonol-4-reductase, Flavonol synthase-like protein, NADPH dihydroflavonol reductase, Leucoanthocyanidin dioxygenase (LDOX), anthocyanidin synthase (ANS), flavanone 4-reductase, anthocyanidin 3-O-glucosyltransferase, glutathione S-transferase, anthocyanin acyltransferase1, and pale aleurone color1. In one embodiment, the rate limiting anthocyanin pathway enzyme is chalcone synthase.

In one embodiment, a modified plant is provided wherein the plant comprises a stress inducible regulatory element operably linked to a rate limiting anthocyanin pathway enzyme encoded from a sequence selected from the group consisting of Zm00001d052673 (SEQ ID NO: 55), Zm00001d007403 (SEQ ID NO: 56), Zm00001d034635, (SEQ ID NO: 57), Zm00001d012972, (SEQ ID NO: 58), Zm00001d018278, (SEQ ID NO: 59), Zm00001d016144, (SEQ ID NO: 60), Zm00001d001960, (SEQ ID NO: 61), Zm00001d029218, (SEQ ID NO: 62), Zm00001d017077, (SEQ ID NO: 63), Zm00001d020970, (SEQ ID NO: 64), Zm00001d031489, (SEQ ID NO: 65), Zm00001d019669, (SEQ ID NO: 66), Zm00001d018184, (SEQ ID NO: 67), Zm00001d018181, (SEQ ID NO: 68), Zm00001d024865, (SEQ ID NO: 69), Zm00001d044122, (SEQ ID NO: 70), Zm00001d014914, (SEQ ID NO: 71), Zm00001d011438, (SEQ ID NO: 72), Zm00001d037383, (SEQ ID NO: 73), Zm00001d053144, (SEQ ID NO: 74), Zm00001d048800, (SEQ ID NO: 75), Zm00001d042980, (SEQ ID NO: 76), Zm00001d035462, (SEQ ID NO: 77), Zm00001d012456, (SEQ ID NO: 78), Zm00001d011107, (SEQ ID NO: 79), Zm00001d045055, (SEQ ID NO: 80), Zm00001d016424, (SEQ ID NO: 81), Zm00001d006683, (SEQ ID NO: 82), Zm00001d052492, (SEQ ID NO: 83), Zm00001d037784, (SEQ ID NO: 84), Zm00001d006446, (SEQ ID NO: 85), Zm00001d019256, (SEQ ID NO: 86), Zm00001d045254, (SEQ ID NO: 87), Zm00001d032969, (SEQ ID NO: 88), Zm00001d034925, (SEQ ID NO: 89), and Zm00001d017617(SEQ ID NO: 90), or a sequence having 95% sequence identity to any of said sequences.

In some embodiments, the modified plant comprises a pathogen inducible regulatory element operably linked to a nucleic acid sequence encoding a transcription factor that enhances production of anthocyanins and a rate limiting anthocyanin pathway enzyme. In some embodiments, the modified plant comprises a first pathogen inducible regulatory element operably linked a nucleic acid sequence encoding a transcription factor that enhances the production of anthocyanins and a second pathogen inducible regulatory element operably linked to a nucleic acid sequence encoding a rate limiting anthocyanin pathway enzyme. In some embodiments, the first and second pathogen inducible regulatory element are identical, or have at least 95% similar sequence identity. In some embodiments, the first and second pathogen inducible regulatory element are different, sharing less than 60% sequence identity. In some embodiments, the first and the second pathogen inducible regulatory element are both endogenous to the modified plant. In some embodiments, the first or the second pathogen inducible promoter is exogenous to the modified plant.

In one embodiment a modified plant or plant part is provided comprising two or more cisgenic constructs, wherein a first cisgenic construct comprises a first stress inducible regulatory element operably linked to a nucleic acid sequence encoding a first signaling moiety and a second cisgenic construct comprising a second stress inducible regulator element operably linked to a nucleic acid sequence encoding a second signaling moiety. In one embodiment the first and second stress inducible regulatory elements respond to the same inducing agent. In an alternative embodiment the first and second stress inducible regulatory elements respond to different inducing agents. In one further embodiment the stress inducible regulatory element of the first and second stress inducible regulatory elements is a pathogen inducible regulatory element. In one embodiment at least one of the first and second signaling moieties is an anthocyanin pathway factor.

In one embodiment, a modified plant is generated by inserting a pathogen inducible regulatory element upstream of a nucleic acid sequence encoding an anthocyanin pathway factor in a manner that operably links the regulatory element to the coding sequence. Alternatively, in one embodiment a modified plant is generated by inserting a nucleic acid sequence encoding an anthocyanin pathway factor downstream of a pathogen inducible regulatory element in a manner that operably links the regulatory element to the nucleic acid sequence encoding an anthocyanin pathway factor. Targeted insertion of a nucleic acid sequence into the genome of a plant cell can be accomplished using standard transformation and homologous recombination techniques. In particular, targeted insertion can be accomplished through the use of site specific nucleases (e.g., Zinc Finger Nucleases (ZFNs), Meganucleases, Transcription Activator-Like Effector Nucelases (TALENS) and Clustered Regularly Interspaced Short Palindromic Repeats/CRISPR-associated nuclease (CRISPR/Cas) with an engineered crRNA/tracer RNA), to facilitate targeted recombination of a donor DNA polynucleotide within a predetermined genomic locus. See, for example, U.S. Patent Publication No. 20030232410; 20050208489; 20050026157; 20050064474; and 20060188987, and International Patent Publication No. WO 2007/014275, the disclosures of which are incorporated by reference in their entireties for all purposes.

Suitable methods for plant transformation for use with the current invention are believed to include virtually any method by which DNA can be introduced into a cell, such as by direct delivery of DNA by PEG-mediated transformation of protoplasts, by desiccation/inhibition-mediated DNA uptake by electroporation, by agitation with silicon carbide fibers, by *Agrobacterium*-mediated transformation, and by acceleration of DNA coated particles. Through the application of techniques such as these, tomato cells, as well as those of virtually any other plant species, may be stably transformed, and these cells developed into engineered plants.

*Agrobacterium*-mediated plant transformation is a widely used method for transferring genes into plants. *Agrobacterium* is a naturally occurring pathogenic bacteria found in the soil that has the ability to transfer its DNA into a plant genome.

In accordance with one embodiment, plant protoplasts are transfected directly with a CRISPR/CAS nucleoprotein.

In some embodiments, a modified plant is generated by selectively inserting a pathogen inducible regulatory element into a plant's DNA to operably link the pathogen inducible regulatory element to a nucleic acid sequence encoding an endogenous anthocyanin pathway factor. Alternatively, in one embodiment, a modified plant is generated by selectively inserting a nucleic acid sequence encoding an endogenous anthocyanin pathway factor into a pathogen inducible gene to operably link the pathogen inducible regulatory element of the pathogen inducible gene to the DNA encoding an endogenous anthocyanin pathway factor. In some embodiments, a modified plant is generated by selectively inserting a nucleic acid sequence encoding an anthocyanin pathway factor into a plant's DNA to operably link an endogenous pathogen inducible regulatory element to the anthocyanin pathway factor. Methods of selectively inserting nucleic acid sequences are known to those skilled in the art of plant genetics. The modified plants according to embodiments of the present disclosure can be prepared by genome editing, through introduction into a plant cell one or more nucleic acids encoding a nuclease, or by directly introducing the nuclease into protoplasts, wherein the nuclease includes, but is not limited to, a Transcription Activator-Like Effector Nuclease ("TALEN"), a zinc finger nuclease ("ZFN"), or a Clustered Regularly Interspaced Short Palindromic Repeats ("CRISPR") associated ("Cas") nuclease. In one embodiment the cisgenic construct is prepared outside the cell and the entire construct is introduced into the genome of a plant cell.

In one embodiment, the modified plant will exhibit a detectable change in color (e.g., exhibit an increase in a red or purple color) when the inducible regulatory element is induced by the presence of a pathogen or pathogen related compound. In some embodiments, the modified plant will turn red when induced by a fungus. In some embodiments, the modified plant will turn purple when induced by a fungus. In some embodiments, the modified plant will exhibit a first detectable change in color when contacted with a fungus or fungus specific compound and will exhibit a second detectable change in color (distinct from the first detectable change in color) when contacted by a non-fungus pathogen such as an insect pest or bacteria. In one embodiment the first and second detectable change in color are visually distinct from one another, and accordingly an insect infestation vs a fungal infection can be determined at an early stage by visual inspection of the plant. In some embodiments, the modified plant will turn purple when induced by a fungus and red when induced by a different pathogen such as an insect pest or bacteria.

In one embodiment, a modified plant is provided that comprises a first pathogen inducible regulatory element operably linked to a nucleic acid sequence encoding a first anthocyanin pathway factor; and a second pathogen inducible regulatory element operably linked to a nucleic acid sequence encoding a second anthocyanin pathway factor wherein the first and second pathogen inducible regulatory elements are induced by separate and distinct moieties, further wherein induction of the first pathogen inducible regulatory element produces a plant that is visibly distinct from a plant having the second pathogen inducible regulatory element induced. In one embodiment the first pathogen inducible regulatory element is activated by a compound specific to fungal pathogens and the second pathogen inducible regulatory element is activated by a compound specific to insect pathogens. In one embodiment the pathogen is a nematode. In one embodiment the first and second anthocyanin pathway factors are each anthocyanin transcription factors, wherein the respective first and second transcription factors activate different sets of genes involved in the biosynthesis of anthocyanins.

In some embodiments, a system of determining when to apply fungicide or insecticide treatments to a field comprising a plurality of plants is provided. The system comprises a plurality of sentry plants and a detection system, wherein the sentry plants comprise a modified plant cell as disclosed herein. The system notifies an end user of the need to apply fungicide or insecticide treatments to a field upon detection of a predetermined signal produced by the sentry pants. In some embodiments, the sentry plants comprise plant cells that have a cisgenic construct present in their genomic DNA wherein the cisgenic construct comprises a stress inducible regulatory element operably linked to a nucleic acid sequence encoding an signaling moiety. In some embodiments, the sentry plants comprise plant cells that have a recombinant construct present in their genomic DNA wherein the recombinant construct comprises a pathogen inducible regulatory element operably linked to a nucleic acid sequence encoding an anthocyanin pathway factor. In some embodiments, the anthocyanin pathway factor is a transcription factor that enhances the production of anthocyanins.

In some embodiments, the plants further comprise a nucleic acid sequence encoding a rate limiting anthocyanin pathway enzyme operably linked to the pathogen inducible regulatory element. In some embodiments, the plant further comprises a second pathogen inducible regulatory element operably linked to a nucleic acid sequence encoding a rate limiting anthocyanin pathway enzyme. In some embodiments, the rate limiting anthocyanin pathway enzyme is chalcone synthase.

In some embodiments, the anthocyanin pathway factor comprises an endogenous nucleic acid sequence encoding a transcription factor that enhances production of anthocyanins, and wherein the endogenous nucleic acid sequence is operably linked to the pathogen inducible regulatory element, optionally where in the pathogen inducible regulatory element is also native to the plant.

In some embodiments, the detection component of the system used to determine when to apply fungicide or insecticide treatments to a field comprises a remote device for monitoring the plants to detect any change in color in the sentry plants. In some embodiments, the detection system further comprises a computer having software, wherein the computer is configured to communicate with the remote device to receive data from the remote device. In some embodiments, the software analyzes the data to detect changes in color in the sentry plants resulting from an induction of the pathogen inducible promoter. The changes in color are relative to non-modified plants.

In some embodiments, the remote device is a camera that captures visual images, including for example still pictures or video. In one embodiment the remote device is mounted onto a mobile vehicle that can move around, through and/or over a field of crop plants. The mobile vehicle can either be manned or unmanned. In some embodiments, the camera is mounted on an unmanned vehicle. In some embodiments, the remote camera is fixed onto a drone. In some embodiments, the camera is fixed on a satellite. In some embodiments, the camera is mounted on a static object such as a pole. In some embodiments, the visual images are streamed from the remote device to the computer. In some embodiments, the software provides an analysis of visual images captured by the remote camera.

In some embodiments, the detection system comprises a wireless controller including a processor; a memory storing a program and a communication unit; and a remote device configured to detect color changes in the plants and to communicate with the wireless controller. In some embodiments, the program, when executed by the processor, analyzes data received from the remote device and produces a signal when the data indicates the presence of plants with an altered change in color relative to adjacent signal or non-signal crop plants. In some embodiments, the altered change is color is determined relative to plants that are not sentry plants.

In some embodiments, a method of treating pathogen-infected plants is disclosed. In some embodiments, the method comprises the steps of planting sentry plants in a field, wherein the sentry plants comprise a modifying gene construct; planting plants lacking the modifying gene construct adjacent to the sentry plants; monitoring the field comprising the sentry plants for alteration in color relative to the plants lacking the modifying gene construct; applying an anti-pathogen treatment to the field in response to a detected alteration in color in the sentry plants relative to the plants lacking the modifying gene construct. In some embodiments, the modifying gene construct comprises a pathogen inducible regulatory element operably linked to a nucleic acid sequence encoding an anthocyanin pathway factor.

In some embodiments, the anti-pathogen treatment comprises an anti-fungal or insecticidal agent. In some embodiments, the anti-pathogen treatment comprises both an anti-fungal and an insecticidal. In some embodiments, the anti-pathogen treatment is antibacterial. Examples of anti-pathogen treatment include fungicides sold by Bayer Crop Science include Stratego YLD for use on corn and soybeans; Aliette for use in vegetable and fruit crops; Gem for use in tree nuts, citrus, stone fruits, potatoes, vegetables, rice, and sugarbeets; Pevicur Flex for use in potatoes, tomato, cucurbits, peppers, lettuce and greenhouse-grown crops; and others. Fungicides sold by Syngenta include Trivapro for protection in corn, wheat, and soybeans, and Miravis Top for soybean fungal diseases, among others. Many other products are available from additional suppliers.

In some embodiments, the anti-pathogen treatment is applied to the entire field. In some embodiments, the anti-pathogen treatment is applied to a portion of the field most closely associated with the sentry plants that have changed color.

In some embodiments, the sentry plants are of the same genetic background as the plants lacking the modifying gene construct. In some embodiments, the sentry plants are of a different genetic background than the plants lacking the modifying gene construct but are the same species.

In some embodiments, the percentage of the sentry plants relative to the total plants in the field is less than about 25%, less than about 20%, less than about 15%, less than about 10%, less than about 5%, or less than about 1%. In some embodiments, the field comprises a single sentry plant. In some embodiments, the field comprises at least about 75%, at least about 80%, at least about 85%, at least about 90%, at least about 95%, at least about 98%, or at least about 99% plants lacking said modifying gene construct. In some embodiments, the field comprises between about 75% to about 99%, about 80% to about 98%, about 80% to about 95%, about 85% to about 95%, or about 90% to about 95% plants lacking said modifying gene construct. In some embodiments, the field comprises between about 0.5% to about 20%, about 1% to about 25%, about 2% to about 20%, about 5% to about 20%, about 5% to about 15%, about 5% to about 10%, about 2% to about 10%, about 1% to about 10%, about 0.5% to about 10%, about 0.5% to about 5%, or about 1% to about 5% sentry plants relative to the total plants in the field.

In some embodiments, the field of plants comprises up to about 95% sentry plants, up to about 96% sentry plants, up to about 97% sentry plants, up to about 98% sentry plants, up to about 99% sentry plants, or up to 100% sentry plants.

In some embodiments, the sentry plants are interspersed with plants having a similar genetic background but lacking the modifying gene construct. In one embodiment, the sentry plants are planted on the perimeter of a field, optionally forming a border that completely surrounds plants of the same species, and optionally having the same genetic background as the non-sentry plants planted adjacent to the sentry plants.

Various functions and advantages of these and other embodiments of the present disclosure will be more fully understood from the examples shown below. The examples are intended to illustrate the benefits of the present disclosure, but do not exemplify the full scope of the disclosure.

EXAMPLES

Example 1. Identification of Pathogen-Induced Tomato Genes

Pathogen-induced (PI) genes from tomato were selected from publicly available data, such as publications (for example, Zuluaga et al., 2016. Analysis of the tomato leaf transcriptome during successive hemibiotrophic stages of a compatible interaction with the oomycete pathogen *Phytophthora infestans*. Molecular Plant Pathology 17, 42-54) and GEO datasets (for example, www.ncbi.nlm.nih.gov/geo/query/acc.cgi?acc=GSE40214). Genes induced in at least three such lists were further screened for expression during normal growth and development using the Tomato eFP Browser (bar.utoronto.ca/efp_tomato/cgi-bin/efpWeb.cgi) and removed. Genes likely to systemically activate in response to a local pathogen infection were manually chosen. The promoter regions of these genes were obtained from the Sol Genomics Network (solgenomics.net), tomato genome version SL3.0.

Example 2. Construction of Vectors and Tomato Transformation

Anthocyanins are a class of red to purple plant pigments that can be produced in nearly all flowering plants. The ANT1 (ANTHOCYANIN1) gene encodes an R2R3 MYB transcription factor that activates the expression of a number of genes in the anthocyanin biosynthetic and transportation pathway. When ANT1 is overexpressed using the Cauliflower Mosaic Virus 35S promoter, most plant tissues hyperaccumulate anthocyanins (Mathews et al., 2003. Activation Tagging in Tomato Identifies a Transcriptional Regulator of Anthocyanin Biosynthesis, Modification, and Transport. The Plant Cell 15, 1689-1703).

ANT1 with its genomic terminator sequence and the selected promoters of the PIs (pPIs) from Example 1 will be synthesized by GenScript, Inc. (www.genscript.com) and cloned into the pRI909 binary vector from Takara Bio USA, INC. (www.takarabio.com), which includes a NOS:NPTII selectable marker gene. The ANT1 gene/terminator, preceded by pPIs, will be inserted into the pRI909 vector by restriction digestion and ligation. Constructs will be confirmed by diagnostic restriction enzyme digestion and by PCR. The pRI909 vectors containing various pPI:ANT1 constructs will be transformed into *Agrobacterium tumefaciens* strain LBA4404.

Tomatoes (var. Micro-Tom) will be transformed as described in Sun et al. (2006. A Highly Efficient Transformation Protocol for Micro-Tom, a Model Cultivar for Tomato Functional Genomics. Plant Cell Physiology 47, 426-431).

Transformants will be verified by PCR.

Example 3. Assessment of Transformed Plants' Reactivity to Pathogens

Transformed plants harboring the pPI:ANT1 construct will be subjected to a series of assessments over multiple generations. Using a sterile disposable syringe, a leaf will be infiltrated with salicylic acid (a phytohormone used in pathogen defense), chitin oligosaccharides (a fungal cell wall component released during fungal infection), or other elicitors. In each assay, the accumulation of anthocyanins will be measured in both local and distil tissues by digital photography, using a modified color checker as a standard.

In addition, transformed plants will be routinely monitored with a colorimeter. L*a*b* coordinates will be recorded and compared to previous data taken from the same plant and compared to non-sentry plants grown beside the sentry plant.

Example 4. Production of Gene-Edited Pathogen-Responsive Tomato Plants

The coding region of ANT1 will be inserted between the promoter and coding region of a pathogen-induced gene (PI). Genes will be selected as described in Example 3. Plants will be edited as described in Dahan-Meir et al. (2018. Efficient in planta gene targeting in tomato using geminiviral replicons and the CRISPR/Cas9 system. The Plant Journal 95, 5-16). Briefly, CRISPR/Cas9 will be used to create a double strand break (DSB) near the transcription start site of the PI. The geminiviral system will be used to create many copies of a repair template sequence for homology-directed repair (HDR) of the break.

Geminiviruses normally replicate by a rolling circle replication mechanism. The viral replication initiator protein (Rep) binds to the large intergenic region (LIR) and creates a single-strand nick. Rep separates a single DNA strand from the double strand until it reaches another LIR, when it circularizes the single strand. Host DNA replication machinery copies each single strand into double strands. Rep again separates the circularized DNA, and many copies of the replicon are formed.

For HDR applications, the virus will be deconstructed. Elements normally found within the replicons, such as the viral coat protein gene, will be removed except for a short intergenic region (SIR), which is still required for efficient replicon formation. The remaining sequence between the LIR regions will consist of the repair template sequence: ~1000 bp of the PI promoter upstream of the DSB (5' homology arm), the ANT1 gene from translation start site to stop sites, and ~1000 bp of the PI gene's sequence downstream of the DSB (3' homology arm).

Binary vectors will be constructed containing a NOS promoter expressing an NPTII hygomycin-resistance gene, *Arabidopsis thaliana* U6 RNA Pol III promoter expressing a guide RNA with homology to a site within the PI, LIR, the template repair sequence, SIR, LIR, 35S promoter expressing Rep, and the Ubiquitin10 promoter from *Solanum lycopersicum* expressing Cas9.

Tomato explants will be transformed using *Agrobacterium tumefaciens* strain LBA4404 harboring this vector. Regenerated T0 plants will be screened for successful HDR by PCR and sequencing. T1 plants will be selected for homozygous HDR mutations but without the T-DNA insertions from the vector.

Gene targeted plants will be analyzed for pathogen reactivity as described in Example 3. Similar methodologies may be used to edit monocot genomes. A different geminivirus, wheat dwarf virus, has been used as a heterologous gene expression platform for wheat, rice, and maize, and in addition was used to perform gene editing by HDR in wheat (Gil-Humanes et al., 2016. High-efficiency gene targeting in hexaploid wheat using DNA replicons and CRISPR/Cas9. The Plant Journal 89, 1251-1262). Another group used the same wheat dwarf virus to perform gene editing by HDR in rice (Wang et al., 2017. Gene Targeting by Homology-Directed Repair in Rice Using a Geminivirus-Based CRISPR/Cas9 System. Molecular Plant 10, 1007-1010). Researchers at Pioneer (Svitashev et al., 2015. Targeted Mutagenesis, Precise Gene Editing, and Site-Specific Gene Insertion in Maize Using Cas9 and Guide RNA. Plant Physiology 169, 931-941) demonstrated that gene editing by HDR in maize using CRISPR/Cas9 is possible. Deconstructed geminiviral systems, such as the wheat dwarf virus, will also be used to perform gene editing in maize.

*Glycine max* will be edited in a similar way. Li et al. (2015. Cas9-Guide RNA Directed Genome Editing in Soybean. Plant Physiology 169, 960-970) first demonstrated that soybean may be gene edited and genes integrated using CRISPR/Cas9. Gene editing by HDR was successful using a deconstructed bean yellow dwarf geminivirus system in tobacco (Baltes et al., 2014. DNA Replicons for Plant Genome Engineering. The Plant Cell 26, 151-163) and in tomato (Čermák et al., 2015. High-frequency, precise modification of the tomato genome. Genome Biology 16, 232), and this system is likely to also be successful in soy and alfalfa.

Example 5. Construction of Vectors and Maize Transformation

Pathogen induced gene promoters (pPI) were selected for maize similar to Example 1 and retrieved from Maize GDB (maizegdb.org) from the B73 reference genome. Anthocyanin biosynthesis can be enhanced by overexpression of genes encoding transcription factors such as B1 and P11, (Chandler et al., 1989. Two Regulatory Genes of the Maize Anthocyanin Pathway Are Homologous: isolation of B Utilizing R Genomic Sequences. The Plant Cell 1, 1175-1183; Hollick et al., 1995. Paramutation Alters Regulatory Control of the Maize pl Locus. Genetics 154, 1827-1838). Promoters and genes were synthesized by Genscript, Inc. Genes were cloned individually or in tandem (fused and spaced by a DNA sequence encoding six alanines, P11/B1) driven by a pPI into the pMCG1005 vector, which contains a 35S:BAR selectable marker. All constructs included the first ADH1 intron (Callis et al., 1987. Introns increase gene expression in cultured maize cells. Genes & Development 1, 1183-1200) between the inducible promoter and the reporter gene. The pMCG1005 vector, lacking a reporter gene, was used as a negative control (FIG. 1). All cloning was performed using Type II and Type IIS restriction endonucleases. Each vector was transformed into *Agrobacterium tumefaciens* strain EHA 105. Maize line B104 was transformed according to Raji et al. (2018. *Agrobacterium*- and Biolistic-Mediated Transformation of Maize B104 Inbred. Maize: Methods and Protocols, Methods in Molecular Biology 1676, 15-40). Transformed maize plants were confirmed by PCR using gene and promoter specific primers and analyzed for pathogen reactivity as described in Examples 3 and 6.

Figure 2:
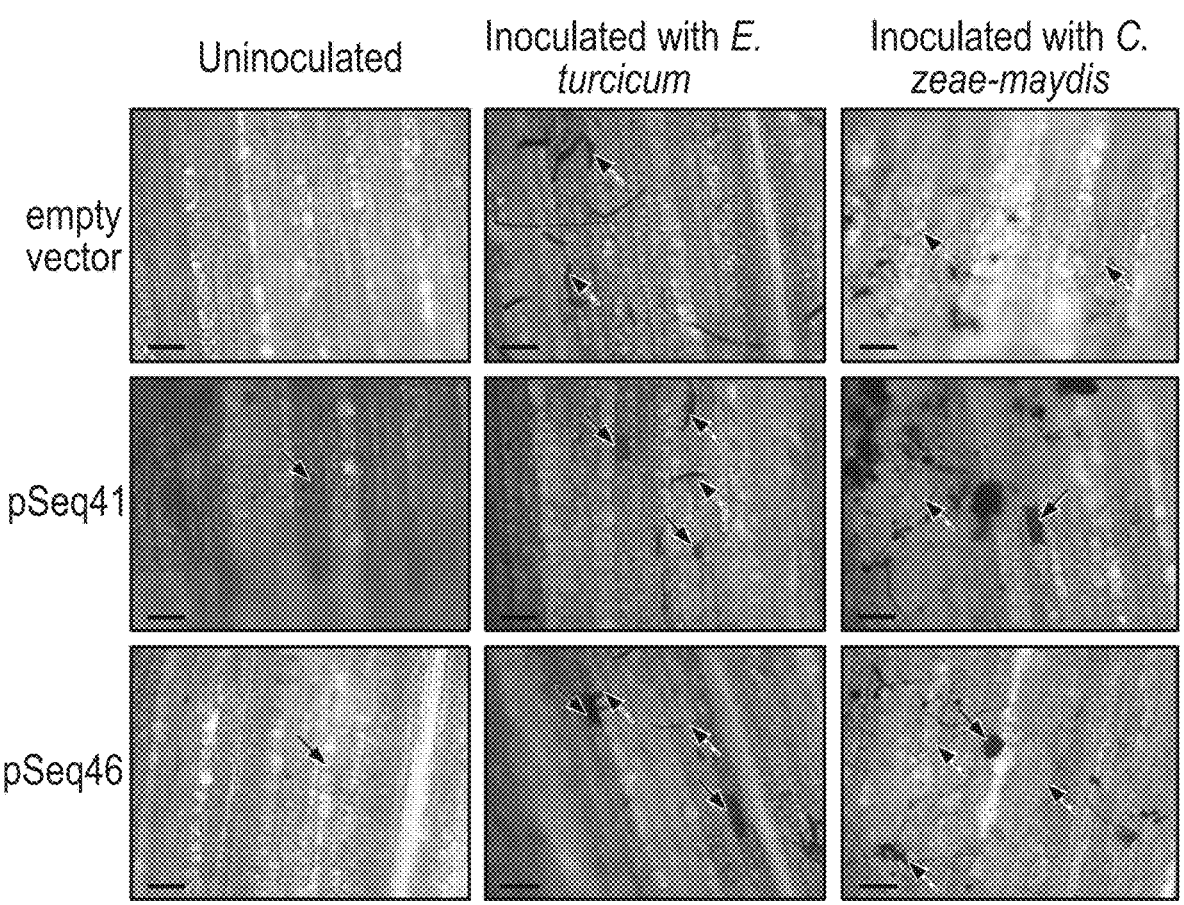
FIG. 2 is a series of micrographs revealing individual bombarded cells producing anthocyanin pigments. Some cells contain a higher concentration of anthocyanins than others, resulting in a darker phenotype. Solid arrows indicate cells producing anthocyanin following transformation. Dotted arrows indicate pathogens. The top row of micrographs depict cells bombarded with negative control plasmid. The middle row of micrographs depict cells bombarded with pSeq41:P11/B1 plasmid. The bottom row of micrographs depict cells bombarded with pSeq46:P11/B1 plasmid. The first column of micrographs depict cells not inoculated, but grown in a non-sterile environment. The second column of micrographs depict cells inoculated with *E. turcicum* immediately following bombardment. The third column of micrographs depict cells inoculated with *C. zeae-maydis* immediately following bombardment. Images taken five DAB. Scale bar=100 μm

Example 6. Assessment of Biolistically Transformed Plants' Reactivity to Pathogens A biolistic transformation device was constructed as described in Tsugama and Takano (2020. Developing a tool to shoot genes by a man-made air pressure. Journal of Genetic Engineering and Biotechnology 18, 48). The first and second leaves of 12-14 days-old maize B104 plants at V2 growth stage were bombarded with gold particles carrying pPI:P11/B1. Some plants were inoculated immediately after bombardment with a drop of *Exserohilum turcicum* or *Cercospora zeae-maydis* grown axenically and blended in water. Plant cells were assessed for red or purple color development by microscopy 4-5 days after bombardment (DAB) (FIG. 2). In leaves bombarded with pPI:P11/B1 constructs, significantly more cells synthesizing anthocyanins were observed in plants that were inoculated with either *E. turcicum* or *C. zeae-maydis* than in uninoculated plants (Table 1). No cells synthesizing anthocyanins were observed in the inoculated or uninoculated negative controls. These results were repeated in an additional experiment for each pathogen. Uninoculated plants displayed a low number of cells containing anthocyanins, possibly due to pathogens present in the non-sterile greenhouse. This demonstrates the efficacy of our system whereby a pathogen inducible promoter drives the expression of an anthocyanin transcription factor gene to identify and report the presence of a plant pathogen.

TABLE 1

In biolistically transformed plants, the number of cells containing anthocyanin increases following inoculation with E. turcicum 5 DAB in Experiments 1, and 2, and 4 DAB in Experiment 3. Uninoculated and inoculated groups (Experiments 1 and 2, n = 6; Experiment 3, n = 10) were compared using t tests, and the P-value is indicated.

| Inducible promoter | Difference between E. turcicum treated and uninoculated (±SE) | p-value | Difference between C. zeae-maydis treated and uninoculated (±SE) | p-value |
|---|---|---|---|---|
| Experiment 1 | | | | |
| empty vector | 0.0 ± 0.0 | N/A | not tested | |
| SEQ41 | 1.5 ± 0.9 | 0.071 | | |
| SEQ46 | 2.1 ± 0.9 | 0.025 | | |
| Experiment 2 | | | | |
| empty vector | not tested | | 0.0 ± 0.0 | N/A |
| SEQ41 | | | 2.9 ± 1.7 | 0.065 |
| SEQ46 | | | 1.5 ± 0.7 | 0.032 |
| Experiment 3 | | | | |
| empty vector | 0.0 ± 0.0 | N/A | 0.0 ± 0.0 | N/A |
| SEQ41 | 1.3 ± 0.8 | 0.091 | 1.5 ± 0.8 | 0.037 |
| SEQ46 | 3.2 ± 0.7 | 8E−05 | 1.8 ± 0.4 | 1E−04 |

The invention claimed is:

1. A modified plant cell comprising a cisgenic construct, said construct comprising:
a promoter comprising a pathogen inducible regulatory element, wherein said promoter comprises a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 and SEQ ID NO: 47, operably linked to a nucleic acid sequence encoding a signaling moiety, wherein said promoter and said nucleic acid sequence encoding the signaling moiety are both endogenous to said plant cell but are not operably linked to one another in the native plant cell.

2. The modified plant cell of claim 1 wherein the cisgenic construct is generated by inserting either the promoter or the nucleic acid sequence encoding a signaling moiety into a genomic location that results in the operable linkage of the promoter to the nucleic acid sequence encoding a signaling moiety.

3. The modified plant cell of claim 1 wherein said cisgenic construct is inserted into a novel genomic site of said plant cell.

4. A plant or plant part comprising a plurality of the modified plant cells according to claim 1.

5. The plant or plant part of claim 4, wherein said signaling moiety is an anthocyanin pathway factor.

6. The plant or plant part of claim 5 wherein said anthocyanin pathway factor is i) a transcription factor that enhances production of anthocyanins; or
ii) a rate limiting anthocyanin pathway enzyme.

7. The plant or plant part of claim 5, wherein said anthocyanin pathway factor is a transcription factor that enhances production of anthocyanins, said transcription factor being
i) selected from the group consisting of C1, R, P11, and B1, or alleles of these genes; or
ii) a nucleic acid encoding an amino acid sequence selected from the group consisting of anthocyanin1 transcription factor (ANT1; SEQ ID NO: 34), Zm00001d044975 (SEQ ID NO: 27), Zm00001d026147 (SEQ ID NO: 28), Zm00001d000236 (SEQ ID NO: 29), Zm00001d028842 (SEQ ID NO: 30), Zm00001d008695 (SEQ ID NO: 31), Zm00001d037118 (SEQ ID NO: 33), Zm00001d019170 (SEQ ID NO: 33), and Glyma09g36990 (SEQ ID NO: 35).

8. The plant or plant part of claim 5 wherein said plant or plant part is
a corn plant wherein a plurality of cells of the corn plant comprise said promoter operably linked to said nucleic acid sequence encoding an anthocyanin transcription factor, wherein the transcription factor has a sequence comprising SEQ ID NO: 28 and said promoter comprises a sequence selected from the group consisting of SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 and SEQ ID NO: 47.

9. The plant or plant part of claim 8, further comprising a nucleic acid sequence encoding a rate limiting anthocyanin pathway enzyme operably linked to a second promoter comprising a pathogen inducible regulatory element, wherein said promoter is native to corn cells.

10. The plant or plant part of claim 5, comprising a first cisgenic construct comprising a first pathogen inducible regulatory element operably linked to a nucleic acid sequence encoding a first signaling moiety and a second cisgenic construct comprising a pathogen inducible regulator element operably linked to a nucleic acid sequence encoding a second signaling moiety.

11. The plant or plant part of claim 10 wherein the first and second pathogen inducible regulatory elements respond to different inducing agents.

12. The plant or plant part of claim 5, wherein said anthocyanin pathway factor is an enzyme selected from the group consisting of chalcone synthase, chalcone flavanone isomerase1, chalcone flavanone isomerase2, chalcone flavanone isomerase3, chalcone flavanone isomerase4, chalcone flavanone isomerase5, flavanone 3β-hydroxylase1, flavanone 3β-hydroxylase2, flavonoid 3'-hydroxylase, dihydroflavonol reductase1, dihydroflavonol 4-reductase, anthocyanin synthase, UDP-glucose flavonoid 3-O-glycosyltransferase, isoflavonoid synthase, flavonol synthase1, flavonol synthase2, cncr2 (cinnamoyl CoA reductase2), CCR4, dihydroflavonol-4-reductase, Flavonol synthase-like protein, NADPH dihydroflavonol reductase, Leucoanthocyanidin dioxygenase (LDOX), anthocyanidin synthase (ANS), flavanone 4-reductase, anthocyanidin 3-O-glucosyltransferase, glutathione S-transferase, anthocyanin acyltransferase1, and pale aleurone color1.

13. The plant or plant cell of claim 10 comprising a first pathogen inducible regulatory element operably linked to a nucleic acid sequence encoding a transcription factor that enhances production of anthocyanins, and a second pathogen inducible regulator element operably linked to a nucleic acid sequence encoding a rate limiting anthocyanin pathway enzyme.

14. The plant of claim 4, wherein said plant is a corn plant and said cisgenic construct of the modified plant cells comprise a promoter sequence selected from the group consisting of SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46 and SEQ ID NO: 47.

15. A system for determining when to apply fungicide or insecticide treatments to a field comprising a plurality of plants, said system comprising:
one or more sentry plants, wherein said sentry plants comprise the cisgenic construct of claim 1; and
a detection system comprising a remote device for monitoring said plants to detect the expression of a detectable marker associated with said signaling moiety in said sentry plants.

16. The system of claim 15 wherein said stress inducible regulatory element is a pathogen inducible regulatory element.

17. The system of claim 16 wherein said signaling moiety is an anthocyanin pathway factor and the detection system detects changes in color in the cells of said sentry plants.

18. The system of claim 17 wherein said detection system further comprises a computer having software, and said computer being configured to communicate with said remote device to receive data from the remote device and analyze said data to detect changes in color in said sentry plants resulting from an induction of said pathogen inducible promoter.

19. The system of claim 18, wherein the remote device is a camera that captures visual images, wherein the camera is
  i) mounted on a stationary pole; or
  ii) mounted on an unmanned vehicle; or
  iii) is fixed onto a drone or satellite.

20. The system of claim 15 wherein said sentry plants further comprise a nucleic acid sequence encoding a rate limiting anthocyanin pathway enzyme operably linked to a second pathogen inducible regulatory element, optionally wherein said rate limiting anthocyanin pathway enzyme is chalcone synthase.

21. The system of claim 19 wherein said detection system comprises
a wireless controller including a processor;
a memory storing a program and a communication unit; and
a remote device configured to detect color changes in said plants and to communicate with the wireless controller, wherein the program, when executed by the processor, analyzes data received from the remote device and produce a signal when the data indicates the presence of plants with an altered change in color and optionally, the location of said plants with an altered change in color.

22. A method of treating pathogen-infected plants, said method comprising the steps of:
planting a sentry plant in a field, wherein said sentry plant comprises a plurality of the modified plant cells according to claim 1;
planting plants lacking said cisgenic construct adjacent to said sentry plant;
monitoring said field comprising said sentry plant for detection of said signaling moiety relative to said plants lacking said cisgenic construct;
applying an anti-pathogen treatment to said field in response to a detected alteration in expression of a detectable marker associated with said signaling moiety in said sentry plants relative to said plants lacking said cisgenic construct.

23. The method of claim 22 wherein said signaling moiety is an anthocyanin pathway factor and the detectable marker is an alteration in color, and -the anti-pathogen treatment comprises an anti-fungal or insecticidal agent.

24. The method of claim 23, wherein the percentage of said sentry plants relative to the total plants in said field is less than about 25%, optionally wherein said sentry plants are interspersed with plants having a similar genetic background but lacking said cisgenic construct.

* * * * *